US006858426B1

(12) United States Patent
Zhu et al.

(10) Patent No.: US 6,858,426 B1
(45) Date of Patent: Feb. 22, 2005

(54) GRAPEVINE LEAFROLL VIRUS (TYPE 2) PROTEINS AND THEIR USES

(75) Inventors: Hai-Ying Zhu, Geneva, NY (US); Kai-Shu Ling, Geneva, NY (US); Dennis Gonsalves, Geneva, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/613,486

(22) Filed: Jul. 11, 2000

Related U.S. Application Data

(63) Continuation of application No. 09/080,983, filed on May 19, 1998, now Pat. No. 6,197,948.
(60) Provisional application No. 60/047,194, filed on May 20, 1997.

(51) Int. Cl.[7] .......................... C12N 15/00; C12N 1/20; C12N 5/00; C12P 21/06; C07H 21/02

(52) U.S. Cl. .................. 435/320.1; 435/69.1; 435/410; 435/419; 435/468; 435/469; 435/252.2; 536/23.1; 536/23.72

(58) Field of Search .............................. 435/69.1, 320.1, 435/410, 419, 468, 469, 252.2, 414, 430.1, 470, 172.3; 536/23.1, 23.72; 800/260, 280, 294, 316, 205; 530/350

(56) References Cited

U.S. PATENT DOCUMENTS

| | | | |
|---|---|---|---|
| 4,358,535 A | 11/1982 | Falkow et al. .................. | 435/5 |
| 4,480,040 A | 10/1984 | Owens et al. ................ | 436/504 |
| 5,043,272 A | 8/1991 | Hartley ......................... | 435/91 |
| 5,104,792 A | 4/1992 | Silver et al. ................... | 435/6 |
| 5,106,727 A | 4/1992 | Hartley et al. ................ | 435/6 |
| 5,196,305 A | 3/1993 | Findlay et al. ................. | 435/6 |
| 5,288,611 A | 2/1994 | Kohne ........................... | 435/6 |
| 5,322,770 A | 6/1994 | Gelfand ......................... | 435/6 |
| 5,328,825 A | 7/1994 | Warren, III et al. ............ | 435/6 |
| 5,714,312 A | 2/1998 | Nuno Bardosa Nolasco et al. ............................... | 435/5 |
| 5,872,241 A | 2/1999 | Pyle et al. ................... | 536/245 |
| 5,907,085 A | 5/1999 | Gonsalves et al. | |
| 5,965,355 A | 10/1999 | Monis et al. ................... | 435/5 |
| 5,990,388 A | 11/1999 | Roth et al. .................. | 800/301 |
| 6,197,948 B1 | 3/2001 | Zhu et al. | |
| 6,558,953 B1 | 5/2003 | Gonsalves et al. .......... | 435/419 |
| 6,638,720 B1 | 10/2003 | Gonsalves et al. ............. | 435/6 |

FOREIGN PATENT DOCUMENTS

| | | |
|---|---|---|
| EP | 0 769 696 A2 | 4/1997 |
| EP | 0769696 | 4/1997 |
| IT | 1268561 | 3/1997 |
| WO | WO 97/22700 | 6/1997 |
| WO | WO 98/53055 | 11/1998 |
| WO | WO 99/55880 | 11/1999 |

OTHER PUBLICATIONS

PTO Sequence search report for Seq ID No:15 by STIC, Oct. 11, 2003.*
Abou–Ghanem et al., "Physico–Chemical and Molecular Characterization of Grapevine Leafroll–Associated Virus 2," 12th Meeting of the International Council for the Study of Viruses and Virus–Like Diseases of the Grapevine, Sep.–Oct., pp. 15–16 (1997).
Agrios, *Plant Pathology*, Third Ed. Excerpt of Chapter 14, pp. 622–623 and 648–655. Academic Press, San Diego (1988).
Beachy et al., "Coat Protein–Mediated Resistance Against Virus Infection," *Annu. Rev. Plant Pathol.*, 28:451–474 (1990).
Abou–Ghanem et al., "Some Properties of Grapevine Leafroll–Associated Virus 2 and Molecular Organization of the 3' Region of the Viral Genome," *Journal of Plant Pathology* 80:37–46 (1998).
Abou–Ghanem et al., "Grapevine Leafroll–Associated 2 Genes Encoding RNA Polymerase and Coat Protein, hsp70, hsp90 Gene and ORF2, ORF7 and ORF8," DataBase EMBL Online Accession No. Y14131 (Sep. 2, 1997).
Habill et al., "Identification of a cDNA Clone Specific to Grapevine Leafroll–Associated Virus 1, and Occurence of the Virus in Australia," *Plant Pathology* 46:516–522 (1997).
Namba et al., "Purification and Properties of Closterovirus–Like Particles Associated With Grapevine Corky Bark Disease," BIOSIS DataBase Accession No. PREV199192116654 (Abstract) (1991).
Namba et al., "Purification and Properties of Closterovirus–Like Particles Associated With Grapevine Corky Bark Disease," *Phytopathology* 81:964–970 (1991).
Zhu et al., "Nucleotide Sequence and Genome Organization of Grapevine Leafroll–Associated Virus–2 are Similar to Beet Yellows Virus, the Closterovirus Type Member," Database EMBL Online Accession No. AF039204 (May 11, 1998).
Boscia et al., "Nomenclature of Grapevine Leafroll–Associated Putative Closteroviruses," *Vitis* 34:171–175 (1995).
Boscia et al., "Characterization of Grape Leafroll Associated Closterovirus (GLRaV) Serotype II and Comparison with GLRaV Serotype III," *Phytopathology* 80:117 (1990).

(List continued on next page.)

Primary Examiner—Jeffrey Fredman
Assistant Examiner—Sumesh Kaushal
(74) Attorney, Agent, or Firm—Clark & Elbing LLP

(57) ABSTRACT

The present invention relates to isolated proteins or polypeptides of grapevine leafroll virus (type 2). The encoding DNA molecules either alone in isolated form or in an expression system, a host cell, or a transgenic grape plant are also disclosed. Other aspects of the present invention relates to a method of imparting grapevine leafroll resistance, to grape and tobacco plants by transforming them with the DNA molecules of the present invention, a method of imparting beet yellows virus resistance to a beet plant, a method of imparting tristeza virus resistance to a citrus plant, and a method of detecting the presence of a grapevine leafroll virus, such as GRLaV-2, in a sample.

6 Claims, 15 Drawing Sheets

OTHER PUBLICATIONS

Boston et al., Molecular Chaperones and Protein Folding in Plants, *Plant Mol. Biol.* 32:191–222 (1996).

Candresse et al., "Virus Taxonomy–Classification and Nomenclature. Part II. The Viruses–Closterovirus," *Archives of Virology* S10:461–464 (1995).

Credi et al., "Grapevine Leafroll–associated Viruses and Grapevine Virus A in Selected *Vitis vinifera* Cultivars in Northern Italy," *Plant Pathology* 45:1110–1116 (1996).

Dolja et al., "Molecular Biology and Evolution of Closteroviruses: Sophisticated Build–Up of Large RNA Genomes," *Annu. Rev. Phytopath.*, 32:261–285 (1994).

Engelbrecht, et al., "Association of a Closterovirus with Grapevines Indexing Positive for Grapevine Leafroll Disease and Evidence for its Natural Spread in Grapevine," *Phytopath. medit.* 24:101–105 (1985).

Frazeli et al., "Efficient Cloning of cDNA From Grapevine Leafroll–associated Virus 4 and Demonstration of Probe Specificity by the Viral Antibody," *J. Virological Methods* 70:201–211 (1998).

Forsline et al., "Comparative Effectiveness of Symptomatology and ELISA for Detecting Two Isolates of Grapevine Leafroll on Graft–inoculated Cabernet franc," *Am. J. Enol.. Vitic.*, 47:239–243 (1996).

Genbank Sequence accession U22170 for Grapevine Leafroll Associated Virus Type III p20 Protein.

Genbank Sequence accession U22158 for Grapevine Leafroll Associated Virus RNA6 Gene.

Goszczynski et al., "Detection of Two Strains of Grapevine Leafroll–Associated Virus 2," *Vitis* 35:133–135 (1996).

Goszczynski et al., "Production and Use of Antisera Specific to Grapevine Leafroll–Associated Viruses Following Electrophoretic Separation of Their Proteins and Transfer to Nitrocellulose," *African Plant Protection* 1:1–8 (1995).

Goszczynski et al., "Grapevine Leafroll–Associated Virus 2 (GLRaV–2)–Mechanical Transmission, Purification, Production and Properties of Antisera, Detection by ELISA," *S. Afr. J. Enol. Vitic.* 17:15–26 (1996).

Gugerli et al., "L'Enroulement de la Vigne: Mise en Évidence de Particules Virales et Développement d' une Méthode Immuno–Enzymatique Pour le Diagnostic Rapide," *Rev. Suisse Vitic. Arboric. Hortic.*, 16:299–304 (1984).

Gugerli et al., "Grapevine Leafroll Associated Virus II Analyzed by Monoclonal Antibodies," 11*th* Meeting of the International Council for the Study of Viruses and Virus–Like Disease of the Grapevine pp. 23–24 (1993).

Gugerli et al., "Identification Immuno–Chimique du 6*e* Virus Associé à la Maladie de L'Enroulement de la Vigne et Amélioration des Techniques de Diagnostic Pour la Sélection Sanitaire en Viticulture," *Rev. Suisse Vitic. Arboric. Hortic.*, 29:137–141 (1997).

Habili et al., "Natural Spread and Molecular Analysis of Grapevine Leafroll–Associated Virus 3 in Australia," *Phytopathology* 85:1418–1422 (1995).

Hu et al., "Use of Monoclonal Antibodies to Characterize Grapevine Leafroll Associated Closteroviruses," *Phytopathology* 80:920–925 (1990).

Hu et al., "Characterization of Closterovirus–like Particles Associated with Grapevine Leafroll Disease," *J. Phytopathology* 128:1–14 (1990).

Karasev et al., "Screening of the Closterovirus Genome by Degenerate Primer–Mediated Polymerase Chain Reaction," *Journal of General Virology* 75:1415–1422 (1994).

Krastanova et al., "Transformation of Grapevine Rootstocks With the Coat Protein Gene of Grapevine Fanleaf Nepovirus," *Plant Cell Reports* 14:550–554 (1995).

Krustanova et al., *Rastenievud, Nauki.* 29(1–2):90–94 (1992) (Abstract).

Lazar et al., "Occurrence of Grapevine Leafroll Associated Closteroviruses (GLRAV–S) in Hungary," *Med. Fac. Landbouww. Univ. Gen.* 60:307–308 (1995).

Le Gall et al., "Agrobacterium–Mediated Genetic Transformation of Grapevine Somatic Embryos and Regeneration of Transgenic Plants Expressing the Coat Proteins of Grapevine Chrome Mosaic Nepovirus (GCMV)," *Plant Science* 102:161–170 (1994).

Levy et al., "Simple and Rapid Preparation of Infected Plant Tissue Extracts for PCR Amplification of Virus, Viroid, and MLO Nucleic Acids," *J. Virological Methods* 49:295–304 (1994).

Ling et al., "Molecular Cloning and Detection of Grapevine Leafroll Virus By Nucleic Acid Hybridization and Polymerase Chain Reaction," *Phytopathology* 83:245 (1993).

Ling et al., "Identification of Coat Protein Gene and Partial Genome Organization of Grapevine Leafroll–Associated Closterovirus Type III," *Phytopathology* 84:1372 (1994).

Ling et al., "Partial Genome Organization of Grapevine Leafroll–Associated Closterovirus 3," *Phytopathology* 85:1152 (1995).

Ling et al., "Coat Protein Gene Identification, Genome Organization, and PCR Detection of Grapevine Leafroll Associated Closterovirus–3 and Study Towards Transgenic Grapevines", *The American Chemical Society* 125:138016 (Abstract) (1996).

Ling et al., "Coat Protein Gene Identification, Genome Organization, and PCR Detection of Grapevine Leafroll Associated Closterovirus–3 and Study Towards Transgenic Grapevines (Vitis)", *Dissertation Abstracts International* 57(3):1539 (1996).

Ling et al., "The coat protein gene of grapevine leafroll associated closterovirus–3: cloning, nucleotide sequencing and expression in transgenic plants," *Archives of Virology* 142:1101–1116 (1997).

Ling et al., "Nucleotide Sequence of the 3' Terminal Two–thirds of the Grapevine—Leafroll–associated Virus–3 Genome Reveals a Typical Monopartite Closterovirus" *Journal General Virology* 79:1299–1307 (1998).

Maningas et al., "Use of Immunocapture–Polymerase Chain Reaction (IC–PCR) in the Diagnosis of Grapevine Leafroll Virus (GLRV) Disease in Grapevine Field Samples," *Am. J. Enol. Vitic..*, 45:357 (1994).

Minafra et al., "Detection of Grapevine Closterovirus A in Infected Grapevine Tissue by Reverse Transcription–Polymerase Chain Reaction," *Vitis* 31:221–227 (1992).

Minafra et al., "Sensitive Detection of Grapevine Virus A, B or Leafroll–Associated III From Viruliferous Mealybugs and Infected Tissue by cDNA Amplification," *Journal of Virological Methods* 47:175–188 (1994).

Minafra, et al., "Improved PCR Procedures for Multiple Identification of Some Artichoke and Grapevine Viruses," *Bulletin OEPP/EPPO Bulletin* 25:283–287 (1995).

Monis et al., "Detection and Localization of Grapevine Leafroll Assoicated Closteroviruses in Greenhouse and Tissue Culture Grown Plants," *Am. J. Enol. Vitic.*, 47:199–205 (1996).

Monis et al., "Production of Antibodies Specific to a 37 kD Polypeptide Associated with Grapevine Leafroll Associated Virus," *Am. J. Enol. Vitic.*, 47:351 (1996).

Monis et al., "Relationship Between Grapevine Leafroll Associated Virus–2 Grapevine Corky Bark Associated Virus, and the Rootstock–Scion Incompatibility Syndrome," *Am. J. Enol. Vitic.*, 48:393 (1997).

Monis, et al., "Serological Detection of Grapevine Associated Closteroviruses in Infected Grapevine Cultivars," *Plant Disease*, vol. 81, No. 7, pp. 802–808 (1997).

Nejidat, A. et al., "Engineered Resistance Against Plant Virus Diseases," *Physiologia Plantarum* 80: 662–668 (1990).

Rowhani et al., "A Comparison Between ELISA and Bioassay Indexing on Cabernet franc Indicator for Detecting Grapevine Leafroll Associated Viruses," *Am. J. Enol. Vitic.*, 47:349–350 (1996).

Rowhani et al., "A Comparison Between Serological and Biological Assays in Detecting Grapevine Leafroll Associated Viruses," *Plant Disease* 81:799–801 (1997).

Saldarelli et al., "Detection of Grapevine Leafroll–Associated Closterovirus III By Molecular Hybridization," *Plant Pathology* 43:91–96 (1994).

Saldarelli et al., "Use of Degenerate Primers in a RT–PCR Assay for the Identification and Analysis of Some Filamentous Viruses, with Special Reference to Clostero– and Vitiviruses of the Grapevine," *Eur. J. Plant Pathology* 104:945–950 (1998).

Schell et al., "Transformation of 'Nova' Tangelo With the Coat Protein Gene of Citrus Tristeza Closterovirus," *Phytopathology* 84:1076 (1994).

Shlamovitz et al., "Unique and Quick in Vitro Procedure to Detect Grapevine Virus Diseases," *Hortscience* 30:783 (1995).

Stam et al., "The Silence of Genes in Transgenic Plants" *Ann. Bot.*, 79:3–12 (1997).

Teliz, "Field Serological Detection of Viral Antigens Associated with Grapevine Leafroll Disease," *Plant Disease* 71:704–709 (1987).

Wetzel et al., A Highly Sensitive Immunocapture Polymerase Chain Reaction Method for Plum Pox Potyvirus Detection,: *Journal of Virological Methods* 39:27–37 (1992).

Zee et al., "Cytopathology of Leafroll–Diseased Grapevines and the Purification and Serology of Associated Closteroviruslike Particles," *Phytopathology* 77:1427–1434 (1987).

Zhang et al., "A Strategy for Rapid cDNA Cloning From double–stranded RNA Templates Isolated From Plants Infected with RNA Viruses by Using Taq DNA Polymerase," *J. Virol. Methods* 84:59–63 (2000).

Zhu et al., "Nucleotide Sequence and Genome Organization of Grapevine Leafroll Associated Closterovirus 2" 12th Meeting of the International Council for the Study of Viruses and Virus–Like Diseases of the Grapevine, Sep.–Oct. (1997).

Zhu et al., "Production and Application of An Antibody to the Grapevine Leafroll Associated Clostervirus 2 Coat Protein Expressed in *Escherichia Coli*," 12th Meeting of the International Council for the Study of Viruses and Virus–Like Diseases of the Grapevine, Sep.–Oct. (1997).

Zhu et al., "Nucleotide Sequence and Genome Organization of Grapevine Leafroll–Associated Virus–2 Are Similar to Beet Yellows Virus, The Closterovirus Type Member," *Journal of General Virology* 79:1289–1298 (1998).

Zimmermann et al., "Characterization and Serological Detection of Four Closterovirus–like Particles Associated with Leafroll Disease on Grapevine," *J. Phytopathology* 130:205–218 (1990).

Zimmermann et al., "Production and Characterization of Monoclonal Antibodies Specific to Closterovirus–like Particles Associated with Grapevine Leafroll Disease," *J. Phytopathology* 130:277–288 (1990).

Agranovsky et al., "Beet Yellows Closterovirus: Complete Genome Structure and Identification of a Leader Papain–Like Thiol Protease," *Virology* 199:311–324 (1994).

Fajardo et al., "Partial Molecular Characterization of an Isolate of Grapevine Leafroll–Associated Virus 3 in Grapes," (Abstract 980) *Fitopatol. Bras.* 26:535 (2001).

GenBank Accession No. CAA51871.

GenBank Accession No. AF037268.

GenBank Accession No. AF283103.

Melzer et al., "Nucleotide Sequence, Genome Organization and Phylogenetic Analysis of Pineapple Mealybug Wilt–Associated Virus–2," *Journal of General Virology* 82:1–7 (2001).

Maiti et al., "Plants that Express a Potyvirus Proteinase Gene Are Resistant to Virus Infection," *Proc. Natl. Acad. Sci.* USA 90:6110–6114 (1993).

Vardi et al., "Plants Transformed with a Cistron of a Potato Virus Y Protease (Nla) Are Resistant to Virus Infection," *Proc. Natl. Acad. Sci.* USA 90:7513–7517 (1993).

Doerks et al., "Protein Annotation: Detective Work for Function Prediction," *Trends in Genetics* 14(6):248–250 (1998).

U.S. Appl. No.: 09/301,906, filed Apr. 29, 1999, Gonsalves et al.

U.S. Appl. No.: 10/039,112, filed Dec. 31, 2001, Gonsalves et al.

\* cited by examiner

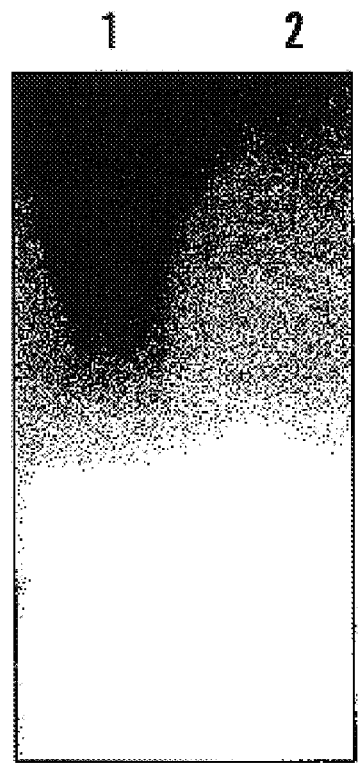
*FIG. 1A*  *FIG. 1B*

```
              |                                                          |
GLRaV2-PRO1   SRVIYPDGRCYLAHNRYLCAFYCRPFRESDYALGMWPTVARLRACVEKNFGVEACGIALRGYYTSRNVYHCDYDSAYVKYFRNLSGRIG/G
GLRaV2-PRO2   TRIRYPNGFCYLAHCRYACAFLLRGFDPKRPDIGAFPTAAKLRNRHVSELGERSLGLNLYGAYTSRGVPHCDYDAKFIKDLRLMSAVIA/G
BYV-P-PRO     LQYRPGEGLCYLAHAALCCALQKRTFREEDPFVGNYPTKFVFAKRLTEKLGPSALKHPVRGRQVSRSLFHCDVASAFSSPFYSLPRFIG/G
Consensus     .......G.CYLAH....CA...R.P.......G..PT............G.........G...SR...HCD..............I./G
```

*FIG. 3A*

```
              MT I                    MT Ia                 MT II
GLRaV2-MTR    MSEATQNSLTRFYPQPELKPSHSSHSDHPAAAASRLLENETLVRLCGNSVSDIGGCPLFHLHSKTQRRVHVCRPVLDGKDAQRRVVRDLQ
BYV-MTR       MGEAVQSGLTRAYPQFNLSPTHSVYSDHPAAAGSRLLENETLASMAKSSPSDIGGCPLFHIK-RGSTDYHVCRPIYDMKDAQRRVSRELQ
                             MT IIa          MT III
GLRaV2-MTR    YSNVRLG-DDDKILEGPRNIDICHYPLGACDHESSAMMMVQVYDASLYEICGAMIKKKSRITYLTMVTPGEFLDGRECVYMESLDCEIEV
BYV-MTR       ARGLVENLSREQLVEAQARVSVCPHTLGNCNVKSDVLIMVQVYDASLNEIASAMVLKESKVAYLTMVTPGELLDEREAFAIDALGCDVVV
                              MT IV
GLRaV2-MTR    DVHADVVMYKFGSSCYSHKLSIIKDIMTTPYLTLGGFLFSVEMYEVRMGVNYFKITKSEVSPSISCTKLLRYRRANSDVVKVKLPRFD
BYV-MTR       DTRRDMVQYKFGSSCYCHKLSNIKSIMLTPAPTPSGNLFSVEMYENRMGVNYYKITRSAYSPEIRGVKTLRYRRACTEVVQVKLPRFD
```

*FIG. 3B*

```
              HEL I                   HEL Ia
GLRaV2-Hel    FVFTNSSVDILLYEAPPGGGKTTTLIDSFLKVFKKGEVSTMILTANKSSQVEILKKVEKEVSNIECQKRKDKRSPKKSIYTIDAYLMHHR
BYV-Hel       FTFTNLSANVLLYEAPPGGGKTTTLIKVFCETFSK--VNSLILTANKSSREEILAKVNRIVLD-EGDTPLQTRDR---ILTIDSYLMNNR
               HEL II          HEL III                        HEL IV
GLRaV2-Hel    GCDADVLFIDECFMVHAGSVLACIEFTRCHKVMIFGDSRQIHYIERNELDKCLYGDLDRFVDLQCRVYGNISYRCPWDVCAWLSTVYGNL
BYV-Hel       GLTCKVLYLDECFMVHAGAAVACIEPTKCDSAILFGDSRQIRYGRCSELDTAVLSDLNRFVDDESRVYGEVSYRCPWDVCAWLSTPYPKT
                                                                   HEL V
GLRaV2-Hel    IATVKGESEGKSSMRINEINSVDDLVPDVGSTPLCMLQSEKLEISKHF---IRKGLTKLNVLTVHEAQGETYARVNLVRLKFQEDEPPKS
BYV-Hel       VATTNLVSAGQSSMQVREIESVDDVEYSSEFVYLTMLQSEKKDLLKSFGKRSRSSVEKPTVLTVHEAQGETYRKVNLVRTKFQEDDPFRS
                     HEL VI
GLRaV2-Hel    IRHITVALSRHTDSLTYNVLAARRGDATCDAIQKAAELVNKFRVFPTSFGGS
BYV-Hel       ENHITVALSRHVESLTYSVLSSKRDDAIAQAIVKAKQLVDAYRVYPTSFGGS
```

*FIG. 3C*

```
              RdRP I                 RdRP II                        RdRP III
GLRaV2-RdRP   ICRFKLMVKRDAKVKLDSSCLTKHSAAQNIMFHRKSINAIFSPIFNEVKNRIMCCLKPNIKFPFTEMTNRDFASVVSNMLGDDDVYHIGEV
BYV-RdRP      ITTFKLMVKRDAKVKLDSSCLVKHPPAQNIMFHRKAVNAIFSPCFDEFKNRVITCTNSNIVFFTEMTNSTLASIAKEMLGSEHVYNVGEI
                RdRP IV                                          RdRP V
GLRaV2-RdRP   DFSKYDKSQDAFVKAFEEVMYKELGVDEELLAIWMCGERLSIANTLDGQLSFTIENQRKSGASNTWIGNSLVTLGILSLYYDVRNPEALY
BYV-RdRP      DFSKFDKSQDAFIKSFERTLYSAFGFPDEDLLDVWMQGEYTSNATTLDGQLSFSVDNQRKSGASNTWIGNSIETLGILSMFYYTNRFKALF
                 RdRP VI              RdRP VII        RdRP VIII
GLRaV2-RdRP   ISGDDSLIFSRSEISNYADDICTDMGFETKFMSPSVPYFCSKFVVMCGHKTPFFVPDPYKLFVKLGAVKEDVSMDFLFETFTSFKDLTSDF
BYV-RdRP      VSGDDSLIFSESPIRNSADAMCTELGFETKFLTPSVPYFCSKFFVMTGHDVFFVPDPYKLLVKLGASKDEVDDEFLFEVFPTSFRDLTKDL

GLRaV2-RdRP   NDERLIQKLAELVALKYEVQTGNTTLAL
BYV-RdRP      VDERVIELLTHLVHSKYGYESGDTYAAL
```

*FIG. 3D*

```
GLRaV-2    CAUGAUAAGCAGCGUGUUUAGCGUAGUUCGGUCGCAGGCGAUUCCGCGUAGA
BYV        CACGACCCGCAGCGGGUUUAGCUCGAUUCGCUCGCAGGCGAUUCCUAAGAGG
BYSV       CACGAUGAACAGCGCGUUUAGCGUAGUUAGGUCGCAGGCCAUCCCUAAAAGG
CTV        CACGAACCGGCUCGCGUUCGGCGUAGUAAGGUCACAAGCAAUUCCUCCAAGA
Consensus  CA.GA.......CG.GUU..GC....U....UC.CA.GC.AU.CC....AG.
```

*FIG. 4A*

```
GLRaV-2    H D K Q R V S V V R S Q A I P R R
BYV        H D P Q R V S S I R S Q A I P K R
BYSV       H D E Q R V S V V R S Q A I P K R
CTV        H E P A R V G V V R S Q A I P P R
Consensus  H . . . R V . . . R S Q A I P . R
```

*FIG. 4B*

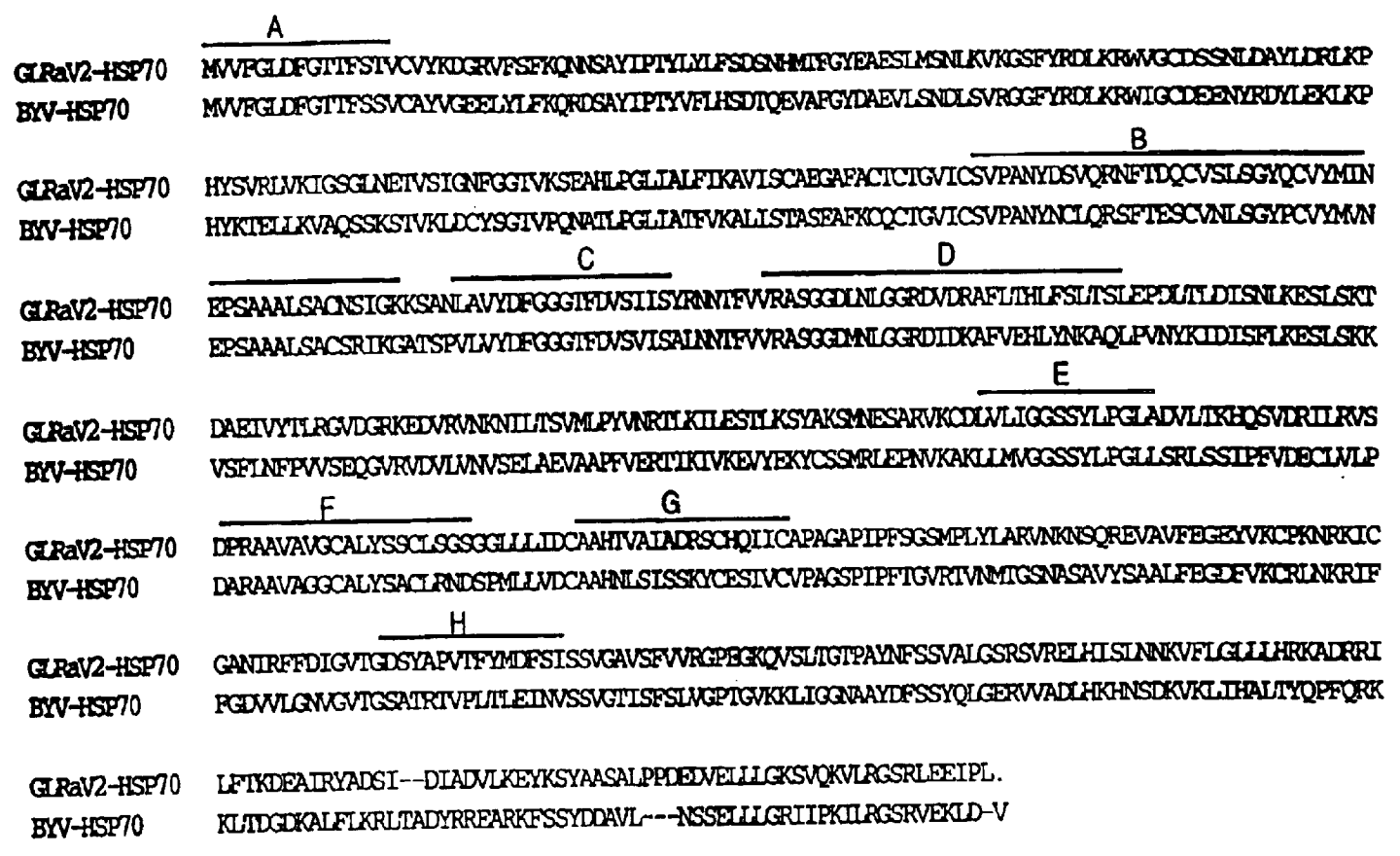

|   |   |
|---|---|
| GLRaV2-HSP70 | MVVFGLDFGTIFSIVC

```
GLRaV2-HSp90  MS-------NYSWESLFKKFYGEADWKKYLSRSIAAHSSEIKTLPDIRLYGGRVVKKSEFESALP
BYV-HSP90     MTTRFSTPANYYWGELFRRFFGGQEWKNLMSEAASVSRPRYSS--DFRFSDGVILSRKTFGESTG
BYSV-HSP90    MSRR--PTFAGYSWGSLFKRHYGEPEWKSYLTETSMRYKPLKSE--SITFYDGSSLTSAELRPARS
CTV-HSP90     MSSH------HVWGSLFRKFYGEAIWKEYLSESTRNFDERNVSL-DHTLSSGVVVRRQSLLNAPQ
Consensus     M...........W..LF....G...WK.......................G............

GLRaV2-HSp90  NSFEQE--LGLFILSEREVGWS-KLCGITVEEAAYDLTNPKAYKFTAETCSPDVKGEGQKYSMED
BYV-HSP90     ESFVREFSL-LLTFPKTYE--VCKLCGVAMELALNGMNRLSDYN-VSEFNIVDVKTVGCKFNIQS
BYSV-HSP90    GT--AEYEIALLIPSDSITKWSEKL-ERSIYRGLNQINNHSIYA-ETELEVTDVKTIGCKFTISA
CTV-HSP90     GTPENE--LALLYNSVVINDFVE-LTGMPLKSLMTGIEDRKV---PDELISVDPHEVGCRFTLND
Consensus     .....E....L..............L..................E....D....G.......

GLRaV2-HSp90  VMNFMRLSNLDVNDKMLTEQCWSLSNSCGELINPDDKGRFVALTFKDRDTADDTGAANVECRVGD
BYV-HSP90     VTEFVKKINGNVAEPSLVEHCWSLSNSCGELINPKDTKRFVSLIFKGKDLAESTDEAIVSSSYLD
BYSV-HSP90    VESFM----GGRASAAQVEHCWSLSNSCGELINPNDTARFIQLVFKDKAVTEQAQ-VNTSGSVSD
CTV-HSP90     VESYLMSRGEDFADLAAVEHSWCLSNSCGRLLSSTEIDAYKTLVFT-KNF--DSNVSGVTTKLET
Consensus     V................E..W.LSNSCG.L...........L.F..................

GLRaV2-HSp90  YLVYAMSLFEQRTQKSQSGNISLYEKYCEYIRTYLGSTDLFFTAPDRIPLLTGILYDFCKEYNVF
BYV-HSP90     YLSHCLNLYETCNLSSNSGKKSLYDEFLKHVIDYLENSDLEYRSPSDNPLVAGILYDMCFEYNTL
BYSV-HSP90    YLVYCLQLYDNSKKKSNAGRTQLMESYVSFIRDFFQHSDLYYRSPLDNPLLTGVLYDLCIEHNVL
CTV-HSP90     YLSYCISLYKKHCMKDD-DYFNLILPMFNCLMKVLASLGLFYEKHADNPLLTGMLIEFCLENKVY
Consensus     YL.....L................L.................L........PL..G.L...

I
                                                            ─────────────────
GLRaV2-HSp90  YSSYKRNVDNFRFFLANYMPLISDVFVFQWVKPAPDV----RLLFELSAAELTLEVPTLSLIDSQ
BYV-HSP90     KSTYLKNIESFDCFLSLYLPLLSEVFSMNWERPAPDV----RLLFELDAAELLLKVPTINMHDST
BYSV-HSP90    RGSYLKNLDNFRLFKQTYLPMIDDIFDYSWELYAPDE----RLLFPIDPYEIIKEVPTMSVIDAN
CTV-HSP90     YSTFKVNLDNVRLFPKSKVLFVVLTV----WDISEPDDPMDERVLIPFDPTDFVLDLPKLNIHDTM
Consensus     ......N......F.....P........W....PD.....R.L..........P.....D..

──────────I──────────                          ─────────II─────────
GLRaV2-HSp90  VVVGHILRYVESYTSDPAIDALEDKLEAILKSSNPRLSTAQLWVGFFCYYGEFRTAQSRVVQRPG
BYV-HSP90     FLYKNKLRYLESYFEDDSNELIKVKVDSLLTRDNPELKLAQRWVGFHCYYGVFRTAQTRKVKRDA
BYSV-HSP90    VVLSNKLVYLDSYLENNSILALEKKIISILCRDNEGIDEGALWAAFFCYYGTYRTARQRVVKRPD
CTV-HSP90     VVVGNQIRQLEYVVESDALDDLSQHVDLRLAADNPDLRVGLRWAGMFVYYGVYRCVVDRAVERPT
Consensus     ...................L....N........W.....YYG..R....R.V.R..

─────────II─────────
GLRaV2-HSp90  VYKTPDSV------GGFEINMKDVEKFFDKLQRELPNVSLRRQFNGARAHEAFKIFKNGNISFRP
BYV-HSP90     EYKLPPAL------GEFVINMSGVEEFFEELQKKMPSISVRRRFCGSLSHEAFSVFKRFGVGFPP
BYSV-HSP90    TYELDGIF------SKPIV-MSGVELFFDELQKRVPDVSLRRRFNGAKAGEAITVFKKLGISFPP
CTV-HSP90     LFRLPQKLLSQDDGESCSLHMGSVEALFNLVQKVNKDINVRRQFMGRHSEVALRLYRNLGLRFPP
Consensus     ....................M..VE..F...Q........RR.F.G.....A..........F.P ─────────II─────────
GLRaV2-HSp90  ISRLNVPREFWYLNIDYFRHANRSGLTEEEILILNNISVDVRKLCAERACN------TLPSAKR
BYV-HSP90     ITRLNVPVKYSYLNVDYYRHVKRVGLTQDELTILSNIEFDVAEMCCEREVALQAR--RAQRGEKP
BYSV-HSP90    ITRLNAPSKYSYLNIDYFKQANSLGLTEPEKIILCNIAKDVDMMCAQRISSVKA---------KP
CTV-HSP90     ISSVRLPAHHGYLYVDFYKRVPDGAVTADELESLRQLRSSVDVMCKDRVSITPPPFNRLRRGSSR
Consensus     I.....P....YL..D..........T..E...L......V...C..R..............

GLRaV2-HSp90  FSKNHKSNIQSSRQERRIKDPLVVLKDTLYEFQHKRAGWGSRSTRDLGSRADHAKGSG.
BYV-HSP90     FQGWKGTKNEISPHARSSIRVKKNNDSLLNILWKDVGARSQRRLNPLHRK-------H
BYSV-HSP90    IAQRNG--EAINSAKIRTLPTNTLVRALEKCLLNQAPSWWNTTLTNLR
CTV-HSP90     TFRGRGARGASSRHMSRDVATSGFNLPYHGRLY-----------------STS
Consensus     ..........................................................
```

| | | |
|---|---|---|
| GLRaV2 3'-UTR | TTAAGCTGTTACTGAGTAATAAACCAACAAGTGTTGGTGTAATGTGTATGTTGATGTGTAGA | 135 |
| BYS 3'-UTR | TTAAGTCGTCACAGAGTGACAAGCGGCACCAAGTGGTGCTTAGTGCGTATGTAAATTACGAA | 95 |
| BYSV 3'-UTR | TTAAGCCCTCACAGAGCGAGAACGTTGGCAAGAGCCAATTAGTGTGTGTAGTATAATTA | 181 |
| CTV 3'-UTR | CTAAGCTCCCACAGAGTGGTAGTGGTCTCAAGTGAGGCTTAACGTATGCGTGAACCAAAGA | 208 |
| Consensus | .TAAG.....AC.CAG............CAAG.G....T..............A | |

SEQUENCE LISTING

<160> NUMBER OF SEQ ID NOS: 48

<210> SEQ ID NO 1
<211> LENGTH: 15500
<212> TYPE: DNA
<213> ORGANISM: Grapevine Leafroll Virus (type 2)

<400> SEQUENCE: 1

```
taaacattgc gagagaaccc cattagcgtc tccggggtga acttgggaag gtctgccgcc      60
gctcaggtta tttatttcgg cagtttcacg cagcccttcg cgttgtatcc gcgccaagag     120
agcgcgatcg taaaaacgca acttccaccg gtcagtgtag tgaaggtgga gtgcgtagct     180
gcggaggtag ctcccgacag gggcgtggtc gacaagaaac ctacgtctgt tggcgttccc     240
ccgcagcgcg gtgtgctttc ttttccgacg gtggttcgga accgcggcga cgtgataatc     300
acaggggtgg tgcatgaagc cctgaagaaa attaaagacg ggctcttacg cttccgcgta     360
ggcggtgaca tgcgtttttc gagatttttc tcatcgaact acggctgcag attcgtcgcg     420
agcgtgcgta cgaacactac agtttggcta aattgcacga aagcgagtgg tgagaaattc     480
tcactcgccg ccgcgtgcac ggcggattac gtggcgatgc tgcgttatgt gtgtggcggg     540
aaatttccac tcgtcctcat gagtagagtt atttacccgg atgggcgctg ttacttggcc     600
catatgaggt atttgtgcgc cttttactgt cgcccgttta gagagtcgga ttatgccctc     660
ggaatgtggc ctacggtggc gcgtctcagg gcatgcgttg agaagaactt cggtgtcgaa     720
gcttgtggca tagctcttcg tggctattac acctctcgca atgtttatca ctgtgattat     780
gactctgctt atgtaaaata ttttagaaac ctttccggcc gcattggcgg tggttcgttc     840
gatccgacat ctttaacctc cgtaataacg gtgaagatta gcggtcttcc aggtggtctt     900
cctaaaaata tagcgtttgg tgccttcctg tgcgatatac gttacgtcga accggtagac     960
tcgggcggca ttcaatcgag cgttaagacg aaacgtgaag atgcgcaccg aaccgtagag    1020
gaacgggcgg ccggcggatc cgtcgagcaa ccgcgacaaa agaggataga tgagaaaggt    1080
tgcggcagag ttcctagtgg aggttttttcg catctcctgg tcggcaacct taacgaagtt    1140
aggaggaagg tagctgccgg acttctacgc tttcgcgttg gcggtgatat ggattttcat    1200
cgctcgttct ccacccaagc gggccaccgc ttgctggtgt ggcgccgctc gagccggagc    1260
gtgtgccttg aactttactc accatctaaa aacttttttgc gttacgatgt cttgccctgt    1320
tctggagact atgcagcgat gttttctttc gcggcgggcg gccgtttccc tttagttttg    1380
atgactagaa ttagatacccc gaacgggttt tgttacttgg ctcactgccg gtacgcgtgc    1440
gcgtttctct taagggtttt tgatccgaag cgtttcgaca tcggtgcttt ccccaccgcg    1500
gccaagctca gaaaccgtat ggtttcggag cttggtgaaa gaagtttagg tttgaacttg    1560
tacggcgcat atacgtcacg cggcgtcttt cactgcgatt atgacgctaa gtttataaag    1620
gatttgcgtc ttatgtcagc agttatagct ggaaaggacg gggtggaaga ggtggtacct    1680
tctgacataa ctcctgccat gaagcagaaa acgatcgaag ccgtgtatga tagattatat    1740
```

```
ggcggcactg actcgttgct gaaactgagc atcgagaaag acttaatcga tttcaaaaat   1800
gacgtgcaga gtttgaagaa agatcggccg attgtcaaag tgcccttta catgtcggaa    1860
gcaacacaga attcgctgac gcgtttctac cctcagttcg aacttaagtt ttcgcactcc   1920
tcgcattcag atcatcccgc cgccgccgct tctagactgc tggaaaatga aacgttagtg   1980
cgcttatgtg gtaatagcgt ttcagatatt ggaggttgtc ctcttttcca tttgcattcc   2040
aagacgcaaa gacgggttca cgtatgtagg cctgtgttgg atggcaagga tgcgcagcgt   2100
cgcgtggtgc gtgatttgca gtattccaac gtgcgtttgg gagacgatga taaaattttg   2160
gaagggccac gcaatatcga catttgccac tatcctctgg gcgcgtgtga ccacgaaagt   2220
agtgctatga tgatggtgca ggtgtatgac gcgtcccttt atgagatatg tggcgccatg   2280
atcaagaaga aaagccgcat aacgtactta accatggtca cgcccggcga gtttcttgac   2340
ggacgcgaat gcgtctacat ggagtcgtta gactgtgaga ttgaagttga tgtgcacgcg   2400
gacgtcgtaa tgtacaaatt cggtagttct tgctattcgc acaagctttc aatcatcaag   2460
gacatcatga ccactccgta cttgacacta ggtggttttc tattcagcgt ggagatgtat   2520
gaggtgcgta tgggcgtgaa ttacttcaag attacgaagt ccgaagtatc gcctagcatt   2580
agctgcacca agctcctgag ataccgaaga gctaatagtg acgtggttaa agttaaactt   2640
ccacgtttcg ataagaaacg tcgcatgtgt ctgcctgggt atgacaccat atacctagat   2700
tcgaagtttg tgagtcgcgt tttcgattat gtcgtgtgta attgctctgc cgtgaactca   2760
aaaactttcg agtgggtgtg gagtttcatt aagtctagta agtcgagggt gattattagc   2820
ggtaaaataa ttcacaagga tgtgaatttg gacctcaagt acgtcgagag tttcgccgcg   2880
gttatgttgg cctctggcgt gcgcagtaga ctagcgtccg agtaccttgc taagaacctt   2940
agtcattttt cgggagattg ctcctttatt gaagccacgt ctttcgtgtt gcgtgagaaa   3000
atcagaaaca tgactctgaa ttttaacgaa agactttac agttagtgaa gcgcgttgcc    3060
tttgcgacct tggacgtgag ttttctagat ttagattcaa ctcttgaatc aataactgat   3120
tttgccgagt gtaaggtagc gattgaactc gacgagttgg gttgcttgag agcggaggcc   3180
gagaatgaaa aaatcaggaa tctggcggga gattcgattg cggctaaact cgcgagcgag   3240
atagtggtcg atattgactc taagccttca ccgaagcagg tgggtaattc gtcatccgaa   3300
aacgccgata agcgggaagt tcagaggccc ggtttgcgtg gtggttctag aaacggggtt   3360
gttggggagt tccttcactt cgtcgtggat tctgccttgc gtcttttcaa atacgcgacg   3420
gatcaacaac ggatcaagtc ttacgtgcgt ttcttggact cggcggtctc attcttggat   3480
tacaactacg ataatctatc gtttatactg cgagtgcttt cggaaggtta ttcgtgtatg   3540
ttcgcgtttt tggcgaatcg cggcgactta tctagtcgtg tccgtagcgc ggtgtgtgct   3600
gtgaaagaag ttgctacctc atgcgcgaac gcgagcgttt ctaaagccaa ggttatgatt   3660
accttcgcag cggccgtgtg tgctatgatg tttaatagct gcggttttc aggcgacggt    3720
cgggagtata atcgtatat acatcgttac acgcaagtat tgtttgacac tatctttttt    3780
gaggacagca gttacctacc catagaagtt ctgagttcgg cgatatgcgg tgctatcgtc   3840
acacttttct cctcgggctc gtccataagt ttaaacgcct tcttacttca aattaccaaa   3900
ggattctccc tagaggttgt cgtccggaat gttgtgcgag tcacgcatgg tttgagcacc   3960
acagcgaccg acggcgtcat acgtgggtt ttctcccaaa ttgtgtctca cttacttgtt    4020
ggaaatacgg gtaatgtggc ttaccagtca gctttcattg ccggggtggt gcctctttta   4080
gttaaaaagt gtgtgagctt aatcttcatc ttgcgtgaag atacttattc cggttttatt   4140
```

-continued

```
aagcacggaa tcagtgaatt ctctttcctt agtagtattc tgaagttctt gaagggtaag    4200
cttgtggacg agttgaaatc gattattcaa ggggtttttg attccaacaa gcacgtgttt    4260
aaagaagcta ctcaggaagc gattcgtacg acggtcatgc aagtgcctgt cgctgtagtg    4320 gatgcccta agagcgccgc gggaaaaatt tataacaatt ttactagtcg acgtacctt     4380 ggtaaggatg aaggctcctc tagcgacggc gcatgtgaag agtatttctc atgcgacgaa    4440
ggtgaaggtc cgggtctgaa aggggttcc agctatggct tctcaattt agcgttcttt     4500 tcacgcatta tgtggggagc tcgtcggctt attgttaagg tgaagcatga gtgttttggg    4560 aaacttttg aatttctatc gctcaagctt cacgaattca ggactcgcgt ttttgggaag     4620
aatagaacgg acgtgggagt ttacgatttt tgcccacgg gcatcgtgga aacgctctca     4680
tcgatagaag agtgcgacca aattgaagaa cttctcggcg acgacctgaa aggtgacaag    4740
gatgcttcgt tgaccgatat gaattacttt gagttctcag aagacttctt agcctctatc    4800
gaggagccgc ctttcgctgg attgcgagga ggtagcaaga acatcgcgat tttggcgatt    4860
ttggaatacg cgcataattt gtttcgcatt gtcgcaagca agtgttcgaa acgacctta    4920 tttcttgctt tcgccgaact ctcaagcgcc cttatcgaga aatttaagga ggttttccct    4980
cgtaagagcc agtcgtcgc tatcgtgcgc gagtatactc agagattcct ccgaagtcgc    5040
atgcgtgcgt tgggtttgaa taacgagttc gtggtaaaat ctttcgccga tttgctaccc    5100
gcattaatga agcggaaggt ttcaggttcg ttcttagcta gtgtttatcg cccacttaga    5160
ggtttctcat atatgtgtgt ttcagcggag cgacgtgaaa agttttttgc tctcgtgtgt    5220
ttaatcgggt taagtctccc tttcttcgtg cgcatcgtag agcgaaagc gtgcgaagaa    5280 ctcgtgtcct cagcgcgtcg cttttatgag cgtattaaaa ttttctaag gcagaagtat    5340 gtctctcttt ctaatttctt ttgtcacttg tttagctctg acgttgatga cagttccgca    5400 tctgcaggg tgaaaggtgg tgcgtcgcga atgacgctct ccaccttct ggttcgcctt     5460 gctagtgccc tcctatcgtt agggtgggaa gggttaaagc tactcttatc gcaccacaac    5520
ttgttatttt tgtgttttgc attggttgac gatgtgaacg tccttatcaa agttcttggg    5580
ggtctttctt tctttgtgca accaatcttt tccttgtttg cggcgatgct tctacaaccg    5640
gacaggtttg tggagtattc cgagaaactt gttacagcgt tgaatttttt cttaaaatgt    5700
tcgcctcgcg cgcctgcact actcaaaggg ttttttgagt gcgtggcgaa cagcactgtg    5760
tcaaaaaccg ttcgaagact tcttcgctgt ttcgtgaaga tgctcaaact tcgaaagg     5820 cgagggttgc gtgcggatgg tagggtctc catcggcaga aagccgtacc cgtcatacct    5880
tctaatcggg tcgtgaccga cggggttgaa agactttcgg taaagatgca aggagttgaa    5940
gcgttgcgta ccgaattgag aatcttagaa gatttagatt ctgccgtgat cgaaaaactc    6000
aatagacgca gaaatcgtga cactaatgac gacgaattta cgcgccctgc tcatgagcag    6060
atgcaagaag tcaccacttt ctgttcgaaa gccaactctg ctggtttggc cctggaaagg    6120
gcagtgcttg tggaagacgc tataaagtcg gagaaacttt ctaagacggt taatgagatg    6180
gtgaggaaag ggagtaccac cagcgaagaa gtggccgtcg ctttgtcgga cgatgaagcc    6240
gtggaagaaa tctctgttgc tgacgagcga acgattcgc ctaagacagt caggataagc     6300
gaatacctaa ataggttaaa ctcaagcttc gaattcccga agcctattgt tgtggacgac    6360
aacaaggata ccgggggtct aacgaacgcc gtgagggagt tttattatat gcaagaactt    6420 gctctttcg aaatccacag caaactgtgc acctactacg atcaactgcg catagtcaac     6480
```

```
ttcgatcgtt ccgtagcacc atgcagcgaa gatgctcagc tgtacgtacg gaagaacggc    6540
tcaacgatag tgcagggtaa agaggtacgt ttgcacatta aggatttcca cgatcacgat    6600
ttcctgtttg acggaaaaat ttctattaac aagcggcggc gaggcggaaa tgttttatat    6660
cacgacaacc tcgcgttctt ggcgagtaat ttgttcttag ccggctaccc cttttcaagg    6720
agcttcgtct tcacgaattc gtcggtcgat attctcctct acgaagctcc acccggaggt    6780
ggtaagacga cgacgctgat tgactcgttc ttgaaggtct tcaagaaagg tgaggtttcc    6840
accatgatct taaccgccaa caaaagttcg caggttgaga tcctaaagaa agtggagaag    6900
gaagtgtcta acattgaatg ccagaaacgt aaagacaaaa gatctccgaa aaagagcatt    6960
tacaccatcg acgcttattt aatgcatcac cgtggttgtg atgcagacgt tcttttcatc    7020
gatgagtgtt tcatggttca tgcgggtagc gtactagctt gcattgagtt cacgaggtgt    7080
cataaagtaa tgatcttcgg ggatagccgg cagattcact acattgaaag gaacgaattg    7140
gacaagtgtt tgtatgggga tctcgacagg ttcgtggacc tgcagtgtcg ggtttatggt    7200
aatatttcgt accgttgtcc atgggatgtg tgcgcttggt taagcacagt gtatggcaac    7260
ctaatcgcca ccgtgaaggg tgaaagcgaa ggtaagagca gcatgcgcat taacgaaatt    7320
aattcagtcg acgatttagt ccccgacgtg ggttccacgt ttctgtgtat gcttcagtcg    7380
gagaagttgg aaatcagcaa gcactttatt cgcaagggtt tgactaaaact taacgttcta    7440 acggtgcatg aggcgcaagg tgagacgtat gcgcgtgtga accttgtgcg acttaagttt    7500
caggaggatg aaccctttaa atctatcagg cacataaccg tcgctctttc tcgtcacacc    7560
gacagcttaa cttataacgt cttagctgct cgtcgaggtg acgccacttg cgatgccatc    7620
cagaaggctc cggaattggt gaacaagttt cgcgtttttc ctacatcttt tggtggtagt    7680
gttatcaatc tcaacgtgaa gaaggacgtg gaagataaca gtaggtgcaa ggcttcgtcg    7740
gcaccattga gcgtaatcaa cgactttttg aacgaagtta atcccggtac tgcggtgatt    7800
gattttggtg atttgtccgc ggacttcagt actgggcctt ttgagtgcgg tgccagcggt    7860
attgtggtgc gggacaacat ctcctccagc aacatcactg atcacgataa gcagcgtgtt    7920
tagcgtagtt cggtcgcagg cgattccgcg tagaaaacct tctctacaag aaaatttgta    7980
ttcgtttgaa gcgcggaatt ataacttctc gacttgcgac cgtaacacat ctgcttcaat    8040
gttcggagag gctatggcga tgaactgtct tcgtcgttgc ttcgacctag atgcctttc    8100 gtccctgcgt gatgatgtga ttagtatcac acgttcaggc atcgaacaat ggctggagaa    8160
acgtactcct agtcagatta aagcattaat gaaggatgtt gaatcgcctt tggaaattga    8220
cgatgaaatt tgtcgtttta agttgatggt gaagcgtgac gctaaggtga agttagactc    8280
ttcttgttta actaaacaca gcgccgctca aaatatcatg tttcatcgca agagcattaa    8340
tgctatcttc tctcctatct ttaatgaggt gaaaaaccga ataatgtgct gtcttaagcc    8400
taacataaag ttttttacgg agatgactaa cagggatttt gcttctgttg tcagcaacat    8460
gcttggtgac gacgatgtgt accatatagg tgaagttgat ttctcaaagt acgacaagtc    8520
tcaagatgct ttcgtgaagg cttttgaaga agtaatgtat aaggaactcg gtgttgatga    8580
agagttgctg gctatctgga tgtgcggcga gcggttatcg atagctaaca ctctcgatgg    8640
tcagttgtcc ttcacgatcg agaatcaaag gaagtcggga gcttcgaaca cttggattgg    8700
taactctctc gtcactttgg gtattttaag tctttactac gacgttagaa atttcgaggc    8760
gttgtacatc tcgggcgatg attctttaat ttttctcgc agcgagattt cgaattatgc    8820
cgacgacata tgcactgaca tgggttttga gacaaaattt atgtccccaa gtgtcccgta    8880
```

-continued

```
cttttgttct aaatttgttg ttatgtgtgg tcataagacg ttttttgttc ccgacccgta    8940
caagcttttt gtcaagttgg gagcagtcaa agaggatgtt tcaatggatt tccttttcga    9000
gacttttacc tcctttaaag acttaacctc cgattttaac gacgagcgct taattcaaaa    9060
gctcgctgaa cttgtggctt taaaatatga ggttcaaacc ggcaacacca ccttggcgtt    9120
aagtgtgata cattgtttgc gttcgaattt cctctcgttt agcaagttat atcctcgcgt    9180
gaagggatgg caggttttttt acacgtcggt taagaaagcg cttctcaaga gtgggtgttc    9240
tctcttcgac agtttcatga ccccttttgg tcaggctgtc atggtttggg atgatgagta    9300
gcgctaactt gtgcgcagtt tctttgttcg tgacatacac cttgtgtgtc accgtgcgtt    9360
tataatgaat caggttttgc agtttgaatg tttgtttctg ctgaatctcg cggttttgc     9420
tgtgactttc attttcattc ttctggtctt ccgcgtgatt aagtcttttc gccagaaggg    9480
tcacgaagca cctgttcccg ttgttcgtgg cgggggtttt tcaaccgtag tgtagtcaaa    9540
agacgcgcat atggtagttt tcggtttgga ctttggcacc acattctcta cggtgtgtgt    9600
gtacaaggat ggacgagttt tttcattcaa gcagaataat tcggcgtaca tccccactta    9660
cctctatctc ttctccgatt ctaaccacat gacttttggt tacgaggccg aatcactgat    9720
gagtaatctg aaagttaaag gttcgtttta tagagattta aaacgttggg tgggttgcga    9780
ttcgagtaac ctcgacgcgt accttgaccg tttaaaacct cattactcgg tccgcttggt    9840
taagatcggc tctggcttga acgaaactgt ttcaattgga aacttcgggg gcactgttaa    9900
gtctgaggct catctgccag ggttgatagc tctctttatt aaggctgtca ttagttcgc     9960
ggagggcgcg tttgcgtgca cttgcaccgg ggttatttgt tcagtacctg ccaattatga    10020
tagcgttcaa aggaatttca ctgatcagtg tgtttcactc agcggttatc agtgcgtata    10080
tatgatcaat gaaccttcag cggctgcgct atctgcgtgt aattcgattg gaaagaagtc    10140
cgcaaatttg gctgtttacg atttcggtgg tgggaccttc gacgtgtcta tcatttcata    10200
ccgcaacaat acttttgttg tgcgagcttc tggaggcgat ctaaatctcg gtggaaggga    10260
tgttgatcgt gcgtttctca cgcacctctt ctctttaaca tcgctggaac ctgacctcac    10320
tttggatatc tcgaatctga aagaatcttt atcaaaaacg gacgcagaga tagtttacac    10380
tttgagaggt gtcgatggaa gaaaagaaga cgttagagta aacaaaaaca ttcttacgtc    10440
ggtgatgctc ccctacgtga acagaacgct taagatatta gagtcaacct taaaatcgta    10500
tgctaagagt atgaatgaga gtgcgcgagt taagtgcgat ttagtgctga taggaggatc    10560
ttcatatctt cctggcctgg cagacgtact aacgaagcat cagagcgttg atcgtatctt    10620
aagagtttcg gatcctcggg ctgccgtggc cgtcggttgc gcattatatt cttcatgcct    10680
ctcaggatct gggggttgc tactgatcga ctgtgcagct cacactgtcg ctatagcgga     10740
cagaagttgt catcaaatca tttgcgctcc agcgggggca ccgatcccct tttcaggaag    10800
catgcctttg tacttagcca gggtcaacaa gaactcgcag cgtgaagtcg ccgtgtttga    10860
agggagtac gttaagtgcc ctaagaacag aaagatctgt ggagcaaata taagattttt     10920
tgatatagga gtgacgggtg attcgtacgc acccgttacc ttctatatgg atttctccat    10980
ttcaagcgta ggagccgttt cattcgtggt gagaggtcct gagggtaagc aagtgtcact    11040
cactggaact ccagcgtata acttttcgtc tgtggctctc ggatcacgca gtgtccgaga    11100
attgcatatt agtttaaata ataaagtttt tctcggtttg cttctacata gaaaggcgga    11160
tcgacgaata cttttcacta aggatgaagc gattcgatac gccgattcaa ttgatatcgc    11220
```

```
ggatgtgcta aaggaatata aaagttacgc ggccagtgcc ttaccaccag acgaggatgt    11280
cgaattactc ctgggaaagt ctgttcaaaa agttttacgg ggaagcagac tggaagaaat    11340
acctctctag gagcatagca gcacactcaa gtgaaattaa aactctacca gacattcgat    11400
tgtacggcgg tagggttgta aagaagtccg aattcgaatc agcacttcct aattcttttg    11460
aacaggaatt aggactgttc atactgagcg aacgggaagt gggatggagc aaattatgcg    11520
gaataacggt ggaagaagca gcatacgatc ttacgaatcc caaggcttat aaattcactg    11580
ccgagacatg tagcccggat gtaaaaggtg aaggacaaaa atactctatg gaagacgtga    11640
tgaatttcat gcgtttatca aatctggatg ttaacgacaa gatgctgacg gaacagtgtt    11700
ggtcgctgtc caattcatgc ggtgaattga tcaacccaga cgacaaaggg cgattcgtgg    11760
ctctcacctt taaggacaga gacacagctg atgacacggg tgccgccaac gtggaatgtc    11820
gcgtgggcga ctatctagtt tacgctatgt ccctgtttga gcagaggacc caaaaatcgc    11880
agtctggcaa catctctctg tacgaaaagt actgtgaata catcaggacc tacttaggga    11940
gtacagacct gttcttcaca gcgccggaca ggattccgtt acttacgggc atcctatacg    12000
attttttgtaa ggaatacaac gttttctact cgtcatataa gagaaacgtc gataatttca    12060
gattcttctt ggcgaattat atgcctttga tatctgacgt cttgtgtcttc cagtgggtaa    12120
aacccgcgcc ggatgttcgg ctgcttttg agttaagtgc agcggaacta acgctggagg    12180
ttcccacact gagtttgata gattctcaag ttgtggtagg tcatatctta agatacgtag    12240
aatcctacac atcagatcca gccatcgacg cgttagaaga caaactggaa gcgatactga    12300
aaagtagcaa tccccgtcta tcgacagcgc aactatgggt tggtttcttt tgttactatg    12360
gtgagtttcg tacggctcaa agtagagtag tgcaaagacc aggcgtatac aaaacacctg    12420
actcagtggg tggatttgaa ataaacatga aagatgttga gaaattcttc gataaacttc    12480
agagagaatt gcctaatgta tctttgcggc gtcagtttaa cggagctaga gcgcatgagg    12540
cttttcaaaat atttaaaaac ggaaatataa gtttcagacc tatatcgcgt ttaaacgtgc    12600
ctagagagtt ctggtatctg aacatagact acttcaggca cgcgaatagg tccgggttaa    12660
ccgaagaaga aatactcatc ctaaacaaca taagcgttga tgttaggaag ttatgcgctg    12720
agagagcgtg caatacccta cctagcgcga agcgctttag taaaaatcat aagagtaata    12780
tacaatcatc acgccaagag cggaggatta aagacccatt ggtagtcctg aaagacactt    12840
tatatgagtt ccaacacaag cgtgccggtt gggggtctcg aagcactcga gacctcggga    12900
gtcgtgctga ccacgcgaaa ggaagcggtt gataagtttt ttaatgaact aaaaaacgaa    12960
aattactcat cagttgacag cagccgatta agcgattcgg aagtaaaaga agtgttagag    13020
aaaagtaaag aaagtttcaa aagcgaactg gcctccactg acgagcactt cgtctaccac    13080
attatatttt tcttaatccg atgtgctaag atatcgacaa gtgaaaaggt gaagtacgtt    13140
ggtagtcata cgtacgtggt cgacggaaaa acgtacaccg ttcttgacgc ttgggtattc    13200
aacatgatga aaagtctcac gaagaagtac aaacgagtga atggtctgcg tgcgttctgt    13260
tgcgcgtgcg aagatctata tctaaccgtc gcaccaataa tgtcagaacg ctttaagact    13320
aaagccgtag ggatgaaagg tttgcctgtt ggaaaggaat acttaggcgc cgactttctt    13380
tcgggaacta gcaaactgat gagcgatcac gacagggcgg tctccatcgt tgcagcgaaa    13440
aacgctgtcg atcgtagcgc tttcacgggt ggggagagaa agatagttag tttgtatgat    13500
ctagggaggt actaagcacg gtgtgctata gtgcgtgcta taataataaa cactagtgct    13560
taagtcgcgc agaagaaaac gctatggagt tgatgtccga cagcaacctt agcaacctgg    13620
```

```
tgataaccga cgcctctagt ctaaatggtg tcgacaagaa gcttttatct gctgaagttg    13680
aaaaaatgtt ggtgcagaaa ggggctccta acgagggtat agaagtggtg ttcggtctac    13740
tcctttacgc actcgcggca agaaccacgt ctcctaaggt tcagcgcgca gattcagacg    13800
ttatattttc aaatagtttc ggagagagga atgtggtagt aacagagggt gaccttaaga    13860
aggtactcga cgggtgtgcg cctctcacta ggttcactaa taaacttaga acgttcggtc    13920
gtactttcac tgaggcttac gttgactttt gtatcgcgta taagcacaaa ttaccccaac    13980
tcaacgccgc ggcggaattg gggattccag ctgaagattc gtacttagct gcagattttc    14040
tgggtacttg cccgaagctc tctgaattac agcaaagtag gaagatgttc gcgagtatgt    14100
acgctctaaa aactgaaggt ggagtggtaa atacaccagt gagcaatctg cgtcagctag    14160
gtagaaggga agttatgtaa tggaagatta cgaagaaaaa tccgaatcgc tcatactgct    14220
acgcacgaat ctgaacacta tgcttttagt ggtcaagtcc gatgctagtg tagagctgcc    14280
taaactacta atttgcggtt acttacgagt gtcaggacgt ggggaggtga cgtgttgcaa    14340
ccgtgaggaa ttaacaagag attttgaggg caatcatcat acggtgatcc gttctagaat    14400
catacaatat gacagcgagt ctgcttttga ggaattcaac aactctgatt gcgtagtgaa    14460 gttttttccta gagactggta gtgtcttttg gttttttcctt cgaagtgaaa ccaaaggtag    14520
agcggtgcga catttgcgca ccttcttcga agctaacaat ttcttctttg gatcgcattg    14580
cggtaccatg gagtattgtt tgaagcaggt actaactgaa actgaatcta taatcgattc    14640
tttttgcgaa gaaagaaatc gttaagatga gggttatagt gtctccttat gaagctgaag    14700
acattctgaa aagatcgact gacatgttac gaaacataga cagtggggtc ttgagcacta    14760
aagaatgtat caaggcattc tcgacgataa cgcgagacct acattgtgcg aaggcttcct    14820
accagtgggg tgttgacact gggttatatc agcgtaattg cgctgaaaaa cgtttaattg    14880
acacggtgga gtcaaacata cggttggctc aacctctcgt gcgtgaaaaa gtggcggttc    14940 attttttgtaa ggatgaacca aaagagctag tagcattcat cacgcgaaag tacgtggaac    15000
tcacgggcgt gggagtgaga gaagcggtga agagggaaat gcgctctctt accaaaacag    15060
ttttaaataa aatgtctttg gaaatggcgt tttacatgtc accacgagcg tggaaaaacg    15120
ctgaatggtt agaactaaaa ttttcacctg tgaaaatctt tagagatctg ctattagacg    15180
tggaaacgct caacgaattg tgcgccgaag atgatgttca cgtcgacaaa gtaaatgaga    15240
atggggacga aaatcacgac ctcgaactcc aagacgaatg ttaaacattg gttaagttta    15300
acgaaaatga ttagtaaata ataaatcgaa cgtgggtgta tctacctgac gtatcaactt    15360
aagctgttac tgagtaatta aaccaacaag tgttggtgta atgtgtatgt tgatgtagag    15420
aaaaatccgt ttgtagaacg gtgttttttct cttctttatt tttaaaaaaa aaataaaaaa    15480
aaaaaaaaaa aagcggccgc                                                 15500
```

<210> SEQ ID NO 2
<211> LENGTH: 7920
<212> TYPE: DNA
<213> ORGANISM: Grapevine Leafroll Virus (type 2)

<400> SEQUENCE: 2

```
acattgcgag agaaccccat tagcgtctcc ggggtgaact tgggaaggtc tgccgccgct     60
caggttattt atttcggcag tttcacgcag cccttcgcgt tgtatccgcg ccaagagagc    120
gcgatcgtaa aaacgcaact tccaccggtc agtgtagtga aggtggagtg cgtagctgcg    180
```

```
gaggtagctc cgacaggggg cgtggtcgac aagaaaccta cgtctgttgg cgttcccccg    240
cagcgcggtg tgctttcttt tccgacggtg gttcggaacc gcggcgacgt gataatcaca    300
ggggtggtgc atgaagccct gaagaaaatt aaagacgggc tcttacgctt ccgcgtaggc    360
ggtgacatgc gttttcgag attttttctca tcgaactacg gctgcagatt cgtcgcgagc    420
gtgcgtacga acactacagt ttggctaaat tgcacgaaag cgagtggtga gaaattctca    480
ctcgccgccg cgtgcacggc ggattacgtg gcgatgctgc gttatgtgtg tggcgggaaa    540
tttccactcg tcctcatgag tagagttatt tacccggatg ggcgctgtta cttggcccat    600
atgaggtatt tgtgcgcctt ttactgtcgc ccgtttagag agtcggatta tgccctcgga    660
atgtggccta cggtggcgcg tctcagggca tgcgttgaga agaacttcgg tgtcgaagct    720
tgtggcatag ctcttcgtgg ctattacacc tctcgcaatg tttatcactg tgattatgac    780
tctgcttatg taaaatattt tagaaacctt tccggccgca ttggcggtgg ttcgttcgat    840
ccgacatctt taacctccgt aataacggtg aagattagcg gtcttccagg tggtcttcct    900
aaaaatatag cgtttggtgc cttcctgtgc gatatacgtt acgtcgaacc ggtagactcg    960
ggcggcattc aatcgagcgt taagacgaaa cgtgaagatg cgcaccgaac cgtagaggaa   1020
cgggcggccg gcggatccgt cgagcaaccg cgacaaaaga ggatagatga gaaaggttgc   1080
ggcagagttc ctagtggagg ttttttcgcat ctcctggtcg gcaaccttaa cgaagttagg   1140
aggaaggtag ctgccggact tctacgcttt cgcgttggcg gtgatatgga ttttcatcgc   1200
tcgttctcca cccaagcggg ccaccgcttg ctggtgtggc gccgctcgag ccggagcgtg   1260
tgccttgaac tttactcacc atctaaaaac tttttgcgtt acgatgtctt gccctgttct   1320
ggagactatg cagcgatgtt ttctttcgcg gcgggcggcc gtttcccttt agttttgatg   1380
actagaatta gatacccgaa cgggttttgt tacttggctc actgccggta cgcgtgcgcg   1440
tttctcttaa ggggttttga tccgaagcgt ttcgacatcg gtgctttccc caccgcggcc   1500
aagctcagaa accgtatggt ttcggagctt ggtgaaagaa gtttaggttt gaacttgtac   1560
ggcgcatata cgtcacgcgg cgtctttcac tgcgattatg acgctaagtt tataaaggat   1620
ttgcgtctta tgtcagcagt tatagctgga aaggacgggg tggaagaggt ggtaccttct   1680
gacataactc ctgccatgaa gcagaaaacg atcgaagccg tgtatgatag attatatggc   1740
ggcactgact cgttgctgaa actgagcatc gagaaagact taatcgattt caaaaatgac   1800
gtgcagagtt tgaagaaaga tcggccgatt gtcaaagtgc ccttttacat gtcggaagca   1860
acacagaatt cgctgacgcg tttctaccct cagttcgaac ttaagttttc gcactcctcg   1920
cattcagatc atcccgccgc cgccgcttct agactgctgg aaaatgaaac gttagtgcgc   1980
ttatgtggta atagcgtttc agatattgga ggttgtcctc ttttccattt gcattccaag   2040
acgcaaagac gggttcacgt atgtaggcct gtgttggatg gcaaggatgc gcagcgtcgc   2100
gtggtgcgtg atttgcagta ttccaacgtg cgtttgggag acgatgataa aattttggaa   2160
gggccacgca atatcgacat ttgccactat cctctgggcg cgtgtgacca cgaaagtagt   2220
gctatgatga tggtgcaggt gtatgacgcg tccctttatg agatatgtgg cgccatgatc   2280
aagaagaaaa gccgcataac gtacttaacc atggtcacgc ccggcgagtt tcttgacgga   2340
cgcgaatgcg tctacatgga gtcgttagac tgtgagattg aagttgatgt gcacgcggac   2400
gtcgtaatgt acaaattcgg tagttcttgc tattcgcaca agctttcaat catcaaggac   2460
atcatgacca ctccgtactt gacactaggt ggttttctat tcagcgtgga gatgtatgag   2520
gtgcgtatgg gcgtgaatta cttcaagatt acgaagtccg aagtatcgcc tagcattagc   2580
```

```
tgcaccaagc tcctgagata ccgaagagct aatagtgacg tggttaaagt taaacttcca   2640
cgtttcgata agaaacgtcg catgtgtctg cctgggtatg acaccatata cctagattcg   2700
aagtttgtga gtcgcgtttt cgattatgtc gtgtgtaatt gctctgccgt gaactcaaaa   2760
actttcgagt gggtgtggag tttcattaag tctagtaagt cgaggtgat tattagcggt    2820 aaaataattc acaaggatgt gaatttggac ctcaagtacg tcgagagttt cgccgcggtt   2880
atgttggcct ctggcgtgcg cagtagacta gcgtccgagt accttgctaa gaaccttagt   2940 cattttcgg  gagattgctc ctttattgaa gccacgtctt tcgtgttgcg tgagaaaatc   3000
agaaacatga ctctgaattt taacgaaaga cttttacagt tagtgaagcg cgttgccttt   3060
gcgaccttgg acgtgagttt tctagattta gattcaactc ttgaatcaat aactgatttt   3120
gccgagtgta aggtagcgat tgaactcgac gagttgggtt gcttgagagc ggaggccgag   3180
aatgaaaaaa tcaggaatct ggcgggagat tcgattgcgg ctaaactcgc gagcgagata   3240
gtggtcgata ttgactctaa gccttcaccg aagcaggtgg gtaattcgtc atccgaaaac   3300
gccgataagc gggaagttca gaggcccggt ttgcgtggtg gttctagaaa cggggttgtt   3360
ggggagttcc ttcacttcgt cgtggattct gccttgcgtc ttttcaaata cgcgacggat   3420
caacaacgga tcaagtctta cgtgcgtttc ttggactcgg cggtctcatt cttggattac   3480
aactacgata atctatcgtt tatactgcga gtgctttcgg aaggttattc gtgtatgttc   3540
gcgtttttgg cgaatcgcgg cgacttatct agtcgtgtcc gtagcgcggt gtgtgctgtg   3600
aaagaagttg ctacctcatg cgcgaacgcg agcgtttcta aagccaaggt tatgattacc   3660
ttcgcagcgg ccgtgtgtgc tatgatgttt aatagctgcg gttttcagg  cgacggtcgg   3720 gagtataaat cgtatataca tcgttacacg caagtattgt ttgacactat ctttttgag   3780 gacagcagtt acctacccat agaagttctg agttcggcga tatgcggtgc tatcgtcaca   3840
cttttctcct cgggctcgtc cataagttta aacgccttct tacttcaaat taccaaagga   3900
ttctccctag aggttgtcgt ccggaatgtt gtgcgagtca cgcatggttt gagcaccaca   3960
gcgaccgacg gcgtcatacg tggggttttc tcccaaattg tgtctcactt acttgttgga   4020
aatacgggta atgtggctta ccagtcagct ttcattgccg gggtggtgcc tcttttagtt   4080
aaaaagtgtg tgagcttaat cttcatcttg cgtgaagata cttattccgg ttttattaag   4140
cacggaatca gtgaattctc tttccttagt agtattctga agttcttgaa gggtaagctt   4200
gtggacgagt tgaaatcgat tattcaaggg gttttttgatt ccaacaagca cgtgtttaaa   4260
gaagctactc aggaagcgat tcgtacgacg gtcatgcaag tgcctgtcgc tgtagtggat   4320
gcccttaaga gcgccgcggg aaaaatttat aacaattta ctagtcgacg tacctttggt    4380
aaggatgaag gctcctctag cgacggcgca tgtgaagagt atttctcatg cgacgaaggt   4440
gaaggtccgg gtctgaaagg gggttccagc tatggcttct caattttagc gttcttttca   4500
cgcattatgt ggggagctcg tcggcttatt gttaaggtga agcatgagtg ttttgggaaa   4560 cttttgaat ttctatcgct caagcttcac gaattcagga ctcgcgtttt tgggaagaat    4620
agaacggacg tgggagttta cgattttttg cccacgggca tcgtggaaac gctctcatcg   4680
atagaagagt gcgaccaaat tgaagaactt ctcggcgacg acctgaaagg tgacaaggat   4740
gcttcgttga ccgatatgaa ttactttgag ttctcagaag acttcttagc ctctatcgag   4800
gagccgcctt tcgctggatt gcgaggaggt agcaagaaca tcgcgatttt ggcgatttttg   4860 gaatacgcgc ataatttgtt tcgcattgtc gcaagcaagt gttcgaaacg accttatttt   4920
```

```
cttgctttcg ccgaactctc aagcgccctt atcgagaaat ttaaggaggt tttccctcgt    4980
aagagccagc tcgtcgctat cgtgcgcgag tatactcaga gattcctccg aagtcgcatg    5040
cgtgcgttgg gtttgaataa cgagttcgtg gtaaaatctt tcgccgattt gctacccgca    5100
ttaatgaagc ggaaggtttc aggttcgttc ttagctagtg tttatcgccc acttagaggt    5160
ttctcatata tgtgtgtttc agcggagcga cgtgaaaagt tttttgctct cgtgtgttta    5220
atcgggttaa gtctcccttt cttcgtgcgc atcgtaggag cgaaagcgtg cgaagaactc    5280
gtgtcctcag cgcgtcgctt ttatgagcgt attaaaattt ttctaaggca gaagtatgtc    5340
tctctttcta atttcttttg tcacttgttt agctctgacg ttgatgacag ttccgcatct    5400
gcagggttga aggtggtgc gtcgcgaatg acgctcttcc accttctggt tcgccttgct    5460
agtgccctcc tatcgttagg gtgggaaggg ttaaagctac tcttatcgca ccacaacttg    5520
ttatttttgt gttttgcatt ggttgacgat gtgaacgtcc ttatcaaagt tcttgggggt    5580 cttctctttct ttgtgcaacc aatcttttcc ttgtttgcgg cgatgcttct acaaccggac    5640
aggtttgtgg agtattccga gaaacttgtt acagcgtttg aattttttctt aaaatgttcg    5700 cctcgcgcgc ctgcactact caaagggttt tttgagtgcg tggcgaacag cactgtgtca    5760
aaaaccgttc gaagacttct tcgctgtttc gtgaagatgc tcaaacttcg aaaagggcga    5820
gggttgcgtg cggatggtag gggtctccat cggcagaaag ccgtacccgt catacccttct    5880 aatcgggtcg tgaccgacgg ggttgaaaga ctttcggtaa agatgcaagg agttgaagcg    5940
ttgcgtaccg aattgagaat cttagaagat ttagattctg ccgtgatcga aaaactcaat    6000
agacgcagaa atcgtgacac taatgacgac gaatttacgc gccctgctca tgagcagatg    6060
caagaagtca ccactttctg ttcgaaagcc aactctgctg gtttggccct ggaaagggca    6120
gtgcttgtgg aagacgctat aaagtcggag aaactttcta agacggttaa tgagatggtg    6180
aggaaaggga gtaccaccag cgaagaagtg gccgtcgctt tgtcggacga tgaagccgtg    6240
gaagaaatct ctgttgctga cgagcgagac gattcgccta agacagtcag gataagcgaa    6300
tacctaaata ggttaaactc aagcttcgaa ttcccgaagc ctattgttgt ggacgacaac    6360
aaggataccg ggggtctaac gaacgccgtg agggagtttt attatatgca agaacttgct    6420
cttttcgaaa tccacagcaa actgtgcacc tactacgatc aactgcgcat agtcaacttc    6480
gatcgttccg tagcaccatg cagcgaagat gctcagctgt acgtacggaa gaacggctca    6540
acgatagtgc agggtaaaga ggtacgtttg cacattaagg atttccacga tcacgatttc    6600
ctgtttgacg gaaaaatttc tattaacaag cggcggcgag gcggaaatgt tttatatcac    6660
gacaacctcg cgttcttggc gagtaatttg ttcttagccg gctaccccttt ttcaaggagc    6720 ttcgtcttca cgaattcgtc ggtcgatatt tcctctacg aagctccacc cggaggtggt    6780
aagacgacga cgctgattga ctcgttcttg aaggtcttca agaaaggtga ggtttccacc    6840
atgatcttaa ccgccaacaa aagttcgcag gttgagatcc taaagaaagt gggagaaggaa    6900 gtgtctaaca ttgaatgcca gaaacgtaaa gacaaaagat ctccgaaaaa gagcatttac    6960
accatcgacg cttatttaat gcatcaccgt ggttgtgatg cagacgttct tttcatcgat    7020
gagtgtttca tggttcatgc gggtagcgta ctagcttgca ttgagttcac gaggtgtcat    7080
aaagtaatga tcttcgggga tagccggcag attcactaca ttgaaaggaa cgaattggac    7140 aagtgttttgt atggggatct cgacaggttc gtggacctgc agtgtcgggt ttatggtaat    7200
atttcgtacc gttgtccatg ggatgtgtgc gcttggttaa gcacagtgta tggcaaccta    7260
atcgccaccg tgaagggtga aagcgaaggt aagagcagca tgcgcattaa cgaaattaat    7320
```

-continued

```
tcagtcgacg atttagtccc cgacgtgggt tccacgtttc tgtgtatgct tcagtcggag    7380
aagttggaaa tcagcaagca ctttattcgc aagggtttga ctaaacttaa cgttctaacg    7440
gtgcatgagg cgcaaggtga gacgtatgcg cgtgtgaacc ttgtgcgact taagtttcag    7500
gaggatgaac cctttaaatc tatcaggcac ataaccgtcg ctctttctcg tcacaccgac    7560
agcttaactt ataacgtctt agctgctcgt cgaggtgacg ccacttgcga tgccatccag    7620
aaggctgcgg aattggtgaa caagtttcgc gttttttccta catcttttgg tggtagtgtt    7680
atcaatctca acgtgaagaa ggacgtggaa gataacagta ggtgcaaggc ttcgtcggca    7740
ccattgagcg taatcaacga cttttgaac gaagttaatc ccggtactgc ggtgattgat    7800
tttggtgatt tgtccgcgga cttcagtact gggccttttg agtgcggtgc cagcggtatt    7860
gtggtgcggg acaacatctc ctccagcaac atcactgatc acgataagca gcgtgtttag    7920
```

<210> SEQ ID NO 3
<211> LENGTH: 2639
<212> TYPE: PRT
<213> ORGANISM: Grapevine Leafroll Virus (type 2)

<400> SEQUENCE: 3

```
Thr Leu Arg Glu Asn Pro Ile Ser Val Ser Gly Val Asn Leu Gly Arg
 1               5                  10                  15

Ser Ala Ala Ala Gln Val Ile Tyr Phe Gly Ser Phe Thr Gln Pro Phe
            20                  25                  30

Ala Leu Tyr Pro Arg Gln Glu Ser Ala Ile Val Lys Thr Gln Leu Pro
        35                  40                  45

Pro Val Ser Val Val Lys Val Glu Cys Val Ala Ala Glu Val Ala Pro
    50                  55                  60

Asp Arg Gly Val Val Asp Lys Lys Pro Thr Ser Val Gly Val Pro Pro
65                  70                  75                  80

Gln Arg Gly Val Leu Ser Phe Pro Thr Val Arg Asn Arg Gly Asp
                85                  90                  95

Val Ile Ile Thr Gly Val Val His Glu Ala Leu Lys Lys Ile Lys Asp
            100                 105                 110

Gly Leu Leu Arg Phe Arg Val Gly Gly Asp Met Arg Phe Ser Arg Phe
        115                 120                 125

Phe Ser Ser Asn Tyr Gly Cys Arg Phe Val Ala Ser Val Arg Thr Asn
    130                 135                 140

Thr Thr Val Trp Leu Asn Cys Thr Lys Ala Ser Gly Glu Lys Phe Ser
145                 150                 155                 160

Leu Ala Ala Ala Cys Thr Ala Asp Tyr Val Ala Met Leu Arg Tyr Val
                165                 170                 175

Cys Gly Gly Lys Phe Pro Leu Val Leu Met Ser Arg Val Ile Tyr Pro
            180                 185                 190

Asp Gly Arg Cys Tyr Leu Ala His Met Arg Tyr Leu Cys Ala Phe Tyr
        195                 200                 205

Cys Arg Pro Phe Arg Glu Ser Asp Tyr Ala Leu Gly Met Trp Pro Thr
    210                 215                 220

Val Ala Arg Leu Arg Ala Cys Val Glu Lys Asn Phe Gly Val Glu Ala
225                 230                 235                 240

Cys Gly Ile Ala Leu Arg Gly Tyr Tyr Thr Ser Arg Asn Val Tyr His
                245                 250                 255

Cys Asp Tyr Asp Ser Ala Tyr Val Lys Tyr Phe Arg Asn Leu Ser Gly
            260                 265                 270
```

```
Arg Ile Gly Gly Gly Ser Phe Asp Pro Thr Ser Leu Thr Ser Val Ile
        275                 280                 285

Thr Val Lys Ile Ser Gly Leu Pro Gly Gly Leu Pro Lys Asn Ile Ala
    290                 295                 300

Phe Gly Ala Phe Leu Cys Asp Ile Arg Tyr Val Glu Pro Val Asp Ser
305                 310                 315                 320

Gly Gly Ile Gln Ser Ser Val Lys Thr Lys Arg Glu Asp Ala His Arg
                325                 330                 335

Thr Val Glu Glu Arg Ala Ala Gly Gly Ser Val Glu Gln Pro Arg Gln
            340                 345                 350

Lys Arg Ile Asp Glu Lys Gly Cys Gly Arg Val Pro Ser Gly Gly Phe
        355                 360                 365

Ser His Leu Leu Val Gly Asn Leu Asn Glu Val Arg Arg Lys Val Ala
    370                 375                 380

Ala Gly Leu Leu Arg Phe Arg Val Gly Gly Asp Met Asp Phe His Arg
385                 390                 395                 400

Ser Phe Ser Thr Gln Ala Gly His Arg Leu Leu Val Trp Arg Arg Ser
                405                 410                 415

Ser Arg Ser Val Cys Leu Glu Leu Tyr Ser Pro Ser Lys Asn Phe Leu
            420                 425                 430

Arg Tyr Asp Val Leu Pro Cys Ser Gly Asp Tyr Ala Ala Met Phe Ser
        435                 440                 445

Phe Ala Ala Gly Gly Arg Phe Pro Leu Val Leu Met Thr Arg Ile Arg
    450                 455                 460

Tyr Pro Asn Gly Phe Cys Tyr Leu Ala His Cys Arg Tyr Ala Cys Ala
465                 470                 475                 480

Phe Leu Leu Arg Gly Phe Asp Pro Lys Arg Phe Asp Ile Gly Ala Phe
                485                 490                 495

Pro Thr Ala Ala Lys Leu Arg Asn Arg Met Val Ser Glu Leu Gly Glu
            500                 505                 510

Arg Ser Leu Gly Leu Asn Leu Tyr Gly Ala Tyr Thr Ser Arg Gly Val
        515                 520                 525

Phe His Cys Asp Tyr Asp Ala Lys Phe Ile Lys Asp Leu Arg Leu Met
    530                 535                 540

Ser Ala Val Ile Ala Gly Lys Asp Gly Val Glu Glu Val Val Pro Ser
545                 550                 555                 560

Asp Ile Thr Pro Ala Met Lys Gln Lys Thr Ile Glu Ala Val Tyr Asp
                565                 570                 575

Arg Leu Tyr Gly Gly Thr Asp Ser Leu Leu Lys Leu Ser Ile Glu Lys
            580                 585                 590

Asp Leu Ile Asp Phe Lys Asn Asp Val Gln Ser Leu Lys Lys Asp Arg
        595                 600                 605

Pro Ile Val Lys Val Pro Phe Tyr Met Ser Glu Ala Thr Gln Asn Ser
    610                 615                 620

Leu Thr Arg Phe Tyr Pro Gln Phe Glu Leu Lys Phe Ser His Ser Ser
625                 630                 635                 640

His Ser Asp His Pro Ala Ala Ala Ser Arg Leu Leu Glu Asn Glu
                645                 650                 655

Thr Leu Val Arg Leu Cys Gly Asn Ser Val Ser Asp Ile Gly Gly Cys
            660                 665                 670

Pro Leu Phe His Leu His Ser Lys Thr Gln Arg Arg Val His Val Cys
        675                 680                 685

Arg Pro Val Leu Asp Gly Lys Asp Ala Gln Arg Arg Val Val Arg Asp
```

-continued

```
                690                 695                 700
Leu Gln Tyr Ser Asn Val Arg Leu Gly Asp Asp Lys Ile Leu Glu
705                 710                 715                 720

Gly Pro Arg Asn Ile Asp Ile Cys His Tyr Pro Leu Gly Ala Cys Asp
                725                 730                 735

His Glu Ser Ser Ala Met Met Met Val Gln Val Tyr Asp Ala Ser Leu
                740                 745                 750

Tyr Glu Ile Cys Gly Ala Met Ile Lys Lys Lys Ser Arg Ile Thr Tyr
                755                 760                 765

Leu Thr Met Val Thr Pro Gly Glu Phe Leu Asp Gly Arg Glu Cys Val
770                 775                 780

Tyr Met Glu Ser Leu Asp Cys Glu Ile Glu Val Asp Val His Ala Asp
785                 790                 795                 800

Val Val Met Tyr Lys Phe Gly Ser Ser Cys Tyr Ser His Lys Leu Ser
                805                 810                 815

Ile Ile Lys Asp Ile Met Thr Thr Pro Tyr Leu Thr Leu Gly Gly Phe
                820                 825                 830

Leu Phe Ser Val Glu Met Tyr Glu Val Arg Met Gly Val Asn Tyr Phe
                835                 840                 845

Lys Ile Thr Lys Ser Glu Val Ser Pro Ser Ile Ser Cys Thr Lys Leu
                850                 855                 860

Leu Arg Tyr Arg Arg Ala Asn Ser Asp Val Val Lys Val Lys Leu Pro
865                 870                 875                 880

Arg Phe Asp Lys Lys Arg Met Cys Leu Pro Gly Tyr Asp Thr Ile
                885                 890                 895

Tyr Leu Asp Ser Lys Phe Val Ser Arg Val Phe Asp Tyr Val Val Cys
                900                 905                 910

Asn Cys Ser Ala Val Asn Ser Lys Thr Phe Glu Trp Val Trp Ser Phe
                915                 920                 925

Ile Lys Ser Ser Lys Ser Arg Val Ile Ile Ser Gly Lys Ile Ile His
                930                 935                 940

Lys Asp Val Asn Leu Asp Leu Lys Tyr Val Glu Ser Phe Ala Ala Val
945                 950                 955                 960

Met Leu Ala Ser Gly Val Arg Ser Arg Leu Ala Ser Glu Tyr Leu Ala
                965                 970                 975

Lys Asn Leu Ser His Phe Ser Gly Asp Cys Ser Phe Ile Glu Ala Thr
                980                 985                 990

Ser Phe Val Leu Arg Glu Lys Ile Arg Asn Met Thr Leu Asn Phe Asn
                995                 1000                1005

Glu Arg Leu Leu Gln Leu Val Lys Arg Val Ala Phe Ala Thr Leu Asp
1010                1015                1020

Val Ser Phe Leu Asp Leu Asp Ser Thr Leu Glu Ser Ile Thr Asp Phe
1025                1030                1035                1040

Ala Glu Cys Lys Val Ala Ile Glu Leu Asp Glu Leu Gly Cys Leu Arg
                1045                1050                1055

Ala Glu Ala Glu Asn Glu Lys Ile Arg Asn Leu Ala Gly Asp Ser Ile
                1060                1065                1070

Ala Ala Lys Leu Ala Ser Glu Ile Val Val Asp Ile Asp Ser Lys Pro
                1075                1080                1085

Ser Pro Lys Gln Val Gly Asn Ser Ser Glu Asn Ala Asp Lys Arg
                1090                1095                1100

Glu Val Gln Arg Pro Gly Leu Arg Gly Gly Ser Arg Asn Gly Val Val
1105                1110                1115                1120
```

-continued

```
Gly Glu Phe Leu His Phe Val Val Asp Ser Ala Leu Arg Leu Phe Lys
                1125                1130                1135

Tyr Ala Thr Asp Gln Gln Arg Ile Lys Ser Tyr Val Arg Phe Leu Asp
                1140            1145                1150

Ser Ala Val Ser Phe Leu Asp Tyr Asn Tyr Asp Asn Leu Ser Phe Ile
                1155                1160            1165

Leu Arg Val Leu Ser Glu Gly Tyr Ser Cys Met Phe Ala Phe Leu Ala
    1170                1175                1180

Asn Arg Gly Asp Leu Ser Ser Arg Val Arg Ser Ala Val Cys Ala Val
1185                1190                1195                1200

Lys Glu Val Ala Thr Ser Cys Ala Asn Ala Ser Val Ser Lys Ala Lys
                1205                1210                1215

Val Met Ile Thr Phe Ala Ala Ala Val Cys Ala Met Met Phe Asn Ser
                1220                1225                1230

Cys Gly Phe Ser Gly Asp Gly Arg Glu Tyr Lys Ser Tyr Ile His Arg
                1235                1240                1245

Tyr Thr Gln Val Leu Phe Asp Thr Ile Phe Phe Glu Asp Ser Ser Tyr
    1250                1255                1260

Leu Pro Ile Glu Val Leu Ser Ser Ala Ile Cys Gly Ala Ile Val Thr
1265                1270                1275                1280

Leu Phe Ser Ser Gly Ser Ser Ile Ser Leu Asn Ala Phe Leu Leu Gln
                1285                1290                1295

Ile Thr Lys Gly Phe Ser Leu Glu Val Val Arg Asn Val Val Arg
                1300                1305                1310

Val Thr His Gly Leu Ser Thr Thr Ala Thr Asp Gly Val Ile Arg Gly
                1315                1320                1325

Val Phe Ser Gln Ile Val Ser His Leu Leu Val Gly Asn Thr Gly Asn
    1330                1335                1340

Val Ala Tyr Gln Ser Ala Phe Ile Ala Gly Val Val Pro Leu Leu Val
1345                1350                1355                1360

Lys Lys Cys Val Ser Leu Ile Phe Ile Leu Arg Glu Asp Thr Tyr Ser
                1365                1370                1375

Gly Phe Ile Lys His Gly Ile Ser Glu Phe Ser Phe Leu Ser Ser Ile
                1380                1385                1390

Leu Lys Phe Leu Lys Gly Lys Leu Val Asp Glu Leu Lys Ser Ile Ile
                1395                1400                1405

Gln Gly Val Phe Asp Ser Asn Lys His Val Phe Lys Glu Ala Thr Gln
    1410                1415                1420

Glu Ala Ile Arg Thr Thr Val Met Gln Val Pro Val Ala Val Val Asp
1425                1430                1435                1440

Ala Leu Lys Ser Ala Ala Gly Lys Ile Tyr Asn Asn Phe Thr Ser Arg
                1445                1450                1455

Arg Thr Phe Gly Lys Asp Glu Gly Ser Ser Asp Gly Ala Cys Glu
                1460                1465                1470

Glu Tyr Phe Ser Cys Asp Glu Gly Gly Pro Gly Leu Lys Gly Gly
                1475                1480                1485

Ser Ser Tyr Gly Phe Ser Ile Leu Ala Phe Phe Ser Arg Ile Met Trp
    1490                1495                1500

Gly Ala Arg Arg Leu Ile Val Lys Val Lys His Glu Cys Phe Gly Lys
1505                1510                1515                1520

Leu Phe Glu Phe Leu Ser Leu Lys Leu His Glu Phe Arg Thr Arg Val
                1525                1530                1535
```

```
Phe Gly Lys Asn Arg Thr Asp Val Gly Val Tyr Asp Phe Leu Pro Thr
            1540                1545                1550
Gly Ile Val Glu Thr Leu Ser Ser Ile Glu Glu Cys Asp Gln Ile Glu
        1555                1560                1565
Glu Leu Leu Gly Asp Asp Leu Lys Gly Asp Lys Asp Ala Ser Leu Thr
    1570                1575                1580
Asp Met Asn Tyr Phe Glu Phe Ser Glu Asp Phe Leu Ala Ser Ile Glu
1585                1590                1595                1600
Glu Pro Pro Phe Ala Gly Leu Arg Gly Ser Lys Asn Ile Ala Ile
                1605                1610                1615
Leu Ala Ile Leu Glu Tyr Ala His Asn Leu Phe Arg Ile Val Ala Ser
            1620                1625                1630
Lys Cys Ser Lys Arg Pro Leu Phe Leu Ala Phe Ala Glu Leu Ser Ser
        1635                1640                1645
Ala Leu Ile Glu Lys Phe Lys Glu Val Phe Pro Arg Lys Ser Gln Leu
    1650                1655                1660
Val Ala Ile Val Arg Glu Tyr Thr Gln Arg Phe Leu Arg Ser Arg Met
1665                1670                1675                1680
Arg Ala Leu Gly Leu Asn Asn Glu Phe Val Val Lys Ser Phe Ala Asp
                1685                1690                1695
Leu Leu Pro Ala Leu Met Lys Arg Lys Val Ser Gly Ser Phe Leu Ala
            1700                1705                1710
Ser Val Tyr Arg Pro Leu Arg Gly Phe Ser Tyr Met Cys Val Ser Ala
        1715                1720                1725
Glu Arg Arg Glu Lys Phe Phe Ala Leu Val Cys Leu Ile Gly Leu Ser
    1730                1735                1740
Leu Pro Phe Phe Val Arg Ile Val Gly Ala Lys Ala Cys Glu Glu Leu
1745                1750                1755                1760
Val Ser Ser Ala Arg Arg Phe Tyr Glu Arg Ile Lys Ile Phe Leu Arg
                1765                1770                1775
Gln Lys Tyr Val Ser Leu Ser Asn Phe Phe Cys His Leu Phe Ser Ser
            1780                1785                1790
Asp Val Asp Ser Ser Ala Ser Ala Gly Leu Lys Gly Gly Ala Ser
            1795                1800                1805
Arg Met Thr Leu Phe His Leu Leu Val Arg Leu Ala Ser Ala Leu Leu
        1810                1815                1820
Ser Leu Gly Trp Glu Gly Leu Lys Leu Leu Ser His His Asn Leu
1825                1830                1835                1840
Leu Phe Leu Cys Phe Ala Leu Val Asp Asp Val Asn Val Leu Ile Lys
                1845                1850                1855
Val Leu Gly Gly Leu Ser Phe Phe Val Gln Pro Ile Phe Ser Leu Phe
            1860                1865                1870
Ala Ala Met Leu Leu Gln Pro Asp Arg Phe Val Glu Tyr Ser Glu Lys
        1875                1880                1885
Leu Val Thr Ala Phe Glu Phe Phe Leu Lys Cys Ser Pro Arg Ala Pro
    1890                1895                1900
Ala Leu Leu Lys Gly Phe Phe Glu Cys Val Ala Asn Ser Thr Val Ser
1905                1910                1915                1920
Lys Thr Val Arg Arg Leu Leu Arg Cys Phe Val Lys Met Leu Lys Leu
                1925                1930                1935
Arg Lys Gly Arg Gly Leu Arg Ala Asp Gly Arg Gly Leu His Arg Gln
            1940                1945                1950
Lys Ala Val Pro Val Ile Pro Ser Asn Arg Val Val Thr Asp Gly Val
```

-continued

```
                1955                1960                1965
Glu Arg Leu Ser Val Lys Met Gln Gly Val Ala Leu Arg Thr Glu
    1970                1975                1980

Leu Arg Ile Leu Glu Asp Leu Asp Ser Ala Val Ile Glu Lys Leu Asn
1985                1990                1995                2000

Arg Arg Arg Asn Arg Asp Thr Asn Asp Asp Glu Phe Thr Arg Pro Ala
            2005                2010                2015

His Glu Gln Met Gln Glu Val Thr Thr Phe Cys Ser Lys Ala Asn Ser
                2020                2025                2030

Ala Gly Leu Ala Leu Glu Arg Ala Val Leu Val Glu Asp Ala Ile Lys
        2035                2040                2045

Ser Glu Lys Leu Ser Lys Thr Val Asn Glu Met Val Arg Lys Gly Ser
    2050                2055                2060

Thr Thr Ser Glu Glu Val Ala Val Ala Leu Ser Asp Asp Glu Ala Val
2065                2070                2075                2080

Glu Glu Ile Ser Val Ala Asp Glu Arg Asp Ser Pro Lys Thr Val
            2085                2090                2095

Arg Ile Ser Glu Tyr Leu Asn Arg Leu Asn Ser Ser Phe Glu Phe Pro
            2100                2105                2110

Lys Pro Ile Val Val Asp Asp Asn Lys Asp Thr Gly Gly Leu Thr Asn
            2115                2120                2125

Ala Val Arg Glu Phe Tyr Tyr Met Gln Glu Leu Ala Leu Phe Glu Ile
        2130                2135                2140

His Ser Lys Leu Cys Thr Tyr Tyr Asp Gln Leu Arg Ile Val Asn Phe
2145                2150                2155                2160

Asp Arg Ser Val Ala Pro Cys Ser Glu Asp Ala Gln Leu Tyr Val Arg
            2165                2170                2175

Lys Asn Gly Ser Thr Ile Val Gln Gly Lys Glu Val Arg Leu His Ile
            2180                2185                2190

Lys Asp Phe His Asp His Asp Phe Leu Phe Asp Gly Lys Ile Ser Ile
            2195                2200                2205

Asn Lys Arg Arg Arg Gly Gly Asn Val Leu Tyr His Asp Asn Leu Ala
2210                2215                2220

Phe Leu Ala Ser Asn Leu Phe Leu Ala Gly Tyr Pro Phe Ser Arg Ser
2225                2230                2235                2240

Phe Val Phe Thr Asn Ser Ser Val Asp Ile Leu Leu Tyr Glu Ala Pro
            2245                2250                2255

Pro Gly Gly Gly Lys Thr Thr Thr Leu Ile Asp Ser Phe Leu Lys Val
            2260                2265                2270

Phe Lys Lys Gly Glu Val Ser Thr Met Ile Leu Thr Ala Asn Lys Ser
        2275                2280                2285

Ser Gln Val Glu Ile Leu Lys Lys Val Glu Lys Glu Val Ser Asn Ile
    2290                2295                2300

Glu Cys Gln Lys Arg Lys Asp Lys Arg Ser Pro Lys Lys Ser Ile Tyr
2305                2310                2315                2320

Thr Ile Asp Ala Tyr Leu Met His His Arg Gly Cys Asp Ala Asp Val
            2325                2330                2335

Leu Phe Ile Asp Glu Cys Phe Met Val His Ala Gly Ser Val Leu Ala
            2340                2345                2350

Cys Ile Glu Phe Thr Arg Cys His Lys Val Met Ile Phe Gly Asp Ser
        2355                2360                2365

Arg Gln Ile His Tyr Ile Glu Arg Asn Glu Leu Asp Lys Cys Leu Tyr
    2370                2375                2380
```

-continued

Gly Asp Leu Asp Arg Phe Val Asp Leu Gln Cys Arg Val Tyr Gly Asn
2385                2390                2395                2400

Ile Ser Tyr Arg Cys Pro Trp Asp Val Cys Ala Trp Leu Ser Thr Val
            2405                2410                2415

Tyr Gly Asn Leu Ile Ala Thr Val Lys Gly Glu Ser Glu Gly Lys Ser
        2420                2425                2430

Ser Met Arg Ile Asn Glu Ile Asn Ser Val Asp Leu Val Pro Asp
    2435                2440                2445

Val Gly Ser Thr Phe Leu Cys Met Leu Gln Ser Glu Lys Leu Glu Ile
2450                2455                2460

Ser Lys His Phe Ile Arg Lys Gly Leu Thr Lys Leu Asn Val Leu Thr
2465                2470                2475                2480

Val His Glu Ala Gln Gly Glu Thr Tyr Ala Arg Val Asn Leu Val Arg
            2485                2490                2495

Leu Lys Phe Gln Glu Asp Glu Pro Phe Lys Ser Ile Arg His Ile Thr
        2500                2505                2510

Val Ala Leu Ser Arg His Thr Asp Ser Leu Thr Tyr Asn Val Leu Ala
        2515                2520                2525

Ala Arg Arg Gly Asp Ala Thr Cys Asp Ala Ile Gln Lys Ala Ala Glu
        2530                2535                2540

Leu Val Asn Lys Phe Arg Val Phe Pro Thr Ser Phe Gly Gly Ser Val
2545                2550                2555                2560

Ile Asn Leu Asn Val Lys Lys Asp Val Glu Asp Asn Ser Arg Cys Lys
            2565                2570                2575

Ala Ser Ser Ala Pro Leu Ser Val Ile Asn Asp Phe Leu Asn Glu Val
            2580                2585                2590

Asn Pro Gly Thr Ala Val Ile Asp Phe Gly Asp Leu Ser Ala Asp Phe
        2595                2600                2605

Ser Thr Gly Pro Phe Glu Cys Gly Ala Ser Gly Ile Val Val Arg Asp
        2610                2615                2620

Asn Ile Ser Ser Ser Asn Ile Thr Asp His Asp Lys Gln Arg Val
2625                2630                2635

<210> SEQ ID NO 4
<211> LENGTH: 1380
<212> TYPE: DNA
<213> ORGANISM: Grapevine Leafroll Virus (type 2)

<400> SEQUENCE: 4
agcgtagttc ggtcgcaggc gattccgcgt agaaaacctt ctctacaaga aaatttgtat 60
tcgtttgaag cgcggaatta taacttctcg acttgcgacc gtaacacatc tgcttcaatg 120
ttcggagagg ctatggcgat gaactgtctt cgtcgttgct cgacctaga tgccttttcg 180 tccctgcgtg atgatgtgat tagtatcaca cgttcaggca tcgaacaatg gctggagaaa 240
cgtactccta gtcagattaa agcattaatg aaggatgttg aatcgccttt ggaaattgac 300
gatgaaattt gtcgttttaa gttgatggtg aagcgtgacg ctaaggtgaa gttagactct 360
tcttgtttaa ctaaacacag cgccgctcaa atatcatgt tcatcgcaa gagcattaat 420 gctatcttct ctcctatctt taatgaggtg aaaaaccgaa taatgtgctg tcttaagcct 480
aacataaagt tttttacgga gatgactaac agggattttg cttctgttgt cagcaacatg 540
cttggtgacg acgatgtgta ccatataggt gaagttgatt tctcaaagta cgacaagtct 600
caagatgctt tcgtgaaggc ttttgaagaa gtaatgtata aggaactcgg tgttgatgaa 660

-continued

```
gagttgctgg ctatctggat gtgcggcgag cggttatcga tagctaacac tctcgatggt  720
cagttgtcct tcacgatcga gaatcaaagg aagtcgggag cttcgaacac ttggattggt  780
aactctctcg tcactttggg tattttaagt ctttactacg acgttagaaa tttcgaggcg  840
ttgtacatct cgggcgatga ttctttaatt ttttctcgca gcgagatttc gaattatgcc  900
gacgacatat gcactgacat gggttttgag acaaaattta tgtccccaag tgtcccgtac  960
ttttgttcta aatttgttgt tatgtgtggt cataagacgt tttttgttcc cgacccgtac 1020 aagcttttttg tcaagttggg agcagtcaaa gaggatgttt caatggattt ccttttcgag 1080
acttttacct cctttaaaga cttaacctcc gattttaacg acgagcgctt aattcaaaag 1140
ctcgctgaac ttgtggcttt aaaatatgag gttcaaaccg gcaacaccac cttggcgtta 1200
agtgtgatac attgtttgcg ttcgaatttc ctctcgttta gcaagttata tcctcgcgtg 1260
aagggatggc aggtttttta cacgtcggtt aagaaagcgc ttctcaagag tgggtgttct 1320
ctcttcgaca gtttcatgac ccctttggt caggctgtca tggtttggga tgatgagtag 1380
```

<210> SEQ ID NO 5
<211> LENGTH: 459
<212> TYPE: PRT
<213> ORGANISM: Grapevine Leafroll Virus (type 2)

<400> SEQUENCE: 5

```
Ser Val Val Arg Ser Gln Ala Ile Pro Arg Arg Lys Pro Ser Leu Gln
1               5                   10                  15

Glu Asn Leu Tyr Ser Phe Glu Ala Arg Asn Tyr Asn Phe Ser Thr Cys
            20                  25                  30

Asp Arg Asn Thr Ser Ala Ser Met Phe Gly Glu Ala Met Ala Met Asn
        35                  40                  45

Cys Leu Arg Arg Cys Phe Asp Leu Asp Ala Phe Ser Ser Leu Arg Asp
    50                  55                  60

Asp Val Ile Ser Ile Thr Arg Ser Gly Ile Glu Gln Trp Leu Glu Lys
65                  70                  75                  80

Arg Thr Pro Ser Gln Ile Lys Ala Leu Met Lys Asp Val Glu Ser Pro
                85                  90                  95

Leu Glu Ile Asp Asp Glu Ile Cys Arg Phe Lys Leu Met Val Lys Arg
            100                 105                 110

Asp Ala Lys Val Lys Leu Asp Ser Ser Cys Leu Thr Lys His Ser Ala
        115                 120                 125

Ala Gln Asn Ile Met Phe His Arg Lys Ser Ile Asn Ala Ile Phe Ser
    130                 135                 140

Pro Ile Phe Asn Glu Val Lys Asn Arg Ile Met Cys Cys Leu Lys Pro
145                 150                 155                 160

Asn Ile Lys Phe Phe Thr Glu Met Thr Asn Arg Asp Phe Ala Ser Val
                165                 170                 175

Val Ser Asn Met Leu Gly Asp Asp Val Tyr His Ile Gly Glu Val
            180                 185                 190

Asp Phe Ser Lys Tyr Asp Lys Ser Gln Asp Ala Phe Val Lys Ala Phe
        195                 200                 205

Glu Glu Val Met Tyr Lys Glu Leu Gly Val Asp Glu Glu Leu Leu Ala
    210                 215                 220

Ile Trp Met Cys Gly Glu Arg Leu Ser Ile Ala Asn Thr Leu Asp Gly
225                 230                 235                 240

Gln Leu Ser Phe Thr Ile Glu Asn Gln Arg Lys Ser Gly Ala Ser Asn
                245                 250                 255
```

```
Thr Trp Ile Gly Asn Ser Leu Val Thr Leu Gly Ile Leu Ser Leu Tyr
        260                 265                 270

Tyr Asp Val Arg Asn Phe Glu Ala Leu Tyr Ile Ser Gly Asp Asp Ser
    275                 280                 285

Leu Ile Phe Ser Arg Ser Glu Ile Ser Asn Tyr Ala Asp Asp Ile Cys
    290                 295                 300

Thr Asp Met Gly Phe Glu Thr Lys Phe Met Ser Pro Ser Val Pro Tyr
305                 310                 315                 320

Phe Cys Ser Lys Phe Val Met Cys Gly His Lys Thr Phe Phe Val
                325                 330                 335

Pro Asp Pro Tyr Lys Leu Phe Val Lys Leu Gly Ala Val Lys Glu Asp
                340                 345                 350

Val Ser Met Asp Phe Leu Phe Glu Thr Phe Thr Ser Phe Lys Asp Leu
            355                 360                 365

Thr Ser Asp Phe Asn Asp Glu Arg Leu Ile Gln Lys Leu Ala Glu Leu
        370                 375                 380

Val Ala Leu Lys Tyr Glu Val Gln Thr Gly Asn Thr Thr Leu Ala Leu
385                 390                 395                 400

Ser Val Ile His Cys Leu Arg Ser Asn Phe Leu Ser Phe Ser Lys Leu
                405                 410                 415

Tyr Pro Arg Val Lys Gly Trp Gln Val Phe Tyr Thr Ser Val Lys Lys
                420                 425                 430

Ala Leu Leu Lys Ser Gly Cys Ser Leu Phe Asp Ser Phe Met Thr Pro
                435                 440                 445

Phe Gly Gln Ala Val Met Val Trp Asp Asp Glu
    450                 455

<210> SEQ ID NO 6
<211> LENGTH: 171
<212> TYPE: DNA
<213> ORGANISM: Grapevine Leafroll Virus (type 2)

<400> SEQUENCE: 6
atgaatcagg ttttgcagtt tgaatgtttg tttctgctga atctcgcggt ttttgctgtg      60
actttcattt tcattcttct ggtcttccgc gtgattaagt cttttcgcca gaagggtcac     120
gaagcacctg ttcccgttgt tcgtggcggg ggttttttcaa ccgtagtgta g             171

<210> SEQ ID NO 7
<211> LENGTH: 56
<212> TYPE: PRT
<213> ORGANISM: Grapevine Leafroll Virus (type 2)

<400> SEQUENCE: 7

Met Asn Gln Val Leu Gln Phe Glu Cys Leu Phe Leu Leu Asn Leu Ala
  1               5                  10                  15

Val Phe Ala Val Thr Phe Ile Phe Ile Leu Leu Val Phe Arg Val Ile
             20                  25                  30

Lys Ser Phe Arg Gln Lys Gly His Glu Ala Pro Val Pro Val Val Arg
         35                  40                  45

Gly Gly Gly Phe Ser Thr Val Val
     50                  55

<210> SEQ ID NO 8
<211> LENGTH: 1800
<212> TYPE: DNA
<213> ORGANISM: Grapevine Leafroll Virus (type 2)
```

<400> SEQUENCE: 8

```
atggtagttt tcggtttgga ctttggcacc acattctcta cggtgtgtgt gtacaaggat      60
ggacgagttt tttcattcaa gcagaataat tcggcgtaca tccccactta cctctatctc     120
ttctccgatt ctaaccacat gacttttggt tacgaggccg aatcactgat gagtaatctg     180
aaagttaaag gttcgtttta tagagattta aaacgttggg tgggttgcga ttcgagtaac     240
ctcgacgcgt accttgaccg tttaaaacct cattactcgg tccgcttggt taagatcggc     300
tctggcttga acgaaactgt tcaattgga acttcggggg cactgttaa gtctgaggct       360
catctgccag ggttgatagc tctctttatt aaggctgtca ttagttgcgc ggagggcgcg     420
tttgcgtgca cttgcaccgg ggttatttgt tcagtacctg ccaattatga tagcgttcaa     480
aggaatttca ctgatcagtg tgtttcactc agcggttatc agtgcgtata tatgatcaat     540
gaaccttcag cggctgcgct atctgcgtgt aattcgattg gaaagaagtc cgcaaatttg     600
gctgtttacg atttcggtgg tgggaccttc gacgtgtcta tcatttcata ccgcaacaat     660
acttttgttg tgcgagcttc tggaggcgat ctaaatctcg gtggaaggga tgttgatcgt     720
gcgtttctca cgcacctctt ctctttaaca tcgctggaac ctgacctcac tttggatatc     780
tcgaatctga aagaatcttt atcaaaaacg gacgcagaga tagtttacac tttgagaggt     840
gtcgatggaa gaaaagaaga cgttagagta aacaaaaaca ttcttacgtc ggtgatgctc     900
ccctacgtga acagaacgct taagatatta gagtcaacct aaaatcgta tgctaagagt      960
atgaatgaga gtgcgcgagt taagtgcgat ttagtgctga taggaggatc ttcatatctt    1020
cctggcctgg cagacgtact aacgaagcat cagagcgttg atcgtatctt aagagtttcg    1080
gatcctcggg ctgccgtggc cgtcggttgc gcattatatt cttcatgcct ctcaggatct    1140
gggggggttgc tactgatcga ctgtgcagct cacactgtcg ctatagcgga cagaagttgt   1200
catcaaatca tttgcgctcc agcgggggca ccgatcccct tttcaggaag catgcctttg    1260
tacttagcca gggtcaacaa gaactcgcag cgtgaagtcg ccgtgtttga aggggagtac    1320
gttaagtgcc ctaagaacag aaagatctgt ggagcaaata taagattttt tgatatagga    1380
gtgacgggtg attcgtacgc acccgttacc ttctatatgg atttctccat ttcaagcgta    1440
ggagccgttt cattcgtggt gagaggtcct gagggtaagc aagtgtcact cactggaact    1500
ccagcgtata acttttcgtc tgtggctctc ggatcacgca gtgtccgaga attgcatatt    1560
agtttaaata ataaagtttt tctcggtttg cttctacata gaaaggcgga tcgacgaata    1620
cttttcacta aggatgaagc gattcgatac gccgattcaa ttgatatcgc ggatgtgcta    1680
aaggaatata aaagttacgc ggccagtgcc ttaccaccag acgaggatgt cgaattactc    1740
ctgggaaagt ctgttcaaaa agttttacgg ggaagcagac tggaagaaat acctctctag   1800
```

<210> SEQ ID NO 9
<211> LENGTH: 599
<212> TYPE: PRT
<213> ORGANISM: Grapevine Leafroll Virus (type 2)

<400> SEQUENCE: 9

```
Met Val Val Phe Gly Leu Asp Phe Gly Thr Thr Phe Ser Thr Val Cys
  1               5                  10                  15

Val Tyr Lys Asp Gly Arg Val Phe Ser Phe Lys Gln Asn Asn Ser Ala
             20                  25                  30

Tyr Ile Pro Thr Tyr Leu Tyr Leu Phe Ser Asp Ser Asn His Met Thr
         35                  40                  45
```

```
Phe Gly Tyr Glu Ala Glu Ser Leu Met Ser Asn Leu Lys Val Lys Gly
     50                  55                  60
Ser Phe Tyr Arg Asp Leu Lys Arg Trp Val Gly Cys Asp Ser Ser Asn
 65                  70                  75                  80
Leu Asp Ala Tyr Leu Asp Arg Leu Lys Pro His Tyr Ser Val Arg Leu
                 85                  90                  95
Val Lys Ile Gly Ser Gly Leu Asn Glu Thr Val Ser Ile Gly Asn Phe
                100                 105                 110
Gly Gly Thr Val Lys Ser Glu Ala His Leu Pro Gly Leu Ile Ala Leu
            115                 120                 125
Phe Ile Lys Ala Val Ile Ser Cys Ala Glu Gly Ala Phe Ala Cys Thr
    130                 135                 140
Cys Thr Gly Val Ile Cys Ser Val Pro Ala Asn Tyr Asp Ser Val Gln
145                 150                 155                 160
Arg Asn Phe Thr Asp Gln Cys Val Ser Leu Ser Gly Tyr Gln Cys Val
                165                 170                 175
Tyr Met Ile Asn Glu Pro Ser Ala Ala Leu Ser Ala Cys Asn Ser
                180                 185                 190
Ile Gly Lys Lys Ser Ala Asn Leu Ala Val Tyr Asp Phe Gly Gly Gly
        195                 200                 205
Thr Phe Asp Val Ser Ile Ile Ser Tyr Arg Asn Asn Thr Phe Val Val
    210                 215                 220
Arg Ala Ser Gly Gly Asp Leu Asn Leu Gly Gly Arg Asp Val Asp Arg
225                 230                 235                 240
Ala Phe Leu Thr His Leu Phe Ser Leu Thr Ser Leu Glu Pro Asp Leu
                245                 250                 255
Thr Leu Asp Ile Ser Asn Leu Lys Glu Ser Leu Ser Lys Thr Asp Ala
                260                 265                 270
Glu Ile Val Tyr Thr Leu Arg Gly Val Asp Gly Arg Lys Glu Asp Val
            275                 280                 285
Arg Val Asn Lys Asn Ile Leu Thr Ser Val Met Leu Pro Tyr Val Asn
290                 295                 300
Arg Thr Leu Lys Ile Leu Glu Ser Thr Leu Lys Ser Tyr Ala Lys Ser
305                 310                 315                 320
Met Asn Glu Ser Ala Arg Val Lys Cys Asp Leu Val Leu Ile Gly Gly
                325                 330                 335
Ser Ser Tyr Leu Pro Gly Leu Ala Asp Val Leu Thr Lys His Gln Ser
            340                 345                 350
Val Asp Arg Ile Leu Arg Val Ser Asp Pro Arg Ala Ala Val Ala Val
        355                 360                 365
Gly Cys Ala Leu Tyr Ser Ser Cys Leu Ser Gly Ser Gly Gly Leu Leu
    370                 375                 380
Leu Ile Asp Cys Ala Ala His Thr Val Ala Ile Ala Asp Arg Ser Cys
385                 390                 395                 400
His Gln Ile Ile Cys Ala Pro Ala Gly Ala Pro Ile Pro Phe Ser Gly
                405                 410                 415
Ser Met Pro Leu Tyr Leu Ala Arg Val Asn Lys Asn Ser Gln Arg Glu
            420                 425                 430
Val Ala Val Phe Glu Gly Glu Tyr Val Lys Cys Pro Lys Asn Arg Lys
        435                 440                 445
Ile Cys Gly Ala Asn Ile Arg Phe Phe Asp Ile Gly Val Thr Gly Asp
    450                 455                 460
```

```
Ser Tyr Ala Pro Val Thr Phe Tyr Met Asp Phe Ser Ile Ser Ser Val
465                 470                 475                 480

Gly Ala Val Ser Phe Val Arg Gly Pro Glu Gly Lys Gln Val Ser
                485                 490                 495

Leu Thr Gly Thr Pro Ala Tyr Asn Phe Ser Ser Val Ala Leu Gly Ser
            500                 505                 510

Arg Ser Val Arg Glu Leu His Ile Ser Leu Asn Asn Lys Val Phe Leu
        515                 520                 525

Gly Leu Leu His Arg Lys Ala Asp Arg Arg Ile Leu Phe Thr Lys
    530                 535                 540

Asp Glu Ala Ile Arg Tyr Ala Asp Ser Ile Asp Ile Ala Asp Val Leu
545                 550                 555                 560

Lys Glu Tyr Lys Ser Tyr Ala Ala Ser Ala Leu Pro Pro Asp Glu Asp
                565                 570                 575

Val Glu Leu Leu Leu Gly Lys Ser Val Gln Lys Val Leu Arg Gly Ser
            580                 585                 590

Arg Leu Glu Glu Ile Pro Leu
        595

<210> SEQ ID NO 10
<211> LENGTH: 1656
<212> TYPE: DNA
<213> ORGANISM: Grapevine Leafroll Virus (type 2)

<400> SEQUENCE: 10
atgtcgaatt actcctggga agtctgttc aaaagtttt acggggaagc agactggaag      60
aaatacctct ctaggagcat agcagcacac tcaagtgaaa ttaaaactct accagacatt     120
cgattgtacg gcgtagggt tgtaaagaag tccgaattcg aatcagcact tcctaattct     180
tttgaacagg aattaggact gttcatactg agcgaacggg aagtgggatg gagcaaatta     240
tgcggaataa cggtggaaga agcagcatac gatcttacga atcccaaggc ttataaattc     300
actgccgaga catgtagccc ggatgtaaaa ggtgaaggac aaaaatactc tatggaagac     360
gtgatgaatt tcatgcgttt atcaaatctg gatgttaacg acaagatgct gacggaacag     420
tgttggtcgc tgtccaattc atgcggtgaa ttgatcaacc cagacgacaa agggcgattc     480
gtggctctca cctttaagga cagagacaca gctgatgaca cgggtgccgc caacgtggaa     540
tgtcgcgtgg gcgactatct agtttacgct atgtccctgt ttgagcagag gacccaaaaa     600
tcgcagtctg gcaacatctc tctgtacgaa aagtactgtg aatacatcag gacctactta     660
gggagtacag acctgttctt cacagcgccg acaggattcc gttacttac gggcatccta     720 tacgattttt gtaaggaata caacgttttc tactcgtcat ataagagaaa cgtcgataat     780
ttcagattct tcttggcgaa ttatatgcct ttgatatctg acgtctttgt cttccagtgg     840
gtaaaacccg cgccggatgt tcggctgctt tttgagttaa gtgcagcgga actaacgctg     900
gaggttccca cactgagttt gatagattct caagttgtgg taggtcatat cttaagatac     960
gtagaatcct acacatcaga tccagccatc gacgcgttag aagacaaact ggaagcgata    1020
ctgaaaagta gcaatccccg tctatcgaca gcgcaactat gggttggttt cttttgttac    1080
tatggtgagt tcgtacggc tcaaagtaga gtagtgcaaa gaccaggcgt atacaaaaca    1140
cctgactcag tgggtggatt tgaaataaac atgaaagatg ttgagaaatt cttcgataaa    1200
cttcagagag aattgcctaa tgtatctttg cggcgtcagt ttaacggagc tagagcgcat    1260
gaggctttca aaatatttaa aaacggaaat ataagtttca gacctatatc gcgtttaaac    1320
```

-continued

```
gtgcctagag agttctggta tctgaacata gactacttca ggcacgcgaa taggtccggg   1380
ttaaccgaag aagaaatact catcctaaac aacataagcg ttgatgttag gaagttatgc   1440
gctgagagag cgtgcaatac cctacctagc gcgaagcgct ttagtaaaaa tcataagagt   1500
aatatacaat catcacgcca agagcggagg attaaagacc cattggtagt cctgaaagac   1560
actttatatg agttccaaca caagcgtgcc ggttgggggt ctcgaagcac tcgagacctc   1620
gggagtcgtg ctgaccacgc gaaaggaagc ggttga                             1656
```

<210> SEQ ID NO 11
<211> LENGTH: 551
<212> TYPE: PRT
<213> ORGANISM: Grapevine Leafroll Virus (type 2)

<400> SEQUENCE: 11

```
Met Ser Asn Tyr Ser Trp Glu Ser Leu Phe Lys Lys Phe Tyr Gly Glu
 1               5                  10                  15

Ala Asp Trp Lys Lys Tyr Leu Ser Arg Ser Ile Ala Ala His Ser Ser
            20                  25                  30

Glu Ile Lys Thr Leu Pro Asp Ile Arg Leu Tyr Gly Gly Arg Val Val
        35                  40                  45

Lys Lys Ser Glu Phe Glu Ser Ala Leu Pro Asn Ser Phe Glu Gln Glu
 50                  55                  60

Leu Gly Leu Phe Ile Leu Ser Glu Arg Glu Val Gly Trp Ser Lys Leu
 65                  70                  75                  80

Cys Gly Ile Thr Val Glu Glu Ala Ala Tyr Asp Leu Thr Asn Pro Lys
                85                  90                  95

Ala Tyr Lys Phe Thr Ala Glu Thr Cys Ser Pro Asp Val Lys Gly Glu
            100                 105                 110

Gly Gln Lys Tyr Ser Met Glu Asp Val Met Asn Phe Met Arg Leu Ser
        115                 120                 125

Asn Leu Asp Val Asn Asp Lys Met Leu Thr Glu Gln Cys Trp Ser Leu
130                 135                 140

Ser Asn Ser Cys Gly Glu Leu Ile Asn Pro Asp Asp Lys Gly Arg Phe
145                 150                 155                 160

Val Ala Leu Thr Phe Lys Asp Arg Asp Thr Ala Asp Thr Gly Ala
                165                 170                 175

Ala Asn Val Glu Cys Arg Val Gly Asp Tyr Leu Val Tyr Ala Met Ser
            180                 185                 190

Leu Phe Glu Gln Arg Thr Gln Lys Ser Gln Ser Gly Asn Ile Ser Leu
        195                 200                 205

Tyr Glu Lys Tyr Cys Glu Tyr Ile Arg Thr Tyr Leu Gly Ser Thr Asp
    210                 215                 220

Leu Phe Phe Thr Ala Pro Asp Arg Ile Pro Leu Leu Thr Gly Ile Leu
225                 230                 235                 240

Tyr Asp Phe Cys Lys Glu Tyr Asn Val Phe Tyr Ser Ser Tyr Lys Arg
                245                 250                 255

Asn Val Asp Asn Phe Arg Phe Phe Leu Ala Asn Tyr Met Pro Leu Ile
            260                 265                 270

Ser Asp Val Phe Val Phe Gln Trp Val Lys Pro Ala Pro Asp Val Arg
        275                 280                 285

Leu Leu Phe Glu Leu Ser Ala Ala Glu Leu Thr Leu Glu Val Pro Thr
    290                 295                 300

Leu Ser Leu Ile Asp Ser Gln Val Val Val Gly His Ile Leu Arg Tyr
305                 310                 315                 320
```

Val Glu Ser Tyr Thr Ser Asp Pro Ala Ile Asp Ala Leu Glu Asp Lys
            325                 330                 335

Leu Glu Ala Ile Leu Lys Ser Ser Asn Pro Arg Leu Ser Thr Ala Gln
        340                 345                 350

Leu Trp Val Gly Phe Phe Cys Tyr Tyr Gly Glu Phe Arg Thr Ala Gln
    355                 360                 365

Ser Arg Val Val Gln Arg Pro Gly Val Tyr Lys Thr Pro Asp Ser Val
370                 375                 380

Gly Gly Phe Glu Ile Asn Met Lys Asp Val Glu Lys Phe Phe Asp Lys
385                 390                 395                 400

Leu Gln Arg Glu Leu Pro Asn Val Ser Leu Arg Arg Gln Phe Asn Gly
            405                 410                 415

Ala Arg Ala His Glu Ala Phe Lys Ile Phe Lys Asn Gly Asn Ile Ser
        420                 425                 430

Phe Arg Pro Ile Ser Arg Leu Asn Val Pro Arg Glu Phe Trp Tyr Leu
    435                 440                 445

Asn Ile Asp Tyr Phe Arg His Ala Asn Arg Ser Gly Leu Thr Glu Glu
450                 455                 460

Glu Ile Leu Ile Leu Asn Asn Ile Ser Val Asp Val Arg Lys Leu Cys
465                 470                 475                 480

Ala Glu Arg Ala Cys Asn Thr Leu Pro Ser Ala Lys Arg Phe Ser Lys
            485                 490                 495

Asn His Lys Ser Asn Ile Gln Ser Ser Arg Gln Glu Arg Arg Ile Lys
        500                 505                 510

Asp Pro Leu Val Val Leu Lys Asp Thr Leu Tyr Glu Phe Gln His Lys
    515                 520                 525

Arg Ala Gly Trp Gly Ser Arg Ser Thr Arg Asp Leu Gly Ser Arg Ala
530                 535                 540

Asp His Ala Lys Gly Ser Gly
545                 550

<210> SEQ ID NO 12
<211> LENGTH: 672
<212> TYPE: DNA
<213> ORGANISM: Grapevine Leafroll Virus (type 2)

<400> SEQUENCE: 12
atgagttcca acacaagcgt gccggttggg ggtctcgaag cactcgagac ctcgggagtc      60
gtgctgacca cgcgaaagga agcggttgat aagttttta atgaactaaa aaacgaaaat     120
tactcatcag ttgacagcag ccgattaagc gattcggaag taaagaagt gttagagaaa     180 agtaaagaaa gtttcaaaag cgaactggcc tccactgacg agcacttcgt ctaccacatt    240 atattttct taatccgatg tgctaagata tcgacaagtg aaaggtgaa gtacgttggt      300 agtcatacgt acgtggtcga cggaaaaacg tacaccgttc ttgacgcttg ggtattcaac    360
atgatgaaaa gtctcacgaa gaagtacaaa cgagtgaatg gtctgcgtgc gttctgttgc    420
gcgtgcgaag atctatatct aaccgtcgca ccaataatgt cagaacgctt taagactaaa    480
gccgtaggga tgaaaggttt gcctgttgga aaggaatact taggcgccga ctttctttcg    540
ggaactagca aactgatgag cgatcacgac agggcggtct ccatcgttgc agcgaaaaac    600
gctgtcgatc gtagcgcttt cacgggtggg gagagaaaga tagttagttt gtatgatcta    660
gggaggtact aa                                                        672

<210> SEQ ID NO 13
<211> LENGTH: 223
<212> TYPE: PRT
<213> ORGANISM: Grapevine Leafroll Virus (type 2)

<400> SEQUENCE: 13

```
Met Ser Ser Asn Thr Ser Val Pro Val Gly Gly Leu Glu Ala Leu Glu
1               5                   10                  15

Thr Ser Gly Val Val Leu Thr Thr Arg Lys Glu Ala Val Asp Lys Phe
            20                  25                  30

Phe Asn Glu Leu Lys Asn Glu Asn Tyr Ser Ser Val Asp Ser Ser Arg
        35                  40                  45

Leu Ser Asp Ser Glu Val Lys Glu Val Leu Glu Lys Ser Lys Glu Ser
    50                  55                  60

Phe Lys Ser Glu Leu Ala Ser Thr Asp Glu His Phe Val Tyr His Ile
65                  70                  75                  80

Ile Phe Phe Leu Ile Arg Cys Ala Lys Ile Ser Thr Ser Glu Lys Val
                85                  90                  95

Lys Tyr Val Gly Ser His Thr Tyr Val Val Asp Gly Lys Thr Tyr Thr
            100                 105                 110

Val Leu Asp Ala Trp Val Phe Asn Met Met Lys Ser Leu Thr Lys Lys
        115                 120                 125

Tyr Lys Arg Val Asn Gly Leu Arg Ala Phe Cys Cys Ala Cys Glu Asp
    130                 135                 140

Leu Tyr Leu Thr Val Ala Pro Ile Met Ser Glu Arg Phe Lys Thr Lys
145                 150                 155                 160

Ala Val Gly Met Lys Gly Leu Pro Val Gly Lys Glu Tyr Leu Gly Ala
                165                 170                 175

Asp Phe Leu Ser Gly Thr Ser Lys Leu Met Ser Asp His Asp Arg Ala
            180                 185                 190

Val Ser Ile Val Ala Ala Lys Asn Ala Val Asp Arg Ser Ala Phe Thr
        195                 200                 205

Gly Gly Glu Arg Lys Ile Val Ser Leu Tyr Asp Leu Gly Arg Tyr
    210                 215                 220
```

<210> SEQ ID NO 14
<211> LENGTH: 597
<212> TYPE: DNA
<213> ORGANISM: Grapevine Leafroll Virus (type 2)

<400> SEQUENCE: 14

```
atggagttga tgtccgacag caaccttagc aacctggtga taaccgacgc ctctagtcta    60
aatggtgtcg acaagaagct tttatctgct gaagttgaaa aaatgttggt gcagaaaggg   120
gctcctaacg agggtataga agtggtgttc ggtctactcc tttacgcact cgcggcaaga   180
accacgtctc ctaaggttca gcgcgcagat tcagacgtta tattttcaaa tagtttcgga   240
gagaggaatg tggtagtaac agagggtgac cttaagaagg tactcgacgg tgtgtgcgcct  300
ctcactaggt tcactaataa acttagaacg ttcggtcgta cttttcactga ggcttacgtt   360
gacttttgta tcgcgtataa gcacaaatta ccccaactca acgccgcggc ggaattgggg   420
attccagctg aagattcgta cttagctgca gattttctgg gtacttgccc gaagctctct   480
gaattacagc aaagtaggaa gatgttcgcg agtatgtacg ctctaaaaac tgaaggtgga   540
gtggtaaata caccagtgag caatctgcgt cagctaggta agggaagt tatgtaa        597
```

<210> SEQ ID NO 15

<211> LENGTH: 198
<212> TYPE: PRT
<213> ORGANISM: Grapevine Leafroll Virus (type 2)

<400> SEQUENCE: 15

Met Glu Leu Met Ser Asp Ser Asn Leu Ser Asn Leu Val Ile Thr Asp
 1               5                  10                  15

Ala Ser Ser Leu Asn Gly Val Asp Lys Lys Leu Leu Ser Ala Glu Val
            20                  25                  30

Glu Lys Met Leu Val Gln Lys Gly Ala Pro Asn Glu Gly Ile Glu Val
        35                  40                  45

Val Phe Gly Leu Leu Leu Tyr Ala Leu Ala Ala Arg Thr Thr Ser Pro
 50                  55                  60

Lys Val Gln Arg Ala Asp Ser Asp Val Ile Phe Ser Asn Ser Phe Gly
65                  70                  75                  80

Glu Arg Asn Val Val Thr Glu Gly Asp Leu Lys Lys Val Leu Asp
                85                  90                  95

Gly Cys Ala Pro Leu Thr Arg Phe Thr Asn Lys Leu Arg Thr Phe Gly
            100                 105                 110

Arg Thr Phe Thr Glu Ala Tyr Val Asp Phe Cys Ile Ala Tyr Lys His
        115                 120                 125

Lys Leu Pro Gln Leu Asn Ala Ala Ala Glu Leu Gly Ile Pro Ala Glu
130                 135                 140

Asp Ser Tyr Leu Ala Ala Asp Phe Leu Gly Thr Cys Pro Lys Leu Ser
145                 150                 155                 160

Glu Leu Gln Gln Ser Arg Lys Met Phe Ala Ser Met Tyr Ala Leu Lys
                165                 170                 175

Thr Glu Gly Gly Val Val Asn Thr Pro Val Ser Asn Leu Arg Gln Leu
            180                 185                 190

Gly Arg Arg Glu Val Met
        195

<210> SEQ ID NO 16
<211> LENGTH: 486
<212> TYPE: DNA
<213> ORGANISM: Grapevine Leafroll Virus (type 2)

<400> SEQUENCE: 16
atggaagatt acgaagaaaa atccgaatcg ctcatactgc tacgcacgaa tctgaacact      60 atgctttag tggtcaagtc cgatgctagt gtagagctgc ctaaactact aatttgcggt     120
tacttacgag tgtcaggacg tggggaggtg acgtgttgca accgtgagga attaacaaga     180
gattttgagg gcaatcatca tacggtgatc cgttctagaa tcatacaata tgacagcgag     240
tctgcttttg aggaattcaa caactctgat tgcgtagtga agttttttcct agagactggt     300 agtgtctttt ggttttttcct tcgaagtgaa accaaaggta gagcggtgcg acatttgcgc     360
accttcttcg aagctaacaa tttcttcttt ggatcgcatt gcggtaccat ggagtattgt     420
ttgaagcagg tactaactga aactgaatct ataatcgatt ctttttgcga agaaagaaat     480
cgttaa                                                               486

<210> SEQ ID NO 17
<211> LENGTH: 161
<212> TYPE: PRT
<213> ORGANISM: Grapevine Leafroll Virus (type 2)

<400> SEQUENCE: 17

```
Met Glu Asp Tyr Glu Glu Lys Ser Glu Ser Leu Ile Leu Leu Arg Thr
 1               5                  10                  15

Asn Leu Asn Thr Met Leu Leu Val Val Lys Ser Asp Ala Ser Val Glu
                 20                  25                  30

Leu Pro Lys Leu Leu Ile Cys Gly Tyr Leu Arg Val Ser Gly Arg Gly
             35                  40                  45

Glu Val Thr Cys Cys Asn Arg Glu Glu Leu Thr Arg Asp Phe Glu Gly
         50                  55                  60

Asn His His Thr Val Ile Arg Ser Arg Ile Ile Gln Tyr Asp Ser Glu
 65                  70                  75                  80

Ser Ala Phe Glu Glu Phe Asn Asn Ser Asp Cys Val Val Lys Phe Phe
                 85                  90                  95

Leu Glu Thr Gly Ser Val Phe Trp Phe Phe Leu Arg Ser Glu Thr Lys
             100                 105                 110

Gly Arg Ala Val Arg His Leu Arg Thr Phe Phe Glu Ala Asn Asn Phe
         115                 120                 125

Phe Phe Gly Ser His Cys Gly Thr Met Glu Tyr Cys Leu Lys Gln Val
     130                 135                 140

Leu Thr Glu Thr Glu Ser Ile Ile Asp Ser Phe Cys Glu Glu Arg Asn
145                 150                 155                 160

Arg
```

<210> SEQ ID NO 18
<211> LENGTH: 618
<212> TYPE: DNA
<213> ORGANISM: Grapevine Leafroll Virus (type 2)

<400> SEQUENCE: 18

```
atgagggtta tagtgtctcc ttatgaagct gaagacattc tgaaaagatc gactgacatg    60
ttacgaaaca tagacagtgg ggtcttgagc actaaagaat gtatcaaggc attctcgacg   120
ataacgcgag acctacattg tgcgaaggct tcctaccagt ggggtgttga cactgggtta   180
tatcagcgta attgcgctga aaacgtttta attgacacgg tggagtcaaa catacggttg   240
gctcaacctc tcgtgcgtga aaagtggcg gttcattttt gtaaggatga accaaaagag   300
ctagtagcat tcatcacgcg aaagtacgtg gaactcacgg gcgtgggagt gagagaagcg   360
gtgaagaggg aaatgcgctc tcttaccaaa acagttttaa ataaaatgtc tttggaaatg   420
gcgttttaca tgtcaccacg agcgtggaaa aacgctgaat ggttagaact aaaattttca   480
cctgtgaaaa tctttagaga tctgctatta gacgtggaaa cgctcaacga attgtgcgcc   540
gaagatgatg ttcacgtcga caaagtaaat gagaatgggg acgaaaatca cgacctcgaa   600
ctccaagacg aatgttaa                                                618
```

<210> SEQ ID NO 19
<211> LENGTH: 205
<212> TYPE: PRT
<213> ORGANISM: Grapevine Leafroll Virus (type 2)

<400> SEQUENCE: 19

```
Met Arg Val Ile Val Ser Pro Tyr Glu Ala Glu Asp Ile Leu Lys Arg
 1               5                  10                  15

Ser Thr Asp Met Leu Arg Asn Ile Asp Ser Gly Val Leu Ser Thr Lys
                 20                  25                  30

Glu Cys Ile Lys Ala Phe Ser Thr Ile Thr Arg Asp Leu His Cys Ala
             35                  40                  45
```

-continued

```
Lys Ala Ser Tyr Gln Trp Gly Val Asp Thr Gly Leu Tyr Gln Arg Asn
 50                  55                  60
Cys Ala Glu Lys Arg Leu Ile Asp Thr Val Glu Ser Asn Ile Arg Leu
 65                  70                  75                  80
Ala Gln Pro Leu Val Arg Glu Lys Val Ala Val His Phe Cys Lys Asp
                 85                  90                  95
Glu Pro Lys Glu Leu Val Ala Phe Ile Thr Arg Lys Tyr Val Glu Leu
            100                 105                 110
Thr Gly Val Gly Val Arg Glu Ala Val Lys Arg Glu Met Arg Ser Leu
        115                 120                 125
Thr Lys Thr Val Leu Asn Lys Met Ser Leu Glu Met Ala Phe Tyr Met
130                 135                 140
Ser Pro Arg Ala Trp Lys Asn Ala Glu Trp Leu Glu Leu Lys Phe Ser
145                 150                 155                 160
Pro Val Lys Ile Phe Arg Asp Leu Leu Asp Val Glu Thr Leu Asn
                165                 170                 175
Glu Leu Cys Ala Glu Asp Asp Val His Val Asp Lys Val Asn Glu Asn
            180                 185                 190
Gly Asp Glu Asn His Asp Leu Glu Leu Gln Asp Glu Cys
        195                 200                 205
```

<210> SEQ ID NO 20
<211> LENGTH: 21
<212> TYPE: DNA
<213> ORGANISM: Artificial Sequence
<220> FEATURE:
<223> OTHER INFORMATION: Artificially Synthesized Oligonucleotide
      Sequence

<400> SEQUENCE: 20
tgctggagct tgaggttctg c                                              21

<210> SEQ ID NO 21
<211> LENGTH: 31
<212> TYPE: DNA
<213> ORGANISM: Artificial Sequence
<220> FEATURE:
<223> OTHER INFORMATION: Artificially Synthesized Oligonucleotide
      Sequence

<400> SEQUENCE: 21
cggaattcac catggagttg atgtccgaca g                                   31

<210> SEQ ID NO 22
<211> LENGTH: 33
<212> TYPE: DNA
<213> ORGANISM: Artificial Sequence
<220> FEATURE:
<223> OTHER INFORMATION: Artificially Synthesized Oligonucleotide
      Sequence

<400> SEQUENCE: 22
agcggatcca tggcagattc gtgcgtagca gta                                 33

<210> SEQ ID NO 23
<211> LENGTH: 216
<212> TYPE: DNA
<213> ORGANISM: Grapevine Leafroll Virus (type 2)

<400> SEQUENCE: 23
acattggtta agtttaacga aaatgattag taaataataa atcgaacgtg ggtgtatcta    60

```
cctgacgtat caacttaagc tgttactgag taattaaacc aacaagtgtt ggtgtaatgt      120
gtatgttgat gtagagaaaa atccgtttgt agaacggtgt ttttctcttc tttatttta      180 aaaaaaaaat aaaaaaaaaa aaaaaaagc ggccgc                                216
```

<210> SEQ ID NO 24
<211> LENGTH: 90
<212> TYPE: PRT
<213> ORGANISM: Beet Yellows Virus

<400> SEQUENCE: 24

```
Leu Gln Tyr Arg Pro Gly Glu Gly Leu Cys Tyr Leu Ala His Ala Ala
 1               5                  10                  15

Leu Cys Cys Ala Leu Gln Lys Arg Thr Phe Arg Glu Glu Asp Phe Phe
            20                  25                  30

Val Gly Met Tyr Pro Thr Lys Phe Val Phe Ala Lys Arg Leu Thr Glu
        35                  40                  45

Lys Leu Gly Pro Ser Ala Leu Lys His Pro Val Arg Gly Arg Gln Val
    50                  55                  60

Ser Arg Ser Leu Phe His Cys Asp Val Ala Ser Ala Phe Ser Ser Pro
65                  70                  75                  80

Phe Tyr Ser Leu Pro Arg Phe Ile Gly Gly
                85                  90
```

<210> SEQ ID NO 25
<211> LENGTH: 267
<212> TYPE: PRT
<213> ORGANISM: Beet Yellows Virus

<400> SEQUENCE: 25

```
Met Gly Glu Ala Val Gln Ser Gly Leu Thr Arg Ala Tyr Pro Gln Phe
 1               5                  10                  15

Asn Leu Ser Phe Thr His Ser Val Tyr Ser Asp His Pro Ala Ala Ala
            20                  25                  30

Gly Ser Arg Leu Leu Glu Asn Glu Thr Leu Ala Ser Met Ala Lys Ser
        35                  40                  45

Ser Phe Ser Asp Ile Gly Gly Cys Pro Leu Phe His Ile Lys Arg Gly
    50                  55                  60

Ser Thr Asp Tyr His Val Cys Arg Pro Ile Tyr Asp Met Lys Asp Ala
65                  70                  75                  80

Gln Arg Arg Val Ser Arg Glu Leu Gln Ala Arg Gly Leu Val Glu Asn
                85                  90                  95

Leu Ser Arg Glu Gln Leu Val Glu Ala Gln Ala Arg Val Ser Val Cys
            100                 105                 110

Pro His Thr Leu Gly Asn Cys Asn Val Lys Ser Asp Val Leu Ile Met
        115                 120                 125

Val Gln Val Tyr Asp Ala Ser Leu Asn Glu Ile Ala Ser Ala Met Val
    130                 135                 140

Leu Lys Glu Ser Lys Val Ala Tyr Leu Thr Met Val Thr Pro Gly Glu
145                 150                 155                 160

Leu Leu Asp Glu Arg Glu Ala Phe Ala Ile Asp Ala Leu Gly Cys Asp
                165                 170                 175

Val Val Val Asp Thr Arg Arg Asp Met Val Gln Tyr Lys Phe Gly Ser
            180                 185                 190

Ser Cys Tyr Cys His Lys Leu Ser Asn Ile Lys Ser Ile Met Leu Thr
        195                 200                 205
```

```
Pro Ala Phe Thr Phe Ser Gly Asn Leu Phe Ser Val Glu Met Tyr Glu
    210                 215                 220

Asn Arg Met Gly Val Asn Tyr Tyr Lys Ile Thr Arg Ser Ala Tyr Ser
225                 230                 235                 240

Pro Glu Ile Arg Gly Val Lys Thr Leu Arg Tyr Arg Arg Ala Cys Thr
                245                 250                 255

Glu Val Val Gln Val Lys Leu Pro Arg Phe Asp
            260                 265
```

<210> SEQ ID NO 26
<211> LENGTH: 316
<212> TYPE: PRT
<213> ORGANISM: Beet Yellows VIrus

<400> SEQUENCE: 26

```
Phe Thr Phe Thr Asn Leu Ser Ala Asn Val Leu Leu Tyr Glu Ala Pro
1               5                   10                  15

Pro Gly Gly Gly Lys Thr Thr Thr Leu Ile Lys Val Phe Cys Glu Thr
            20                  25                  30

Phe Ser Lys Val Asn Ser Leu Ile Leu Thr Ala Asn Lys Ser Ser Arg
        35                  40                  45

Glu Glu Ile Leu Ala Lys Val Asn Arg Ile Val Leu Asp Glu Gly Asp
50                  55                  60

Thr Pro Leu Gln Thr Arg Asp Arg Ile Leu Thr Ile Asp Ser Tyr Leu
65                  70                  75                  80

Met Asn Asn Arg Gly Leu Thr Cys Lys Val Leu Tyr Leu Asp Glu Cys
                85                  90                  95

Phe Met Val His Ala Gly Ala Val Ala Cys Ile Glu Phe Thr Lys
                100                 105                 110

Cys Asp Ser Ala Ile Leu Phe Gly Asp Ser Arg Gln Ile Arg Tyr Gly
            115                 120                 125

Arg Cys Ser Glu Leu Asp Thr Ala Val Leu Ser Asp Leu Asn Arg Phe
130                 135                 140

Val Asp Asp Glu Ser Arg Val Tyr Gly Glu Val Ser Tyr Arg Cys Pro
145                 150                 155                 160

Trp Asp Val Cys Ala Trp Leu Ser Thr Phe Tyr Pro Lys Thr Val Ala
                165                 170                 175

Thr Thr Asn Leu Val Ser Ala Gly Gln Ser Ser Met Gln Val Arg Glu
            180                 185                 190

Ile Glu Ser Val Asp Asp Val Glu Tyr Ser Ser Glu Phe Val Tyr Leu
        195                 200                 205

Thr Met Leu Gln Ser Glu Lys Lys Asp Leu Leu Lys Ser Phe Gly Lys
210                 215                 220

Arg Ser Arg Ser Ser Val Glu Lys Pro Thr Val Leu Thr Val His Glu
225                 230                 235                 240

Ala Gln Gly Glu Thr Tyr Arg Lys Val Asn Leu Val Arg Thr Lys Phe
                245                 250                 255

Gln Glu Asp Asp Pro Phe Arg Ser Glu Asn His Ile Thr Val Ala Leu
            260                 265                 270

Ser Arg His Val Glu Ser Leu Thr Tyr Ser Val Leu Ser Ser Lys Arg
        275                 280                 285

Asp Asp Ala Ile Ala Gln Ala Ile Val Lys Ala Lys Gln Leu Val Asp
290                 295                 300

Ala Tyr Arg Val Tyr Pro Thr Ser Phe Gly Gly Ser
305                 310                 315
```

<210> SEQ ID NO 27
<211> LENGTH: 298
<212> TYPE: PRT
<213> ORGANISM: Beet Yellows Virus

<400> SEQUENCE: 27

```
Ile Thr Thr Phe Lys Leu Met Val Lys Arg Asp Ala Lys Val Lys Leu
  1               5                  10                  15

Asp Ser Ser Cys Leu Val Lys His Pro Pro Ala Gln Asn Ile Met Phe
             20                  25                  30

His Arg Lys Ala Val Asn Ala Ile Phe Ser Pro Cys Phe Asp Glu Phe
         35                  40                  45

Lys Asn Arg Val Ile Thr Cys Thr Asn Ser Asn Ile Val Phe Phe Thr
     50                  55                  60

Glu Met Thr Asn Ser Thr Leu Ala Ser Ile Ala Lys Glu Met Leu Gly
 65                  70                  75                  80

Ser Glu His Val Tyr Asn Val Gly Glu Ile Asp Phe Ser Lys Phe Asp
                 85                  90                  95

Lys Ser Gln Asp Ala Phe Ile Lys Ser Phe Glu Arg Thr Leu Tyr Ser
            100                 105                 110

Ala Phe Gly Phe Asp Glu Asp Leu Leu Asp Val Trp Met Gln Gly Glu
        115                 120                 125

Tyr Thr Ser Asn Ala Thr Thr Leu Asp Gly Gln Leu Ser Phe Ser Val
    130                 135                 140

Asp Asn Gln Arg Lys Ser Gly Ala Ser Asn Thr Trp Ile Gly Asn Ser
145                 150                 155                 160

Ile Glu Thr Leu Gly Ile Leu Ser Met Phe Tyr Tyr Thr Asn Arg Phe
                165                 170                 175

Lys Ala Leu Phe Val Ser Gly Asp Asp Ser Leu Ile Phe Ser Glu Ser
            180                 185                 190

Pro Ile Arg Asn Ser Ala Asp Ala Met Cys Thr Glu Leu Gly Phe Glu
        195                 200                 205

Thr Lys Phe Leu Thr Pro Ser Val Pro Tyr Phe Cys Ser Lys Phe Phe
    210                 215                 220

Val Met Thr Gly His Asp Val Phe Phe Val Pro Asp Pro Tyr Lys Leu
225                 230                 235                 240

Leu Val Lys Leu Gly Ala Ser Lys Asp Glu Val Asp Glu Phe Leu
                245                 250                 255

Phe Glu Val Phe Thr Ser Phe Arg Asp Leu Thr Lys Asp Leu Val Asp
            260                 265                 270

Glu Arg Val Ile Glu Leu Leu Thr His Leu Val His Ser Lys Tyr Gly
        275                 280                 285

Tyr Glu Ser Gly Asp Thr Tyr Ala Ala Leu
    290                 295
```

<210> SEQ ID NO 28
<211> LENGTH: 52
<212> TYPE: DNA
<213> ORGANISM: Grapevine Leafroll Virus

<400> SEQUENCE: 28
caugauaagc agcguguuua gcguaguucg gucgcaggcg auuccgcgua ga        52

<210> SEQ ID NO 29
<211> LENGTH: 52

```
<212> TYPE: DNA
<213> ORGANISM: Beet Yellows Virus

<400> SEQUENCE: 29
cacgacccgc agcggguuua gctcgauucg cucgcaggcg auuccuaaga gg        52

<210> SEQ ID NO 30
<211> LENGTH: 52
<212> TYPE: DNA
<213> ORGANISM: Beet Yellow Stunt Virus

<400> SEQUENCE: 30
cacgaugaac agcgcguuua gcguaguuag gucgcaggcc aucccuaaaa gg        52

<210> SEQ ID NO 31
<211> LENGTH: 52
<212> TYPE: DNA
<213> ORGANISM: Citrus Tristeza Virus

<400> SEQUENCE: 31
cacgaaccgg cucgcguucg gcguaguaag gucacaagca auuccuccaa ga        52

<210> SEQ ID NO 32
<211> LENGTH: 17
<212> TYPE: PRT
<213> ORGANISM: Grapevine Leafroll Virus

<400> SEQUENCE: 32

His Asp Lys Gln Arg Val Ser Val Val Arg Ser Gln Ala Ile Pro Arg
 1               5                  10                  15

Arg

<210> SEQ ID NO 33
<211> LENGTH: 17
<212> TYPE: PRT
<213> ORGANISM: Beet Yellows Virus

<400> SEQUENCE: 33

His Asp Pro Gln Arg Val Ser Ser Ile Arg Ser Gln Ala Ile Pro Lys
 1               5                  10                  15

Arg

<210> SEQ ID NO 34
<211> LENGTH: 17
<212> TYPE: PRT
<213> ORGANISM: Beet Yellow Stunt Virus

<400> SEQUENCE: 34

His Asp Glu Gln Arg Val Ser Val Val Arg Ser Gln Ala Ile Pro Lys
 1               5                  10                  15

Arg

<210> SEQ ID NO 35
<211> LENGTH: 17
<212> TYPE: PRT
<213> ORGANISM: Citrus Tristeza Virus

<400> SEQUENCE: 35

His Glu Pro Ala Arg Val Gly Val Val Arg Ser Gln Ala Ile Pro Pro
 1               5                  10                  15

Arg
```

<210> SEQ ID NO 36
<211> LENGTH: 598
<212> TYPE: PRT
<213> ORGANISM: Beet Yellows Virus

<400> SEQUENCE: 36

```
Met Val Val Phe Gly Leu Asp Phe Gly Thr Thr Phe Ser Ser Val Cys
  1               5                  10                  15

Ala Tyr Val Gly Glu Glu Leu Tyr Leu Phe Lys Gln Arg Asp Ser Ala
             20                  25                  30

Tyr Ile Pro Thr Tyr Val Phe Leu His Ser Asp Thr Gln Glu Val Ala
         35                  40                  45

Phe Gly Tyr Asp Ala Glu Val Leu Ser Asn Asp Leu Ser Val Arg Gly
     50                  55                  60

Gly Phe Tyr Arg Asp Leu Lys Arg Trp Ile Gly Cys Asp Glu Glu Asn
 65                  70                  75                  80

Tyr Arg Asp Tyr Leu Glu Lys Leu Lys Pro His Tyr Lys Thr Glu Leu
                 85                  90                  95

Leu Lys Val Ala Gln Ser Ser Lys Ser Thr Val Lys Leu Asp Cys Tyr
            100                 105                 110

Ser Gly Thr Val Pro Gln Asn Ala Thr Leu Pro Gly Leu Ile Ala Thr
        115                 120                 125

Phe Val Lys Ala Leu Ile Ser Thr Ser Glu Ala Phe Lys Cys Gln
    130                 135                 140

Cys Thr Gly Val Ile Cys Ser Val Pro Ala Asn Tyr Asn Cys Leu Gln
145                 150                 155                 160

Arg Ser Phe Thr Glu Ser Cys Val Asn Leu Ser Gly Tyr Pro Cys Val
                165                 170                 175

Tyr Met Val Asn Glu Pro Ser Ala Ala Leu Ser Ala Cys Ser Arg
            180                 185                 190

Ile Lys Gly Ala Thr Ser Pro Val Leu Val Tyr Asp Phe Gly Gly Gly
        195                 200                 205

Thr Phe Asp Val Ser Val Ile Ser Ala Leu Asn Asn Thr Phe Val Val
    210                 215                 220

Arg Ala Ser Gly Gly Asp Met Asn Leu Gly Gly Arg Asp Ile Asp Lys
225                 230                 235                 240

Ala Phe Val Glu His Leu Tyr Asn Lys Ala Gln Leu Pro Val Asn Tyr
                245                 250                 255

Lys Ile Asp Ile Ser Phe Leu Lys Glu Ser Leu Ser Lys Lys Val Ser
            260                 265                 270

Phe Leu Asn Phe Pro Val Val Ser Glu Gln Gly Val Arg Val Asp Val
        275                 280                 285

Leu Val Asn Val Ser Glu Leu Ala Glu Val Ala Ala Pro Phe Val Glu
    290                 295                 300

Arg Thr Ile Lys Ile Val Lys Glu Val Tyr Glu Lys Tyr Cys Ser Ser
305                 310                 315                 320

Met Arg Leu Glu Pro Asn Val Lys Ala Lys Leu Leu Met Val Gly Gly
                325                 330                 335

Ser Ser Tyr Leu Pro Gly Leu Leu Ser Arg Leu Ser Ser Ile Pro Phe
            340                 345                 350

Val Asp Glu Cys Leu Val Leu Pro Asp Ala Arg Ala Val Ala Gly
        355                 360                 365

Gly Cys Ala Leu Tyr Ser Ala Cys Leu Arg Asn Asp Ser Pro Met Leu
    370                 375                 380
```

-continued

```
Leu Val Asp Cys Ala Ala His Asn Leu Ser Ile Ser Ser Lys Tyr Cys
385                 390                 395                 400

Glu Ser Ile Val Cys Val Pro Ala Gly Ser Pro Ile Pro Phe Thr Gly
                405                 410                 415

Val Arg Thr Val Asn Met Thr Gly Ser Asn Ala Ser Ala Val Tyr Ser
            420                 425                 430

Ala Ala Leu Phe Glu Gly Asp Phe Val Lys Cys Arg Leu Asn Lys Arg
        435                 440                 445

Ile Phe Phe Gly Asp Val Val Leu Gly Asn Val Gly Val Thr Gly Ser
    450                 455                 460

Ala Thr Arg Thr Val Pro Leu Thr Leu Glu Ile Asn Val Ser Ser Val
465                 470                 475                 480

Gly Thr Ile Ser Phe Ser Leu Val Gly Pro Thr Gly Val Lys Lys Leu
                485                 490                 495

Ile Gly Gly Asn Ala Ala Tyr Asp Phe Ser Ser Tyr Gln Leu Gly Glu
            500                 505                 510

Arg Val Val Ala Asp Leu His Lys His Asn Ser Asp Lys Val Lys Leu
        515                 520                 525

Ile His Ala Leu Thr Tyr Gln Pro Phe Gln Arg Lys Lys Leu Thr Asp
    530                 535                 540

Gly Asp Lys Ala Leu Phe Leu Lys Arg Leu Thr Ala Asp Tyr Arg Arg
545                 550                 555                 560

Glu Ala Arg Lys Phe Ser Ser Tyr Asp Asp Ala Val Leu Asn Ser Ser
                565                 570                 575

Glu Leu Leu Leu Gly Arg Ile Ile Pro Lys Ile Leu Arg Gly Ser Arg
            580                 585                 590

Val Glu Lys Leu Asp Val
        595
```

<210> SEQ ID NO 37
<211> LENGTH: 204
<212> TYPE: PRT
<213> ORGANISM: Beet Yellows Virus

<400> SEQUENCE: 37

```
Met Gly Ser Ala Glu Pro Ile Ser Ala Ile Ala Thr Phe Glu Asn Val
 1               5                  10                  15

Ser Leu Ala Asp Gln Thr Cys Leu His Gly Glu Asp Cys Asp Lys Leu
            20                  25                  30

Arg Lys Asn Phe Glu Glu Cys Leu Lys Leu Lys Gly Val Pro Glu Asp
        35                  40                  45

Asn Leu Gly Ile Ala Leu Gly Leu Cys Leu Tyr Ser Cys Ala Thr Ile
    50                  55                  60

Gly Thr Ser Asn Lys Val Asn Val Gln Pro Thr Ser Thr Phe Ile Lys
65                  70                  75                  80

Ala Ser Phe Gly Gly Gly Lys Glu Leu Tyr Leu Thr His Gly Glu Ile
                85                  90                  95

Asn Ser Phe Leu Gly Ser Gln Lys Leu Leu Glu Gly Lys Pro Asn Lys
            100                 105                 110

Leu Arg Cys Phe Cys Arg Thr Phe Gln Lys Asp Tyr Ile Ser Leu Arg
        115                 120                 125

Lys Glu Tyr Arg Gly Lys Leu Pro Pro Ile Ala Arg Ala Asn Arg His
    130                 135                 140

Gly Leu Pro Ala Glu Asp His Tyr Leu Ala Ala Asp Phe Ile Ser Thr
```

```
                145                 150                 155                 160
Ser Thr Glu Leu Thr Asp Leu Gln Gln Ser Arg Leu Leu Ala Arg
                165                 170                 175

Glu Asn Ala Thr His Thr Glu Phe Ser Ser Glu Ser Pro Val Thr Ser
                180                 185                 190

Leu Lys Gln Leu Gly Arg Gly Leu Gly Thr Gly Arg
            195                 200

<210> SEQ ID NO 38
<211> LENGTH: 216
<212> TYPE: PRT
<213> ORGANISM: Beet Yellows Virus

<400> SEQUENCE: 38

Met Leu Ala Pro Glu Ala Arg Gly Asp Leu Ile His Phe Thr Glu Asn
  1               5                  10                  15

Thr Arg Asp Ala Met Glu Thr Phe Phe Asn Ser Tyr Asp Leu Ala Glu
                 20                  25                  30

Tyr Ser Glu Val Asn Pro Asn Lys Leu Asn Arg Lys Glu Thr Asp Glu
             35                  40                  45

Leu Leu Gly Val Ile Arg Glu Arg Phe Lys Ser Glu Leu Val Ile Thr
 50                  55                  60

Asp Glu Asp Phe Val Lys His Leu Ala Phe Ala Leu Ile Arg Ala Ala
 65                  70                  75                  80

Asn Ile Thr Thr Ser Val Lys Val Asn Tyr Val Gly Ala Tyr Glu Tyr
                 85                  90                  95

Thr Ile Gly Gly Lys Lys Phe Leu Val Lys Asp Ala Trp Val Phe Pro
            100                 105                 110

Leu Ile Lys Glu Cys Met Lys Lys Phe Asn Lys Pro Asn Pro Val Arg
        115                 120                 125

Thr Phe Cys Ala Thr Phe Glu Asp Ala Tyr Ile Val Ile Ala Arg Ser
    130                 135                 140

Leu Pro Lys Leu Phe Ile Asn Arg Thr Ile Gly Lys Arg Gly Ile Pro
145                 150                 155                 160

Ser Gly Tyr Glu Phe Leu Gly Ala Asp Phe Leu Thr Ala Thr Ser Val
                165                 170                 175

Cys Leu Asn Asp His Glu Lys Ala Ile Val Leu Gln Ala Ser Arg Ala
            180                 185                 190

Ala Ile Asp Arg Ala Val Ser Ser Val Asp Gly Lys Ile Val Ser
        195                 200                 205

Leu Phe Asp Leu Gly Arg Leu Ser
    210                 215

<210> SEQ ID NO 39
<211> LENGTH: 215
<212> TYPE: PRT
<213> ORGANISM: Beet Yellow Stunt Virus

<400> SEQUENCE: 39

Met Ala Gly Gly Asn Asp Glu Gly Ser Asp Asp Ser Ser Ala Ser Gln
  1               5                  10                  15

Thr Met Thr Ala Lys Asp Met Ile Phe Ala Pro Phe Glu Asn Phe Ala
                 20                  25                  30

Arg Ala Ser Ala Thr Cys Leu Asn Gly Glu Asn Lys Lys Lys Leu Phe
             35                  40                  45
```

-continued

```
Glu Glu Phe Ser Val Arg Val Lys Thr Gln Asp Val Thr Glu Ser Gly
 50                  55                  60

Ile Pro Thr Thr Leu Gly Met Thr Leu Tyr Ala Leu Ala Thr Leu Ser
 65                  70                  75                  80

Thr Ser Ser Lys Ile Asp Ile Glu Asp Lys Thr Pro Leu Val Ser Ala
                 85                  90                  95

Lys Ile Asp Ala Val Asn Val Thr Ile Thr Tyr Glu Asp Ile Lys Asn
                100                 105                 110

Phe Val Asn Ser Leu Thr Leu Leu Lys Asn Tyr Lys Asn Lys Leu Arg
            115                 120                 125

Val Phe Ala Arg Thr Phe Glu Glu Tyr Leu Arg Phe Val Arg Gln
    130                 135                 140

Tyr Lys His Ile Leu Pro Asn Ile Ala Arg Ala Asn Lys His Gly Ile
145                 150                 155                 160

Pro Ala Asp Tyr Ser Tyr Leu Ala Ala Asp Phe Val Gln Thr Ser Asn
                165                 170                 175

Leu Leu Lys Glu His Glu Gln Ala Val Leu Leu Glu Gly Arg Asn Ala
            180                 185                 190

Ala Thr Ala Ser Ser Gly Thr Thr Arg Glu Ser Ala Val Asn Leu Lys
        195                 200                 205

Tyr Leu Gly Gly Ser Ser Lys
    210                 215

<210> SEQ ID NO 40
<211> LENGTH: 226
<212> TYPE: PRT
<213> ORGANISM: Beet Yellow Stunt Virus

<400> SEQUENCE: 40

Met Pro Pro Gln Pro Gly Ala Glu Leu Val Glu His Asn Ala Asn Lys
  1               5                  10                  15

Ser Ser Leu Glu Val Phe Ser Glu Thr Arg Glu Lys Val Gly Lys
                20                  25                  30

Phe Phe Asn Asn Phe Asp His Lys Thr Phe Lys Gln Val Asn Pro Asn
             35                  40                  45

Leu Leu Asn Glu Asp Glu Leu Arg Glu Val Leu Gly Lys Leu Thr Glu
 50                  55                  60

Leu Lys Thr Asn Leu Lys Ala Leu Asp Glu Asp Ile Tyr His His Val
 65                  70                  75                  80

Ala Phe Phe Leu Leu Arg Ala Ser Val Val Ser Thr Ser Pro Lys Val
                 85                  90                  95

Glu Tyr Lys Gly Ser Tyr Ser Tyr Ser Ile Asp Gln Arg Lys Tyr Thr
                100                 105                 110

Val Asn Asp Ala Trp Ile Phe Pro Gln Val Lys Ile Leu Ala Ser Lys
            115                 120                 125

His Asn Lys Pro Asn Gly Leu Arg Ala Phe Cys Ala Ser Leu Glu Gly
        130                 135                 140

Met Tyr Leu Ser Val Ala Arg Leu Gly Pro Asp Ala Phe Gly Thr Arg
145                 150                 155                 160

Ser Val Gly Lys Arg Gly Ala Pro Ser Gly Ser Glu Tyr Leu Gly Ala
                165                 170                 175

Asp Phe Leu Thr Ser Thr Cys Pro Leu Met Ser Asp His Asp Arg Ala
            180                 185                 190

Val Ala Leu Ser Ala Ser Arg Asn Ala Leu Asp Arg Ser Ala Ala Ser
        195                 200                 205
```

```
Gln Ile Asp Lys Lys Met Val Ser Leu Tyr Asp Phe Gly Lys Val Val
    210                 215                 220

Tyr Thr
225

<210> SEQ ID NO 41
<211> LENGTH: 223
<212> TYPE: PRT
<213> ORGANISM: Citrus Tristeza Virus

<400> SEQUENCE: 41

Met Asp Asp Glu Thr Lys Lys Leu Lys Asn Lys Asn Lys Glu Thr Lys
  1               5                  10                  15

Glu Gly Asp Asp Val Val Ala Ala Glu Ser Ser Phe Ser Ser Val Asn
                 20                  25                  30

Leu His Ile Asp Pro Thr Leu Ile Thr Met Asn Asp Val Arg Gln Leu
             35                  40                  45

Ser Thr Gln Gln Asn Ala Ala Leu Asn Arg Asp Leu Phe Leu Thr Leu
 50                  55                  60

Lys Gly Lys His Pro Asn Leu Pro Asp Lys Asp Lys Asp Phe Arg Ile
 65                  70                  75                  80

Ala Met Met Leu Tyr Arg Leu Ala Val Lys Ser Ser Ser Leu Gln Ser
                 85                  90                  95

Asp Asp Asp Ala Thr Gly Ile Thr Tyr Thr Arg Glu Gly Val Glu Val
                100                 105                 110

Asp Leu Ser Asp Lys Leu Trp Ile Asp Val Val Phe Asn Ser Lys Gly
            115                 120                 125

Ile Gly Asn Arg Thr Asn Ala Leu Arg Val Trp Gly Arg Thr Asn Asp
        130                 135                 140

Ala Leu Tyr Leu Ala Phe Cys Arg Gln Asn Arg Asn Leu Ser Tyr Gly
145                 150                 155                 160

Gly Arg Pro Leu Asp Ala Gly Ile Pro Ala Gly Tyr His Tyr Leu Cys
                165                 170                 175

Ala Asp Phe Leu Thr Gly Ala Gly Leu Thr Asp Leu Glu Cys Ala Val
                180                 185                 190

Tyr Ile Gln Ala Lys Glu Gln Leu Leu Lys Lys Arg Gly Ala Asp Asp
            195                 200                 205

Val Val Val Thr Asn Val Arg Gln Leu Gly Lys Phe Asn Thr Arg
        210                 215                 220

<210> SEQ ID NO 42
<211> LENGTH: 240
<212> TYPE: PRT
<213> ORGANISM: Citrus Tristeza Virus

<400> SEQUENCE: 42

Met Ala Gly Tyr Thr Val Leu Pro Lys Thr Asp Asp Lys Glu Met Asp
  1               5                  10                  15

Pro Val Ser Ala Ala Val Pro Gly Lys Tyr Pro Asp Val Ile Glu Lys
                 20                  25                  30

Phe Val Ala Asn Arg Ser Val Asp Ala Leu Ile Glu Gly Val Ile Ser
             35                  40                  45

Lys Leu Asp Thr Asn Ser Ile Tyr Glu Asp Ser Thr Glu Lys Phe Thr
 50                  55                  60

Gly Glu His Leu Lys Tyr Val Met Val Thr Met Asp Thr Phe Leu Leu
 65                  70                  75                  80
```

-continued

```
Glu Asn Tyr Lys Thr Lys Thr Glu Asp Leu Leu Val His Leu Thr Met
                 85                  90                  95
Ile Gln Lys Arg Leu Tyr Thr Ile Ser Thr Ser Thr Lys Thr Lys Phe
                100                 105                 110
Arg Asp Lys Gly Cys Ile Ser Tyr Val Gln Gly Gly Leu Arg Tyr Lys
            115                 120                 125
Leu Leu Asp Lys Val Val Phe Pro Phe Ile Leu Ser Lys Phe Thr Asp
130                 135                 140
Arg Glu Thr Pro Asn Ala Leu Arg Lys Phe Ala Cys Thr Phe Glu Glu
145                 150                 155                 160
Leu His Leu Cys Met Ala Arg Leu Arg Pro Asp Leu Tyr Glu Asn Lys
                165                 170                 175
Arg Thr Thr Arg Ala Gly Thr Pro His Leu Lys Gly Tyr Leu Ser Ala
            180                 185                 190
Asp Phe Leu Ser Gly Ser Leu Pro Gly Tyr Ser Glu His Glu Arg Gly
        195                 200                 205
Ile Ile Leu Arg Ala Ser Glu Ser Met Leu Ala Arg Arg Gln Gly Tyr
    210                 215                 220
Glu Glu Ala Thr Glu Leu Leu Asn Leu Arg Asp Leu Gly Lys Tyr Leu
225                 230                 235                 240

<210> SEQ ID NO 43
<211> LENGTH: 553
<212> TYPE: PRT
<213> ORGANISM: Beet Yellows Virus

<400> SEQUENCE: 43

Met Thr Thr Arg Phe Ser Thr Pro Ala Asn Tyr Tyr Trp Gly Glu Leu
1               5                   10                  15
Phe Arg Arg Phe Phe Gly Gly Gln Glu Trp Lys Asn Leu Met Ser Glu
                20                  25                  30
Ala Ala Ser Val Ser Arg Pro Arg Tyr Ser Ser Asp Phe Arg Phe Ser
            35                  40                  45
Asp Gly Val Ile Leu Ser Arg Lys Thr Phe Gly Glu Ser Thr Gly Glu
        50                  55                  60
Ser Phe Val Arg Glu Phe Ser Leu Leu Thr Phe Pro Lys Thr Tyr
65                  70                  75                  80
Glu Val Cys Lys Leu Cys Gly Val Ala Met Glu Leu Ala Leu Asn Gly
                85                  90                  95
Met Asn Arg Leu Ser Asp Tyr Asn Val Ser Glu Phe Asn Ile Val Asp
                100                 105                 110
Val Lys Thr Val Gly Cys Lys Phe Asn Ile Gln Ser Val Thr Glu Phe
            115                 120                 125
Val Lys Lys Ile Asn Gly Asn Val Ala Glu Pro Ser Leu Val Glu His
        130                 135                 140
Cys Trp Ser Leu Ser Asn Ser Cys Gly Glu Leu Ile Asn Pro Lys Asp
145                 150                 155                 160
Thr Lys Arg Phe Val Ser Leu Ile Phe Lys Gly Lys Asp Leu Ala Glu
                165                 170                 175
Ser Thr Asp Glu Ala Ile Val Ser Ser Ser Tyr Leu Asp Tyr Leu Ser
            180                 185                 190
His Cys Leu Asn Leu Tyr Glu Thr Cys Asn Leu Ser Ser Asn Ser Gly
        195                 200                 205
Lys Lys Ser Leu Tyr Asp Glu Phe Leu Lys His Val Ile Asp Tyr Leu
```

```
                210                 215                 220
Glu Asn Ser Asp Leu Glu Tyr Arg Ser Pro Ser Asp Asn Pro Leu Val
225                 230                 235                 240

Ala Gly Ile Leu Tyr Asp Met Cys Phe Glu Tyr Asn Thr Leu Lys Ser
                245                 250                 255

Thr Tyr Leu Lys Asn Ile Glu Ser Phe Asp Cys Phe Leu Ser Leu Tyr
            260                 265                 270

Leu Pro Leu Leu Ser Glu Val Phe Ser Met Asn Trp Glu Arg Pro Ala
            275                 280                 285

Pro Asp Val Arg Leu Leu Phe Glu Leu Asp Ala Ala Glu Leu Leu Leu
290                 295                 300

Lys Val Pro Thr Ile Asn Met His Asp Ser Thr Phe Leu Tyr Lys Asn
305                 310                 315                 320

Lys Leu Arg Tyr Leu Glu Ser Tyr Phe Glu Asp Asp Ser Asn Glu Leu
                325                 330                 335

Ile Lys Val Lys Val Asp Ser Leu Leu Thr Arg Asp Asn Pro Glu Leu
            340                 345                 350

Lys Leu Ala Gln Arg Trp Val Gly Phe His Cys Tyr Tyr Gly Val Phe
            355                 360                 365

Arg Thr Ala Gln Thr Arg Lys Val Lys Arg Asp Ala Glu Tyr Lys Leu
    370                 375                 380

Pro Pro Ala Leu Gly Glu Phe Val Ile Asn Met Ser Gly Val Glu Glu
385                 390                 395                 400

Phe Phe Glu Glu Leu Gln Lys Lys Met Pro Ser Ile Ser Val Arg Arg
                405                 410                 415

Arg Phe Cys Gly Ser Leu Ser His Glu Ala Phe Ser Val Phe Lys Arg
            420                 425                 430

Phe Gly Val Gly Phe Pro Pro Ile Thr Arg Leu Asn Val Pro Val Lys
            435                 440                 445

Tyr Ser Tyr Leu Asn Val Asp Tyr Tyr Arg His Val Lys Arg Val Gly
            450                 455                 460

Leu Thr Gln Asp Glu Leu Thr Ile Leu Ser Asn Ile Glu Phe Asp Val
465                 470                 475                 480

Ala Glu Met Cys Cys Glu Arg Glu Val Ala Leu Gln Ala Arg Arg Ala
                485                 490                 495

Gln Arg Gly Glu Lys Pro Phe Gln Gly Trp Lys Gly Thr Lys Asn Glu
            500                 505                 510

Ile Ser Pro His Ala Arg Ser Ser Ile Arg Val Lys Lys Asn Asn Asp
            515                 520                 525

Ser Leu Leu Asn Ile Leu Trp Lys Asp Val Gly Ala Arg Ser Gln Arg
530                 535                 540

Arg Leu Asn Pro Leu His Arg Lys His
545                 550

<210> SEQ ID NO 44
<211> LENGTH: 534
<212> TYPE: PRT
<213> ORGANISM: Beet Yellow Stunt Virus

<400> SEQUENCE: 44

Met Ser Arg Arg Pro Thr Phe Ala Gly Tyr Ser Trp Gly Ser Leu Phe
  1               5                  10                  15

Lys Arg His Tyr Gly Glu Pro Glu Trp Lys Ser Tyr Leu Thr Glu Thr
                20                  25                  30
```

```
Ser Met Lys Tyr Lys Pro Leu Lys Ser Glu Ile Thr Phe Tyr Asp
        35              40              45

Gly Ser Ser Leu Thr Ser Ala Glu Leu Arg Pro Ala Arg Ser Gly Thr
        50              55              60

Ala Glu Tyr Glu Ile Ala Leu Leu Ile Phe Ser Asp Ser Ile Thr Lys
65              70              75              80

Trp Ser Glu Lys Leu Glu Arg Ser Ile Tyr Arg Gly Leu Asn Gln Ile
                85              90              95

Asn Asn His Ser Ile Tyr Ala Glu Thr Glu Leu Glu Val Thr Asp Val
            100             105             110

Lys Thr Ile Gly Cys Lys Phe Thr Ile Ser Ala Val Glu Ser Phe Met
        115             120             125

Gly Gly Arg Ala Ser Ala Ala Gln Val Glu His Cys Trp Ser Leu Ser
        130             135             140

Asn Ser Cys Gly Glu Leu Ile Asn Pro Asn Asp Thr Ala Arg Phe Ile
145             150             155             160

Gln Leu Val Phe Lys Asp Lys Ala Val Thr Glu Gln Ala Gln Val Asn
                165             170             175

Thr Ser Gly Ser Val Ser Asp Tyr Leu Val Tyr Cys Leu Gln Leu Tyr
            180             185             190

Asp Asn Ser Lys Lys Ser Asn Ala Gly Arg Thr Gln Leu Met Glu
        195             200             205

Ser Tyr Val Ser Phe Ile Arg Asp Phe Phe Gln His Ser Asp Leu Tyr
    210             215             220

Tyr Arg Ser Pro Leu Asp Asn Pro Leu Leu Thr Gly Val Leu Tyr Asp
225             230             235             240

Leu Cys Ile Glu His Asn Val Leu Arg Gly Ser Tyr Leu Lys Asn Leu
                245             250             255

Asp Asn Phe Arg Leu Phe Lys Gln Thr Tyr Leu Pro Met Ile Asp Asp
        260             265             270

Ile Phe Asp Tyr Ser Trp Glu Leu Tyr Ala Pro Asp Glu Arg Leu Leu
        275             280             285

Phe Pro Ile Asp Pro Tyr Glu Ile Ile Lys Glu Val Pro Thr Met Ser
290             295             300

Val Ile Asp Ala Asn Val Val Leu Ser Asn Lys Leu Val Tyr Leu Asp
305             310             315             320

Ser Tyr Leu Glu Asn Asn Ser Ile Leu Ala Leu Glu Lys Lys Ile Ile
                325             330             335

Ser Ile Leu Cys Arg Asp Asn Glu Gly Ile Asp Glu Gly Ala Leu Trp
            340             345             350

Ala Ala Phe Phe Cys Tyr Tyr Gly Thr Tyr Arg Thr Ala Arg Gln Arg
        355             360             365

Val Val Lys Arg Pro Asp Thr Tyr Glu Leu Asp Gly Ile Phe Ser Lys
    370             375             380

Pro Ile Val Met Ser Gly Val Glu Leu Phe Phe Asp Glu Leu Gln Lys
385             390             395             400

Arg Val Pro Asp Val Ser Leu Arg Arg Phe Asn Gly Ala Lys Ala
                405             410             415

Gly Glu Ala Ile Thr Val Phe Lys Lys Leu Gly Ile Ser Phe Pro Pro
            420             425             430

Ile Thr Arg Leu Asn Ala Pro Ser Lys Tyr Ser Tyr Leu Asn Ile Asp
        435             440             445

Tyr Phe Lys Gln Ala Asn Ser Leu Gly Leu Thr Glu Pro Glu Lys Ile
```

-continued

```
    450                 455                 460

Ile Leu Cys Asn Ile Ala Lys Asp Val Asp Met Met Cys Ala Gln Arg
465                 470                 475                 480

Ile Ser Ser Val Lys Ala Lys Pro Ile Ala Gln Arg Asn Gly Glu Ala
                485                 490                 495

Ile Asn Ser Ala Lys Ile Arg Thr Leu Pro Thr Asn Thr Leu Val Arg
            500                 505                 510

Ala Leu Glu Lys Cys Leu Leu Asn Gln Ala Pro Ser Trp Trp Asn Thr
        515                 520                 525

Thr Leu Thr Asn Leu Arg
    530

<210> SEQ ID NO 45
<211> LENGTH: 535
<212> TYPE: PRT
<213> ORGANISM: Citrus Tristeza Virus
<400> SEQUENCE: 45

Met Ser Ser His His Val Trp Gly Ser Leu Phe Arg Lys Phe Tyr Gly
 1               5                  10                  15

Glu Ala Ile Trp Lys Glu Tyr Leu Ser Glu Ser Thr Arg Asn Phe Asp
            20                  25                  30

Glu Arg Asn Val Ser Leu Asp His Thr Leu Ser Ser Gly Val Val Val
        35                  40                  45

Arg Arg Gln Ser Leu Leu Asn Ala Pro Gln Gly Thr Phe Glu Asn Glu
    50                  55                  60

Leu Ala Leu Leu Tyr Asn Ser Val Val Ile Asn Asp Phe Val Glu Leu
65                  70                  75                  80

Thr Gly Met Pro Leu Lys Ser Leu Met Thr Gly Ile Glu Asp Arg Lys
                85                  90                  95

Val Pro Asp Glu Leu Ile Ser Val Asp Pro His Glu Val Gly Cys Arg
            100                 105                 110

Phe Thr Leu Asn Asp Val Glu Ser Tyr Leu Met Ser Arg Gly Glu Asp
        115                 120                 125

Phe Ala Asp Leu Ala Ala Val Glu His Ser Trp Cys Leu Ser Asn Ser
    130                 135                 140

Cys Gly Arg Leu Leu Ser Ser Thr Glu Ile Asp Ala Tyr Lys Thr Leu
145                 150                 155                 160

Val Phe Thr Lys Asn Phe Asp Ser Asn Val Ser Gly Val Thr Thr Lys
                165                 170                 175

Leu Glu Thr Tyr Leu Ser Tyr Cys Ile Ser Leu Tyr Lys Lys His Cys
            180                 185                 190

Met Lys Asp Asp Asp Tyr Phe Asn Leu Ile Leu Pro Met Phe Asn Cys
        195                 200                 205

Leu Met Lys Val Leu Ala Ser Leu Gly Leu Phe Tyr Glu Lys His Ala
    210                 215                 220

Asp Asn Pro Leu Leu Thr Gly Met Leu Ile Glu Phe Cys Leu Glu Asn
225                 230                 235                 240

Lys Val Tyr Tyr Ser Thr Phe Lys Val Asn Leu Asp Asn Val Arg Leu
                245                 250                 255

Phe Lys Ser Lys Val Leu Pro Val Val Leu Thr Val Trp Asp Ile Ser
            260                 265                 270

Glu Pro Asp Asp Pro Met Asp Glu Arg Val Leu Ile Pro Phe Asp Pro
        275                 280                 285
```

```
Thr Asp Phe Val Leu Asp Leu Pro Lys Leu Asn Ile His Asp Thr Met
    290             295                 300

Val Val Val Gly Asn Gln Ile Arg Gln Leu Glu Tyr Val Val Glu Ser
305             310                 315                 320

Asp Ala Leu Asp Leu Ser Gln His Val Asp Leu Arg Leu Ala Ala
            325                 330                 335

Asp Asn Pro Asp Leu Arg Val Gly Leu Arg Trp Ala Gly Met Phe Val
            340                 345                 350

Tyr Tyr Gly Val Tyr Arg Cys Val Val Asp Arg Ala Val Glu Arg Pro
            355                 360                 365

Thr Leu Phe Arg Leu Pro Gln Lys Leu Leu Ser Gln Asp Asp Gly Glu
    370                 375                 380

Ser Cys Ser Leu His Met Gly Ser Val Glu Ala Leu Phe Asn Leu Val
385                 390                 395                 400

Gln Lys Val Asn Lys Asp Ile Asn Val Arg Arg Gln Phe Met Gly Arg
                405                 410                 415

His Ser Glu Val Ala Leu Arg Leu Tyr Arg Asn Leu Gly Leu Arg Phe
            420                 425                 430

Pro Pro Ile Ser Ser Val Arg Leu Pro Ala His Gly Tyr Leu Tyr
            435                 440                 445

Val Asp Phe Tyr Lys Arg Val Pro Asp Gly Ala Val Thr Ala Asp Glu
450                 455                 460

Leu Glu Ser Leu Arg Gln Leu Arg Ser Ser Val Asp Val Met Cys Lys
465                 470                 475                 480

Asp Arg Val Ser Ile Thr Pro Pro Phe Asn Arg Leu Arg Arg Gly
                485                 490                 495

Ser Ser Arg Thr Phe Arg Gly Arg Gly Ala Arg Gly Ala Ser Ser Arg
            500                 505                 510

His Met Ser Arg Asp Val Ala Thr Ser Gly Phe Asn Leu Pro Tyr His
            515                 520                 525

Gly Arg Leu Tyr Ser Thr Ser
530                 535

<210> SEQ ID NO 46
<211> LENGTH: 61
<212> TYPE: DNA
<213> ORGANISM: Beet Yellows Virus

<400> SEQUENCE: 46
ttaagtcgtc acagagtgac aacggcacca agtggtgctt agtgcgtatg taaattacga      60
a                                                                     61

<210> SEQ ID NO 47
<211> LENGTH: 61
<212> TYPE: DNA
<213> ORGANISM: Beet Yellow  Stunt Virus

<400> SEQUENCE: 47
ttaagccctc acagagcgag aacgttggca agagccaatt agtgtgtgtg tagtataatt      60
a                                                                     61

<210> SEQ ID NO 48
<211> LENGTH: 61
<212> TYPE: DNA
<213> ORGANISM: Citrus Tristeza Virus

<400> SEQUENCE: 48
```

-continued

```
ctaagctccc acagagtggt agtggtctca agtgaggctt aacgtatgcg tgaaccaaag      60
a                                                                    61
```

GRAPEVINE LEAFROLL VIRUS (TYPE 2) PROTEINS AND THEIR USES

This application is Continuation of a U.S. application Ser. No. 09/080,983, filed May 19, 1998 now U.S. Pat. No. 6,197,948, which claims the benefit of U.S. Provisional Patent Application Ser. No. 60/047,194, filed May 20, 1997.

This work was supported by the U.S. Department of Agriculture Cooperative Grant No. 58-2349-9-01. The U.S. Government may have certain rights in the invention.

FIELD OF THE INVENTION

The present invention relates to grapevine leafroll virus (type 2) proteins, DNA molecules encoding these proteins, and their uses.

BACKGROUND OF THE INVENTION

The world's most widely grown fruit crop, the grape (*Vitis* sp.), is cultivated on all continents except Antarctica. However, major grape production centers are in European countries (including Italy, Spain, and France), which constitute about 70% of the world grape production (Mullins et al., *Biology of the Grapevine*, Cambridge, U.K.:University Press (1992)). The United States, with 300,000 hectares of grapevines, is the eighth largest grape grower in the world. Although grapes have many uses, a major portion of grape production (~80%) is used for wine production. Unlike cereal crops, most of the world's vineyards are planted with traditional grapevine cultivars, which have been perpetuated for centuries by vegetative propagation. Several important grapevine virus and virus-like diseases, such as grapevine leafroll, corky bark, and *Rupestris* stem pitting, are transmitted and spread through the use of infected vegetatively propagated materials. Thus, propagation of certified, virus-free materials is one of the most important disease control measures. Traditional breeding for disease resistance is difficult due to the highly heterozygous nature and outcrossing behavior of grapevines, and due to polygenic patterns of inheritance. Moreover, introduction of a new cultivar may be prohibited by custom or law. Recent biotechnology developments have made possible the introduction of special traits, such as disease resistance, into an established cultivar without altering its horticultural characteristics.

Many plant pathogens, such as fungi, bacteria, phytoplasmas, viruses, and nematodes can infect grapes, and the resultant diseases can cause substantial losses in production (Pearson et al., *Compendium of Grape Diseases*, American Phytopathological Society Press (1988)). Among these, viral diseases constitute a major hindrance to profitable growing of grapevines. About 34 viruses have been isolated and characterized from grapevines. The major virus diseases are grouped into: (1) the grapevine degeneration caused by the fanleaf nepovirus, other European nepoviruses, and American nepoviruses, (2) the leafroll complex, and (3) rugose wood complex (Martelli, ed., *Graft Transmissible Diseases of Grapevines, Handbook for Detection and Diagnosis*, FAO, UN, Rome, Italy (1993)).

Of the major virus diseases, the grapevine leafroll complex is the most widely distributed throughout the world. According to Goheen ("Grape Leafroll, " in Frazier et al., eds., *Virus Diseases of Small Fruits and Grapevines (A Handbook)*, University of California, Division of Agricultural Sciences, Berkeley, Calif., USA, pp. 209–212 (1970) ("Goheen (1970)"), grapevine leafroll-like disease was described as early as the 1850s in German and French literature. However, the vital nature of the disease was first demonstrated by Scheu (Scheu, "Die Rollkrankheit des Rebstockes (Leafroll of grapevine)," *D. D. Weinbau* 14:222–358 (1935) ("Scheu (1935)")). In 1946, Harmon and Snyder (Harmon et al., "Investigations on the Occurrence, Transmission, Spread and Effect of 'White' Fruit Colour in the Emperor Grape, " *Proc. Am. Soc. Hort. Sci.* 74:190–194 (1946)) determined the viral nature of White Emperor disease in California. It was later proven by Goheen et al. (Goheen et al., "Leafroll (White Emperor Disease) of Grapes in California, *Phytopathology*, 48:51–54(1958), ("Goheen (1958)")) that both leafroll and "White Emperor" diseases were the same, and only the name leafroll was retained.

Leafroll is a serious viral disease of grapes and occurs wherever grapes are grown. This wide distribution of the disease has come about through the propagation of diseased vines. It affects almost all cultivated and rootstock varieties of *Vitis*. Although the disease is not lethal, it causes yield losses and reduction of sugar content. Scheu estimated in 1936 that 80 per cent of all grapevines planted in Germany were infected (Scheu, *Mein Winzerbuch*, Berlin:Reichsnahrstand-Verlags (1936). In many California wine grape vineyards, the incidence of leafroll (based on a survey of field symptoms conducted in 1959) agrees with Scheu's initial observation in German vineyards (Goheen et al., "Studies of Grape Leafroll in California," *Amer. J. Enol. Vitic.*, 10:78–84 (1959)). The current situation on leafroll disease does not seem to be any better (Goheen, "Diseases Caused by Viruses and Viruslike Agents," *The American Phytopathological Society*, St. Paul, Minn.:APS press, 1:47–54 (1988) ("Goheen (1988)"). Goheen also estimated that the disease causes an annual loss of about 5–20 per cent of the total grape production (Goheen (1970) and Goheen (1988)). The amount of sugar in individual berries of infected vines is only about ½ to ⅔ that of berries from noninfected vines (Goheen (1958)).

Symptoms of leafroll disease vary considerably depending upon the cultivar, environment, and time of the year. On red or dark-colored fruit varieties, the typical downward rolling and interveinal reddening of basal, mature leaves is the most prevalent in autumn; but not in spring or early summer. On light-colored fruit varieties however, symptoms are less conspicuous, usually downward rolling accompanied by interveinal chlorosis. Moreover, many infected rootstock cultivars do not develop symptoms. In these cases, the disease is usually diagnosed with a woody indicator indexing assay using *Vitis vivifera* cv. Carbernet Franc (Goheen (1988)).

Ever since Scheu demonstrated that leafroll was graft transmissible, a virus etiology has been suspected (Scheu (1935)). Several virus particle types have been isolated from leafroll diseased vines. These include potyvirus-like (Tanne et al., "Purification and Characterization of a Virus Associated with the Grapevine Leafroll Disease," *Phytopathology*, 67:442–447 (1977)), isometric virus-like (Castellano et al., "Virus-like Particles and Ultrastructural Modifications in the Phloem of Leafroll-affected Grapevines," *Vitis*, 2:23–39 (1983) (Castellano (1983)") and Namba et al., A Small Spherical Virus Associated with the Ajinashika Disease of Koshu Grapevine,*Ann. Phytopathol. Soc. Japan*, 45:-70–73 (1979)), and *closterovirus*-like (Namba, "Grapevine Leafroll Virus, a Possible Member of *Closteroviruses, Ann. Phytopathol, Soc. Japan*, 45.497–502 (1979)) particles. In recent years, however, long flexuous *closteroviruses* ranging from 1,400 to 2,200 nm have been most consistently associated with leafroll disease (FIG. 1) (Castellano (1983), Faoro et al., "Association of a Possible *Closterovirus* with Grapevine Leafroll in Northern Italy," *Riv. Patol. Veg. Ser IV*, 17:183–189 (1981), Gugerli et al., "L'enroulement de la vigne; mise en évidence de particules virales et développement d'une méthode immuno-enzymatique pour le diagnostic rapide (Grapevine Leafroll: Presence of Virus Particles and Development of an Immuno-enzyme method for Diagnosis and Detection)," *Rev. Suisse Viticult. Arboricult, Hort.*, 16:299–304 (1984) ("Gugerli (1984)"), Hu et al., "Characterization of *Closterovirus*-like Particles Associated with Grapevine Leafroll Disease," *J. Phytopathol.*, 128:1–14 (1990) ("Hu (1990)"), Milne et al., "*Closterovirus*-like Particles of Two Types Associated with Diseased Grapevines," *Phytopathol, Z.*, 110:360–368(1984), Zee et al., "Cytopathology of Leafroll-diseased Grapevines and the Purification and Serology of Associated *Closterovirus* like Particles," *Phytopathology*, 77:1427–1434(1987) ("Zee (1987)"), and Zimmerman et al., "Characterization and Serological Detection of Four *Closterovirus*-like Particles Associated with Leafroll Disease on Grapevine," *J. Phyopathol.*, 130:205–218 (1990) ("Zimmermann (1990)")). These *closteroviruses* are referred to as grapevine leafroll associated viruses ("GLRaV"). At least six serologically distinct types of GLRaV's (GLRaV-1 to -6) have been detected from leafroll diseased vines (Table 1) (Boscia et al., "Nomenclature of Grapevine Leafroll-associated Putative *Closteroviruses, Vitis*, 34:171–175 (1995) ("Boscia (1995)") and (Martelli, "Leafroll," pp. 37–44 in Martelli, ed., *Graft Transmissible Diseases of Grapevines, Handbook for Detection and Diagnosis*, FAO, Rome Italy, (1993) ("Martelli I")). The first five of these were confirmed in the 10th Meeting of the International Council for the Study of Virus and Virus Diseases of the Grapevine ("ICVG") (Volos, Greece, 1990).

TABLE 1

| Type | Particle length (nm) | Coat protein Mr (×10³) | Reference |
|---|---|---|---|
| GLRaV-1 | 1,400–2,200 | 39 | Gugerli (1984) |
| GLRaV-2 | 1,400–1,800 | 26 | Gugerli (1984) |
| | | | Zimmermann (1990) |
| GLRaV-3 | 1,400–2,200 | 43 | Zee (1987) |
| GLRaV-4 | 1,400–2,200 | 36 | Hu (1990) |
| GLRaV-5 | 1,400–2,200 | 36 | Zimmermann (1990) |
| GLRaV-6 | 1,400–2,200 | 36 | Gugerli (1993) |

Through the use of monoclonal antibodies, however, the original GLRaV II described in Gugerli (1984) has been shown to be an apparent mixture of at least two components, IIa and IIb (Gugerli et al., "Grapevine Leafroll Associated Virus II Analyzed by Monoclonal Antibodies," 11*th Meeting of the International Council for the Study of Viruses and Virus Diseases of the Grapevine*, Montreux, Switzerland, pp. 23–24 (1993) ("Gugerli (1993)")). Recent investigation with comparative serological assays (Boscia (1995)) demonstrated that the IIb component of cv. Chasselas 8/22 is the same as the GLRaV-2 isolate from France (Zimmermann (1990)) which also include the isolates of grapevine corky bark associated *closteroviruses* from Italy (GCBaV-BA) (Boscia (1995)) and from the United States (GCBaV-NY) (Namba et al., "Purification and Properties of *Closterovirus*-like Particles Associated with Grapevine Corky Bark Disease," *Phytopathology*, 81:964–970 (1991) ("Namba (1991)")). The IIa component of cv. Chasselas 8/22 was given the provisional name of grapevine leafroll associated virus 6 (GLRaV-6). Furthermore, the antiserum to the CA-5 isolate of GLRaV-2 produced by Boscia et al. (Boscia et al., "Characterization of Grape Leafroll Associated *Closterovirus* (GLRaV) Serotype II and Comparison with GLRaV Serotype III, "*Phytopathology*, 80:117 (1990)) was show to contain antibodies to both GLRaV-2 and GLRaV-1, with a prevalence of the latter (Boscia (1995)).

Virions of GLRaV-2 are flexuous, filamentous particles about 1,400–1,800 nm in length (Gugerli et al., "L'enroulement de la Vigne: Mise en Evidence de Particles Virales et Development d'une Methode Immunoenzymatique Pour le Diagnostic Rapide (Grapevine Leafroll: Presence of Virus Particles and Development of an Immuno-enzyme Method for Diagnosis and Detection)," *Rev. Suisse Viticult, Arboricult, Horticult.* 16:299–304 (1984)). A double-stranded RNA (dsRNA) of about 15 kb was consistently isolated from GLRaV-2 infected tissues (Goszczynski et al., Detection of Two Strains of Grapevine Leafroll-Associated Virus 2," *Vitis* 35:133–35 (1996)). The coat protein of GLRaV-2 is ca 22~26 kDa (Zimmermann et al., Characterization and Serological Detection of Four *Closterovirus*-like Particles Associated with Leafroll Disease on Grapevine," *J. Phytopathology* 130:205–18 (1990); Gugerli and Ramel, Extended abstracts: "Grapevine Leafroll Associated Virus II Analyzed by Monoclonal Antibodies," 11th ICVG at Montreux, Switzerland, Gugerli, ed., Federal Agricultural Research Station of Changins, CH-1260 Nyon, Switzerland, p 23–24 (1993); Boscia et al., "Nomenclature of Grapevine Leafroll-Associated Putative *Closteroviruses,*" *Vitis* 34–171–75 (1995)), which is considerably smaller than other GLRaVs (35~43 kDa) (Zee et al., "Cytopathology of Leafroll-Diseased Grapevines and the Purification and Serology of Associated *Closterovirus* Like Particles," *Phytopathology* 77:1427–34 (1987); Hu et al., "Characterization of *Closterovirus*-Like Particles Associated with Grapevine Leafroll Disease," *J. of Phytopathology* 128:1–14(1990); Ling et al., "The Coat Protein Gene of Grapevine Leafroll Associated *Closterovirus*-3Cloning, Nucleotide Sequencing and Expression in Transgenic Plants," *Arch. of Virology* 142:1101–16(1997)). Although GLRaV-2 has been classified as a member of the genus *Closterovirus* based on particle morphology and cytopathology (Martelli, Circular of ICTV-Plant Virus Subcommittee Study Group on *Closterolike* Viruses" (1996)), its molecular and biochemical properties are not well characterized.

In the *closterovirus* group, several viruses have recently been sequences. The partial or complete genome sequences of beet yellows virus (BYV) (Agranovsky et al. "Nucleotide Sequence of the 3'-Terminal Half of Beet Yellows *Closterovirus* RNA Genome Unique Arrangement of Eight Virus Genes," *J. General Virology* 72:15–24 (1991), Agranovsky et al., "Beet Yellows *Closterovirus*: Complete Genome Structure and Identification of a Papain-like Thiol Protease," *Virology* 198:311–24 (1994)), beet yellow stunt virus (BYSV) (Karasev et al., "Organization of the 3'-Terminal Half of Beet Yellow Stunt Virus Genome and Implications for the Evolution of *Closteroviruses,*" *Virology* 221:199–207 (1996)), citrus tristeza virus (CTV) (Pappu et al., "Nucleotide Sequence and Organization of Eight 3' Open Reading Frames of the *Citrus* Tristeza *Closterovirus* Genome," *Virology* 199:35–46 (1994); Karasev et al., "Complete Sequence of the *Citrus* Tristeza Virus RNA Genome," *Virology* 208:511–20 (1995)), lettuce infectious yellows virus (LIYV) (Klaassen et al., "Partial Characterization of the Lettuce Infectious Yellows Virus Genomic RNAs, Identification of the Coat Protein Gene and Comparison of its Amino Acid Sequence With Those of Other Filamentous RNA Plant Viruses," *J. General Virology* 75:1525–33 (1994); Klaassen et al., "Genome Structure and Phylogenetic Analysis of Lettuce Infectious Yellows Virus, a Whitefly-Transmitted, Bipartite *Closterovirus,*" *Virology* 208:99–110 (1995)), little cherry virus (LChV) (Keim and Jelkmann, "Genome Analysis of the 3'-Terminal Part of the Little Cherry Disease Associated dsRNA Reveals a Monopartite Clostero-Like Virus," *Arch. Virology* 141:1437–51 (1996); Jelkmann et al., "Complete Genome Structure and Phylogenetic Analysis of Little Cherry Virus, a Mealybug-Transmissible *Closterovirus,*" *J. General Virology* 78:2067–71 (1997)), and GLRaV-3 (Ling et al., "Nucleotide Sequence of the 3' Terminal Two-Thirds of the Grapevine Leafroll Associated Virus-3-Genome Reveals a Typical Monopartite *Closterovirus,*" *J. Gen. Virology* 79(5): 1289–1301 (1998)) revealed several common features of the *closteroviruses*, including the presence of HSP70 chaperone heat shock protein and a duplicate of the coat protein gene (Agranovsky "Principles of Molecular Organization, Expression, and Evolution of *Closteroviruses*: Over the Barriers," *Adv. in Virus Res.* 47:119–218 (1996); Dolja et al. "Molecular Biology and Evolution of *Closteroviruses*: Sophisticated Build-up of Large RNA Genomes," *Annual Rev. Photopathology* 32:261–85 (1994); Boyko et al., "Coat Protein Gene Duplication in a Filamentous RNA Virus of Plants," *Proc. Nat. Acad. Sci. USA* 89:9156–60 (1992)). Characterization of the genome organization of GLRaVs would provide molecular information on the serologically distinct *closteroviruses* that cause similar leafroll symptoms in grapevine.

Several shorter *closteroviruses* (particle length 800 nm long) have also been isolated from grapevines. One of these, called grapevine virus A ("GVA") has also been found associated, though inconsistently, with the leafroll disease (Agran et al., "Occurrence of Grapevine Virus A (GVA) and Other *Closteroviruses* in Tunisian Grapevines Affected by Leafroll Disease," *Vitis*, 29:43–48 (1990), Conti, et al., "*Closterovirus* Associated with Leafroll and Stem Pitting in Grapevine," *Phytopathol. Mediterr.*, 24:110–113 (1985), and Conti et al., "A *Closterovirus* from a Stem-pitting-diseased Grapevine," *Phytopathology*, 70:394–399 (1980)). The etiology of GVA is not really known; however, it appears to be more consistently associated with rugose wood *serau lato* (Rosciglione at al., "Maladies de l'enroulement et du bois strié de la vigne: analyse microscopique et sérologique Leafroll and Stem Pitting of Grapevine: Microscopical and Serological Analysis)," *Rev. Suisse Vitic Arboric. Hortic.*, 18:207–211 (1986) ("Rosciglione (1986)"), and Zimmermann (1990)). Moreover, another short *closterovirus* (800 nm long) named grapevine virus B ("GVB") has been isolated and characterized from corky bark-affected vines (Boscia et al., "Properties of a Filamentous Virus Isolated from Grapevines Affected by Corky Bark," *Arch. Virol.*, 130:109–120(1993) and Namba(1991)).

As suggested by Martelli I, leafroll symptoms may be induced by more than one virus or they may be simply a general plant physiological response to invasion by an array of phloem-inhabiting viruses. Evidence accumulated in the last 15 years strongly favors the idea that grapevine leafroll is induced by one (or a complex) of long *closteroviruses* (particle length 1,400 to 2,200 nm).

Grapevine leafroll is transmitted primarily by contaminated scions and rootstocks. However, under field conditions, several species of mealybugs have been shown to be the vector of leafroll (Engelbrecht et al., "Transmission of Grapevine Leafroll Disease and Associated *Closteroviruses* by the Vine Mealybug *Planococcus-ficus,*" *Phytophylactica*, 22:341–346 (1990), Rosciglione, et al., "Transmission of Grapevine Leafroll Disease and an Associated *Closterovirus* to Healthy Grapevine by the Mealybug *Planococcus ficus*," (Abstract), *Phytoparasitica*, 17:63–63 (1989), and Tanne, "Evidence for the Transmission by Mealybugs to Healthy Grapevines of a *Closter*-like Particle Associated with Grapevine Leafroll Disease," *Phytoparasitica*, 16:288 (1988)). Natural spread of leafroll by insect vectors is rapid in various parts of the world. In New Zealand, observations of three vineyards showed that the number of infected vines nearly doubled in a single year (Jordan et al., "Spread of Grapevine Leafroll and its Associated Virus in New Zealand Vineyards," 11*th Meeting of the International Council for the Study of Viruses and Virus Diseases of the Grapevine*, Montreux, Switzerland, pp. 113–114 (1993)). One vineyard became 90% infected 5 years after GLRaV-3 was first observed. Prevalence of leafroll worldwide may increase as chemical control of mealybugs becomes more difficult due to the unavailability of effective insecticides.

In view of the serious risk grapevine leafroll virus poses to vineyards and the absence of an effective treatment of it, the need to prevent this affliction continues to exist. The present invention is directed to overcoming this deficiency in the art.

SUMMARY OF INVENTION

The present invention relates to an isolated protein or polypeptide, corresponding to a protein or polypeptide of a grapevine leafroll virus (type 2). The encoding RNA and DNA molecules, in either isolated form or incorporated in an expression system, a host cell, a transgenic *Vitis* or *citrus* scion or rootstock cultivar, or a transgenic *Nicotiana* plant or beet plant are also disclosed.

Another aspect of the present invention relates to a method of imparting grapevine leafroll virus (type 2) resistance to *Vitis* scion or rootstock cultivars or *Nicotiana* plants by transforming them with a DNA molecule encoding the protein or polypeptide corresponding to a protein or polypeptide of a grapevine leafroll virus (type 2). Other aspects of the present invention relate to a method of imparting beet yellows virus resistance to beet plants and a method of imparting tristeza virus resistance to *citrus* scion or rootstock cultivars, both by transforming the plants or cultivars with a DNA molecule encoding the protein or polypeptide corresponding to a protein or polypeptide of a grapevine leafroll virus (type 2).

The present invention also relates to an antibody or binding portion thereof or probe which recognizes the protein or polypeptide.

Grapevine leafroll virus resistant transgenic variants of the current commercial grape cultivars and rootstocks allows for more complete control of the virus, while retaining the varietal characteristics of specific cultivars. Furthermore, these variants permit control of GLRaV-2 transmitted either by contaminated scions or rootstocks or by a presently uncharacterized insect vector. With respect to the latter mode of transmission, the present invention circumvents increased restriction of pesticide use which has made chemical control of insect infestation increasingly difficult. In this manner, the interests of the environment and the economics of grape cultivation and wine making are all furthered by the present invention.

BRIEF DESCRIPTION OF THE DRAWINGS

FIGS. 1A and 1B are a comparison of a double-stranded RNA (dsRNA) profile (FIG. 1A) of GLRaV-2 and its Northern hybridization analysis (FIG. 1B). In FIG. 1A: lane M, lambda HindIII DNA marker; and lane 1, dsRNA pattern in 1% agarose gel stained with ethidium bromide. FIG. 1B is a northern hybridization of isolated high molecular weight dsRNA of GLRaV-2 with a probe prepared with $^{32}$P [α-dATP] labeled cDNA insert from GLRaV-2 specific cDNA clone TC-1. Lane 1, high molecular weight dsRNA of GLRaV-2. Lane 2, total RNA extracted from healthy grapevine.

FIG. 2 displays the genome organization of GLRaV-2 and its sequencing strategy. Boxes represent ORFs encoded by deduced amino acid sequences of GLRaV-2, numbered lines represent nucleotide coordinates, beginning from 5'-terminal of RNA in kilobases (kb). The lines below GLRaV-2 RNA genome represent the cDNA clones used to determine the nucleotide sequences.

FIG. 3A-3D are comparisons between ORF1a/ORF1b of GLRaV-2 and BYV. FIG. 3A-3D show the conserved domains of two papain-like proteases (P-PRO), methyltransferase (MT/MTR), helicase (HEL), and RNA-dependent RNA polymerase (RdRP), respectively (SEQ ID NOS: 3, 5, and 24–27). Exclamation marks indicate the predicted catalytic residues of the leader papain-like protease; slashes indicate the predicted cleavage sites. The conserved motifs of the MT, HEL, and RdRP domains are highlighted with overlines marked with respective letters. The alignment is constructed using the MegAlign program in DNASTAR.

FIGS. 4A and 4B are alignments of the nucleotide (FIG. 4A) and deduced amino acid (FIG. 4B) sequences of ORF1a/ORF1b overlapping region of GLRaV-2, BYV, BYSV, and CTV (SEQ ID NOS: 28–35). Identical nucleotides and amino acids are shown in consensus. GLRaV-2 putative+1 frameshift site (TAGC) and its corresponding sites of BYV (TAGC) and BYSV (TAGC) and CTV (CGGC) at nucleotide and amino acid sequences are highlighted with underlines.

FIG. 5 is an alignment of the amino acid sequence of HSP70 protein of GLRaV-2 and BYV (SEQ ID NOS: 9 and 36). The conserved motifs (A to H) are indicated with overlines and marked with respective letters. The alignment was conducted with the MegAlign program of DNASTAR.

FIG. 6A is a comparison of the coat protein (CP) and coat protein duplicate (CPd) of GLRaV-2 with other closteroviruses (SEQ ID NOS: 13, 15, and 37–42). The amino acid sequence of the GLRaV-2 CP and CPd are aligned with the CP and CPd of BYV, BYSV, and CTV. The conserved amino acid residues are in bold and the consensus sequences are indicated. Sequence alignment and phylogenetic tree were constructed by Clustal Method in the MegAlign Program of DNASTAR. FIG. 6B is a tentative phylogenetic tree of the CP and CPd of GLRaV-2 with BYV, BYSV, CTV, LIYV, LChV, and GLRaV-3. To facilitate the alignment, only the C-terminal 250 amino acids of CP and CPd of LIYV, LChV, and GLRaV-3 were used. The scale beneath the phylogenetic tree represents the distance between sequences. Units indicate the number of substitution events.

FIG. 7 is a comparison of the genome organization of GLRaV-2, BYV, BYSV, CTV, LIYV, LChV, and GLRaV-3. P-PRO, papain-like protease; MT/MTR, methyltransferase; HEL, helicase; RdRP, RNA-dependent RNA polymerase; HSP70, heat shock protein 70; CP, coat protein; CPd, coat protein duplicate.

FIG. 9 is an alignment of the amino acid sequence of HSP90 protein of GLRaV-2 with respect to other closteroviruses, BYS, BYSV, and CTV (SEQ ID NOS: 11 and 43–45). The most conserved motifs (I to II) are indicated with the highlighted lines and marked with respective letters.

Figure 2:
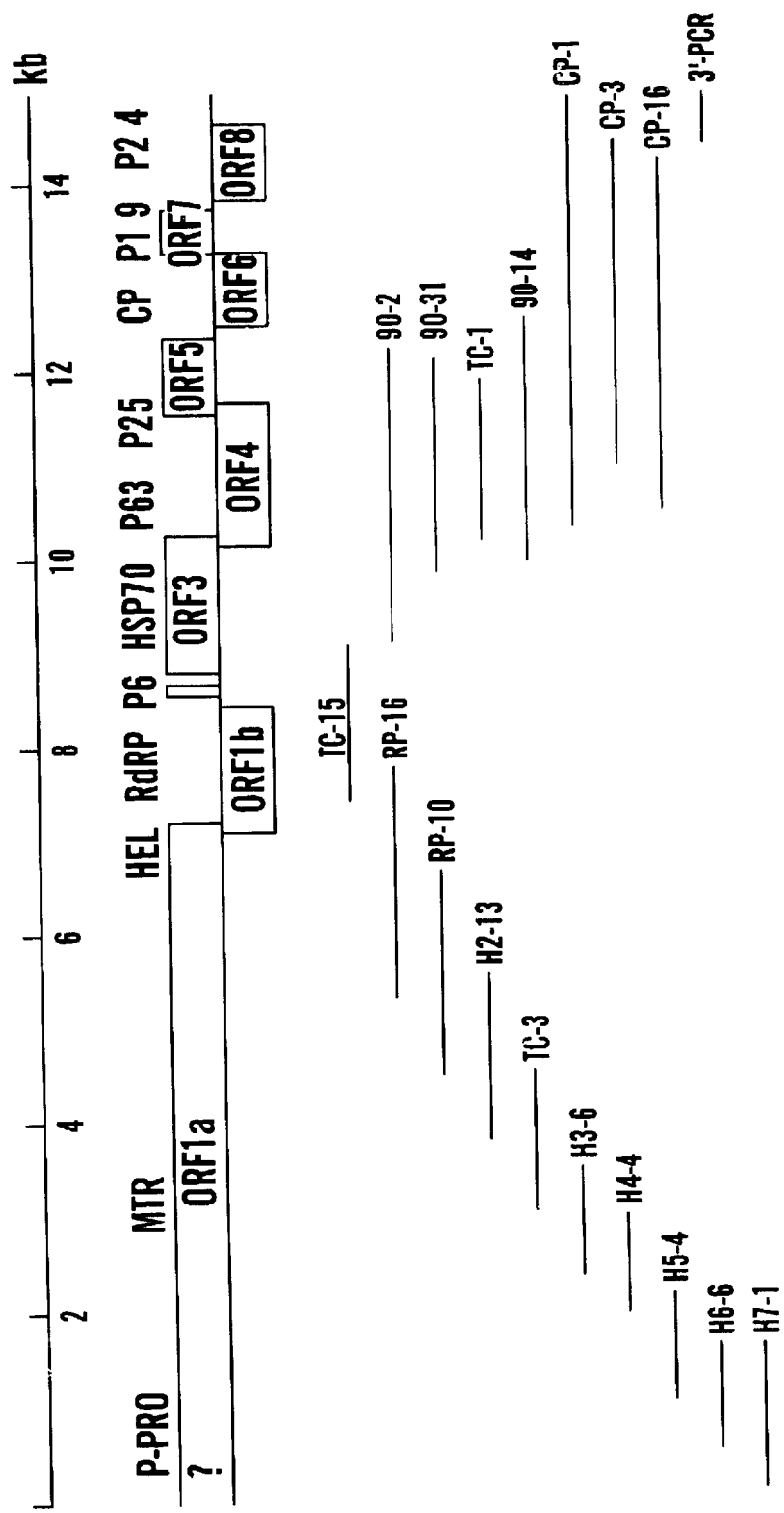

FIG. 10 is an alignment of the nucleotide sequence of 3'-terminal untranslated region of GLRaV-2 with respect to the closteroviruses BYV (Agranovsky et al., "Beet Yellows Closterovirus: Complete Genome Structure and Identification of a Papain-like Thiol Protease," Virology 198:311–24 (1994), which is hereby incorporated by reference), BYSV (Karasev et al., Organization of the 3'-Terminal Half of Beet Yellow Stunt Virus Genome and Implications for the Evolution of Closteroviruses," Virology 221:199–207 (1996), which is hereby incorporated by reference), and CTV (Karasev et al., "Complete Sequence of the Citrus Tristeza Virus RNA Genome," Virology 208:511–20 (1995), which is hereby incorporated by reference) (SEQ ID NOS: 1 and 46–48). The consensus sequences are shown, and the distance to the 3'-end is indicated. A complementary region capable of forming a "hair-pin" structure is underlined.

Figures 11A, 11B:
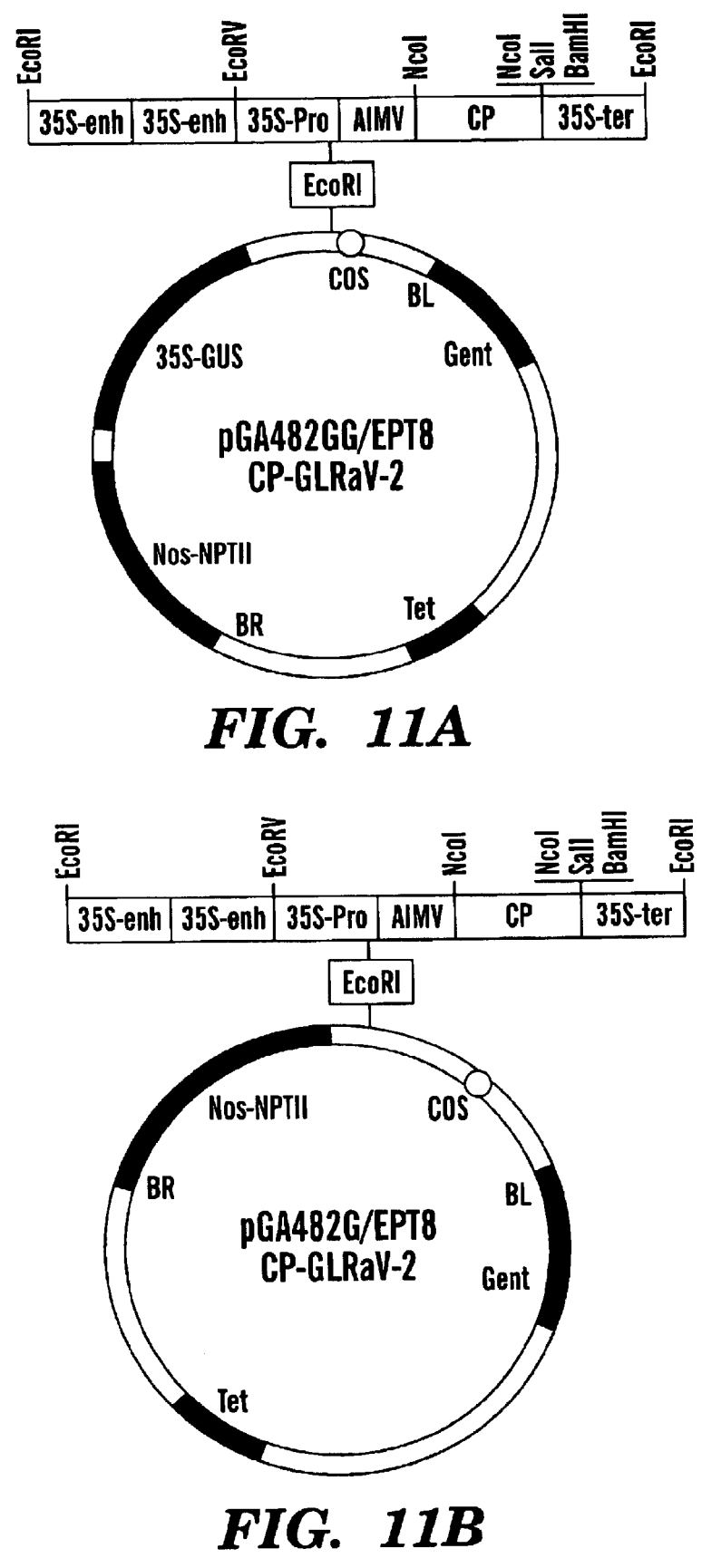

FIGS. 11B and 11B are genetic maps of the transformation vectors pGA482GG/EPT8CP-GLRaV-2 and pGA482G/EPT8CP-GLRaV-2, respectively As shown in FIGS. 11A and 11B, the plant expression cassette (EPT8CP-GLRaV-2), which consists of a double cauliflower mosaic virus (CaMV) 35S-enhancer, a CaMV 35S-promoter, an alfalfa mosaic virus (ALMV) RNA4 5' leader sequence, a coat protein gene of GLRaV-2 (CP-GLRaV-2), and a CaMV 35S 3' untranslated region as a terminator, was cloned into the transformation vector by EcoRI restriction site. The CP of GLRaV-2 was cloned into the plant expression vector by NcoI restriction site.

FIG. 12 is a PCR analysis of DNA molecules extracted from the leaves of putative transgenic plants using both the CP gene of GLRaV-2 and NPT II gene specific primers. An ethidium bromide-stained gel shows a 720 bp amplified DNA fragment for NPT II gene, and a 653 bp DNA fragment for the entire coding sequence of the CP gene. Lane 1, Φ174/Hae III DNA Marker; lanes 2–6, transgenic plants from different lines; lane 7, the cp gene of GLRaV-2 of positive control; and lane 8, NPT II gene of positive control.

FIG. 13 is a comparison of resistant (right side 3 plants) and susceptible (left side 3 plants) transgenic *Nicotiana benthamiana* plants. Plants are shown 48 days after inoculation with GLRaV-2.

FIG. 14 is a northern blot analysis of transgenic *Nicotiana benthamiana* plants. An aliquot of 10 g of total RNA extracted from putative transgenic plants was denatured and loaded onto 1% agarose gel containing formaldehyde. The separated RNAs were transferred to Gene Screen Plus membrane and hybridized with a $^{32}P$-labeled DNA probe containing the 3' one third CP gene sequence. Lanes 1, 3, and 4 represent nontransformed control plants without RNA expression. The remaining lanes represent transgenic plants from different lines: lanes 2, 14–17, and 22–27 represent plants with high RNA expression level which are susceptible to GLRaV-2; all other lanes represent plants with undetectable or low RNA expression level which are resistant to GLRaV-2.

DETAILED DESCRIPTION OF THE INVENTION

The present invention relates to isolated DNA molecules encoding for the proteins or polypeptides of a grapevine leafroll virus (type 2). A substantial portion of the grapevine leafroll virus (type-2) ("GLRaV-2") genome has been sequenced. Within the genome are a plurality of open reading frames ("ORFs") and a 3' untranscribed region ("UTR"), each containing DNA molecules in accordance with the present invention. The DNA molecule which constitutes a substantial portion of the GLRaV-2 genome comprises the nucleotide sequence corresponding to SEQ. ID. No. 1 as follows:

```
TAAACATTGC GAGAGAACCC CATTAGCGTC TCCGGGGTGA ACTTGGGAAG GTCTGCCGCC     60
GCTCAGGTTA TTTATTTCGG CAGTTTCACG CAGCCCTTCG CGTTGTATCC GCGCCAAGAG    120
AGCGCGATCG TAAAAACGCA ACTTCCACCG GTCAGTGTAG TGAAGGTGGA GTGCGTAGCT    180
GCGGAGGTAG CTCCCGACAG GGGCGTGGTC GACAAGAAAC CTACGTCTGT TGGCGTTCCC    240
CCGCAGCGCG GTGTGCTTTC TTTTCCGACG GTGGTTCGGA ACCGCGGCGA CGTGATAATC    300
ACAGGGGTGG TGCATGAAGC CCTGAAGAAA ATTAAAGACG GGCTCTTACG CTTCCGCGTA    360
GGCGGTGACA TGCGTTTTTC GAGATTTTTC TCATCGAACT ACGGCTGCAG ATTCGTCGCG    420
AGCGTGCGTA CGAACACTAC AGTTTGGCTA AATTGCACGA AAGCGAGTGG TGAGAAATTC    480
TCACTCGCCG CCGCGTGCAC GGCGGATTAC GTGGCGATGC TGCGTTATGT GTGTGGCGGG    540
AAATTTCCAC TCGTCCTCAT GAGTAGAGTT ATTTACCCGG ATGGGCGCTG TTACTTGGCC    600
CATATGAGGT ATTTGTGCGC CTTTTACTGT CGCCCGTTTA GAGAGTCGGA TTATGCCCTC    660
GGAATGTGGC CTACGGTGGC GCGTCTCAGG GCATGCGTTG AGAAGAACTT CGGTGTCGAA    720
GCTTGTGGCA TAGCTCTTCG TGGCTATTAC ACCTCTCGCA ATGTTTATCA CTGTGATTAT    780
GACTCTGCTT ATGTAAAATA TTTTAGAAAC CTTTCCGGCC GCATTGGCGG TGGTTCGTTC    840
GATCCGACAT CTTTAACCTC CGTAATAACG GTGAAGATTA GCGGTCTTCC AGGTGGTCTT    900
CCTAAAAATA TAGCGTTTGG TGCCTTCCTG TGCGATATAC GTTACGTCGA ACCGGTAGAC    960
TCGGGCGGCA TTCAATCGAG CGTTAAGACG AAACGTGAAG ATGCGCACCG AACCGTAGAG   1020
GAACGGGCGG CCGGCGGATC CGTCGAGCAA CCGCGACAAA AGAGGATAGA TGAGAAAGGT   1080
TGCGGCAGAG TTCCTAGTGG AGGTTTTTCG CATCTCCTGG TCGGCAACCT TAACGAAGTT   1140
AGGAGGAAGG TAGCTGCCGG ACTTCTACGC TTTCGCGTTG GCGGTGATAT GGATTTTCAT   1200
CGCTCGTTCT CCACCCAAGC GGGCCACCGC TTGCTGGTGT GGCGCCGCTC GAGCCGGAGC   1260
GTGTGCCTTG AACTTTACTC ACCATCTAAA AACTTTTTGC GTTACGATGT CTTGCCCTGT   1320
TCTGGAGACT ATGCAGCGAT GTTTTCTTTC GCGGCGGGCG GCCGTTTCCC TTTAGTTTTG   1380
ATGACTAGAA TTAGATACCC GAACGGGTTT TGTTACTTGG CTCACTGCCG GTACGCGTGC   1440
GCGTTTCTCT TAAGGGGTTT TGATCCGAAG CGTTTCGACA TCGGTGCTTT CCCCACCGCG   1500
GCCAAGCTCA GAAACCGTAT GGTTTCGGAG CTTGGTGAAA GAAGTTTAGG TTTGAACTTG   1560
TACGGCGCAT ATACGTCACG CGGCGTCTTT CACTGCGATT ATGACGCTAA GTTTATAAAG   1620
GATTTGCGTC TTATGTCAGC AGTTATAGCT GGAAAGGACG GGGTGGAAGA GGTGGTACCT   1680
TCTGACATAA CTCCTGCCAT GAAGCAGAAA ACGATCGAAG CCGTGTATGA TAGATTATAT   1740
GGCGGCACTG ACTCGTTGCT GAAACTGAGC ATCGAGAAAG ACTTAATCGA TTTCAAAAAT   1800
GACGTGCAGA GTTTGAAGAA AGATCGGCCG ATTGTCAAAG TGCCCTTTTA CATGTCGGAA   1860
GCAACACAGA ATTCGCTGAC GCGTTTCTAC CCTCAGTTCG AACTTAAGTT TTCGCACTCC   1920
TCGCATTCAG ATCATCCCGC CGCCGCCGCT TCTAGACTGC TGGAAAATGA AACGTTAGTG   1980
CGCTTATGTG GTAATAGCGT TTCAGATATT GGAGGTTGTC CTCTTTTCCA TTTGCATTCC   2040
AAGACGCAAA GACGGGTTCA CGTATGTAGG CCTGTGTTGG ATGGCAAGGA TGCGCAGCGT   2100
CGCGTGGTGC GTGATTTGCA GTATTCCAAC GTGCGTTTGG GAGACGATGA TAAAATTTTG   2160
GAAGGGCCAC GCAATATCGA CATTTGCCAC TATCCTCTGG GCGCGTGTGA CCACGAAAGT   2220
```

-continued

```
AGTGCTATGA TGATGGTGCA GGTGTATGAC GCGTCCCTTT ATGAGATATG TGGCGCCATG    2280

ATCAAGAAGA AAAGCCGCAT AACGTACTTA ACCATGGTCA CGCCCGGCGA GTTTCTTGAC    2340

GGACGCGAAT GCGTCTACAT GGAGTCGTTA GACTGTGAGA TTGAAGTTGA TGTGCACGCG    2400

GACGTCGTAA TGTACAAATT CGGTAGTTCT TGCTATTCGC ACAAGCTTTC AATCATCAAG    2460

GACATCATGA CCACTCCGTA CTTGACACTA GGTGGTTTTC TATTCAGCGT GGAGATGTAT    2520

GAGGTGCGTA TGGGCGTGAA TTACTTCAAG ATTACGAAGT CCGAAGTATC GCCTAGCATT    2580

AGCTGCACCA AGCTCCTGAG ATACCGAAGA GCTAATAGTG ACGTGGTTAA AGTTAAACTT    2640

CCACGTTTCG ATAAGAAACG TCGCATGTGT CTGCCTGGGT ATGACACCAT ATACCTAGAT    2700

TCGAAGTTTG TGAGTCGCGT TTTCGATTAT GTCGTGTGTA ATTGCTCTGC CGTGAACTCA    2760

AAAACTTTCG AGTGGGTGTG GAGTTTCATT AAGTCTAGTA AGTCGAGGGT GATTATTAGC    2820

GGTAAAATAA TTCACAAGGA TGTCAATTTG GACCTCAAGT ACGTCGAGAG TTTCGCCGCG    2880

GTTATGTTGG CCTCTGGCGT GCGCAGTAGA CTAGCGTCCG AGTACCTTGC TAAGAACCTT    2940

AGTCATTTTT CGGGAGATTG CTCCTTTATT GAAGGGAGGT CTTTCGTGTT GCGTGAGAAA    3000

ATCAGAAACA TGACTCTGAA TTTTAACGAA AGACTTTTAC AGTTAGTGAA GCGCGTTGCC    3060

TTTGCGACCT TGGACGTGAG TTTTCTAGAT TTAGATTCAA CTCTTGAATC AATAACTGAT    3120

TTTGCCGAGT GTAAGGTAGC GATTGAACTC GACGAGTTGG GTTGCTTGAG AGCGGAGGCC    3180

GAGAATGAAA AAATCAGGAA TCTGGCGGGA GATTCGATTG CGGCTAAACT CGCGAGCGAG    3240

ATAGTGGTCG ATATTGACTC TAAGCCTTCA CCGAAGCAGG TGGGTAATTC GTCATCCGAA    3300

AACGCCGATA AGCGGGAAGT TCAGAGGCCC GGTTTGCGTG GTGGTTCTAG AAACGGGGTT    3360

GTTGGGGAGT TCCTTCACTT CGTCGTGGAT TCTGCCTTGC GTCTTTTCAA ATACGCGACG    3420

GATCAACAAC GGATCAAGTC TTACGTGCGT TTCTTGGACT CGGCGGTCTC ATTCTTGGAT    3480

TACAACTACG ATAATCTATC GTTTATACTG CGAGTGCTTT CGGAAGGTTA TTCGTGTATG    3540

TTCGCGTTTT TGGCGAATCG CGGCGACTTA TCTAGTCGTG TCCGTAGCGC GGTGTGTGCT    3600

GTGAAAGAAG TTGCTACCTC ATGCGCGAAC GCGAGCGTTT CTAAAGCCAA GGTTATGATT    3660

ACCTTCGCAG CGGCCGTGTG TGCTATGATG TTTAATAGCT GCGGTTTTTC AGGCGACGGT    3720

CGGGAGTATA AATCGTATAT ACATCGTTAC ACGCAAGTAT TGTTTGACAC TATCTTTTTT    3780

GAGGACAGCA GTTACCTACC CATAGAAGTT CTGAGTTCGG CGATATGCGG TGCTATCGTC    3840

ACACTTTTCT CCTCGGGCTC GTCCATAAGT TTAAACGCCT TCTTACTTCA AATTACCAAA    3900

GGATTCTCCC TAGAGGTTGT CGTCCGGAAT GTTGTGCGAG TCACGCATGG TTTGAGCACC    3960

ACAGCGACCG ACGGCGTCAT ACGTGGGGTT TTCTCCCAAA TTGTGTCTCA CTTACTTGTT    4020

GGAAATACGG GTAATGTGGC TTACCAGTCA GCTTTCATTG CCGGGGTGGT GCCTCTTTTA    4080

GTTAAAAAGT GTGTGAGCTT AATCTTCATC TTGCGTGAAG ATACTTATTC CGGTTTTATT    4140

AAGCACGGAA TCAGTGAATT CTCTTTCCTT AGTAGTATTC TGAAGTTCTT GAAGGGTAAG    4200

CTTGTGGACG AGTTGAAATC GATTATTCAA GGGGTTTTTG ATTCCAACAA GCACGTGTTT    4260

AAAGAAGCTA CTCAGGAAGC GATTCGTACG ACGGTCATGC AAGTGCCTGT CGCTGTAGTG    4320

GATGCCCTTA AGAGCGCCGC GGGAAAAATT TATAACAATT TTACTAGTCG ACGTACCTTT    4380

GGTAAGGATG AAGGCTCCTC TAGCGACGGC GCATGTGAAG AGTATTTCTC ATGCGACGAA    4440

GGTGAAGGTC CGGGTCTGAA AGGGGGTTCC AGCTATGGCT TCTCAATTTT AGCGTTCTTT    4500

TCACGCATTA TGTGGGGAGC TCGTCGGCTT ATTGTTAAGG TGAAGCATGA GTGTTTTGGG    4560

AAACTTTTTG AATTTCTATC GCTCAAGCTT CACGAATTCA GGACTCGCGT TTTTGGGAAG    4620
```

-continued

```
AATAGAACGG ACGTGGGAGT TTACGATTTT TTGCCCACGG GCATCGTGGA AACGCTCTCA  4680

TCGATAGAAG AGTGCGACCA AATTGAAGAA CTTCTCGGCG ACGACCTGAA AGGTGACAAG  4740

GATGCTTCGT TGACCGATAT GAATTACTTT GAGTTCTCAG AAGACTTCTT AGCCTCTATC  4800

GAGGAGCCGC CTTTCGCTGG ATTGCGAGGA GGTAGCAAGA ACATCGCGAT TTTGGCGATT  4860

TTGGAATACG CGCATAATTT GTTTCGCATT GTCGCAAGCA AGTGTTCGAA ACGACCTTTA  4920

TTTCTTGCTT TCGCCGAACT CTCAAGCGCC CTTATCGAGA AATTTAAGGA GGTTTTCCCT  4980

CGTAAGAGCC AGCTCGTCGC TATCGTGCGC GAGTATACTC AGAGATTCCT CCGAAGTCGC  5040

ATGCGTGCGT TGGGTTTGAA TAACGAGTTC GTGGTAAAAT CTTTCGCCGA TTTGCTACCC  5100

GCATTAATGA AGCGGAAGGT TTCAGGTTCG TTCTTAGCTA GTGTTTATCG CCCACTTAGA  5160

GGTTTCTCAT ATATGTGTGT TTCAGCGGAG CGACGTGAAA AGTTTTTTGC TCTCGTGTGT  5220

TTAATCGGGT TAAGTCTCCC TTTCTTCGTG CGCATCGTAG GAGCGAAAGC GTGCGAAGAA  5280

CTCGTGTCCT CAGCGCGTCG CTTTTATGAG CGTATTAAAA TTTTTCTAAG GCAGAAGTAT  5340

GTCTCTCTTT CTAATTTCTT TTGTCACTTG TTTAGCTCTG ACGTTGATGA CAGTTCCGCA  5400

TCTGCAGGGT TGAAAGGTGG TGCGTCGCGA ATGACGCTCT TCCACCTTCT GGTTCGCCTT  5460

GCTAGTGCCC TCCTATCGTT AGGGTGGGAA GGGTTAAAGC TACTCTTATC GCACCACAAC  5520

TTGTTATTTT TGTGTTTTGC ATTGGTTGAC GATGTGAACG TCCTTATCAA AGTTCTTGGG  5580

GGTCTTTCTT TCTTTGTGCA ACCAATCTTT TCCTTGTTTG CGGCGATGCT TCTACAACCG  5640

GACAGGTTTG TGGAGTATTC CGAGAAACTT GTTACAGCGT TTGAATTTTT CTTAAAATGT  5700

TCGCCTCGCG CGCCTGCACT ACTCAAAGGG TTTTTTGAGT GCGTGGCGAA CAGCACTGTG  5760

TCAAAAACCG TTCGAAGACT TCTTCGCTGT TTCGTGAAGA TGCTCAAACT TCGAAAAGGG  5820

CGAGGGTTGC GTGCGGATGG TAGGGGTCTC CATCGGCAGA AAGCCGTACC CGTCATACCT  5880

TCTAATCGGG TCGTGACCGA CGGGGTTGAA AGACTTTCGG TAAAGATGCA AGGAGTTGAA  5940

GCGTTGCGTA CCGAATTGAG AATCTTAGAA GATTTAGATT CTGCCGTGAT CGAAAAACTC  6000

AATAGACGCA GAAATCGTGA CACTAATGAC GACGAATTTA CGCGCCCTGC TCATGAGCAG  6060

ATGCAAGAAG TCACCACTTT CTGTTCGAAA GCCAACTCTG CTGGTTTGGC CCTGGAAAGG  6120

GCAGTGCTTG TGGAAGACGC TATAAAGTCG GAGAAACTTT CTAAGACGGT TAATGAGATG  6180

GTGAGGAAAG GGAGTACCAC CAGCGAAGAA GTGGCCGTCG CTTTGTCGGA CGATGAAGCC  6240

GTGGAAGAAA TCTCTGTTGC TGACGAGCGA GACGATTCGC CTAAGACAGT CAGGATAAGC  6300

GAATACCTAA ATAGGTTAAA CTCAAGCTTC GAATTCCCGA AGCCTATTGT TGTGGACGAC  6360

AACAAGGATA CCGGGGGTCT AACGAACGCC GTGAGGGAGT TTTATTATAT GCAAGAACTT  6420

GCTCTTTTCG AAATCCACAG CAAACTGTGC ACCTACTACG ATCAACTGCG CATAGTCAAC  6480

TTCGATCGTT CCGTAGCACC ATGCAGCGAA GATGCTCAGC TGTACGTACG GAAGAACGGC  6540

TCAACGATAG TGCAGGGTAA AGAGGTACGT TTGCACATTA AGGATTTCCA CGATCACGAT  6600

TTCCTGTTTG ACGGAAAAAT TTCTATTAAC AAGCGGCGGC GAGGCGGAAA TGTTTTATAT  6660

CACGACAACC TCGCGTTCTT GGCGAGTAAT TTGTTCTTAG CCGGCTACCC CTTTTCAAGG  6720

AGCTTCGTCT TCACGAATTC GTCGGTCGAT ATTCTCCTCT ACGAAGCTCC ACCCGGAGGT  6780

GGTAAGACGA CGACGCTGAT TGACTCGTTC TTGAAGGTCT TCAAGAAAGG TGAGGTTTCC  6840

ACCATGATCT TAACCGCCAA CAAAAGTTCG CAGGTTGAGA TCCTAAAGAA AGTGGACAAG  6900

GAAGTGTCTA ACATTGAATG CCAGAAACGT AAAGACAAAA GATCTCCGAA AAAGAGCATT  6960

TACACCATCG ACGCTTATTT AATGCATCAC CGTGGTTGTG ATGCAGACGT TCTTTTCATC  7020
```

```
                          -continued
GATGAGTGTT TCATGGTTCA TGCGGGTAGC GTACTAGCTT GCATTGAGTT CACGAGGTGT     7080

CATAAAGTAA TGATCTTCGG GGATAGCCGG CAGATTCACT ACATTGAAAG GAACGAATTG     7140

GACAAGTGTT TGTATGGGGA TCTCGACAGG TTCGTGGACC TGCAGTGTCG GGTTTATGGT     7200

AATATTTCGT ACCGTTGTCC ATGGGATGTG TGCGCTTGGT TAAGCACAGT GTATGGCAAC     7260

CTAATCGCCA CCGTGAAGGG TGAAAGCGAA GGTAAGAGCA GCATGCGCAT TAACGAAATT     7320

AATTCAGTCG ACGATTTAGT CCCCGACGTG GGTTCCACGT TTCTGTGTAT GCTTCAGTCG     7380

GAGAAGTTGG AAATCAGCAA GCACTTTATT CGCAAGGGTT TGACTAAACT TAACGTTCTA     7440

ACGGTGCATG AGGCGCAAGG TGAGACGTAT GCGCGTGTGA ACCTTGTGCG ACTTAAGTTT     7500

CAGGAGGATG AACCCTTTAA ATCTATCAGG CACATAACCG TCGCTCTTTC TCGTCACACC     7560

GACAGCTTAA CTTATAACGT CTTAGCTGCT CGTCGAGGTG ACGCCACTTG CGATGCCATC     7620

CAGAAGGCTG CGGAATTGGT GAACAAGTTT CGCGTTTTTC CTACATCTTT TGGTGGTAGT     7680

GTTATCAATC TCAACGTGAA GAAGGACGTG GAAGATAACA GTAGGTGCAA GGCTTCGTCG     7740

GCACCATTGA GCGTAATCAA CGACTTTTTG AACGAAGTTA ATCCCGGTAC TGCGGTGATT     7800

GATTTTGGTG ATTTGTCCGC GGACTTCAGT ACTGGGCCTT TGAGTGCGG TGCCAGCGGT     7860

ATTGTGGTGC GGGACAACAT CTCCTCCAGC AACATCACTG ATCACGATAA GCAGCGTGTT     7920

TAGCGTAGTT CGGTCGCAGG CGATTCCGCG TAGAAAACCT TCTCTACAAG AAAATTTGTA     7980

TTCGTTTGAA GCGCGGAATT ATAACTTCTC GACTTGCGAC CGTAACACAT CTGCTTCAAT     8040

GTTCGGAGAG GCTATGGCGA TGAACTGTCT TCGTCGTTGC TTCGACCTAG ATGCCTTTTC     8100

GTCCCTGCGT GATGATGTGA TTAGTATCAC ACGTTCAGGC ATCGAACAAT GGCTGGAGAA     8160

ACGTACTCCT AGTCAGATTA AAGCATTAAT GAAGGATGTT GAATCGCCTT TGGAAATTGA     8220

CGATGAAATT TGTCGTTTTA AGTTGATGGT GAAGCGTGAC GCTAAGGTGA AGTTAGACTC     8280

TTCCTTGTTTA ACTAAACACA GCGCCGCTCA AAATATCATG TTTCATCGCA AGAGCATTAA     8340

TGCTATCTTC TCTCCTATCT TTAATGAGGT GAAAAACCGA ATAATGTGCT GTCTTAAGCC     8400

TAACATAAAG TTTTTTACGG AGATGACTAA CAGGGATTTT GCTTCTGTTG TCAGCAACAT     8460

GCTTGGTGAC GACGATGTGT ACCATATAGG TGAAGTTGAT TTCTCAAAGT ACGACAAGTC     8520

TCAAGATGCT TTCGTGAAGG CTTTTGAAGA AGTAATGTAT AAGGAACTCG GTGTTGATGA     8580

AGAGTTGCTG GCTATCTGGA TGTGCGGCGA GCGGTTATCG ATAGCTAACA CTCTCGATGG     8640

TCAGTTGTCC TTCACGATCG AGAATCAAAG GAAGTCGGGA GCTTCGAACA CTTGGATTGG     8700

TAACTCTCTC GTCACTTTGG GTATTTTAAG TCTTTACTAC GACGTTAGAA ATTTCGAGGC     8760

GTTGTACATC TCGGGCGATG ATTCTTTAAT TTTTTCTCGC AGCGAGATTT CGAATTATGC     8820

CGACGACATA TGCACTGACA TGGGTTTTGA GACAAAATTT ATGTCCCCAA GTGTCCCGTA     8880

CTTTTGTTCT AAATTTGTTG TTATGTGTGG TCATAAGACG TTTTTTGTTC CCGACCCGTA     8940

CAAGCTTTTT GTCAAGTTGG GAGCAGTCAA AGAGGATGTT TCAATGGATT TCCTTTTCGA     9000

GACTTTTACC TCCTTTAAAG ACTTAACCTC CGATTTTAAC GACGAGCGCT TAATTCAAAA     9060

GCTCGCTGAA CTTGTGGCTT TAAAATATGA GGTTCAAACC GGCAACACCA CCTTGGCGTT     9120

AAGTGTGATA CATTGTTTGC GTTCGAATTT CCTCTCGTTT AGCAAGTTAT ATCCTCGCGT     9180

GAAGGGATGG CAGGTTTTTT ACACGTCGGT TAAGAAAGCG CTTCTCAAGA GTGGGTGTTC     9240

TCTCTTCGAC AGTTTCATGA CCCCTTTTGG TCAGGCTGTC ATGGTTTGGG ATGATGAGTA     9300

GCGCTAACTT GTGCGCAGTT TCTTTGTTCG TGACATACAC CTTGTGTGTC ACCGTGCGTT     9360

TATAATGAAT CAGGTTTTGC AGTTTGAATG TTTGTTTCTG CTGAATCTCG CGGTTTTTGC     9420
```

-continued

```
TGTGACTTTC ATTTTCATTC TTCTGGTCTT CCGCGTGATT AAGTCTTTTC GCCAGAAGGG   9480

TCACGAAGCA CCTGTTCCCG TTGTTCGTGG CGGGGGTTTT TCAACCGTAG TGTAGTCAAA   9540

AGACGCGCAT ATGGTAGTTT TCGGTTTGGA CTTTGGCACC ACATTCTCTA CGGTGTGTGT   9600

GTACAAGGAT GGACGAGTTT TTTCATTCAA GCAGAATAAT TCGGCGTACA TCCCCACTTA   9660

CCTCTATCTC TTCTCCGATT CTAACCACAT GACTTTTGGT TACGAGGCCG AATCACTGAT   9720

GAGTAATCTG AAAGTTAAAG GTTCGTTTTA TAGAGATTTA AAACGTTGGG TGGGTTGCGA   9780

TTCGAGTAAC CTCGACGCGT ACCTTGACCG TTTAAAACCT CATTACTCGG TCCGCTTGGT   9840

TAAGATCGGC TCTGGCTTGA ACGAAACTGT TTCAATTGGA AACTTCGGGG GCACTGTTAA   9900

GTCTGAGGCT CATCTGCCAG GGTTGATAGC TCTCTTTATT AAGGCTGTCA TTAGTTGCGC   9960

GGAGGGCGCG TTTGCGTGCA CTTGCACCGG GGTTATTTGT TCAGTACCTG CCAATTATGA  10020

TAGCGTTCAA AGGAATTTCA CTGATCAGTG TGTTTCACTC AGCGGTTATC AGTGCGTATA  10080

TATGATCAAT GAACCTTCAG CGGCTGCGCT ATCTGCGTGT AATTCGATTG GAAAGAAGTC  10140

CGCAAATTTG GCTGTTTACG ATTTCGGTGG TGGGACCTTC GACGTGTCTA TCATTTCATA  10200

CCGCAACAAT ACTTTTGTTG TGCGAGCTTC TGGAGGCGAT CTAAATCTCG GTGGAAGGGA  10260

TGTTGATCGT GCGTTTCTCA CGCACCTCTT CTCTTTAACA TCGCTGGAAC CTGACCTCAC  10320

TTTGGATATC TCGAATCTGA AAGAATCTTT ATCAAAAACG GACGCAGAGA TAGTTTACAC  10380

TTTGAGAGGT GTCGATGGAA GAAAAGAAGA CGTTAGAGTA AACAAAAACA TTCTTACGTC  10440

GGTGATGCTC CCCTACGTGA ACAGAACGCT TAAGATATTA GAGTCAACCT TAAAATCGTA  10500

TGCTAAGAGT ATGAATGAGA GTGCGCGAGT TAAGTGCGAT TTAGTGCTGA TAGGAGGATC  10560

TTCATATCTT CCTGGCCTGG CAGACGTACT AACGAAGCAT CAGAGCGTTG ATCGTATCTT  10620

AAGAGTTTCG GATCCTCGGG CTGCCGTGGC CGTCGGTTGC GCATTATATT CTTCATGCCT  10680

CTCAGGATCT GGGGGGTTGC TACTGATCGA CTGTGCAGCT CACACTGTCG CTATAGCGGA  10740

CAGAAGTTGT CATCAAATCA TTTGCGCTCC AGCGGGGCA CCGATCCCCT TTTCAGGAAG  10800

CATGCCTTTG TACTTAGCCA GGGTCAACAA GAACTCGCAG CGTGAAGTCG CCGTGTTTGA  10860

AGGGGAGTAC GTTAAGTGCC CTAAGAACAG AAAGATCTGT GGAGCAAATA TAAGATTTTT  10920

TGATATAGGA GTGACGGGTG ATTCGTACGC ACCCGTTACC TTCTATATGG ATTTCTCCAT  10980

TTCAAGCGTA GGAGCCGTTT CATTCGTGGT GAGAGGTCCT GAGGGTAAGC AAGTGTCACT  11040

CACTGGAACT CCAGCGTATA ACTTTTCGTC TGTGGCTCTC GGATCACGCA GTGTCCGAGA  11100

ATTGCATATT AGTTTAAATA ATAAAGTTTT TCTCGGTTTG CTTCTACATA GAAAGGCGGA  11160

TCGACGAATA CTTTTCACTA AGGATGAAGC GATTCGATAC GCCGATTCAA TTGATATCGC  11220

GGATGTGCTA AAGGAATATA AAAGTTACGC GGCCAGTGCC TTACCACCAG ACGAGGATGT  11280

CGAATTACTC CTGGGAAAGT CTGTTCAAAA AGTTTTACGG GGAAGCAGAC TGGAAGAAAT  11340

ACCTCTCTAG GAGCATAGCA GCACACTCAA GTGAAATTAA AACTCTACCA GACATTCGAT  11400

TGTACGGCGG TAGGGTTGTA AAGAAGTCCG AATTCGAATC AGCACTTCCT AATTCTTTTG  11460

AACAGGAATT AGGACTGTTC ATACTGAGCG AACGGGAAGT GGGATGGAGC AAAATTATGCG  11520

GAATAACGGT GGAAGAAGCA GCATACGATC TTACGAATCC CAAGGCTTAT AAATTCACTG  11580

CCGAGACATG TAGCCCGGAT GTAAAAGGTG AAGGACAAAA ATACTCTATG GAAGACGTGA  11640

TGAATTTCAT GCGTTTATCA AATCTGGATG TTAACGACAA GATGCTGACG GAACAGTGTT  11700

GGTCGCTGTC CAATTCATGC GGTGAATTGA TCAACCCAGA CGACAAAGGG CGATTCGTGG  11760

CTCTCACCTT TAAGGACAGA GACACAGCTG ATGACACGGG TGCCGCCAAC GTGGAATGTC  11820
```

```
                            -continued
GCGTGGGCGA CTATCTAGTT TACGCTATGT CCCTGTTTGA GCAGAGGACC CAAAAATCGC    11880

AGTCTGGCAA CATCTCTCTG TACGAAAAGT ACTGTGAATA CATCAGGACC TACTTAGGGA    11940

GTACAGACCT GTTCTTCACA GCGCCGGACA GGATTCCGTT ACTTACGGGC ATCCTATACG    12000

ATTTTTGTAA GGAATACAAC GTTTTCTACT CGTCATATAA GAGAAACGTC GATAATTTCA    12060

GATTCTTCTT GGCGAATTAT ATGCCTTTGA TATCTGACGT CTTTGTCTTC CAGTGGGTAA    12120

AACCCGCGCC GGATGTTCGG CTGCTTTTTG AGTTAAGTGC AGCGGAACTA ACGCTGGAGG    12180

TTCCCACACT GAGTTTGATA GATTCTCAAG TTGTGGTAGG TCATATCTTA AGATACGTAG    12240

AATCCTACAC ATCAGATCCA GCCATCGACG CGTTAGAAGA CAAACTGGAA GCGATACTGA    12300

AAAGTAGCAA TCCCCGTCTA TCGACAGCGC AACTATGGGT TGGTTTCTTT TGTTACTATG    12360

GTGAGTTTCG TACGGCTCAA AGTAGAGTAG TGCAAAGACC AGGCGTATAC AAAACACCTG    12420

ACTCAGTGGG TGGATTTGAA ATAAACATGA AAGATGTTGA GAAATTCTTC GATAAACTTC    12480

AGAGAGAATT GCCTAATGTA TCTTTGCGGC GTCAGTTTAA CGGAGCTAGA GCGCATGAGG    12540

CTTTCAAAAT ATTTAAAAAC GGAAATATAA GTTTCAGACC TATATCGCGT TTAAACGTGC    12600

CTAGAGAGTT CTGGTATCTG AACATAGACT ACTTCAGGCA CGCGAATAGG TCCGGGTTAA    12660

CCGAAGAAGA AATACTCATC CTAAACAACA TAAGCGTTGA TGTTAGGAAG TTATGCGCTG    12720

AGAGAGCGTG CAATACCCTA CCTAGCGCGA AGCGCTTTAG TAAAAATCAT AAGAGTAATA    12780

TACAATCATC ACGCCAAGAG CGGAGGATTA AGACCCATT GGTAGTCCTG AAAGACACTT     12840

TATATGAGTT CCAACACAAG CGTGCCGGTT GGGGGTCTCG AAGCACTCGA GACCTCGGGA    12900

GTCGTGCTGA CCACGCGAAA GGAAGCGGTT GATAAGTTTT TTAATGAACT AAAAAACGAA    12960

AATTACTCAT CAGTTGACAG CAGCCGATTA AGCGATTCGG AAGTAAAAGA AGTGTTAGAG    13020

AAAAGTAAAG AAAGTTTCAA AAGCGAACTG GCCTCCACTG ACGAGCACTT CGTCTACCAC    13080

ATTATATTTT TCTTAATCCG ATGTGCTAAG ATATCGACAA GTGAAAAGGT GAAGTACGTT    13140

GGTAGTCATA CGTACGTGGT CGACGGAAAA ACGTACACCG TTCTTGACGC TTGGGTATTC    13200

AACATGATGA AAAGTCTCAC GAAGAAGTAC AAACGAGTGA ATGGTCTGCG TGCGTTCTGT    13260

TGCGCGTGCG AAGATCTATA TCTAACCGTC GCACCAATAA TGTCAGAACG CTTTAAGACT    13320

AAAGCCGTAG GGATGAAAGG TTTGCCTGTT GGAAAGGAAT ACTTAGGCGC CGACTTTCTT    13380

TCGGAACTA GCAAACTGAT GAGCGATCAC GACAGGGCGG TCTCCATCGT TGCAGCGAAA     13440

AACGCTGTCG ATCGTAGCGC TTTCACGGGT GGGGAGAGAA AGATAGTTAG TTTGTATGAT    13500

CTAGGGAGGT ACTAAGCACG GTGTGCTATA GTGCGTGCTA TAATAATAAA CACTAGTGCT    13560

TAAGTCGCGC AGAAGAAAAC GCTATGGAGT TGATGTCCGA CAGCAACCTT AGCAACCTGG    13620

TGATAACCGA CGCCTCTAGT CTAAATGGTG TCGACAAGAA GCTTTTATCT GCTGAAGTTG    13680

AAAAAATGTT GGTGCAGAAA GGGGCTCCTA ACGAGGGTAT AGAAGTGGTG TTCGGTCTAC    13740

TCCTTTACGC ACTCGCGGCA AGAACCACGT CTCCTAAGGT TCAGCGCGCA GATTCAGACG    13800

TTATATTTTC AAATAGTTTC GGAGAGAGGA ATGTGGTAGT AACAGAGGGT GACCTTAAGA    13860

AGGTACTCGA CGGGTGTGCG CCTCTCACTA GGTTCACTAA TAAACTTAGA ACGTTCGGTC    13920

GTACTTTCAC TGAGGCTTAC GTTGACTTTT GTATCGCGTA TAAGCACAAA TTACCCCAAC    13980

TCAACGCCGC GGCGGAATTG GGGATTCCAG CTGAAGATTC GTACTTAGCT GCAGATTTTC    14040

TGGGTACTTG CCCGAAGCTC TCTGAATTAC AGCAAAGTAG GAAGATGTTC GCGAGTATGT    14100

ACGCTCTAAA AACTGAAGGT GGAGTGGTAA ATACACCAGT GAGCAATCTG CGTCAGCTAG    14160

GTAGAAGGGA AGTTATGTAA TGGAAGATTA CGAAGAAAAA TCCGAATCGC TCATACTGCT    14220
```

-continued

```
ACGCACGAAT CTGAACACTA TGCTTTTAGT GGTCAAGTCC GATGCTAGTG TAGAGCTGCC   14280

TAAACTACTA ATTTGCGGTT ACTTACGAGT GTCAGGACGT GGGGAGGTGA CGTGTTGCAA   14340

CCGTGAGGAA TTAACAAGAG ATTTTGAGGG CAATCATCAT ACGGTGATCC GTTCTAGAAT   14400

CATACAATAT GACAGCGAGT CTGCTTTTGA GGAATTCAAC AACTCTGATT GCGTAGTGAA   14460

GTTTTTCCTA GAGACTGGTA GTGTCTTTTG GTTTTTCCTT CGAAGTGAAA CCAAAGGTAG   14520

AGCGGTGCGA CATTTGCGCA CCTTCTTCGA AGCTAACAAT TTCTTCTTTG GATCGCATTG   14580

CGGTACCATG GAGTATTGTT TGAAGCAGGT ACTAACTGAA ACTGAATCTA TAATCGATTC   14640

TTTTTGCGAA GAAAGAAATC GTTAAGATGA GGGTTATAGT GTCTCCTTAT GAAGCTGAAG   14700

ACATTCTGAA AAGATCGACT GACATGTTAC GAAACATAGA CAGTGGGGTC TTGAGCACTA   14760

AAGAATGTAT CAAGGCATTC TCGACGATAA CGCGAGACCT ACATTGTGCG AAGGCTTCCT   14820

ACCAGTGGGG TGTTGACACT GGGTTATATC AGCGTAATTG CGCTGAAAAA CGTTTAATTG   14880

ACACGGTGGA GTCAAACATA CGGTTGGCTC AACCTCTCGT GCGTGAAAAA GTGGCGGTTC   14940

ATTTTTGTAA GGATGAACCA AAAGAGCTAG TAGCATTCAT CACGCGAAAG TACGTGGAAC   15000

TCACGGGCGT GGGAGTGAGA GAAGCGGTGA AGAGGGAAAT GCGCTCTCTT ACCAAAACAG   15060

TTTTAAATAA AATGTCTTTG GAAATGGCGT TTTACATGTC ACCACGAGCG TGGAAAAACG   15120

CTGAATGGTT AGAACTAAAA TTTTCACCTG TGAAAATCTT TAGAGATCTG CTATTAGACG   15180

TGGAAACGCT CAACGAATTG TGCGCCGAAG ATGATGTTCA CGTCGACAAA GTAAATGAGA   15240

ATGGGGACGA AAATCACGAC CTCGAACTCC AAGAGGAATG TTAAACATTG GTTAAGTTTA   15300

ACGAAAATGA TTAGTAAATA ATAAATCGAA CGTGGGTGTA TCTACCTGAC GTATCAACTT   15360

AAGCTGTTAC TGAGTAATTA AACCAACAAG TGTTGGTGTA ATGTGTATGT TGATGTAGAG   15420

AAAAATCCGT TTGTAGAACG GTGTTTTTCT CTTCTTTATT TTTAAAAAAA AAATAAAAAA   15480

AAAAAAAAAA AAGCGGCCGC                                             15500
```

Another DNA molecule of the present invention (GLRaV-2 ORF1a) includes nucleotides 4–7923 of SEQ. ID. No. 1 and is believed to code for a large, grapevine leafroll virus polyprotein containing the conserved domains characteristic of two papain-like proteases, a methyltransferase, and a helicase. This DNA molecule comprises the nucleotide sequence corresponding to SEQ. ID. No. 2 as follows:

```
ACATTGCGAG AGAACCCCAT TAGCGTCTCC GGGGTGAACT TGGGAAGGTC TGCCGCCGCT    60

CAGGTTATTT ATTTCGGCAG TTTCACGCAG CCCTTCGCGT TGTATCCGCG CCAAGAGAGC   120

GCGATCGTAA AAACGCAACT TCCACCGGTC AGTGTAGTGA AGGTGGAGTG CGTAGCTGCG   180

GAGGTAGCTC CCGACAGGGG CGTGGTCGAC AAGAAACCTA CGTCTGTTGG CGTTCCCCCG   240

CAGCGCGGTG TGCTTTCTTT TCCGACGGTG GTTCGGAACC GCGGCGACGT GATAATCACA   300

GGGGTGGTGC ATGAAGCCCT GAAGAAAATT AAAGACGGGC TCTTACGCTT CCGCGTAGGC   360

GGTGACATGC GTTTTTCGAG ATTTTTCTCA TCGAACTACG GCTGCAGATT CGTCGCGAGC   420

GTGCGTACGA ACACTACAGT TTGGCTAAAT TGCACGAAAG CGAGTGGTGA GAAATTCTCA   480

CTCGCCGCCG CGTGCACGGC GGATTACGTG GCGATGCTGC GTTATGTGTG TGGCGGGAAA   540

TTTCCACTCG TCCTCATGAG TAGAGTTATT TACCCGGATG GGCGCTGTTA CTTGGCCCAT   600

ATGAGGTATT TGTGCGCCTT TTACTGTCGC CCGTTTAGAG AGTCGGATTA TGCCCTCGGA   660

ATGTGGCCTA CGGTGGCGCG TCTCAGGGCA TGCGTTGAGA GAACTTCGG TGTCGAAGCT   720

TGTGGCATAG CTCTTCGTGG CTATTACACC TCTCGCAATG TTTATCACTG TGATTATGAC   780

TCTGCTTATG TAAAATATTT TAGAAACCTT TCCGGCCGCA TTGGCGGTGG TTCGTTCGAT   840
```

-continued

```
CCGACATCTT TAACCTCCGT AATAACGGTG AAGATTAGCG GTCTTCCAGG TGGTCTTCCT    900

AAAAATATAG CGTTTGGTGC CTTCCTGTGC GATATACGTT ACGTCGAACC GGTAGACTCG    960

GGCGGCATTC AATCGAGCGT TAAGACGAAA CGTGAAGATG CGCACCGAAC CGTAGAGGAA   1020

CGGGCGGCCG GCGGATCCGT CGAGCAACCG CGACAAAAGA GGATAGATGA GAAAGGTTGC   1080

GGCAGAGTTC CTAGTGGAGG TTTTTCGCAT CTCCTGGTCG GCAACCTTAA CGAAGTTAGG   1140

AGGAAGGTAG CTGCCGGACT TCTACGCTTT CGCGTTGGCG GTGATATGGA TTTTCATCGC   1200

TCGTTCTCCA CCCAAGCGGG CCACCGCTTG CTGGTGTGGC GCCCCTCGAG CCGGAGCGTG   1260

TGCCTTGAAC TTTACTCACC ATCTAAAAAC TTTTTGCGTT ACGATGTCTT GCCCTGTTCT   1320

GGAGACTATG CAGCGATGTT TTCTTTCGCG GCGGGCGGCC GTTTCCCTTT AGTTTTGATG   1380

ACTAGAATTA GATACCCGAA CGGGTTTTGT TACTTGGCTC ACTGCCGGTA CGCGTGCGCG   1440

TTTCTCTTAA GGGGTTTTGA TCCGAAGCGT TTCGACATCG GTGCTTTCCC CACCGCGGCC   1500

AAGCTCAGAA ACCGTATGGT TTCGGAGCTT GGTGAAAGAA GTTAGGTTT GAACTTGTAC   1560

GGCGCATATA CGTCACGCGG CGTCTTTCAC TGCGATTATG ACGCTAAGTT TATAAAGGAT   1620

TTGCGTCTTA TGTCAGCAGT TATAGCTGGA AAGGACGGGG TGGAAGAGGT GGTACCTTCT   1680

GACATAACTC CTGCCATGAA GCAGAAAACG ATCGAAGCCG TGTATGATAG ATTATATGGC   1740

GGCACTGACT CGTTGCTGAA ACTGAGCATC GAGAAAGACT TAATCGATTT CAAAAATGAC   1800

GTGCAGAGTT TGAAGAAAGA TCGGCCGATT GTCAAAGTGC CCTTTTACAT GTCGGAAGCA   1860

ACACAGAATT CGCTGACGCG TTTCTACCCT CAGTTCGAAC TTAAGTTTTC GCACTCCTCG   1920

CATTCAGATC ATCCCGCCGC CGCCGCTTCT AGACTGCTGG AAAATGAAAC GTTAGTGCGC   1980

TTATGTGGTA ATAGCGTTTC AGATATTGGA GGTTGTCCTC TTTTCCATTT GCATTCCAAG   2040

ACGCAAAGAC GGGTTCACGT ATGTAGGCCT GTGTTGGATG GCAAGGATGC GCAGCGTCGC   2100

GTGGTGCGTG ATTTGCAGTA TTCCAACGTG CGTTTGGGAG ACGATGATAA AATTTTGGAA   2160

GGGCCACGCA ATATCGACAT TGCCACTAT CCTCTGGGCG CGTGTGACCA CGAAAGTAGT   2220

GCTATGATGA TGGTGCAGGT GTATGACGCG TCCCTTTATG AGATATGTGG CGCCATGATC   2280

AAGAAGAAAA GCCGCATAAC GTACTTAACC ATGGTCACGC CCGGCGAGTT TCTTGACGGA   2340

CGCGAATGCG TCTACATGGA GTCGTTAGAC TGTGAGATTG AAGTTGATGT GCACGCGGAC   2400

GTCGTAATGT ACAAATTCGG TAGTTCTTGC TATTCGCACA AGCTTTCAAT CATCAAGGAC   2460

ATCATGACCA CTCCGTACTT GACACTAGGT GGTTTTCTAT TCAGCGTGGA GATGTATGAG   2520

GTGCGTATGG GCGTGAATTA CTTCAAGATT ACGAAGTCCG AAGTATCGCC TAGCATTAGC   2580

TGCACCAAGC TCCTGAGATA CCGAAGAGCT AATAGTGACG TGGTTAAAGT TAAACTTCCA   2640

CGTTTCGATA AGAAACGTCG CATGTGTCTG CCTGGGTATG ACACCATATA CCTAGATTCG   2700

AAGTTTGTGA GTCGCGTTTT CGATTATGTC GTGTGTAATT GCTCTGCCGT GAACTCAAAA   2760

ACTTTCGAGT GGGTGTGGAG TTTCATTAAG TCTAGTAAGT CGAGGGTGAT TATTAGCGGT   2820

AAAATAATTC ACAAGGATGT GAATTTGGAC CTCAAGTACG TCGAGAGTTT CGCCGCGGTT   2880

ATGTTGGCCT CTGGCGTGCG CAGTAGACTA GCGTCCGAGT ACCTTGCTAA GAACCTTAGT   2940

CATTTTTCGG GAGATTGCTC CTTTATTGAA GCCACGTCTT TCGTGTTGCG TGAGAAAATC   3000

AGAAACATGA CTCTGAATTT TAACGAAAGA CTTTTACAGT TAGTGAAGCG CGTTGCCTTT   3060

GCGACCTTGG ACGTGAGTTT TCTAGATTTA GATTCAACTC TTGAATCAAT AACTGATTTT   3120

GCCGAGTGTA AGGTAGCGAT TGAACTCGAC GAGTTGGGTT GCTTGAGAGC GGAGGCCGAG   3180

AATGAAAAAA TCAGGAATCT GGCGGGAGAT TCGATTGCGG CTAAACTCGC GAGCGAGATA   3240
```

-continued

```
GTGGTCGATA TTGACTCTAA GCCTTCACCG AAGCAGGTGG GTAATTCGTC ATCCGAAAAC  3300

GCCGATAAGC GGGAAGTTCA GAGGCCCGGT TTGCGTGGTG GTTCTAGAAA CGGGGTTGTT  3360

GGGGAGTTCC TTCACTTCGT CGTGGATTCT GCCTTGCGTC TTTTCAAATA CGCGACGGAT  3420

CAACAACGGA TCAAGTCTTA CGTGCGTTTC TTGGACTCGG CGGTCTCATT CTTGGATTAC  3480

AACTACGATA ATCTATCGTT TATACTGCGA GTGCTTTCGG AAGGTTATTC GTGTATGTTC  3540

GCGTTTTTGG CCAATCCCGG CCACTTATCT AGTCGTGTCC GTAGCGCGGT GTGTGCTGTG  3600

AAAGAAGTTG CTACCTCATG CGCGAACGCG AGCGTTTCTA AAGCCAAGGT TATGATTACC  3660

TTCGCAGCGG CCGTGTGTGC TATGATGTTT AATAGCTGCG GTTTTTCAGG CGACGGTCGG  3720

GAGTATAAAT CGTATATACA TCGTTACACG CAAGTATTGT TTGACACTAT CTTTTTTGAG  3780

GACAGCAGTT ACCTACCCAT AGAAGTTCTG AGTTCGGCGA TATGCGGTGC TATCGTCACA  3840

CTTTTCTCCT CGGGCTCGTC CATAAGTTTA AACGCCTTCT TACTTCAAAT TACCAAAGGA  3900

TTCTCCCTAG AGGTTGTCGT CCGGAATGTT GTGCGAGTCA CGCATGGTTT GAGCACCACA  3960

GCGACCGACG GCGTCATACG TGGGGTTTTC TCCCAAATTG TGTCTCACTT ACTTGTTGGA  4020

AATACGGGTA ATGTGGCTTA CCAGTCAGCT TTCATTGCCG GGGTGGTGCC TCTTTTAGTT  4080

AAAAAGTGTG TGAGCTTAAT CTTCATCTTG CGTGAAGATA CTTATTCCGG TTTTATTAAG  4140

CACGGAATCA GTGAATTCTC TTTCCTTAGT AGTATTCTGA AGTTCTTGAA GGGTAAGCTT  4200

GTGGACGAGT TGAAATCGAT TATTCAAGGG GTTTTTGATT CCAACAAGCA CGTGTTTAAA  4260

GAAGCTACTC AGGAAGCGAT TCGTACGACG GTCATGCAAG TGCCTGTCGC TGTAGTGGAT  4320

GCCCTTAAGA GCGCCGCGGG AAAAATTTAT AACAATTTTA CTAGTCGACG TACCTTTGGT  4380

AAGGATGAAG GCTCCTCTAG CGACGGCGCA TGTGAAGAGT ATTTCTCATG CGACGAAGGT  4440

GAAGGTCCGG GTCTGAAAGG GGGTTCCAGC TATGGCTTCT CAATTTTAGC GTTCTTTTCA  4500

CGCATTATGT GGGGAGCTCG TCGGCTTATT GTTAAGGTGA AGCATGAGTG TTTTGGGAAA  4560

CTTTTTGAAT TTCTATCGCT CAAGCTTCAC GAATTCAGGA CTCGCGTTTT TGGGAAGAAT  4620

AGAACGGACG TGGGAGTTTA CGATTTTTTG CCCACGGGCA TCGTGGAAAC GCTCTCATCG  4680

ATAGAAGAGT GCGACCAAAT TGAAGAACTT CTCGGCGACG ACCTGAAAGG TGACAAGGAT  4740

GCTTCGTTGA CCGATATGAA TTACTTTGAG TTCTCAGAAG ACTTCTTAGC CTCTATCGAG  4800

GAGCCGCCTT TCGCTGGATT GCGAGGAGGT AGCAAGAACA TCGCGATTTT GGCGATTTTG  4860

GAATACGCGC ATAATTTGTT TCGCATTGTC GCAAGCAAGT GTTCGAAACG ACCTTTATTT  4920

CTTGCTTTCG CCGAACTCTC AAGCGCCCTT ATCGAGAAAT TTAAGGAGGT TTTCCCTCGT  4980

AAGAGCCAGC TCGTCGCTAT CGTGCGCGAG TATACTCAGA GATTCCTCCG AAGTCGCATG  5040

CGTGCGTTGG GTTTGAATAA CGAGTTCGTG GTAAAATCTT TCGCCGATTT GCTACCCGCA  5100

TTAATGAAGC GGAAGGTTTC AGGTTCGTTC TTAGCTAGTG TTTATCGCCC ACTTAGAGGT  5160

TTCTCATATA TGTGTGTTTC AGCGGAGCGA CGTGAAAAGT TTTTTGCTCT CGTGTCTTTA  5220

ATCGGGTTAA GTCTCCCTTT CTTCGTGCGC ATCGTAGGAG CGAAAGCGTG CGAAGAACTC  5280

GTGTCCTCAG CGCGTCGCTT TTATGAGCGT ATTAAAATTT TTCTAAGGCA GAAGTATGTC  5340

TCTCTTTCTA ATTTCTTTTG TCACTTGTTT AGCTCTGACG TTGATGACAG TTCCGCATCT  5400

GCAGGGTTGA AAGGTGGTGC GTCGCGAATG ACGCTCTTCC ACCTTCTGGT TCGCCTTGCT  5460

AGTGCCCTCC TATCGTTAGG GTGGGAAGGG TTAAAGCTAC TCTTATCGCA CCACAACTTG  5520

TTATTTTTGT GTTTTGCATT GGTTGACGAT GTGAACGTCC TTATCAAAGT TCTTGGGGGT  5580

CTTTCTTTCT TTGTGCAACC AATCTTTTCC TTGTTTGCGG CGATGCTTCT ACAACCGGAC  5640
```

```
AGGTTTGTGG AGTATTCCGA GAAACTTGTT ACAGCGTTTG AATTTTTCTT AAAATGTTCG   5700

CCTCGCGCGC CTGCACTACT CAAAGGGTTT TTTGAGTGCG TGGCGAACAG CACTGTGTCA   5760

AAAACCGTTC GAAGACTTCT TCGCTGTTTC GTGAAGATGC TCAAACTTCG AAAAGGGCGA   5820

GGGTTGCGTG CGGATGGTAG GGGTCTCCAT CGGCAGAAAG CCGTACCCGT CATACCTTCT   5880

AATCGGGTCG TGACCGACGG GGTTGAAAGA CTTTCGGTAA AGATGCAAGG AGTTGAAGCG   5940

TTGCGTACCG AATTGAGAAT CTTAGAAGAT TTAGATTCTG CCGTGATCGA AAAACTCAAT   6000

AGACGCAGAA ATCGTGACAC TAATGACGAC GAATTTACGC GCCCTGCTCA TGAGCAGATG   6060

CAAGAAGTCA CCACTTTCTG TTCGAAAGCC AACTCTGCTG GTTTGGCCCT GGAAAGGGCA   6120

GTGCTTGTGG AAGACGCTAT AAAGTCGGAG AAACTTTCTA AGACGGTTAA TGAGATGGTG   6180

AGGAAAGGGA GTACCACCAG CGAAGAAGTG GCCGTCGCTT TGTCGGACGA TGAAGCCGTG   6240

GAAGAAATCT CTGTTGCTGA CGAGCGAGAC GATTCGCCTA AGACAGTCAG GATAAGCGAA   6300

TACCTAAATA GGTTAAACTC AAGCTTCGAA TTCCCGAAGC CTATTGTTGT GGACGACAAC   6360

AAGGATACCG GGGGTCTAAC GAACGCCGTG AGGGAGTTTT ATTATATGCA AGAACTTGCT   6420

CTTTTCGAAA TCCACAGCAA ACTGTGCACC TACTACGATC AACTGCGCAT AGTCAACTTC   6480

GATCGTTCCG TAGCACCATG CAGCGAAGAT GCTCAGCTGT ACGTACGGAA GAACGGCTCA   6540

ACGATAGTGC AGGGTAAAGA GGTACGTTTG CACATTAAGG ATTTCCACGA TCACGATTTC   6600

CTGTTTGACG GAAAAATTTC TATTAACAAG CGGCGGCGAG GCGGAAATGT TTTATATCAC   6660

GACAACCTCG CGTTCTTGGC GAGTAATTTG TTCTTAGCCG GCTACCCCTT TTCAAGGAGC   6720

TTCGTCTTCA CGAATTCGTC GGTCGATATT CTCCTCTACG AAGCTCCACC CGGAGGTGGT   6780

AAGACGACGA CGCTGATTGA CTCGTTCTTG AAGGTCTTCA AGAAAGGTGA GGTTTCCACC   6840

ATGATCTTAA CCGCCAACAA AAGTTCGCAG GTTGAGATCC TAAAGAAAGT GGAGAAGGAA   6900

GTGTCTAACA TTGAATGCCA GAAACGTAAA GACAAAAGAT CTCCGAAAAA GAGCATTTAC   6960

ACCATCGACG CTTATTTAAT GCATCACCGT GGTTGTGATG CAGACGTTCT TTTCATCGAT   7020

GAGTGTTTCA TGGTTCATGC GGGTAGCGTA CTAGCTTGCA TTGAGTTCAC GAGGTGTCAT   7080

AAAGTAATGA TCTTCGGGGA TAGCCGGCAG ATTCACTACA TTGAAAGGAA CGAATTGGAC   7140

AAGTGTTTGT ATGGGGATCT CGACAGGTTC GTGGACCTGC AGTGTCGGGT TTATGGTAAT   7200

ATTTCGTACC GTTGTCCATG GGATGTGTGC GCTTGGTTAA GCACAGTGTA TGGCAACCTA   7260

ATCGCCACCG TGAAGGGTGA AAGCGAAGGT AAGAGCAGCA TGCGCATTAA CGAAATTAAT   7320

TCAGTCGACG ATTTAGTCCC CGACGTGGGT TCCACGTTTC TGTGTATGCT TCAGTCGGAG   7380

AAGTTGGAAA TCAGCAAGCA CTTTATTCGC AAGGGTTTGA CTAAACTTAA CGTTCTAACG   7440

GTGCATGAGG CGCAAGGTGA GACGTATGCG CGTGTGAACC TTGTGCGACT TAAGTTTCAG   7500

GAGGATGAAC CCTTTAAATC TATCAGGCAC ATAACCGTCG CTCTTTCTCG TCACACCGAC   7560

AGCTTAACTT ATAACGTCTT AGCTGCTCGT CGAGGTGACG CCACTTGCGA TGCCATCCAG   7620

AAGGCTGCGG AATTGGTGAA CAAGTTTCGC GTTTTTCCTA CATCTTTTGG TGGTAGTGTT   7680

ATCAATCTCA ACGTGAAGAA GGACGTGGAA GATAACAGTA GGTGCAAGGC TTCGTCGGCA   7740

CCATTGAGCG TAATCAACGA CTTTTTGAAC GAAGTTAATC CCGGTACTGC GGTGATTGAT   7800

TTTGGTGATT TGTCCGCGGA CTTCAGTACT GGGCCTTTTG AGTGCGGTGC CAGCGGTATT   7860

GTGGTGCGGG ACAACATCTC CTCCAGCAAC ATCACTGATC ACGATAAGCA GCGTGTTTAG   7920
```

The large polyprotein (papain-like proteases, methyltransferase, and helicase) has an amino acid sequence corresponding to SEQ. ID. No. 3 as follows:

```
Thr Leu Arg Glu Asn Pro Ile Ser Val Ser Gly Val Asn Leu Gly Arg
1               5                   10                  15

Ser Ala Ala Gln Val Ile Tyr Phe Gly Ser Phe Thr Gln Pro Phe
            20                  25                  30

Ala Leu Tyr Pro Arg Gln Glu Ser Ala Ile Val Lys Thr Gln Leu Pro
            35                  40                  45

Pro Val Ser Val Lys Val Glu Cys Val Ala Ala Glu Val Ala Pro
    50                  55                  60

Asp Arg Gly Val Val Asp Lys Lys Pro Thr Ser Val Gly Val Pro Pro
65                  70                  75                  80

Gln Arg Gly Val Leu Ser Phe Pro Thr Val Val Arg Asn Arg Gly Asp
                85                  90                  95

Val Ile Ile Thr Gly Val Val His Glu Ala Leu Lys Lys Ile Lys Asp
                100                 105                 110

Gly Leu Leu Arg Phe Arg Val Gly Gly Asp Met Arg Phe Ser Arg Phe
            115                 120                 125

Phe Ser Ser Asn Tyr Gly Cys Arg Phe Val Ala Ser Val Arg Thr Asn
    130                 135                 140

Thr Thr Val Trp Leu Asn Cys Thr Lys Ala Ser Gly Glu Lys Phe Ser
145                 150                 155                 160

Leu Ala Ala Cys Thr Ala Asp Tyr Val Ala Met Leu Arg Tyr Val
                165                 170                 175

Cys Gly Gly Lys Phe Pro Leu Val Leu Met Ser Arg Val Ile Tyr Pro
            180                 185                 190

Asp Gly Arg Cys Tyr Leu Ala His Met Arg Tyr Leu Cys Ala Phe Tyr
            195                 200                 205

Cys Arg Pro Phe Arg Glu Ser Asp Tyr Ala Leu Gly Met Trp Pro Thr
    210                 215                 220

Val Ala Arg Leu Arg Ala Cys Val Glu Lys Asn Phe Gly Val Glu Ala
225                 230                 235                 240

Cys Gly Ile Ala Leu Arg Gly Tyr Tyr Thr Ser Arg Asn Val Tyr His
                245                 250                 255

Cys Asp Tyr Asp Ser Ala Tyr Val Lys Tyr Phe Arg Asn Leu Ser Gly
            260                 265                 270

Arg Ile Gly Gly Gly Ser Phe Asp Pro Thr Ser Leu Thr Ser Val Ile
        275                 280                 285

Thr Val Lys Ile Ser Gly Leu Pro Gly Gly Leu Pro Lys Asn Ile Ala
    290                 295                 300

Phe Gly Ala Phe Leu Cys Asp Ile Arg Tyr Val Glu Pro Val Asp Ser
305                 310                 315                 320

Gly Gly Ile Gln Ser Ser Val Lys Thr Lys Arg Glu Asp Ala His Arg
                325                 330                 335

Thr Val Glu Glu Arg Ala Ala Gly Gly Ser Val Glu Gln Pro Arg Gln
            340                 345                 350

Lys Arg Ile Asp Glu Lys Gly Cys Gly Arg Val Pro Ser Gly Gly Phe
            355                 360                 365

Ser His Leu Leu Val Gly Asn Leu Asn Glu Val Arg Arg Lys Val Ala
        370                 375                 380

Ala Gly Leu Leu Arg Phe Arg Val Gly Gly Asp Met Asp Phe His Arg
385                 390                 395                 400
```

-continued

```
Ser Phe Ser Thr Gln Ala Gly His Arg Leu Leu Val Trp Arg Arg Ser
                405                 410                 415

Ser Arg Ser Val Cys Leu Glu Leu Tyr Ser Pro Ser Lys Asn Phe Leu
            420                 425                 430

Arg Tyr Asp Val Leu Pro Cys Ser Gly Asp Tyr Ala Ala Met Phe Ser
        435                 440                 445

Phe Ala Ala Gly Gly Arg Phe Pro Leu Val Leu Met Thr Arg Ile Arg
    450                 455                 460

Tyr Pro Asn Gly Phe Cys Tyr Leu Ala His Cys Arg Tyr Ala Cys Ala
465                 470                 475                 480

Phe Leu Leu Arg Gly Phe Asp Pro Lys Arg Phe Asp Ile Gly Ala Phe
            485                 490                 495

Pro Thr Ala Ala Lys Leu Arg Asn Arg Met Val Ser Glu Leu Gly Glu
        500                 505                 510

Arg Ser Leu Gly Leu Asn Leu Tyr Gly Ala Tyr Thr Ser Arg Gly Val
    515                 520                 525

Phe His Cys Asp Tyr Asp Ala Lys Phe Ile Lys Asp Leu Arg Leu Met
530                 535                 540

Ser Ala Val Ile Ala Gly Lys Asp Gly Val Glu Glu Val Val Pro Ser
545                 550                 555                 560

Asp Ile Thr Pro Ala Met Lys Gln Lys Thr Ile Glu Ala Val Tyr Asp
            565                 570                 575

Arg Leu Tyr Gly Gly Thr Asp Ser Leu Leu Lys Leu Ser Ile Glu Lys
        580                 585                 590

Asp Leu Ile Asp Phe Lys Asn Asp Val Gln Ser Leu Lys Lys Asp Arg
    595                 600                 605

Pro Ile Val Lys Val Pro Phe Tyr Met Ser Glu Ala Thr Gln Asn Ser
610                 615                 620

Leu Thr Arg Phe Tyr Pro Gln Phe Glu Leu Lys Phe Ser His Ser Ser
625                 630                 635                 640

His Ser Asp His Pro Ala Ala Ala Ser Arg Leu Leu Glu Asn Glu
            645                 650                 655

Thr Leu Val Arg Leu Cys Gly Asn Ser Val Ser Asp Ile Gly Gly Cys
        660                 665                 670

Pro Leu Phe His Leu His Ser Lys Thr Gln Arg Arg Val His Val Cys
    675                 680                 685

Arg Pro Val Leu Asp Gly Lys Asp Ala Gln Arg Arg Val Val Arg Asp
690                 695                 700

Leu Gln Tyr Ser Asn Val Arg Leu Gly Asp Asp Lys Ile Leu Glu
705                 710                 715                 720

Gly Pro Arg Asn Ile Asp Ile Cys His Tyr Pro Leu Gly Ala Cys Asp
            725                 730                 735

His Glu Ser Ser Ala Met Met Val Gln Val Tyr Asp Ala Ser Leu
        740                 745                 750

Tyr Glu Ile Cys Gly Ala Met Ile Lys Lys Ser Arg Ile Thr Tyr
    755                 760                 765

Leu Thr Met Val Thr Pro Gly Glu Phe Leu Asp Gly Arg Glu Cys Val
    770                 775                 780

Tyr Met Glu Ser Leu Asp Cys Glu Ile Glu Val Asp Val His Ala Asp
785                 790                 795                 800

Val Val Met Tyr Lys Phe Gly Ser Ser Cys Tyr Ser His Lys Leu Ser
            805                 810                 815

Ile Ile Lys Asp Ile Met Thr Thr Pro Tyr Leu Thr Leu Gly Gly Phe
        820                 825                 830
```

-continued

Leu Phe Ser Val Glu Met Tyr Glu Val Arg Met Gly Val Asn Tyr Phe
            835                 840                 845
Lys Ile Thr Lys Ser Glu Val Ser Pro Ser Ile Ser Cys Thr Lys Leu
            850                 855                 860
Leu Arg Tyr Arg Arg Ala Asn Ser Asp Val Val Lys Val Lys Leu Pro
865                 870                 875                 880
Arg Phe Asp Lys Lys Arg Arg Met Cys Leu Pro Gly Tyr Asp Thr Ile
            885                 890                 895
Tyr Leu Asp Ser Lys Phe Val Ser Arg Val Phe Asp Tyr Val Val Cys
            900                 905                 910
Asn Cys Ser Ala Val Asn Ser Lys Thr Phe Glu Trp Val Trp Ser Phe
            915                 920                 925
Ile Lys Ser Ser Lys Ser Arg Val Ile Ile Ser Gly Lys Ile Ile His
            930                 935                 940
Lys Asp Val Asn Leu Asp Leu Lys Tyr Val Glu Ser Phe Ala Ala Val
945                 950                 955                 960
Met Leu Ala Ser Gly Val Arg Ser Arg Leu Ala Ser Glu Tyr Leu Ala
            965                 970                 975
Lys Asn Leu Ser His Phe Ser Gly Asp Cys Ser Phe Ile Glu Ala Thr
            980                 985                 990
Ser Phe Val Leu Arg Glu Lys Ile Arg Asn Met Thr Leu Asn Phe Asn
            995                 1000                1005
Glu Arg Leu Leu Gln Leu Val Lys Arg Val Ala Phe Ala Thr Leu Asp
            1010                1015                1020
Val Ser Phe Leu Asp Leu Asp Ser Thr Leu Glu Ser Ile Thr Asp Phe
1025                1030                1035                1040
Ala Glu Cys Lys Val Ala Ile Glu Leu Asp Glu Leu Gly Cys Leu Arg
            1045                1050                1055
Ala Glu Ala Glu Asn Glu Lys Ile Arg Asn Leu Ala Gly Asp Ser Ile
            1060                1065                1070
Ala Ala Lys Leu Ala Ser Glu Ile Val Asp Ile Asp Ser Lys Pro
            1075                1080                1085
Ser Pro Lys Gln Val Gly Asn Ser Ser Glu Asn Ala Asp Lys Arg
            1090                1095                1100
Glu Val Gln Arg Pro Gly Leu Arg Gly Gly Ser Arg Asn Gly Val Val
1105                1110                1115                1120
Gly Glu Phe Leu His Phe Val Val Asp Ser Ala Leu Arg Leu Phe Lys
            1125                1130                1135
Tyr Ala Thr Asp Gln Gln Arg Ile Lys Ser Tyr Val Arg Phe Leu Asp
            1140                1145                1150
Ser Ala Val Ser Phe Leu Asp Tyr Asn Tyr Asp Asn Leu Ser Phe Ile
            1155                1160                1165
Leu Arg Val Leu Ser Glu Gly Tyr Ser Cys Met Phe Ala Phe Leu Ala
            1170                1175                1180
Asn Arg Gly Asp Leu Ser Ser Arg Val Arg Ser Ala Val Cys Ala Val
1185                1190                1195                1200
Lys Glu Val Ala Thr Ser Cys Ala Asn Ala Ser Val Ser Lys Ala Lys
            1205                1210                1215
Val Met Ile Thr Phe Ala Ala Val Cys Ala Met Met Phe Asn Ser
            1220                1225                1230
Cys Gly Phe Ser Gly Asp Gly Arg Glu Tyr Lys Ser Tyr Ile His Arg
            1235                1240                1245
Tyr Thr Gln Val Leu Phe Asp Thr Ile Phe Phe Glu Asp Ser Ser Tyr

-continued

```
                1250                1255                1260
Leu Pro Ile Glu Val Leu Ser Ser Ala Ile Cys Gly Ala Ile Val Thr
1265                1270                1275                1280
Leu Phe Ser Ser Gly Ser Ser Ile Ser Leu Asn Ala Phe Leu Leu Gln
                1285                1290                1295
Ile Thr Lys Gly Phe Ser Leu Glu Val Val Arg Asn Val Val Arg
                1300                1305                1310
Val Thr His Gly Leu Ser Thr Thr Ala Thr Asp Gly Val Ile Arg Gly
                1315                1320                1325
Val Phe Ser Gln Ile Val Ser His Leu Leu Val Gly Asn Thr Gly Asn
                1330                1335                1340
Val Ala Tyr Gln Ser Ala Phe Ile Ala Gly Val Val Pro Leu Leu Val
1345                1350                1355                1360
Lys Lys Cys Val Ser Leu Ile Phe Ile Leu Arg Glu Asp Thr Tyr Ser
                1365                1370                1375
Gly Phe Ile Lys His Gly Ile Ser Glu Phe Ser Phe Leu Ser Ser Ile
                1380                1385                1390
Leu Lys Phe Leu Lys Gly Lys Leu Val Asp Glu Leu Lys Ser Ile Ile
                1395                1400                1405
Gln Gly Val Phe Asp Ser Asn Lys His Val Phe Lys Glu Ala Thr Gln
                1410                1415                1420
Glu Ala Ile Arg Thr Thr Val Met Gln Val Pro Val Ala Val Val Asp
1425                1430                1435                1440
Ala Leu Lys Ser Ala Ala Gly Lys Ile Tyr Asn Asn Phe Thr Ser Arg
                1445                1450                1455
Arg Thr Phe Gly Lys Asp Glu Gly Ser Ser Ser Asp Gly Ala Cys Glu
                1460                1465                1470
Glu Tyr Phe Ser Cys Asp Glu Gly Glu Pro Gly Leu Lys Gly Gly
                1475                1480                1485
Ser Ser Tyr Gly Phe Ser Ile Leu Ala Phe Phe Ser Arg Ile Met Trp
                1490                1495                1500
Gly Ala Arg Arg Leu Ile Val Lys Val Lys His Glu Cys Phe Gly Lys
1505                1510                1515                1520
Leu Phe Glu Phe Leu Ser Leu Lys Leu His Glu Phe Arg Thr Arg Val
                1525                1530                1535
Phe Gly Lys Asn Arg Thr Asp Val Gly Val Tyr Asp Phe Leu Pro Thr
                1540                1545                1550
Gly Ile Val Glu Thr Leu Ser Ser Ile Glu Glu Cys Asp Gln Ile Glu
                1555                1560                1565
Glu Leu Leu Gly Asp Asp Leu Lys Gly Asp Lys Asp Ala Ser Leu Thr
                1570                1575                1590
Asp Met Asn Tyr Phe Glu Phe Ser Glu Asp Phe Leu Ala Ser Ile Glu
1585                1580                1595                1600
Glu Pro Pro Phe Ala Gly Leu Arg Gly Gly Ser Lys Asn Ile Ala Ile
                1605                1610                1615
Leu Ala Ile Leu Glu Tyr Ala His Asn Leu Phe Arg Ile Val Ala Ser
                1620                1625                1630
Lys Cys Ser Lys Arg Pro Leu Phe Leu Ala Phe Ala Glu Leu Ser Ser
                1635                1640                1645
Ala Leu Ile Glu Lys Phe Lys Glu Val Phe Pro Arg Lys Ser Gln Leu
                1650                1655                1660
Val Ala Ile Val Arg Glu Tyr Thr Gln Arg Phe Leu Arg Ser Arg Met
1665                1670                1675                1680
```

-continued

```
Arg Ala Leu Gly Leu Asn Asn Glu Phe Val Val Lys Ser Phe Ala Asp
            1685                1690                1695
Leu Leu Pro Ala Leu Met Lys Arg Lys Val Ser Gly Ser Phe Leu Ala
            1700                1705                1710
Ser Val Tyr Arg Pro Leu Arg Gly Phe Ser Tyr Met Cys Val Ser Ala
            1715                1720                1725
Glu Arg Arg Glu Lys Phe Phe Ala Leu Val Cys Leu Ile Gly Leu Ser
            1730                1735                1740
Leu Pro Phe Phe Val Arg Ile Val Gly Ala Lys Ala Cys Glu Glu Leu
1745                1750                1755                1760
Val Ser Ser Ala Arg Arg Phe Tyr Glu Arg Ile Lys Ile Phe Leu Arg
            1765                1770                1775
Gln Lys Tyr Val Ser Leu Ser Asn Phe Phe Cys His Leu Phe Ser Ser
            1780                1785                1790
Asp Val Asp Asp Ser Ser Ala Ser Ala Gly Leu Lys Gly Gly Ala Ser
            1795                1800                1805
Arg Met Thr Leu Phe His Leu Leu Val Arg Leu Ala Ser Ala Leu Leu
            1810                1815                1820
Ser Leu Gly Trp Glu Gly Leu Lys Leu Leu Ser His His Asn Leu
1825                1830                1835                1840
Leu Phe Leu Cys Phe Ala Leu Val Asp Asp Val Asn Val Leu Ile Lys
            1845                1850                1855
Val Leu Gly Gly Leu Ser Phe Phe Val Gln Pro Ile Phe Ser Leu Phe
            1660                1865                1870
Ala Ala Met Leu Leu Gln Pro Asp Arg Phe Val Glu Tyr Ser Glu Lys
            1875                1880                1885
Leu Val Thr Ala Phe Glu Phe Phe Leu Lys Cys Ser Pro Arg Ala Pro
            1890                1895                1900
Ala Leu Leu Lys Gly Phe Phe Glu Cys Val Ala Asn Ser Thr Val Ser
1905                1910                1915                1920
Lys Thr Val Arg Arg Leu Leu Arg Cys Phe Val Lys Met Leu Lys Leu
            1925                1930                1935
Arg Lys Gly Arg Gly Leu Arg Ala Asp Gly Arg Gly Leu His Arg Gln
            1940                1945                1950
Lys Ala Val Pro Val Ile Pro Ser Asn Arg Val Val Thr Asp Gly Val
            1955                1960                1965
Glu Arg Leu Ser Val Lys Met Gln Gly Val Glu Ala Leu Arg Thr Glu
            1970                1975                1980
Leu Arg Ile Leu Glu Asp Leu Asp Ser Ala Val Ile Glu Lys Leu Asn
1985                1990                1995                2000
Arg Arg Arg Asn Arg Asp Thr Asn Asp Asp Glu Phe Thr Arg Pro Ala
            2005                2010                2015
His Glu Gln Met Gln Glu Val Thr Thr Phe Cys Ser Lys Ala Asn Ser
            2020                2025                2030
Ala Gly Leu Ala Leu Glu Arg Ala Val Leu Val Glu Asp Ala Ile Lys
            2035                2040                2045
Ser Glu Lys Leu Ser Lys Thr Val Asn Glu Met Val Arg Lys Gly Ser
            2050                2055                2060
Thr Thr Ser Glu Glu Val Ala Val Ala Leu Ser Asp Glu Ala Val
2065                2070                2075                2080
Glu Glu Ile Ser Val Ala Asp Glu Arg Asp Asp Ser Pro Lys Thr Val
            2085                2090                2095
Arg Ile Ser Glu Tyr Leu Asn Arg Leu Asn Ser Ser Phe Glu Phe Pro
            2100                2105                2110
```

```
Lys Pro Ile Val Val Asp Asp Asn Lys Asp Thr Gly Gly Leu Thr Asn
            2115                2120                2125

Ala Val Arg Glu Phe Tyr Tyr Met Gln Glu Leu Ala Leu Phe Glu Ile
        2130                2135                2140

His Ser Lys Leu Cys Thr Tyr Tyr Asp Gln Leu Arg Ile Val Asn Phe
2145                2150                2155                2160

Asp Arg Ser Val Ala Pro Cys Ser Glu Asp Ala Gln Leu Tyr Val Arg
            2165                2170                2175

Lys Asn Gly Ser Thr Ile Val Gln Gly Lys Glu Val Arg Leu His Ile
        2180                2185                2190

Lys Asp Phe His Asp His Asp Phe Leu Phe Asp Gly Lys Ile Ser Ile
        2195                2200                2205

Asn Lys Arg Arg Arg Gly Gly Asn Val Leu Tyr His Asp Asn Leu Ala
        2210                2215                2220

Phe Leu Ala Ser Asn Leu Phe Leu Ala Gly Tyr Pro Phe Ser Arg Ser
2225                2230                2235                2240

Phe Val Phe Thr Asn Ser Ser Val Asp Ile Leu Leu Tyr Glu Ala Pro
            2245                2250                2255

Pro Gly Gly Gly Lys Thr Thr Leu Ile Asp Ser Phe Leu Lys Val
        2260                2265                2270

Phe Lys Lys Gly Glu Val Ser Thr Met Ile Leu Thr Ala Asn Lys Ser
        2275                2280                2285

Ser Gln Val Glu Ile Leu Lys Lys Val Glu Lys Glu Val Ser Asn Ile
2290                2295                2300

Glu Cys Gln Lys Arg Lys Asp Lys Arg Ser Pro Lys Lys Ser Ile Tyr
2305                2310                2315                2320

Thr Ile Asp Ala Tyr Leu Met His His Arg Gly Cys Asp Ala Asp Val
            2325                2330                2335

Leu Phe Ile Asp Glu Cys Phe Met Val His Ala Gly Ser Val Leu Ala
        2340                2345                2350

Cys Ile Glu Phe Thr Arg Cys His Lys Val Met Ile Phe Gly Asp Ser
            2355                2360                2365

Arg Gln Ile His Tyr Ile Glu Arg Asn Glu Leu Asp Lys Cys Leu Tyr
        2370                2375                2380

Gly Asp Leu Asp Arg Phe Val Asp Leu Gln Cys Arg Val Tyr Gly Asn
2385                2390                2395                2400

Ile Ser Tyr Arg Cys Pro Trp Asp Val Cys Ala Trp Leu Ser Thr Val
            2405                2410                2415

Tyr Gly Asn Leu Ile Ala Thr Val Lys Gly Glu Ser Glu Gly Lys Ser
            2420                2425                2430

Ser Met Arg Ile Asn Glu Ile Asn Ser Val Asp Asp Leu Val Pro Asp
        2435                2440                2445

Val Gly Ser Thr Phe Leu Cys Met Leu Gln Ser Glu Lys Leu Glu Ile
        2450                2455                2460

Ser Lys His Phe Ile Arg Lys Gly Leu Thr Lys Leu Asn Val Leu Thr
2465                2470                2475                2480

Val His Glu Ala Gln Gly Glu Thr Tyr Ala Arg Val Asn Leu Val Arg
            2485                2490                2495

Leu Lys Phe Gln Glu Asp Glu Pro Phe Lys Ser Ile Arg His Ile Thr
            2500                2505                2510

Val Ala Leu Ser Arg His Thr Asp Ser Leu Thr Tyr Asn Val Leu Ala
            2515                2520                2525

Ala Arg Arg Gly Asp Ala Thr Cys Asp Ala Ile Gln Lys Ala Ala Glu
```

```
                          -continued
        2530              2535          2540
Leu Val Asn Lys Phe Arg Val Phe Pro Thr Ser Phe Gly Gly Ser Val
2545                2550              2555              2560

Ile Asn Leu Asn Val Lys Lys Asp Val Glu Asp Asn Ser Arg Cys Lys
                2565              2570              2575

Ala Ser Ser Ala Pro Leu Ser Val Ile Asn Asp Phe Leu Asn Glu Val
            2580              2585              2590

Asn Pro Gly Thr Ala Val Ile Asp Phe Gly Asp Leu Ser Ala Asp Phe
        2595              2600              2605

Ser Thr Gly Pro Phe Glu Cys Gly Ala Ser Gly Ile Val Val Arg Asp
    2610              2615              2620

Asn Ile Ser Ser Ser Asn Ile Thr Asp His Asp Lys Gln Arg Val
2625                2630              2635
``` and has a molecular weight of about 290 to 300 kDa, preferably 294 kDa.

Another such DNA molecule (GLRaV-2 ORF1b) includes nucleotides 7922–9301 of SEQ. ID. No. 1 and codes for a grapevine leafroll virus RNA-dependent RNA polymerase (RdRP). This DNA molecule comprises the nucleotide sequence corresponding to SEQ. ID. No. 4 as follows:

```
AGCGTAGTTC GGTCGCAGGC GATTCCGCGT AGAAAACCTT CTCTACAAGA AAATTTGTAT    60

TCGTTTGAAG CGCGGAATTA TAACTTCTCG ACTTGCGACC GTAACACATC TGCTTCAATG   120

TTCGGAGAGG CTATGGCGAT GAACTGTCTT CGTCGTTGCT TCGACCTAGA TGCCTTTTCG   180

TCCCTGCGTG ATGATGTGAT TAGTATCACA CGTTCAGGCA TCGAACAATG GCTGGAGAAA   240

CGTACTCCTA GTCAGATTAA AGCATTAATG AAGGATGTTG AATCGCCTTT GGAAATTGAC   300

GATGAAATTT GTCGTTTTAA GTTGATGGTG AAGCGTGACG CTAAGGTGAA GTTAGACTCT   360

TCTTGTTTAA CTAAACACAG CGCCGCTCAA AATATCATGT TCATCGCAA GAGCATTAAT   420

GCTATCTTCT CTCCTATCTT TAATGAGGTG AAAAACCGAA TAATGTGCTG TCTTAAGCCT   480

AACATAAAGT TTTTTACGGA GATGACTAAC AGGGATTTTG CTTCTGTTGT CAGCAACATG   540

CTTGGTGACG ACGATGTGTA CCATATAGGT GAAGTTGATT TCTCAAAGTA CGACAAGTCT   600

CAAGATGCTT TCGTGAAGGC TTTTGAAGAA GTAATGTATA AGGAACTCGG TGTTGATGAA   660

GAGTTGCTGG CTATCTGGAT GTGCGGCGAG CGGTTATCGA TAGCTAACAC TCTCGATGGT   720

CAGTTGTCCT TCACGATCGA GAATCAAAGG AAGTCGGGAG CTTCGAACAC TTGGATTGGT   780

AACTCTCTCG TCACTTTGGG TATTTTAAGT CTTTACTACG ACGTTAGAAA TTTCGAGGCG   840

TTGTACATCT CGGGCGATGA TTCTTTAATT TTTTCTCGCA GCGAGATTTC GAATTATGCC   900

GACGACATAT GCACTGACAT GGGTTTTGAG ACAAAATTTA TGTCCCCAAG TGTCCCGTAC   960

TTTTGTTCTA AATTTGTTGT TATGTGTGGT CATAAGACGT TTTTTGTTCC CGACCCGTAC  1020

AAGCTTTTTG TCAAGTTGGG AGCAGTCAAA GAGGATGTTT CAATGGATTT CCTTTTCGAG  1080

ACTTTTACCT CCTTTAAAGA CTTAACCTCC GATTTTAACG ACGAGCGCTT AATTCAAAAG  1140

CTCGCTGAAC TTGTGGCTTT AAAATATGAG GTTCAAACCG GCAACACCAC CTTGGCGTTA  1200

AGTGTGATAC ATTGTTTGCG TTCGAATTTC CTCTCGTTTA GCAAGTTATA TCCTCGCGTG  1260

AAGGGATGGC AGGTTTTTTA CACGTCGGTT AAGAAAGCGC TTCTCAAGAG TGGGTGTTCT  1320

CTCTTCGACA GTTTCATGAC CCCTTTTGGT CAGGCTGTCA TGGTTTGGGA TGATGAGTAG  1380
```

The RNA-dependent RNA polymerase has an amino acid sequence corresponding to SEQ. ID. No. 5 as follows:

```
Ser Val Val Arg Ser Gln Ala Ile Pro Arg Arg Lys Pro Ser Leu Gln
1               5                   10                  15

Glu Asn Leu Tyr Ser Phe Glu Ala Arg Asn Tyr Asn Phe Ser Thr Cys
                20                  25                  30

Asp Arg Asn Thr Ser Ala Ser Met Phe Gly Glu Ala Met Ala Met Asn
            35                  40                  45

Cys Leu Arg Arg Cys Phe Asp Leu Asp Ala Phe Ser Ser Leu Arg Asp
        50                  55                  60

Asp Val Ile Ser Ile Thr Arg Ser Gly Ile Glu Gln Trp Leu Glu Lys
65                  70                  75                  80

Arg Thr Pro Ser Gln Ile Lys Ala Leu Met Lys Asp Val Glu Ser Pro
                85                  90                  95

Leu Glu Ile Asp Asp Glu Ile Cys Arg Phe Lys Leu Met Val Lys Arg
                100                 105                 110

Asp Ala Lys Val Lys Leu Asp Ser Ser Cys Leu Thr Lys His Ser Ala
            115                 120                 125

Ala Gln Asn Ile Met Phe His Arg Lys Ser Ile Asn Ala Ile Phe Ser
        130                 135                 140

Pro Ile Phe Asn Glu Val Lys Asn Arg Ile Met Cys Cys Leu Lys Pro
145                 150                 155                 160

Asn Ile Lys Phe Phe Thr Glu Met Thr Asn Arg Asp Phe Ala Ser Val
                165                 170                 175

Val Ser Asn Met Leu Gly Asp Asp Val Tyr His Ile Gly Glu Val
            180                 185                 190

Asp Phe Ser Lys Tyr Asp Lys Ser Gln Asp Ala Phe Val Lys Ala Phe
        195                 200                 205

Glu Glu Val Met Tyr Lys Glu Leu Gly Val Asp Glu Glu Leu Leu Ala
        210                 215                 220

Ile Trp Met Cys Gly Glu Arg Leu Ser Ile Ala Asn Thr Leu Asp Gly
225                 230                 235                 240

Gln Leu Ser Phe Thr Ile Glu Asn Gln Arg Lys Ser Gly Ala Ser Asn
                245                 250                 255

Thr Trp Ile Gly Asn Ser Leu Val Thr Leu Gly Ile Leu Ser Leu Tyr
                260                 265                 270

Tyr Asp Val Arg Asn Phe Glu Ala Leu Tyr Ile Ser Gly Asp Asp Ser
            275                 280                 285

Leu Ile Phe Ser Arg Ser Glu Ile Ser Asn Tyr Ala Asp Asp Ile Cys
        290                 295                 300

Thr Asp Met Gly Phe Glu Thr Lys Phe Met Ser Pro Ser Val Pro Tyr
305                 310                 315                 320

Phe Cys Ser Lys Phe Val Met Cys Gly His Lys Thr Phe Phe Val
                325                 330                 335

Pro Asp Pro Tyr Lys Leu Phe Val Lys Leu Gly Ala Val Lys Glu Asp
            340                 345                 350

Val Ser Met Asp Phe Leu Phe Glu Thr Phe Thr Ser Phe Lys Asp Leu
        355                 360                 365

Thr Ser Asp Phe Asn Asp Glu Arg Leu Ile Gln Lys Leu Ala Glu Leu
        370                 375                 380

Val Ala Leu Lys Tyr Glu Val Gln Thr Gly Asn Thr Thr Leu Ala Leu
385                 390                 395                 400

Ser Val Ile His Cys Leu Arg Ser Asn Phe Leu Ser Phe Ser Lys Leu
```

```
                    405               410              415
Tyr Pro Arg Val Lys Gly Trp Gln Val Phe Tyr Thr Ser Val Lys Lys
            420              425              430

Ala Leu Leu Lys Ser Gly Cys Ser Leu Phe Asp Ser Phe Met Thr Pro
        435              440              445

Phe Gly Gln Ala Val Met Val Trp Asp Asp Glu
    450              455
``` and a molecular weight from about 50 to about 54 kDa, preferably about 52 kDa.

Another such DNA molecule (GLRaV-2 ORF2) includes nucleotides 9365–9535 of SEQ. ID. No. 1 and codes for a small, grapevine leafroll virus hydrophobic protein or polypeptide. This DNA molecule comprises the nucleotide sequence corresponding to SEQ. ID. No. 6 as follows:

```
ATGAATCAGG TTTTGCAGTT TGAATGTTTG TTTCTGCTGA ATCTCGCGGT TTTTGCTGTG   60
ACTTTCATTT TCATTCTTCT GGTCTTCCGC GTGATTAAGT CTTTTCGCCA GAAGGGTCAC  120
GAAGCACCTG TTCCCGTTGT TCGTGGCGGG GGTTTTTCAA CCGTAGTGTA G           171
```

The small hydrophobic protein or polypeptide has an amino acid sequence corresponding to SEQ. ID. No. 7 as follows:

```
Met Asn Gln Val Leu Gln Phe Glu Cys Leu Phe Leu Leu Asn Leu Ala
1               5                   10                  15

Val Phe Ala Val Thr Phe Ile Phe Ile Leu Leu Val Phe Arg Val Ile
            20                  25                  30

Lys Ser Phe Arg Gln Lys Gly His Glu Ala Pro Val Pro Val Val Arg
                35                  40                  45

Gly Gly Gly Phe Ser Thr Val Val
    50                  55
``` and a molecular weight from about 5 to about 7 kDa, preferably about 6 kDa.

Another such DNA molecule (GLRaV-2 ORF3) includes nucleotides 9551–11350 of SEQ. ID. No. 1 and encodes for a grapevine leafroll virus heat shock 70 protein. This DNA molecule comprises the nucleotide sequence corresponding to SEQ. ID. No. 8 as follows:

```
ATGGTAGTTT TCGGTTTGGA CTTTGGCACC ACATTCTCTA CGGTGTGTGT GTACAAGGAT   60
GGACGAGTTT TTTCATTCAA GCAGAATAAT TCGGCGTACA TCCCCACTTA CCTCTATCTC  120
TTCTCCGATT CTAACCACAT GACTTTTGGT TACGAGGCCG AATCACTGAT GAGTAATCTG  180
AAAGTTAAAG GTTCGTTTTA TAGAGATTTA AAACGTTGGG TGGGTTGCGA TTCGAGTAAC  240
CTCGACGCGT ACCTTGACCG TTTAAAACCT CATTACTCGG TCCGCTTGGT TAAGATCGGC  300
TCTGGCTTGA ACGAAACTGT TTCAATTGGA AACTTCGGGG GCACTGTTAA GTCTGAGGCT  360
CATCTGCCAG GGTTGATAGC TCTCTTTATT AAGGCTGTCA TTAGTTGCGC GGAGGGCGCG  420
TTTGCGTGCA CTTGCACCGG GGTTATTTGT TCAGTACCTG CCAATTATGA TAGCGTTCAA  480
AGGAATTTCA CTGATCAGTG TGTTTCACTC AGCGGTTATC AGTGCGTATA TATGATCAAT  540
GAACCTTCAG CGGCTGCGCT ATCTGCGTGT AATTCGATTG GAAAGAAGTC CGCAAATTTG  600
GCTGTTTACG ATTTCGGTGG TGGGACCTTC GACGTGTCTA TCATTTCATA CCGCAACAAT  660
```

```
                          -continued
ACTTTTGTTG TGCGAGCTTC TGGAGGCGAT CTAAATCTCG GTGGAAGGGA TGTTGATCGT   720

GCGTTTCTCA CGCACCTCTT CTCTTTAACA TCGCTGGAAC CTGACCTCAC TTTGGATATC   780

TCGAATCTGA AAGAATCTTT ATCAAAAACG GACGCAGAGA TAGTTTACAC TTTGAGAGGT   840

GTCGATGGAA GAAAAGAAGA CGTTAGAGTA AACAAAAACA TTCTTACGTC GGTGATGCTC   900

CCCTACGTGA ACAGAACGCT TAAGATATTA GAGTCAACCT TAAAATCGTA TGCTAAGAGT   960

ATGAATGAGA GTGCGCGAGT TAAGTGCGAT TTAGTGCTGA TAGGAGGATC TTCATATCTT  1020

CCTGGCCTGG CAGACGTACT AACGAAGCAT CAGAGCGTTG ATCGTATCTT AAGAGTTTCG  1080

GATCCTCGGG CTGCCGTGGC CGTCGGTTGC GCATTATATT CTTCATGCCT CTCAGGATCT  1140

GGGGGGTTGC TACTGATCGA CTGTGCAGCT CACACTGTCG CTATAGCGGA CAGAAGTTGT  1200

CATCAAATCA TTTGCGCTCC AGCGGGGGCA CCGATCCCCT TTTCAGGAAG CATGCCTTTG  1260

TACTTAGCCA GGGTCAACAA GAACTCGCAG CGTGAAGTCG CCGTGTTTGA AGGGGAGTAC  1320

GTTAAGTGCC CTAAGAACAG AAAGATCTGT GGAGCAAATA TAAGATTTTT TGATATAGGA  1380

GTGACGGGTG ATTCGTACGC ACCCGTTACC TTCTATATGG ATTTCTCCAT TTCAAGCGTA  1440

GGAGCCGTTT CATTCGTGGT GAGAGGTCCT GAGGGTAAGC AAGTGTCACT CACTGGAACT  1500

CCAGCGTATA ACTTTTCGTC TGTGGCTCTC GGATCACGCA GTGTCCGAGA ATTGCATATT  1560

AGTTTAAATA ATAAAGTTTT TCTCGGTTTG CTTCTACATA GAAAGGCGGA TCGACGAATA  1620

CTTTTCACTA AGGATGAAGC GATTCGATAC GCCGATTCAA TTGATATCGC GGATGTGCTA  1680

AAGGAATATA AAAGTTACGC GGCCAGTGCC TTACCACCAG ACGAGGATGT CGAATTACTC  1740

CTGGGAAAGT CTGTTCAAAA AGTTTTACGG GGAAGCAGAC TGGAAGAAAT ACCTCTCTAG  1800
```

The heat shock 70 protein is believed to function as a chaperone protein and has an amino acid sequence corresponding to SEQ. ID. No. 9 as follows:

```
Met Val Val Phe Gly Leu Asp Phe Gly Thr Thr Phe Ser Thr Val Cys
1               5                   10                  15

Val Tyr Lys Asp Gly Arg Val Phe Ser Phe Lys Gln Asn Asn Ser Ala
            20                  25                  30

Tyr Ile Pro Thr Tyr Leu Tyr Leu Phe Ser Asp Ser Asn His Met Thr
        35                  40                  45

Phe Gly Tyr Glu Ala Glu Ser Leu Met Ser Asn Leu Lys Val Lys Gly
    50                  55                  60

Ser Phe Tyr Arg Asp Leu Lys Arg Trp Val Gly Cys Asp Ser Ser Asn
65                  70                  75                  80

Leu Asp Ala Tyr Leu Asp Arg Leu Lys Pro His Tyr Ser Val Arg Leu
                85                  90                  95

Val Lys Ile Gly Ser Gly Leu Asn Glu Thr Val Ser Ile Gly Asn Phe
            100                 105                 110

Gly Gly Thr Val Lys Ser Glu Ala His Leu Pro Gly Leu Ile Ala Leu
        115                 120                 125

Phe Ile Lys Ala Val Ile Ser Cys Ala Glu Gly Ala Phe Ala Cys Thr
    130                 135                 140

Cys Thr Gly Val Ile Cys Ser Val Pro Ala Asn Tyr Asp Ser Val Gln
145                 150                 155                 160

Arg Asn Phe Thr Asp Gln Cys Val Ser Leu Ser Gly Tyr Gln Cys Val
                165                 170                 175

Tyr Met Ile Asn Glu Pro Ser Ala Ala Ala Leu Ser Ala Cys Asn Ser
```

-continued

```
                 180                     185                     190
Ile Gly Lys Lys Ser Ala Asn Leu Ala Val Tyr Asp Phe Gly Gly
            195                     200                 205

Thr Phe Asp Val Ser Ile Ile Ser Tyr Arg Asn Asn Thr Phe Val Val
        210                     215                 220

Arg Ala Ser Gly Gly Asp Leu Asn Leu Gly Gly Arg Asp Val Asp Arg
225                     230                     235                     240

Ala Phe Leu Thr His Leu Phe Ser Leu Thr Ser Leu Glu Pro Asp Leu
                245                     250                     255

Thr Leu Asp Ile Ser Asn Leu Lys Glu Ser Leu Ser Lys Thr Asp Ala
                260                     265                     270

Glu Ile Val Tyr Thr Leu Arg Gly Val Asp Gly Arg Lys Glu Asp Val
            275                     280                     285

Arg Val Asn Lys Asn Ile Leu Thr Ser Val Met Leu Pro Tyr Val Asn
        290                     295                     300

Arg Thr Leu Lys Ile Leu Glu Ser Thr Leu Lys Ser Tyr Ala Lys Ser
305                     310                     315                     320

Met Asn Glu Ser Ala Arg Val Lys Cys Asp Leu Val Leu Ile Gly Gly
                325                     330                     335

Ser Ser Tyr Leu Pro Gly Leu Ala Asp Val Leu Thr Lys His Gln Ser
            340                     345                     350

Val Asp Arg Ile Leu Arg Val Ser Asp Pro Arg Ala Ala Val Ala Val
        355                     360                     365

Gly Cys Ala Leu Tyr Ser Ser Cys Leu Ser Gly Ser Gly Leu Leu
        370                     375                     380

Leu Ile Asp Cys Ala Ala His Thr Val Ala Ile Ala Asp Arg Ser Cys
385                     390                     395                     400

His Gln Ile Ile Cys Ala Pro Ala Gly Ala Pro Ile Pro Phe Ser Gly
                405                     410                     415

Ser Met Pro Leu Tyr Leu Ala Arg Val Asn Lys Asn Ser Gln Arg Glu
            420                     425                     430

Val Ala Val Phe Glu Gly Glu Tyr Val Lys Cys Pro Lys Asn Arg Lys
        435                     440                     445

Ile Cys Gly Ala Asn Ile Arg Phe Phe Asp Ile Gly Val Thr Gly Asp
450                     455                     460

Ser Tyr Ala Pro Val Thr Phe Tyr Met Asp Phe Ser Ile Ser Ser Val
465                     470                     475                     480

Gly Ala Val Ser Phe Val Val Arg Gly Pro Glu Gly Lys Gln Val Ser
            465                     490                     495

Leu Thr Gly Thr Pro Ala Tyr Asn Phe Ser Val Ala Leu Gly Ser
                500                     505                     510

Arg Ser Val Arg Glu Leu His Ile Ser Leu Asn Asn Lys Val Phe Leu
            515                     520                     525

Gly Leu Leu Leu His Arg Lys Ala Asp Arg Arg Ile Leu Phe Thr Lys
        530                     535                     540

Asp Glu Ala Ile Arg Tyr Ala Asp Ser Ile Asp Ile Ala Asp Val Leu
545                     550                     555                     560

Lys Glu Tyr Lys Ser Tyr Ala Ala Ser Ala Leu Pro Pro Asp Glu Asp
                565                     570                     575

Val Glu Leu Leu Leu Gly Lys Ser Val Gln Lys Val Leu Arg Gly Ser
            580                     585                     590

Arg Leu Glu Glu Ile Pro Leu
        595
``` and a molecular weight from about 63 to about 67 kDa, preferably about 65 kDa.

Another such DNA molecule (GLRaV-2 ORF4) includes nucleotides 11277–12932 of SEQ. ID. No. 1 and codes for a putative grapevine leafroll virus heat shock 90 protein. This DNA molecule comprises a nucleotide sequence corresponding to SEQ. ID. No. 10 as follows:

```
ATGTCGAATT ACTCCTGGGA AAGTCTGTTC AAAAAGTTTT ACGGGGAAGC AGACTGGAAG    60
AAATACCTCT CTAGGAGCAT AGCAGCACAC TCAAGTGAAA TTAAAACTCT ACCAGACATT   120
CGATTGTACG GCGGTAGGGT TGTAAAGAAG TCCGAATTCG AATCAGCACT TCCTAATTCT   180
TTTGAACAGG AATTAGGACT GTTCATACTG AGCGAACGGG AAGTGGGATG GAGCAAATTA   240
TGCGGAATAA CGGTGGAAGA AGCAGCATAC GATCTTACGA ATCCCAAGGC TTATAAATTC   300
ACTGCCGAGA CATGTAGCCC GGATGTAAAA GGTGAAGGAC AAAAATACTC TATGGAAGAC   360
GTGATGAATT TCATGCGTTT ATCAAATCTG GATGTTAACG ACAAGATGCT GACGGAACAG   420
TGTTGGTCGC TGTCCAATTC ATGCGGTGAA TTGATCAACC CAGACGACAA AGGGCGATTC   480
GTGGCTCTCA CCTTTAAGGA CAGAGACACA GCTGATGACA CGGGTGCCGC CAACGTGGAA   540
TGTCGCGTGG GCGACTATCT AGTTTACGCT ATGTCCCTGT TGAGCAGAG GACCCAAAAA   600
TCGCAGTCTG GCAACATCTC TCTGTACGAA AAGTACTGTG AATACATCAG GACCTACTTA   660
GGGAGTACAG ACCTGTTCTT CACAGCGCCG GACAGGATTC CGTTACTTAC GGGCATCCTA   720
TACGATTTTT GTAAGGAATA CAACGTTTTC TACTCGTCAT ATAAGAGAAA CGTCGATAAT   780
TTCAGATTCT TCTTGGCGAA TTATATGCCT TTGATATCTG ACGTCTTTGT CTTCCAGTGG   840
GTAAAACCCG CGCCGGATGT TCGGCTGCTT TTTGAGTTAA GTGCAGCGGA ACTAACGCTG   900
GAGGTTCCCA CACTGAGTTT GATAGATTCT CAAGTTGTGG TAGGTCATAT CTTAAGATAC   960
GTAGAATCCT ACACATCAGA TCCAGCCATC GACGCGTTAG AAGACAAACT GGAAGCGATA  1020
CTGAAAAGTA GCAATCCCCG TCTATCGACA GCGCAACTAT GGGTTGGTTT CTTTTGTTAC  1080
TATGGTGAGT TTCGTACGGC TCAAAGTAGA GTAGTGCAAA GACCAGGCGT ATACAAAACA  1140
CCTGACTCAG TGGGTGGATT TGAAATAAAC ATGAAAGATG TTGAGAAATT CTTCGATAAA  1200
CTTCAGAGAG AATTGCCTAA TGTATCTTTG CGGCGTCAGT TTAACGGAGC TAGAGCGCAT  1260
GAGGCTTTCA AAATATTTAA AAACGGAAAT ATAAGTTTCA GACCTATATC GCGTTTAAAC  1320
GTGCCTAGAG AGTTCTGGTA TCTGAACATA GACTACTTCA GGCACGCGAA TAGGTCCGGG  1380
TTAACCGAAG AAGAAATACT CATCCTAAAC AACATAAGCG TTGATGTTAG GAAGTTATGC  1440
GCTGAGAGAG CGTGCAATAC CCTACCTAGC GCGAAGCGCT TTAGTAAAAA TCATAAGAGT  1500
AATATACAAT CATCACGCCA AGAGCGGAGG ATTAAAGACC CATTGGTAGT CCTGAAAGAC  1560
ACTTTATATG AGTTCCAACA CAAGCGTGCC GGTTGGGGGT CTCGAAGCAC TCGAGACCTC  1620
GGGAGTCGTG CTGACCACGC GAAAGGAAGC GGTTGA                            1656
```

The heat shock 90 protein has an amino acid sequence corresponding to SEQ. ID. No. 11 as follows:

```
Met Ser Asn Tyr Ser Trp Glu Ser Leu Phe Lys Lys Phe Tyr Gly Glu
 1               5                  10                  15

Ala Asp Trp Lys Lys Tyr Leu Ser Arg Ser Ile Ala Ala His Ser Ser
                20                  25                  30

Glu Ile Lys Thr Leu Pro Asp Ile Arg Leu Tyr Gly Gly Arg Val Val
            35                  40                  45

Lys Lys Ser Glu Phe Glu Ser Ala Leu Pro Asn Ser Phe Glu Gln Glu
        50                  55                  60
```

```
Leu Gly Leu Phe Ile Leu Ser Glu Arg Glu Val Gly Trp Ser Lys Leu
 65                  70                  75                  80

Cys Gly Ile Thr Val Glu Glu Ala Ala Tyr Asp Leu Thr Asn Pro Lys
             85                  90                  95

Ala Tyr Lys Phe Thr Ala Glu Thr Cys Ser Pro Asp Val Lys Gly Glu
             100                 105                 110

Gly Gln Lys Tyr Ser Met Glu Asp Val Met Asn Phe Met Arg Leu Ser
             115                 120                 125

Asn Leu Asp Val Asn Asp Lys Met Leu Thr Glu Gln Cys Trp Ser Leu
130                 135                 140

Ser Asn Ser Cys Gly Glu Leu Ile Asn Pro Asp Lys Gly Arg Phe
145                 150                 155                 160

Val Ala Leu Thr Phe Lys Asp Arg Asp Thr Ala Asp Thr Gly Ala
             165                 170                 175

Ala Asn Val Glu Cys Arg Val Gly Asp Tyr Leu Val Tyr Ala Met Ser
             180                 185                 190

Leu Phe Glu Gln Arg Thr Gln Lys Ser Gln Ser Gly Asn Ile Ser Leu
     195                 200                 205

Tyr Glu Lys Tyr Cys Glu Tyr Ile Arg Thr Tyr Leu Gly Ser Thr Asp
     210                 215                 220

Leu Phe Phe Thr Ala Pro Asp Arg Ile Pro Leu Leu Thr Gly Ile Leu
225                 230                 235                 240

Tyr Asp Phe Cys Lys Glu Tyr Asn Val Phe Tyr Ser Tyr Lys Arg
             245                 250                 255

Asn Val Asp Asn Phe Arg Phe Phe Leu Ala Asn Tyr Met Pro Leu Ile
             260                 265                 270

Ser Asp Val Phe Val Phe Gln Trp Val Lys Pro Ala Pro Asp Val Arg
     275                 280                 285

Leu Leu Phe Glu Leu Ser Ala Ala Glu Leu Thr Leu Glu Val Pro Thr
     290                 295                 300

Leu Ser Leu Ile Asp Ser Gln Val Val Gly His Ile Leu Arg Tyr
305                 310                 315                 320

Val Glu Ser Tyr Thr Ser Asp Pro Ala Ile Asp Ala Leu Glu Asp Lys
             325                 330                 335

Leu Glu Ala Ile Leu Lys Ser Ser Asn Pro Arg Leu Ser Thr Ala Gln
             340                 345                 350

Leu Trp Val Gly Phe Phe Cys Tyr Tyr Gly Glu Phe Arg Thr Ala Gln
             355                 360                 365

Ser Arg Val Val Gln Arg Pro Gly Val Tyr Lys Thr Pro Asp Ser Val
370                 375                 380

Gly Gly Phe Glu Ile Asn Met Lys Asp Val Glu Lys Phe Phe Asp Lys
385                 390                 395                 400

Leu Gln Arg Glu Leu Prc Asn Val Ser Leu Arg Arg Gln Phe Asn Gly
             405                 410                 415

Ala Arg Ala His Glu Ala Phe Lys Ile Phe Lys Asn Gly Asn Ile Ser
             420                 425                 430

Phe Arg Pro Ile Ser Arg Leu Asn Val Pro Arg Glu Phe Trp Tyr Leu
             435                 440                 445

Asn Ile Asp Tyr Phe Arg His Ala Asn Arg Ser Gly Leu Thr Glu Glu
450                 455                 460

Glu Ile Leu Ile Leu Asn Asn Ile Ser Val Asp Val Arg Lys Leu Cys
465                 470                 475                 480

Ala Glu Arg Ala Cys Asn Thr Leu Pro Ser Ala Lys Arg Phe Ser Lys
```

```
                485                490                495
Asn His Lys Ser Asn Ile Gln Ser Ser Arg Gln Glu Arg Arg Ile Lys
            500                505                510

Asp Pro Leu Val Val Leu Lys Asp Thr Leu Tyr Glu Phe Gln His Lys
            515                520                525

Arg Ala Gly Trp Gly Ser Arg Ser Thr Arg Asp Leu Gly Ser Arg Ala
            530                535                540

Asp His Ala Lys Gly Ser Gly
545                550
``` and a molecular weight from about 61 to about 65 kDa, preferably about 63 kDa.

Yet another DNA molecule of the present invention (GLRaV-2 ORF5) includes nucleotides 12844–13515 of SEQ. ID. No. 1 and codes for a diverged coat protein. This DNA molecule comprises a nucleotide sequence corresponding to SEQ. ID. No. 12 as follows:

```
ATGAGTTCCA ACACAAGCGT GCCGGTTGGG GGTCTCGAAG CACTCGAGAC CTCGGGAGTC    60

GTGCTGACCA CGCGAAAGGA AGCGGTTGAT AAGTTTTTTA ATGAACTAAA AAACGAAAAT   120

TACTCATCAG TTGACAGCAG CCGATTAAGC GATTCGGAAG TAAAAGAAGT GTTAGAGAAA   180

AGTAAAGAAA GTTTCAAAAG CGAACTGGCC TCCACTGACG AGCACTTCGT CTACCACATT   240

ATATTTTTCT TAATCCGATG TGCTAAGATA TCGACAAGTG AAAAGGTGAA GTACGTTGGT   300

AGTCATACGT ACGTGGTCGA CGGAAAAACG TACACCGTTC TTGACGCTTG GGTATTCAAC   360

ATGATGAAAA GTCTCACGAA GAAGTACAAA CGAGTGAATG GTCTGCGTGC GTTCTGTTGC   420

GCGTGCGAAG ATCTATATCT AACCGTCGCA CCAATAATGT CAGAACGCTT TAAGACTAAA   480

GCCGTAGGGA TGAAAGGTTT GCCTGTTGGA AAGGAATACT TAGGCGCCGA CTTTCTTTCG   540

GGAACTAGCA AACTGATGAG CGATCACGAC AGGGCGGTCT CCATCGTTGC AGCGAAAAAC   600

GCTGTCGATC GTAGCGCTTT CACGGGTGGG GAGAGAAAGA TAGTTAGTTT GTATGATCTA   660

GGGAGGTACT AA                                                       672
```

The diverged coat protein has an amino acid sequence corresponding to SEQ. ID. No. 13 as follows:

```
Met Ser Ser Asn Thr Ser Val Pro Val Gly Gly Leu Glu Ala Leu Glu
1                5                  10                  15

Thr Ser Gly Val Val Leu Thr Thr Arg Lys Glu Ala Val Asp Lys Phe
                20                  25                  30

Phe Asn Glu Leu Lys Asn Glu Asn Tyr Ser Ser Val Asp Ser Ser Arg
            35                  40                  45

Leu Ser Asp Ser Glu Val Lys Glu Val Leu Glu Lys Ser Lys Glu Ser
        50                  55                  60

Phe Lys Ser Glu Leu Ala Ser Thr Asp Glu His Phe Val Tyr His Ile
65                  70                  75                  80

Ile Phe Phe Leu Ile Arg Cys Ala Lys Ile Ser Thr Ser Glu Lys Val
                85                  90                  95

Lys Tyr Val Gly Ser His Thr Tyr Val Val Asp Gly Lys Thr Tyr Thr
                100                 105                 110

Val Leu Asp Ala Trp Val Phe Asn Met Met Lys Ser Leu Thr Lys Lys
            115                 120                 125

Tyr Lys Arg Val Asn Gly Leu Arg Ala Phe Cys Cys Ala Cys Glu Asp
        130                 135                 140
```

```
Leu Tyr Leu Thr Val Ala Pro Ile Met Ser Glu Arg Phe Lys Thr Lys
145                 150                 155                 160

Ala Val Gly Met Lys Gly Leu Pro Val Gly Lys Glu Tyr Leu Gly Ala
                165                 170                 175

Asp Phe Leu Ser Gly Thr Ser Lys Leu Met Ser Asp His Asp Arg Ala
                180                 185                 190

Val Ser Ile Val Ala Ala Lys Asn Ala Val Asp Arg Ser Ala Phe Thr
            195                 200                 205

Gly Gly Glu Arg Lys Ile Val Ser Leu Tyr Asp Leu Gly Arg Tyr
210                 215                 220
                                                        15
``` and a molecular weight from about 23 to about 27 kDa, preferably about 25 kDa.

Another such DNA molecule (GLRaV-2 ORF6) includes nucleotides 13584–14180 of SEQ. ID. No. 1 and codes for a grapevine leafroll virus coat protein. This DNA molecule comprises a nucleotide sequence corresponding to SEQ. ID. No.14 as follows:

```
ATGGAGTTGA TGTCCGACAG CAACCTTAGC AACCTGGTGA TAACCGACGC CTCTAGTCTA    60
AATGGTGTCG ACAAGAAGCT TTTATCTGCT GAAGTTGAAA AAATGTTGGT GCAGAAAGGG   120
GCTCCTAACG AGGGTATAGA AGTGGTGTTC GGTCTACTCC TTTACGCACT CGCGGCAAGA   180
ACCACGTCTC CTAAGGTTCA GCGCGCAGAT TCAGACGTTA TATTTTCAAA TAGTTTCGGA   240
GAGAGGAATG TGGTAGTAAC AGAGGGTGAC CTTAAGAAGG TACTCGACGG GTGTGCGCCT   300
CTCACTAGGT TCACTAATAA ACTTAGAACG TTCGGTCGTA CTTTCACTGA GGCTTACGTT   360
GACTTTTGTA TCGCGTATAA GCACAAATTA CCCCAACTCA ACGCCGCGGC GGAATTGGGG   420
ATTCCAGCTG AAGATTCGTA CTTAGCTGCA GATTTTCTGG GTACTTGCCC GAAGCTCTCT   480
GAATTACAGC AAAGTAGGAA GATGTTCGCG AGTATGTACG CTCTAAAAAC TGAAGGTGGA   540
GTGGTAAATA CACCAGTGAG CAATCTGCGT CAGCTAGGTA GAAGGGAAGT TATGTAA      597
```

The coat protein has an amino acid sequence corresponding to SEQ. ID. No. 15 as follows:

```
Met Glu Leu Met Ser Asp Ser Asn Leu Ser Asn Leu Val Ile Thr Asp
1                   5                   10                  15

Ala Ser Ser Leu Asn Gly Val Asp Lys Lys Leu Leu Ser Ala Glu Val
                20                  25                  30

Glu Lys Met Leu Val Gln Lys Gly Ala Pro Asn Glu Gly Ile Glu Val
                35                  40                  45

Val Phe Gly Leu Leu Leu Tyr Ala Leu Ala Ala Arg Thr Thr Ser Pro
            50                  55                  60

Lys Val Gln Arg Ala Asp Ser Asp Val Ile Phe Ser Asn Ser Phe Gly
65                  70                  75                  80

Glu Arg Asn Val Val Val Thr Glu Gly Asp Leu Lys Lys Val Leu Asp
                85                  90                  95

Gly Cys Ala Pro Leu Thr Arg Phe Thr Asn Lys Leu Arg Thr Phe Gly
                100                 105                 110

Arg Thr Phe Thr Glu Ala Tyr Val Asp Phe Cys Ile Ala Tyr Lys His
                115                 120                 125

Lys Leu Pro Gln Leu Asn Ala Ala Glu Leu Gly Ile Pro Ala Glu
                130                 135                 140

Asp Ser Tyr Leu Ala Ala Asp Phe Leu Gly Thr Cys Pro Lys Leu Ser
```

-continued

```
                145                 150                 155                 160
Glu Leu Gln Gln Ser Arg Lys Met Phe Ala Ser Met Tyr Ala Leu Lys
                    165                 170                 175

Thr Glu Gly Gly Val Val Asn Thr Pro Val Ser Asn Leu Arg Gln Leu
                180                 185                 190

Gly Arg Arg Glu Val Met
            195
``` and a molecular weight from about 20 to about 24 kDa, preferably about 22 kDa.

Another such DNA molecule (GLRaV-2 ORF7) includes nucleotides 14180–14665 of SEQ. ID. No. 1 and codes for a second undefined grapevine leafroll virus protein or polypeptide. This DNA molecule comprises a nucleotide sequence corresponding to SEQ. ID. No. 16 as follows:

```
ATGGAAGATT ACGAAGAAAA ATCCGAATCG CTCATACTGC TACGCACGAA TCTGAACACT    60

ATGCTTTTAG TGGTCAAGTC CGATGCTAGT GTAGAGCTGC CTAAACTACT AATTTGCGGT   120

TACTTACGAG TGTCAGGACG TGGGGAGGTG ACGTGTTGCA ACCGTGAGGA ATTAACAAGA   180

GATTTTGAGG GCAATCATCA TACGGTGATC CGTTCTAGAA TCATACAATA TGACAGCGAG   240

TCTGCTTTTG AGGAATTCAA CAACTCTGAT TGCGTAGTGA AGTTTTTCCT AGAGACTGGT   300

AGTGTCTTTT GGTTTTTCCT TCGAAGTGAA ACCAAAGGTA GAGCGGTGCG ACATTTGCGC   360

ACCTTCTTCG AAGCTAACAA TTTCTTCTTT GGATCGCATT GCGGTACCAT GGAGTATTGT   420

TTGAAGCAGG TACTAACTGA AACTGAATCT ATAATCGATT CTTTTTGCGA AGAAAGAAAT   480

CGTTAA                                                              486
```

The second undefined grapevine leafroll virus protein or polypeptide has a deduced amino acid sequence corresponding to SEQ. ID. No. 17 as follows:

```
Met Glu Asp Tyr Glu Glu Lys Ser Glu Ser Leu Ile Leu Leu Arg Thr
1               5                   10                  15

Asn Leu Asn Thr Met Leu Leu Val Val Lys Ser Asp Ala Ser Val Glu
                20                  25                  30

Leu Pro Lys Leu Leu Ile Cys Gly Tyr Leu Arg Val Ser Gly Arg Gly
            35                  40                  45

Glu Val Thr Cys Cys Asn Arg Glu Leu Thr Arg Asp Phe Glu Gly
        50                  55                  60

Asn His His Thr Val Ile Arg Ser Arg Ile Ile Gln Tyr Asp Ser Glu
65                  70                  75                  80

Ser Ala Phe Glu Glu Phe Asn Asn Ser Asp Cys Val Val Lys Phe Phe
                85                  90                  95

Leu Glu Thr Gly Ser Val Phe Trp Phe Leu Arg Ser Glu Thr Lys
                100                 105                 110

Gly Arg Ala Val Arg His Leu Arg Thr Phe Glu Ala Asn Asn Phe
            115                 120                 125

Phe Phe Gly Ser His Cys Gly Thr Mat Glu Tyr Cys Leu Lys Gln Val
            130                 135                 140

Leu Thr Glu Thr Glu Ser Ile Ile Asp Ser Phe Cys Glu Glu Arg Asn
145                 150                 155                 160

Arg
``` and a molecular weight from about 17 to about 21 kDa, preferably about 19 kDa.

Yet another such DNA molecule (GLRaV-2 ORF8) includes nucleotides 14667–15284 of SEQ. ID. No. 1 and codes for a third undefined grapevine leafroll virus protein or polypeptide. This DNA molecule comprises a nucleotide sequence corresponding to SEQ. ID. No. 18 as follows:

and a molecular weight from about 22 to about 26 kDa, preferably about 24 kDa.

Another DNA molecule of the present invention (GLRaV-2 3' UTR) includes nucleotides 15285–15500 of SEQ. ID. No. 1 and comprises a nucleotide sequence corresponding to SEQ. ID. No. 23 as follows:

```
ATGAGGGTTA TAGTGTCTCC TTATGAAGCT GAAGACATTC TGAAAAGATC GACTGACATG   60

TTACGAAACA TAGACAGTGG GGTCTTGAGC ACTAAAGAAT GTATCAAGGC ATTCTCGACG  120

ATAACGCGAG ACCTACATTG TGCGAAGGCT TCCTACCAGT GGGGTGTTGA CACTGGGTTA  180

TATCAGCGTA ATTGCGCTGA AAAACGTTTA ATTGACACGG TGGAGTCAAA CATACGGTTG  240

GCTCAACCTC TCGTGCGTGA AAAAGTGGCG GTTCATTTTT GTAAGGATGA ACCAAAAGAG  300

CTAGTAGCAT TCATCACGCG AAAGTACGTG GAACTCACGG GCGTGGGAGT GAGAGAAGCG  360

GTGAAGAGGG AAATGCGCTC TCTTACCAAA ACAGTTTTAA ATAAAATGTC TTTGGAAATG  420

GCGTTTTACA TGTCACCACG AGCGTGGAAA AACGCTGAAT GGTTAGAACT AAAATTTTCA  480

CCTGTGAAAA TCTTTAGAGA TCTGCTATTA GACGTGGAAA CGCTCAACGA ATTGTGCGCC  540

GAAGATGATG TTCACGTCGA CAAAGTAAAT GAGAATGGGG ACGAAAATCA CGACCTCGAA  600

CTCCAAGACG AATGTTAA                                                618
```

The third undefined protein or polypeptide has a deduced amino acid sequence corresponding to SEQ. ED. No. 19 as follows:

```
Met Arg Val Ile Val Ser Pro Tyr Glu Ala Glu Asp Ile Leu Lys Arg
1               5                   10                  15

Ser Thr Asp Met Leu Arg Asn Ile Asp Ser Gly Val Leu Ser Thr Lys
            20                  25                  30

Glu Cys Ile Lys Ala Phe Ser Thr Ile Thr Arg Asp Leu His Cys Ala
        35                  40                  45

Lys Ala Ser Tyr Gln Trp Gly Val Asp Thr Gly Leu Tyr Gln Arg Asn
    50                  55                  60

Cys Ala Glu Lys Arg Leu Ile Asp Thr Val Glu Ser Asn Ile Arg Leu
65                  70                  75                  80

Ala Gln Pro Leu Val Arg Glu Lys Val Ala Val His Phe Cys Lys Asp
            85                  90                  95

Glu Pro Lys Glu Leu Val Ala Phe Ile Thr Arg Lys Tyr Val Glu Leu
            100                 105                 110

Thr Gly Val Gly Val Arg Glu Ala Val Lys Arg Glu Met Arg Ser Leu
            115                 120                 125

Thr Lys Thr Val Leu Asn Lys Met Ser Leu Glu Met Ala Phe Tyr Met
            130                 135                 140

Ser Pro Arg Ala Trp Lys Asn Ala Glu Trp Leu Glu Leu Lys Phe Ser
145                 150                 155                 160

Pro Val Lys Ile Phe Arg Asp Leu Leu Leu Asp Val Glu Thr Leu Asn
            165                 170                 175

Glu Leu Cys Ala Glu Asp Asp Val His Val Asp Lys Val Asn Glu Asn
            180                 185                 190

Gly Asp Glu Asn His Asp Leu Glu Leu Gln Asp Glu Cys
            195                 200                 205
```

```
ACATTGGTTA AGTTTAACGA AAATGATTAG TAAATAATAA ATCGAACGTG GGTGTATCTA   60

CCTGACGTAT CAACTTAAGC TGTTACTGAG TAATTAAACC AACAAGTGTT GGTGTAATGT  120

GTATGTTGAT GTAGAGAAAA ATCCGTTTGT AGAACGGTGT TTTTCTCTTC TTTATTTTTA  180

AAAAAAAAAT AAAAAAAAAA AAAAAAAAGC GGCCGC                             216
```

Also encompassed by the present invention are fragments of the DNA molecules of the present invention. Suitable fragments capable of imparting grapevine leafroll resistance to grape plants are constructed by using appropriate restriction sites, revealed by inspection of the DNA molecule's sequence, to: (i) insert an interposon (Felley et al., "Interposon Mutagenesis of Soil and Water Bacteria: a Family of DNA Fragments Designed for in vitro Insertion Mutagenesis of Gram-negative Bacteria," *Gene*, 52:147–15 (1987), which is hereby incorporated by reference) such that truncated forms of the grapevine leafroll virus coat polypeptide or protein, that lack various amounts of the C-terminus, can be produced or (ii) delete various internal portions of the protein. Alternatively, the sequence can be used to amplify any portion of the coding region, such that it can be cloned into a vector supplying both transcription and translation start signals.

Suitable DNA molecules are those that hybridize to a DNA molecule comprising a nucleotide sequence of at least 15 continuous bases of SEQ. ID. No. 1 under stringent conditions characterized by a hybridization buffer comprising 0.9M sodium citrate ("SSC") buffer at a temperature of 37° C. and remaining bound when subject to washing with SSC buffer at 37° C.; and preferably in a hybridization buffer comprising 20% formamide in 0.9M saline/0.9M SSC buffer at a temperature of 42° C. and remaining bound when subject to washing at 42° C. with 0.2×SSC buffer at 42° C.

Variants may also (or alternatively) be modified by, for example, the deletion or addition of nucleotides that have minimal influence on the properties, secondary structure and hydropathic nature of the encoded polypeptide. For example, the nucleotides encoding a polypeptide may be conjugated to a signal (or leader) sequence at the N-terminal end of the protein which co-translationally or post-translationally directs transfer of the protein. The nucleotide sequence may also be altered so that the encoded polypeptide is conjugated to a linker or other sequence for ease of synthesis, purification, or identification of the polypeptide.

The protein or polypeptide of the present invention is preferably produced in purified form preferably at least about 80%, more preferably 90%, pure, )by conventional techniques. Typically, the protein or polypeptide of the present invention is isolated by lysing and sonication. After washing, the lysate pellet is resuspended in buffer containing, Tris-HCl. During dialysis, a precipitate forms from this protein solution. The solution is centrifuged, and the pellet is washed and resuspended in the buffer containing, Tris-HCl. Proteins are resolved by electrophoresis through an SDS 12% polyacrylamide gel.

The DNA molecule encoding the grapevine leafroll virus (type 2) protein or polypeptide of the present invention can be incorporated in cells using conventional recombinant DNA technology. Generally, this involves inserting the DNA molecule into an expression system to which the DNA molecule is heterologous (i.e. not normally present). The heterologous DNA molecule is inserted into the expression system or vector in proper sense orientation and correct reading frame. The vector contains the necessary elements for the transcription and translation of the inserted protein-coding sequences.

U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

Recombinant genes may also be introduced into viruses, such as vaccinia virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK+/− or KS+/− (see "Stratagene Cloning Systems" Catalog (1993) from Stratagene, La Jolla. Calif., which is hereby incorporated by reference), pQE, pIH21, pGEX, pET series (see Studier et. al., "Use of T7 RNA Polymerase to Direct Expression of Cloned Genes," *Gene Expression Technology*, Vol. 185 (1990), which is hereby incorporated by reference), and any derivatives thereof. Recombinant molecules can be introduced into cells via transformation, transduction, conjugation, mobilization, or electroporation. The DNA sequences are cloned into the vector using standard cloning procedures in the art, as described by Maniatis et al., *Molecular Cloning: A Laboratory Manual*, Cold Springs Laboratory, Cold Springs Harbor, N.Y. (1982), which is hereby incorporated by reference.

A variety of host vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms, such as yeast containing yeast vectors; mammalian cell systems infected with virus (e.g., vaccinia virus, adenovirus, etc.); insect cell systems infected with virus (e.g., baculovirus); and plant cells infected by bacteria or transformed via particle bombardment (i.e. biolistics). The expression elements of these vectors vary in their strength and specificities. Depending upon the host-vector system utilized, any one of a number of suitable transcription and translation elements can be used.

Different genetic signals sand processing events control many levels of gene expression (e.g., DNA transcription and messenger RNA ("mRNA") translation).

Transcription of DNA is dependent upon the presence of a promoter which is a DNA sequence that directs the binding of RNA polymerase and thereby promotes mRNA synthesis. The DNA sequences of eucaryotic promoters differ from those of procaryotic promoters. Furthermore, eucaryotic promoters and accompanying genetic signals may not be recognized in or may not function in a procaryotic system, and, further, procaryotic promoters are not recognized and do not function in eucaryotic cells.

Similarly, translation of mRNA in procaryotes depends upon the presence of the proper procaryotic signals which differ from those of eucaryotes. Efficient translation of mRNA in procaryotes requires a ribosome binding site called the Shine-Dalgarno ("SD") sequence on the mRNA. This sequence is a short nucleotide sequence of mRNA that is located before the start codon, usually AUG, which encodes tie amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68–473 (1979), which is hereby incorporated by reference.

Promoters vary in their "strength" (i.e. their ability to promote transcription). For the purposes of expressing a cloned gene, it is desirable to use strong promoters in order to obtain a high level transcription and, hence, expression of the gene. Depending upon the host cell system utilized, any one of a number of suitable promoters maybe used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter other *E. coli* promoter produced by recombinant DNA or other synthetic DNA techniques may be used to provide for transcription of the inserted gene.

Bacterial host cell strains and expression vectors may be chosen which inhibit the action of the promoter unless specifically induced. In certain operons, the addition of specific inducers is necessary for efficient transcription of the inserted DNA.

For example, the lac operon is induced by the addition of lactose or IPTG (isopropylthiobeta-D-galactoside). A variety of other operons, such trp, pro, etc., are under different controls.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires a Shine-Dalgarno ("SD") sequence about 7–9 bases 5' to the initiation codon ("ATG") to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Once the isolated DNA molecules encoding the various grapevine leafroll virus (type 2) proteins or polypeptides, as described above, have been cloned into an expression system, they are ready to be incorporated into a host cell. Such incorporation can be carried out by the various forms of transformation noted above, depending upon the vector/host cell system. Suitable host cells include, but are not limited to, bacteria, virus, yeast, mammalian cells, insect, plant, and the like.

The present invention also relates to RNA molecules which encode the various grapevine leafroll virus (type 2) proteins or polypeptides described above. The transcripts can be synthesized using the host cells of the present invention by any of the conventional techniques. The mRNA can be translated either in vitro or in vivo. Cell-free systems typically include wheat-germ or reticulocyte extracts. In vivo translation can be effected, for example, by microinjection into frog oocytes.

One aspect of the present invention involves using one or more of the above DNA molecules encoding the various proteins or polypeptides of a grapevine leafroll virus (type 2) to transform grape plants in order to impart grapevine leafroll resistance to the plants. The mechanism by which resistance is imparted is not known. In one hypothetical mechanism, the transformed plant can express a protein or polypeptide of grapevine leafroll virus (type 2), and, when the transformed plant is inoculated by a grapevine leafroll virus, such as GLRaV-1, GLRaV-2, GLRaV-3, GLRaV-4, GLRaV-5, or GLRaV-6, or combinations of these, the expressed protein or polypeptide prevents translation of the viral DNA.

In this aspect of the present invention the subject DNA molecule incorporated in the plant can be constitutively expressed. Alternatively, expression can be regulated by a promoter which is activated by the presence of grapevine leafroll virus. Suitable promoters for these purposes include those from genes expressed in response to grapevine leafroll virus infiltration.

The isolated DNA molecules of the present invention can be utilized to impart grapevine leafroll virus resistance for a wide variety of grapevine plants. The DNA molecules are particularly well suited to imparting resistance to *Vitis* scion or rootstock cultivars. Scion cultivars which can be protected include those commonly referred to as Table or Raisin Grapes, such as Alden, Almeria, Anab-E-Shahi, Autumn Black, Beauty Seedless, Black Corinth, Black Damascus, Black Malvoisie, Black Prince, Blackrose, Bronx Seedless, Burgrave, Calmeria, Campbell Early, Canner, Cardinal, Catawba, Christmas, Concord, Dattier, Delight, Diamond, Dizmar, Duchess, Early, Muscat, Emerald Seedless, Emperor, Exotic, Ferdinand de Lesseps, Fiesta, Flame seedless, Flame Tokay, Gasconade, Gold, Himrod, Hunisa, Hussiene, Isabella, Italia, July Muscat, Khandahar, Katta, Kourgane, Kishmishi, Loose Perlette, Malaga, Monukka, Muscat of Alexandria, Muscat Flame, Muscat Hamburg, New York Muscat, Niabell, Niagara, Olivette blanche, Ontario, Pierce, Queen, Red Malaga, Ribier, Rish Baba, Romulus, Ruby Seedless, Schuyler, Seneca, Suavis (IP 365), Thompson seedless, land Thomuscat. They also include those used in wine production, such as Aleatico, Alicante Bouschet, Aligote, Alvarelhao, Aramon, Baco blanc (22A), Burger, Cabernet franc, Cabernet, Sauvignon, Calzin, Carignane, Charbono, Chardonnay, Chasselas dore, Chenin blanc, Clairette blanche, Early Burgundy, Emerald Riesling, Feher Szagos, Fernao Pires, Flora, French Colombard, Fresia, Furmint, Gamay, Gewurztraminer, Grand noir, Gray Riesling, Green Hungarian, Green Veltliner, Grenache, Grillo, Helena, Inzolia, Lalgrein, Lambrusco de Salamino, Malbec, Malvasia bianca, Mataro, Melon, Merlot, Meunier, Mission, Montua de Pilas, Muscadelle du Bordelais, Muscat blanc, Muscat Ottonel, Muscat Saint-Vallier, Nebbiolo, Nebbiolo fino, Nebbiolo Lampia, Orange Muscat, Palomino, Pedro Ximenes, Petit Bouschet, Petite Sirah, Peverella, Pinot noir, Pinot Saint-George, Primitivo di Gioa, Red Veltliner, Refosco, Rkatsiteli, Royalty, Rubired, Ruby Cabernet, Saint-Emilion, Saint Macaire, Salvador, Sangiovese, Sauvignon blanc, Sauvignon gris, Sauvignon vert, Scarlet, Seibel 5279, Seibel 9110, Seibel 13053, Semillon, Servant, Shiraz, Souzao, Sultana Crimson, Sylvaner, Tannat, Teroldico, Tinta Madeira, Tinto cao, Touriga, Traminer, Trebbiano Toscano, Trousseau, Valdepen as, Viognier, Walschriesling, White Riesling, and Zinfandel. Rootstock cultivars which can be protected include Couderc 1202, Couderc 1613, Couderc 1616, Couderc 3309, Dog Ridge, Foex 33 EM, Freedom, Ganzin 1 (A×R #1), Harmony, Kober 5BB, LN33, Millardet & de Grasset 41 B, Millardet & de Grasset 420A, Millardet & de Grasset 101-14, Oppenheim 4 (SO4), Paulsen 775, Paulsen 1045, Paulsen 1103, Richter 99, Richter 110, Riparia Gloire, Ruggeri 225, Saint-George, Salt Creek, Teleki 5A, *Vitis rupestris Constantia, Vitis california,* and *Vitis girdiana*.

There exists an extensive similarity in the hsp70-related sequence regions of GLRaV-2 and other *closteroviruses*, such as tristeza virus and beet yellows virus. Consequently, the GLRaV-2 hsp70-related gene can also be used to produce transgenic plants or cultivars other than grape, such as *citrus* or sugar beet, which are resistant to *closteroviruses* other than grapevine leafroll, such as tristeza virus and beet yellows virus.

Suitable *citrus* cultivars include lemon, lime, orange, grapefruit, pineapple, tangerine, and the like, such as Joppa, Maltaise Ovale, Parson (Parson Brown), Pera, Pineapple, Queen, Shamouti, Valencia, Tenerife, Imperial Doblefina, Washington Sanguine, Moro, Sanguinello Moscato, Spanish Sanguinelli, Tarocco, Atwood, Australian, Bahia, Baiana, Cram, Dalmau, Eddy, Fisher, Frost Washington, Gillette, LengNavelina, Washington, Satsuma Mandarin, Dancy, Robinson, Ponkan, Duncan, Marsh, Pink Marsh, Ruby Red, Red Seedless, Smooth Seville, Orlando Tangelo, Eureka, Lisbon, Meyer Lemon, Rough Lemon, Sour Orange, Persian Lime, West Indian Lime, Bearss, Sweet Lime, Troyer Citrange, and *Citrus* Trifoliata. Each of these *citrus* cultivars is suitable for producing transgenic *citrus* plants resistant to tristeza virus.

The economically important species of sugar beet is *Beta vulgaris L.*, which has four important cultivar types: sugar beet, table beet, fodder beet, and Swiss chard. Each of these beet cultivars is suitable for producing transgenic beet plants resistant to beet yellows virus, as described above.

Because GLRaV-2 has been known to infect tobacco plants (e.g., *Nicotiana benthamiana*), it is also desirable to produce transgenic tobacco plants which are resistant to grapevine leafroll viruses, such as GLRaV-2.

Plant tissue suitable for transformation include leaf tissue, root tissue, meristems, zygotic and somatic embryos, and anthers. It is particularly preferred to utilize embryos obtained from anther cultures.

The expression system of the present invention can be used to transform virtually any plant tissue under suitable conditions. Tissue cells transformed in accordance with the present invention can be grown in vitro in a suitable medium to impart grapevine leafroll virus resistance. Transformed cells can be regenerated into whole plants such that the protein or polypeptide imparts resistance to grapevine leafroll virus in the intact transgenic plants. In either case, the plant cells transformed with the recombinant DNA expression system of the present invention are grown and caused to express that DNA molecule to produce one of the above-described grapevine leafroll virus proteins or polypeptides and, thus, to impart grapevine leafroll virus resistance.

In producing transgenic plants, the DNA construct in a vector described above can be microinjected directly into plant cells by use of micropipettes to transfer mechanically the recombinant DNA. Crossway, *Mol. Gen. Genetics*, 202:179–85 (1985), which is hereby incorporated by reference. The genetic material may also be transferred into the plant cell using polyethylene glycol. Krens, et al., *Nature*, 296:72–74 (1982), which is hereby incorporated by reference.

One technique of transforming plants with the DNA molecules in accordance with the present invention is by contacting the tissue of such plants with an inoculum of a bacteria transformed with a vector comprising a gene in accordance with the present invention which imparts grapevine leafroll resistance. Generally, this procedure involves inoculating the plant tissue with a suspension of bacteria and incubating the tissue for 48 to 72 hours on regeneration medium without antibiotics at 25–28° C.

Bacteria from the genus *Agrobacterium* can be utilized to transform plant cells. Suitable species of such bacterium include *Agrobacterium tumefaciens* and *Agrobacterium rhizogenes. Agrobacterium tumefaciens* (e.g., strains C58, LBA4404, or EHA105) is particularly useful due to its well-known ability to transform plants.

Heterologous genetic sequences can be introduced into appropriate plant cells, by means of the Ti plasmid of *A. tumefaciens* or the Ri plasmid of *A. rhizogenes*. The Ti or Ri plasmid is transmitted to plant cells on infection by *Agrobacterium* and is stably integrated into the plant genome. J. Schell, *Science*, 237:1176–83 (1987), which is hereby incorporated by reference.

After transformation, the transformed plant cells must be regenerated.

Plant regeneration from cultured protoplasts is described in Evans eat al., *Handbook of Plant Cell Cultures, Vol.* 1: (MacMillan Publishing Co., New York, 1983); and Vasil I. R. (ed.), *Cell Culture and Somatic Cell Genetics of Plants*, Acad. Press, Orlando, Vol. I, 1984, and Vol. III (1986), which are hereby incorporated by reference.

It is known that practically all plants can be regenerated from cultured cells or tissues, including but not limited to, all major species of sugarcane, sugar beets, cotton, fruit trees, and legumes.

Means for regeneration vary from species to species of plants, but generally suspension of transformed protoplasts or a petri plate containing explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium. Efficient regeneration will depend on the medium, on the genotype, and on the history of the culture. If these three variables are controlled, then regeneration is usually reproducible and repeatable.

After the expression cassette is stably incorporated in transgenic plants, it can be transferred to other plants by sexual crossing. Any of a number of standard breeding techniques can be used, depending upon the species to be crossed.

Once transgenic plants of this type are produced, the plants themselves can be cultivated in accordance with conventional procedure so that the DNA construct is present in the resulting plants. Alternatively, transgenic seeds are recovered from the transgenic plants. These seeds can then be planted in the soil and cultivated using conventional procedures to produce transgenic plants.

Another approach to transforming plant cells with a gene which imparts resistance to pathogens is particle bombardment (also known as biolistic transformation) of the host cell. This can be accomplished in one of several ways. The first involves propelling inert or biologically active particles at cells. This technique is disclosed in U.S. Pat. Nos. 4,945,050, 5,036,006, and 5,100,792, all to Sanford et al., and in Emerschad et al., "Somatic Embryogenesis and Plant Development from Immature Zygotic Embryos of Seedless Grapes (*Vitis vinifera*)," *Plant Cell Reports*, 14:6–12 (1995) ("Emerschad (1995)"), which are hereby incorporated by reference. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant, cells.

Once a grape plant tissue, *citrus* plant tissue, beet plant tissue, or tobacco plant tissue is transformed in accordance with the present invention, the transformed tissue is regenerated to form a transgenic plant. Generally, regeneration is accomplished by culturing transformed tissue on medium containing the appropriate growth regulators and nutrients to allow for the initiation of shoot meristems. Appropriate antibiotics are added to the regeneration medium to inhibit the growth of *Agrobacterium* and to select for the development of transformed cells. Following shoot initiation, shoots are allowed to develop tissue culture and are screened for marker gene activity.

The DNA molecules of the present invention can be made capable of transcription to a messenger RNA, which, although encoding for a grapevine leafroll virus (type 2) protein or polypeptide, does not translate to the protein. This is known as RNA-mediated resistance. When a *Vitis* scion or rootstock cultivar, or a *citrus*, beet, or tobacco cultivar, is transformed with such a DNA molecule, the DNA molecule can be transcribed under conditions effective to maintain the messenger RNA in the plant cell at low level density readings. Density readings of between 15 and 50 using a Hewlet ScanJet and Image Analysis Program are preferred.

A portion of one or more DNA molecules of the present invention as well as other DNA molecules can be used in a transgenic grape plant, *citrus* plant, beet plant, or tobacco plant in accordance with U.S. patent application Ser. No. 09/025,635, which is hereby incorporated herein by reference.

The grapevine leafroll virus (type 2) protein or polypeptide of the present invention can also be used to raise antibodies or binding portions thereof or probes. The antibodies can be monoclonal or polyclonal.

Monoclonal antibody production may be effected by techniques which are well-known in the art. Basically, the process involves first obtaining immune cells (lymphocytes) from the spleen of a mammal (e.g., mouse) which has been previously immunized with the antigen of interest either in vivo or in vitro. The antibody-secreting lymphocytes are then fused with (mouse) myeloma cells or transformed cells, which are capable of replicating indefinitely in cell culture, thereby producing an-immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, *Nature*, 256:495 (1975), which is hereby incorporated by reference.

Mammalian lymphocytes are immunized by in vivo immunization of the animal (e.g., a mouse) with the protein or polypeptide of the present invention. Such immunizations are repeated as necessary at intervals of up to several weeks to obtain a sufficient titer of antibodies. Following the last antigen boost, the animals are sacrificed and spleen cells removed.

Fusion with mammalian myeloma cells or other fusion partners capable of replicating indefinitely in cell culture is effected by standard and well-known techniques, for example, by using polyethylene glycol ("PEG") or other fusing agents. (See Milstein and Kohler, *Eur. J. Immunol.*, 6:511 (1976), which is hereby incorporated by reference.) This immortal cell line, which is preferably murine, but may also be derived from cells of other mammalian species, including but not limited to rats and humans, is selected to be deficient in enzymes necessary for the utilization of certain nutrients, to be capable of rapid growth, and to have good fusion capability. Many such cell lines are known,to those skilled in the art, and others are regularly described.

Procedures for raising polyclonal antibodies are also well known. Typically, such antibodies can be raised by administering the protein or polypeptide of the present invention subcutaneously to New Zealand white rabbits which have first been bled to obtain pre-immune serum. The antigens can be injected at a total volume of 100 $\mu$l per site at six different sites. Each injected material will contain synthetic surfactant adjuvant pluronic polyols, or pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. Ultimately, the rabbits are euthenized with pentobarbital 150 mg/Kg IV. This and other procedures for raising polyclonal antibodies are disclosed in Harlow et. al., editors, *Antibodies: A Laboratory Manual* (1988), which is hereby incorporated by reference.

In addition to utilizing whole antibodies, binding portions of such antibodies can be used. Such binding portions include Fab fragments, $F(ab')_2$ fragments, and Fv fragments. These antibody fragments can be made by conventional procedures, such as proteolytic fragmentation procedures, as described in Goding, *Monoclonal Antibodies: Principles and Practice*, New York: Academic Press, pp. 98–118 (1983), which is hereby incorporated by reference.

The present invention also relates to probes found either in nature or prepared synthetically by recombinant DNA procedures or other biological procedures. Suitable probes are molecules which bind to grapevine leafroll (type 2) viral antigens identified by the monoclonal antibodies of the present invention. Such probes can be, for example, proteins, peptides, lectins, or nucleic acid probes.

The antibodies or binding portions thereof or probes can be administered to grapevine leafroll virus infected scion cultivars or rootstock cultivars. Alternatively, at least the binding portions of these antibodies can be sequenced, and the encoding DNA synthesized. The encoding DNA molecule can be used to transform plants together with a promoter which causes expression of the encoded antibody when the plant is infected by grapevine leafroll virus. In either case, the antibody or binding portion thereof or probe will bind to the virus and help prevent the usual leafroll response.

Antibodies raised against the GLRaV-2 proteins or polypeptides of the present invention or binding portions of these antibodies can be utilized in a method for detection of grapevine leafroll virus in a sample of tissue, such as tissue (e.g., scion or rootstock) from a grape plant or tobacco plant. Antibodies or binding portions thereof suitable for use in the detection method include those raised against a helicase, a methyltransferase, a papain-like protease, an RNA-dependent RNA polymerase, a heat shock 70 protein, a heat shock 90 protein, a coat protein, a diverged coat protein, or other proteins or polypeptides in accordance with the present invention. Any reaction of the sample with the antibody is detected using an assay system which indicates the presence of grapevine leafroll virus in the sample. A variety of assay systems can be employed, such as enzyme-linked immunosorbent assays, radioimmunoassays, gel diffusion precipitin reaction assays, immunodiffusion assays, agglutination assays, fluorescent immunoassays, protein A immunoassays, or immunoelectrophoresis assays.

Alternatively, grapevine leafroll virus can be detected in such a sample using a nucleotide sequence of the DNA molecule, or a fragment thereof, encoding for a protein or polypeptide of the present invention. The nucleotide sequence is provided as a probe in a nucleic acid hybridization assay or a gene amplification detection procedure (e.g., using a polymerase chain reaction procedure). The nucleic acid probes of the present invention may be used in any nucleic acid hybridization assay system known in the art, including, but not limited to, Southern blots (Southern, E. M., "Detection of Specific Sequences Among DNA Fragments Separated by Gel Electrophoresis," *J. Mol. Biol.*, 98:503–17 (1975), which is hereby incorporated by reference), Northern blots (Thomas, P. S., "Hybridization of Denatured RNA and Small DNA Fragments Transferred to Nitrocellulose," *Proc. Nat'l Acad. Sci. USA*, 77:5201–05 (1980), which is hereby incorporated by reference), and Colony blots (Grunstein, M., et al., "Colony Hybridization: A Method for the Isolation of Cloned cDNAs that Contain a Specific Gene," *Proc. Nat'l Acad. Sci. USA*, 72:3961–65 (1975), which is hereby incorporated by reference). Alternatively, the probes can be used in a gene amplification detection procedure (e.g., a polymerase chain reaction). Erlich, H. A., et. al., "Recent Advances in the Polymerase Chain Reaction," *Science* 252:1643–51 (1991), which is hereby incorporated by reference. Any reaction with the probe is detected so that the presence of a grapevine leafroll virus in the sample is indicated. Such detection is facilitated by providing the probe of the present invention with a label. Suitable labels include a radioactive compound, a fluorescent compound, a chemiluminescent compound, an enzymatic compound, or other equivalent nucleic acid labels.

Depending upon the desired scope of detection, it is possible to utilize probes having nucleotide sequences that correspond with conserved or variable regions of the ORF or UTR. For example, to distinguish a grapevine leafroll virus from other related viruses (e.g., other *closteroviruses*), it is desirable to use probes which contain nucleotide sequences that correspond to sequences more highly conserved among all grapevine leafroll viruses. Also, to distinguish between different grapevine leafroll viruses (i.e., GLRaV-2 from GLRaV-1, GLRaV-3, GLRaV-4, GLRaV-5, and GLRaV-6), it is desirable to utilize probes containing nucleotide sequences that correspond to sequences less highly conserve among the different grapevine leafroll viruses.

Nucleic acid (DNA or RNA) probes of the present invention will hybridize to complementary GLRaV-2 nucleic acid under stringent conditions. Generally, stringent conditions are selected to be about 50° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. The $T_m$ is dependent upon the solution conditions and the base composition of the probe, and may be calculated using the following equation:

$$T_m = 79.8° \text{C.} + (18.5 \times \text{Log}[\text{Na}+]) + (58.4° \text{C.} \times \%[G+C]) - (820/\# \text{bp in duplex}) - (0.5 \times \% \text{ formamide})$$

Nonspecific binding may also be controlled using any one of a number of known techniques such as, for example, blocking the membrane with protein-containing solutions, addition of heterologous RNA, DNA, and SDS to the hybridization buffer, and treatment with, RNase. Wash conditions are typically performed at or below stringency. Generally, suitable stringent conditions for nucleic acid hybridization assays or gene amplification detection procedures are as set forth above. More or less stringent conditions may also be selected.

EXAMPLES

The following examples are provided to illustrate embodiments of the present invention but are by no means intended to limit its scope.

Example 1

Northern Hybridization

Specificity of the selected clones was confirmed by Northern hybridization. Northern hybridization was performed after electrophoresis of the dsRNA of GLRaV-2 in 1% agarose non-denaturing condition gel. The agarose gel was denatured by soaking in 50 mM NaOH containing 0.4 M NaCl for 30 min, and then neutralized with 0.1 M Tris-HCl (PH7.5) containing 0.5 M NaCl for another 30 min. RNA was sandwich blotted overnight onto Genescreen™ plus membrane (Dupont NEN Research Product) in 10×SSC buffer and hybridized as described by the manufacturer's instructions (DuPont, NEN).

Example 2

Sequencing and Computer Assisted Nucleotide and Amino Acid Sequence Analysis DNA inserts were sequenced in pBluescript SK+ by using T3 and T7 universal primers for the terminal region sequence and additional oligonucleotide primers designed according to the known sequence for the internal region sequence. Purification of plasmid DNA was performed by a modified mini alkaline-lysis/PEG precipitation procedure described by the manufacturer (Applied Biosystems, Inc.). Nucleotide sequencing was performed on both strands of cDNA by using ABI TaqDyeDeoxy Terminator Cycle Sequencing Kit (Applied Biosystems, Inc.). Automatic sequencing was performed on an ABI373 Automated Sequencer (Applied Biosystems, Inc.) at Cornell University, Geneva, N.Y.

The nucleotide sequences of GLRaV-2 were assembled and analyzed with the programs of EditSeq and SeqMan, respectively, of DNASTAR package (Madison, Wis.). Amino acid sequences deduced from nucleotide sequences and its encoding open reading frames were conducted using the MapDraw program. Multiple alignments of amino acid sequences, identification of consensus amino acid sequences, and generation of phylogenetic trees were performed using the Clustal method in the MegAlign program. The nucleotide and amino acid sequences of other *closteroviruses* were obtained with the Entrez Program; and sequence comparisons with nonredundant databases were searched with the Blast Program from the National Center for Biotechnology Information.

Example 3

Isolation of dsRNA

Several vines of GLRaV-2 infected *Vitis vinifera* cv Pinot Noir that originated from a central New York vineyard served as the source for dsRNA isolation and cDNA cloning. dsRNA was extracted from phloem tissue of infected grapevines according to the method described by Hu et al., "Characterization of *Closterovirus*-Like Particles Associated with Grapevine Leafroll Disease," *J. Phytopathology* 128:1–14 (1990), which is hereby incorporated by reference. Purification of the high molecular weight dsRNA (ca 15 kb) was carried out by electrophoretic separation of the total dsRNA on a 0.7% low melting point agarose gel and extraction by phenol/chloroform following the method described by Sambrook et al., *Molecular Cloning: A Laboratory Manual*, 2nd ed., Cold Spring Harbor Laboratory Press, New York (1989), which is hereby incorporated by reference. Concentration of dsRNA was estimated with UV fluorescent density of an ethidium bromide stained dsRNA band in comparison with a known concentration of DNA marker.

Example 4 cDNA Synthesis and Cloning cDNA synthesis was performed following the method initially described by Jelkmann et al., "Cloning of Four Plant Viruses From Small Quantities of Double-Stranded RNA," *Phytopathology* 79:1250–53 (1989) and modified by Ling et al., "The Coat Protein Gene of Grapevine Leafroll Associated *Closterovirus*-3: Cloning, Nucleotide Sequencing and Expression in Transgenic Plants," *Arch. Virology* 142:1101–16 (1997), both of which are hereby incorporated by reference. About 100 ng of high molecular weight dsRNA purified from low melting agarose gel was denatured in 20 mM methylmercuric hydroxide and incubated at room temperature for 10 min with 350 ng of random primers. First strand cDNA was synthesized by using avian myeloblastosis virus (AMV) reverse transcriptase. Second strand cDNA was obtained by using RNase H and *E.coli* DNA polymerase I. Double-stranded cDNA was blunt ended with T4 DNA polymerase and ligated with EcoRI adapters. The cDNA, which had EcoRI adapters at the ends, was activated by kinase reaction and ligated into Lambda ZAPII/EcoRI prepared arms following the manufacturer's instruction (Stratagene). The recombinant DNA was then packaged in vitro to Gigapack® II packaging extract (Stratagene). The packaged phage particles were amplified and titered according to the manufacturer's instruction.

Two kinds of probes were used to identify GLRaV-2 specific clones from the library. One type was prepared from the synthesized cDNA that was amplified by, PCR after ligation to the specific EcoRI Uni-Amp™ adapters (Clontech); and the other type was DNA inserts or PCR products from already sequenced clones. Clones from the cDNA library were selected by colony-lifting hybridization onto the colony/plaque Screen membrane (NEN Research Product) with the probe described above. The probe was prepared by labeling with $^{32}P$ [α-dATP] using Klenow fragment of *E. coli* DNA polymerase I. Prehybridization, hybridization, and washing steps were carried out at 65° C. according to the manufacturer's instruction (Dupont, NEN Research Product). Selected plaques were converted to recombinant pBluescript by in vivo excision method according to the manufacturer's instruction (Stratagene).

To obtain clones representing the extreme 3'-terminus of GLRaV-2, dsRNA was polyadenylated by yeast poly(A) polymerase. Using poly(A)-tailed dsRNA as template, cDNA was amplified by RT-PCR with oligo(dT)18 and a specific primer, CP-1/T7R, which is derived from the clone CP-1 and has a nucleotide sequence according to SEQ. ID. No. 20 as follows:
TGCTGGAGCT TGAGGTTCTG C 21
The resulting PCR product (3'-PCR) was cloned into a TA vector (Invitrogen) and sequenced.

As shown in FIG. 1A, a high molecular weight dsRNA of ca. 15 kb was consistently identified from GLRaV-2 infected grapevines, but not from healthy vines. In addition, several low molecular weight dsRNAs were also detected from infected tissue. The yield of dsRNA of GLRaV-2 was estimated between 5–10 ng/15 g phloem tissue, which was much lower than that of GLRaV-3 (Hu et al., "Characterization of *Closterovirus*-Like Particles Associated with Grapevine Leafroll Disease," *J. Phytopathology* 128:1–14 (1990), which is hereby incorporated by reference). Only the high molecular weight dsRNA that was purified from low melting point agarose gel was used for cDNA synthesis, cloning and establishment of the Lambda/ZAPII cDNA library.

Two kinds of probes were used for screening the cDNA library. The initial clones were identified by hybridization with Uni-Amp™ PCR-amplified cDNA as probes. The specificity of these clones (e.g., TC-1) ranging from 200 to 1,800 bp in size was confirmed by Northern hybridization to dsRNA of GLRaV-2 as shown in FIG. 1B. Additionally, over 40 different clones ranging form 800 to 7,500 bp in size were identified following hybridization with the probes generated from GLRaV-2 specific cDNA clones or from PCR products. Over 40 clones were then sequenced on the both strands (FIG. 2).

Example 5

Expression of the Coat Protein in *E. coli* and Immunoblotting

To determine that ORF6 was the coat protein gene of GLRaV-2, the complete ORF6 DNA molecule was subcloned from a PCR product and inserted into the fusion protein expression vector pMAL-C2 (New England Biolabs, Inc.). The specific primers used for the PCR reaction were CP-96F and CP-96R, in which an EcoRI or BamHI site was included to facilitate cloning. CP-96F was designed to include the start codon of the CP and comprises a nucleotide sequence according to SEQ. ID. NO. 21 as follows:
CGGAATTCAC CATGGAGTTG ATGTCCGACA G 31
CP-96R was 66 nucleotides downstream of the stop codon of the CP and comprises the nucleotide sequence corresponding to SEQ. ID. No. 22 as follows:
AGCGGATCCA TGGCAGATTC GTGCGTAGCA GTA 33

The coat protein was expressed as a fusion protein with maltose binding protein (MBP) of E. coli under the control of a "tac" promoter and suppressed by the "lac" repressor. The MBP-CP fusion protein was induced by adding 0.3 mM isopropyl-β-D-thio-galoactopyranoside (IPTG) and purified by a one step affinity column according to the manufacturer's instruction (New England, Biolabs, Inc). The MBP-CP fusion protein or the coat protein cleaved from the fusion protein was tested to react with specific antiserum of GLRaV-2 (kindly provided by Dr. Charles Greif of INRA, Colmar, France) on Western blot according to the method described by Hu et al., "Characterization of Closterovirus-Like Particles Associated with Grapevine Leafroll Disease," J. Phytopathology 128:1–14 (1990), which is hereby incorporated by reference. In contrast, the non-recombinant plasmids or uninduced cells did not react to the antiserum of GLRaV-2.

Example 6

Sequence Analysis and Genome Organization of GLRaV-2

A total of 15,500 bp of the RNA genome of GLRaV-2 was sequenced and deposited in GenBank (accession number AF039204). About 85% of the total RNA genome was revealed from at least two different clones. The sequence in the coat protein gene region was determined and confirmed from several different overlapping clones. The genome organization of GLRaV-2, shown in FIG. 2, includes nine open reading frames (e.g., ORF1a, 1b-8).

ORF1a and ORF1b: Analysis of the amino acid sequence of the N-terminal portion of GLRaV-2 ORF1a encoded product revealed two putative papain-like protease domains, which showed significant similarity to the papain-like leader protease of BYV (Agranovsky et al., "Beet Yellows Closterovirus: Complete Genome Structure and Identification of a Papain-like Thiol Protease," Virology 198:311–24 (1994), which is hereby incorporated by reference). Thus, it allowed prediction of the catalytic cysteine and histidine residues for the putative GLRaV-2 protease. Upon alignment of the sequence of the papain-like protease of BYV with that of GLRaV-2, the cleavage site at residues Gly-Gly (amino acid 588–589) of BYV aligned with the corresponding alanine-glycine (Ala-Gly) and Gly-Gly dipeptide of GLRaV-2 (FIG. 3A). Cleavage at this site would result in a leader protein and a 234 kDa (2090 amino acid) C-terminal fragment consisting of MT and HEL domains. However, the region upstream of the papain-like protease domain in GLRaV-2 did not show similarity to the corresponding region of BYV. In addition, variability in the residues located at the scissible bond (Gly in the BYV and Ala in the GLRaV-2) was present. Similar variability of the cleavage site residue in the P-PRO domain has been described ink LChV (Jelkmann et al., "Complete Genome Structure and Phylogenetic Analysis of Little Cherry Virus, a Mealybug-Transmissible Closterovirus. J. General Virology 78:2067–71 (1997), which is hereby incorporated by reference).

Database searching with the deduced amino acid sequence of the ORF1a/1b encoded protein revealed a significant similarity to the MT, HEL and RdRP domains of the other closteroviruses. The region downstream of the P-PRO cleavage site showed a significant similarity (57.4% identity in a 266-residues alignment) to the putative methyltransferase domain of BYV and contained all the conserved motifs typical of positive-strand RNA viral type I MTs (FIG. 3B). The C-terminal portion of the ORF1a was identified as a helicase domain, the sequence of which showed a high similarity (57.1% identity in a 315-residues alignment) to the helicase domain of BYV and contained the seven conserved motifs characteristic of the Superfamily I helicase of positive-strand RNA viruses (FIG. 3C) (Hodgman, "A New Superfamily of Replicative Proteins," Nature 333,:22–23 (1988); Koonin and Dolja, "Evolution and Taxonomy of Positive-strand RNA Viruses: Implications of Comparative Analysis of Amino Acid Sequences," Crit. Rev. in Biochem. and Mol. Biol. 28:375–430 (1993), both of which are hereby incorporated by reference).

ORF1b encoded a 460 amino acid polypeptide with a molecular mass of 52,486 Da, counting from the frameshifting site. Database searching with the RdRP showed a significant similarity to the RdRP domains of positive strand RNA viruses. Comparison of the RdRP domains of GLRaV-2 and BYV showed the presence of the eight conserved motifs of RdRP (FIG. 3D).

Figure 8:
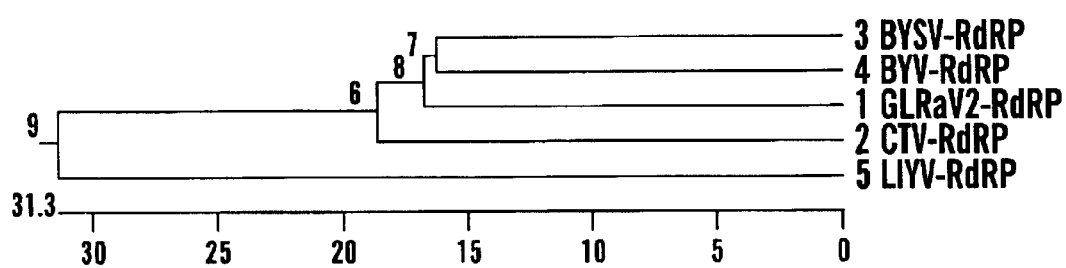
FIG. 8 is a tentative phylogenetic tree showing the relationship of RdRP of GLRaV-2 with respect to BYV, BYSV, CTV, and LIYV. The phylogenetic tree was constructed using the Clustal method with the MegAlign program in DNASTAR.

As shown in FIG. 8, a tentative phylogenetic tree of the RdRP of GLRaV-2 with respect to other closteroviruses shows that it is closely related to the monopartite closteroviruses BYV, BYSV, and CTV.

In closteroviruses, a +1 ribosomal frameshift mechanism has been suggested to be involved in the expression of ORF1b as a large fusion protein with ORF1a (Agranovsky et al., "Beet Yellows Closterovirus: Complete Genome Structure and Identification of a Papain-like Thiol Protease," Virology 198:311–24 (1994); Karasev et al., "Complete Sequence of the Citrus Tristeza Virus RNA Genome," Virology 208:511–20 (1995); Klaassen et al., "Genome Structure and Phylogenetic Analysis of Lettuce Infectious Yellows Virus, a Whitefly-Transmitted, Bipartite Closterovirus," Virology 208:99–110 (1995); Karasev et al., "Organization of the 3'-Terminal Half of Beet Yellow Stunt Virus Genome and Implications for the Evolution of Closteroviruses," Virology 221:199–207 (1996); Jelkmann et al., "Complete Genome Structure and Phylogenetic Analysis of Little Cherry Virus, a Mealybug-Transmissible Closterovirus," J. General Virology 78:2067–71 (1997), all of which are hereby incorporated by reference). In the overlapping ORF1a/1b region of BYV, the slippery sequence of GGGUUUA and two hairpins structure (stem-loop and pseudoknot) ate believed to result in a +1 frameshift (Agranovsky et al., "Beet Yellows Closterovirus: Complete Genome Structure and Identification of a Papain-like Thiol Protease," Virology 198:311–24 (1994), which is hereby incorporated by reference). None of these features are conserved in CTV and BYSV (Karasev et al., "Complete Sequence of the Citrus Tristeza Virus RNA Genome," Virology 208:511–20 (1995); Karasev et al., "Organization of the 3'-Terminal Half of Beet Yellow Stunt Virus Genome and Implications for the Evolution of Closteroviruses," Virology 221:199–207 (1996), both of which are hereby incorporated by reference), in which a ribosomal pausing at a terminator or at a rare codon was suggested to perform the same function. Comparisons of the nucleotide sequence of the C-terminal region of the helicase and the N-terminal region of RdRP of GLRaV-2 with the same region of other closteroviruses revealed a significant similarity to BYV, BYSV, and CTV. As shown in FIG. 4, the terminator UAG at the end of C'-terminal helicase of GLRaV-2 aligned with the terminator UAG of BYV and BYSV, and arginine CGG codon of CTV.

ORF2 encodes a small protein consisting of 171 bp (57 amino acid) with a molecular mass of 6,297 Da. As predicted, the deduced amino acid sequence includes a stretch of nonpolar amino acids, which is presumed to form a transmembrane helix. A small hydrophobic analogous protein is also present in BYV, BYSV, CTV, LIYV, and LChV (Agranovsky et al. "Nucleotide Sequence of the 3'-Terminal Half of Beet Yellows, *Closterovirus* RNA Genome Unique Arrangement of Eight Virus Genes," *J. General Virology* 72:15–24 (1991); Karasev et al., "Organization of the 3'-Terminal Half of Beet Yellow Stunt Virus Genome and Implications for the Evolution of *Closteroviruses*," *Virology* 221:199–207 (1996); Pappu et al., "Nucleotide Sequence and Organization of Eight 3' Open Reading Frames of the *Citrus* Tristeza *Closterovirus* Genome," *Virology* 199:35–46 (1994); Klaassen et al., "Partial Characterization of the Lettuce Infectious Yellows Virus Genomic RNAs, Identification of the Coat Protein Gene and Comparison of its Amino Acid Sequence With Those of Other Filamentous RNA Plant Viruses," *J. General Virology* 75:152,5–33 (1994); Jelkmann et al., "Complete Genome Structure and Phylogenetic Analysis of Little Cherry Virus, a Mealybug-Transmissible *Closterovirus*," *J. General Virology* 78:2067–71 (1997), all of which are hereby incorporated by reference).

ORF3 encodes a 600 amino acid polypeptide with a molecular mass of 65,111 Da, which is homologous to the HSP70 cellular heat shock protein. HSP70 is highly conserved among *closteroviruses* and is probably involved in ATPase activity and, the protein to protein interaction for chaperone activity (Agranovsky et al. "The Beet Yellows *Closterovirus* p65 Homologue of HSP70 Chaperones has ATPase Activity Associated with its Conserved N-terminal Domain but Interact with Unfolded Protein Chains," *J. General Virology* 78:535–42 (1997); Agranovsky et al., "Bacterial Expression and Some Properties of the p65, a Homologue of Cell Heat Shock Protein HSP70 Encoded in RNA Genome of Beet Yellows *Closterovirus*," *Doklady Akademii Nauk.* 340:416–18 (1995); Karasev et al., "HSP70-Related 65-kDa Protein of Beet Yellows *Closterovirus* is a Microtubule-Binding Protein," *FEBS Letters* 304:12–14 (1992), all of which are hereby incorporated by reference). As shown in FIG. 5, alignment of the complete ORF3 of GLRaV-2 with HSP70 homolog of BYV revealed the presence of the eight conserved motifs. The percentage similarity of the HSP70 between GLRaV-2 and that of BYV, BYSV, CTV, LIYV, and LChV is 47.8%, 47.2%, 38.6%, 20.9%, and 17.7%, respectively.

ORF4 encodes a 551 amino acid protein with a molecular mass of 63,349 Da. Database searching with the ORF4 protein product did not identify similar proteins except those of its counterparts in *closteroviruses*, BYV (P64), BYSV (P61), CTV (P61), LIYV (P59), and LChV (P61). This protein is believed to be a putative heat shock 90 protein. As shown in FIG. 9, two conserved motifs which were present in BYV (Agranovsky et al. "Nucleotide Sequence of the 3'-Terminal Half of Beet Yellows *Closterovirus* RNA Genome Unique Arrangement of Eight Virus Genes," *J. General Virology* 72:15–24 (1991), which is hereby incorporated by reference) and CTV (Pappu et al., "Nucleotide Sequence and Organization of Eight 3' Open Reading Frames of the *Citrus* Tristeza *Closterovirus* Genome," *Virology* 199:35–46 (1994), which is hereby incorporated by reference) were also identified in the ORF4 of GLRaV-2.

ORF5 and ORF6 encode polypeptides with molecular mass of 24,803 Da and 21,661 Da, respectively. The start codon for both ORFs is in a favorable context for translation. ORF6 was identified as the coat protein gene of GLRaV-2 based on the sequence comparison with other *closteroviruses*. The calculated molecular mass of the protein product of ORF6 (21,662 Da) is in good agreement with the previously estimated 22~26 kDa based on SDS-PAGE (Zimmermann et al., "Characterization and Serological Detection of Four Closterovirus-like Particles Associated with Leafroll Disease on Grapevine," *J. Phytopathology* 130:205–18 (1990); Boscia et al., "Nomenclature of Grapevine Leafroll-Associated Putative *Closteroviruses*," *Vitis* 34:171–75 (1995), both of which are hereby incorporated by reference).

Figure 6A:
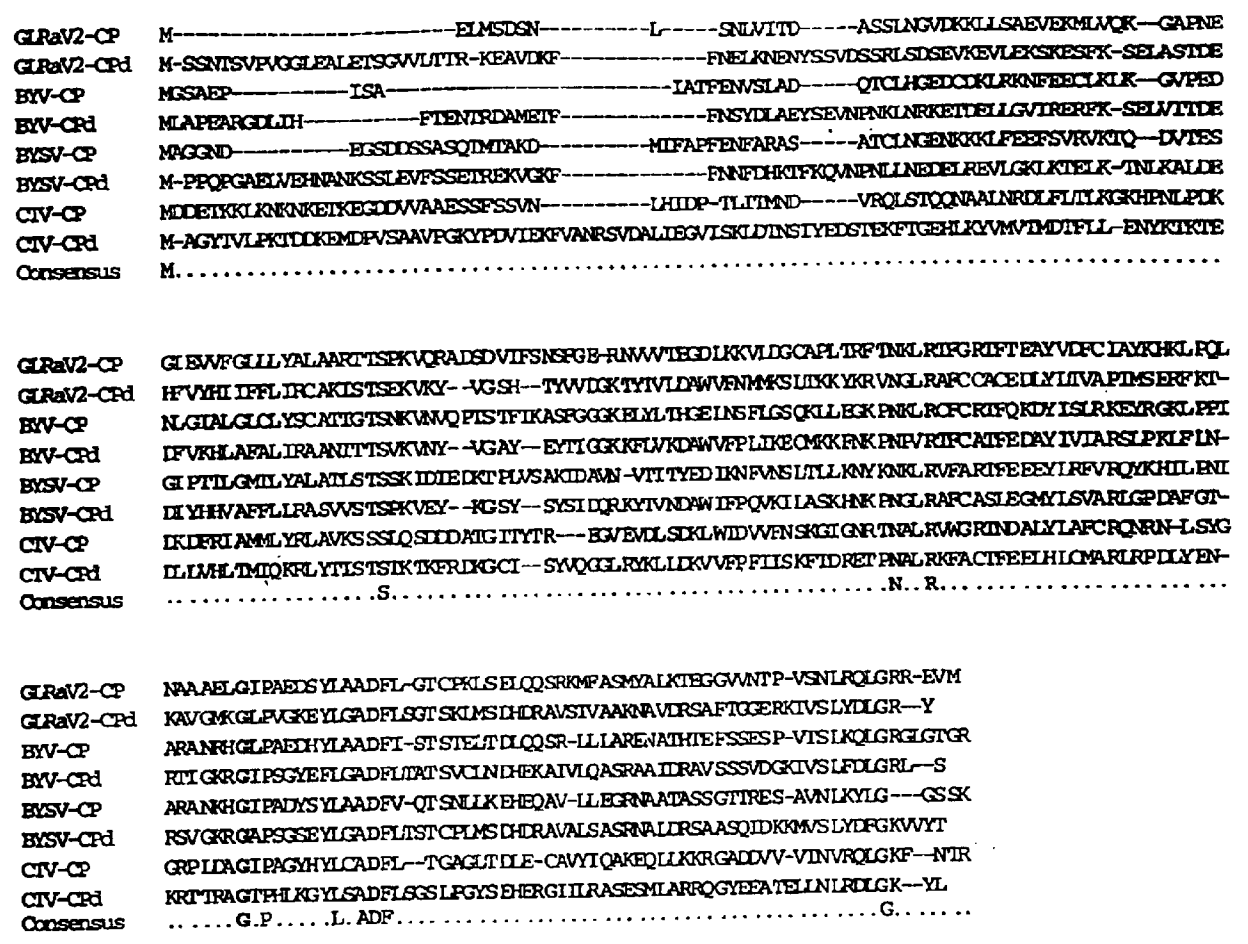

Database searching with the deduced amino acid sequence of the ORF6 of GLRaV-2 showed a similarity with the coat proteins of *closteroviruses*, BYV, BYSV, CTV, LIYV, LChV, and GLRaV-3. At the nucleotide level, the highest percentage similarity was with the coat protein of BYSV (34.8%); at the amino acid level, the highest percentage similarity was with the coat proteins of BYV (32.7%) and BYSV (32.7%). As shown in FIG. 6A, alignment of the amino acid sequence of the coat protein and coat protein duplicate of GLRaV-2 with respect to other *closteroviruses* revealed that the invariant amino acid residues (N. R. G. D.) were present in both ORF5 and ORF6 of GLRaV-2. Two of these amino acid residues (R and D) are believed to be involved in stabilization of molecules by salt bridge formation and proper folding in the most conserved core region of coat proteins of all filamentous plant viruses (Dolja et al., "Phylogeny of Capsid Proteins of Rod-Shaped and Filamentous RNA Plant Viruses Two Families With Distinct Patterns of Sequence and Probably Structure Conservation," *Virology* 184:79–86 (1991), which is hereby incorporated by reference).

Figure 6B:
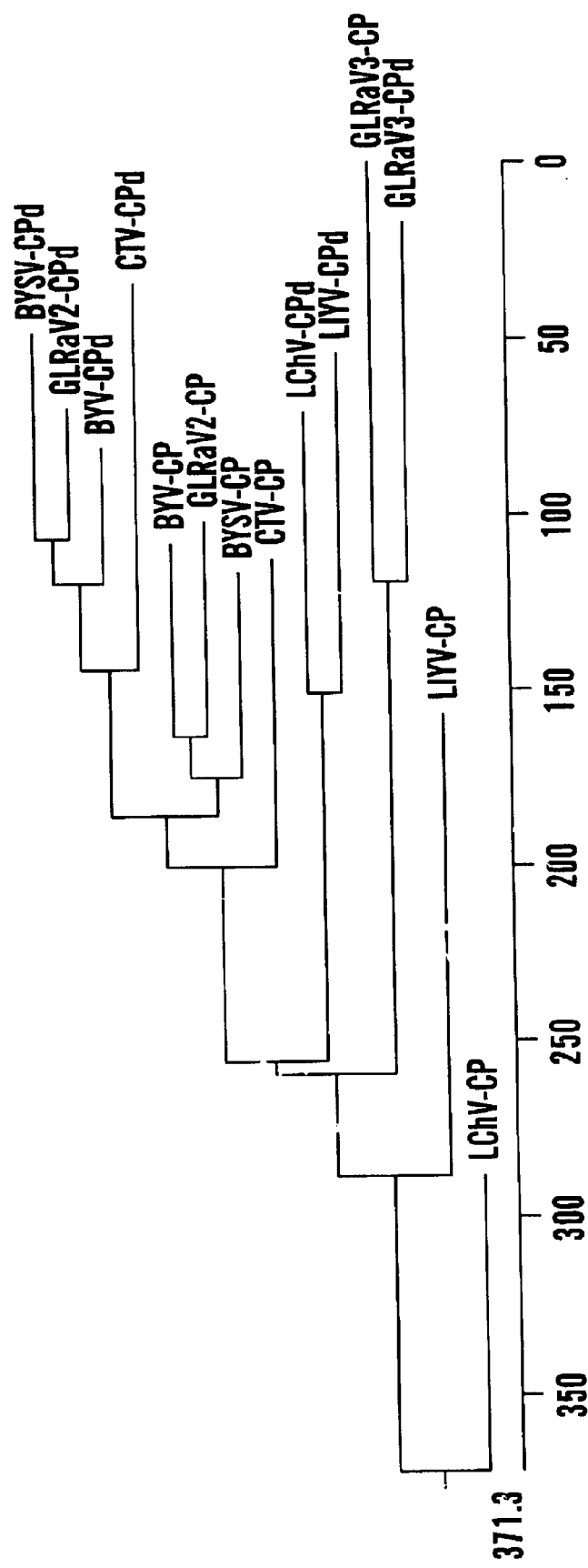

Identification of ORF6 as the coat protein gene was further confirmed by Western blot following expression of a fusion protein, consisting of a 22 kDa of ORF6 CP and a 42 kDa of maltose binding protein, produced by transformed *E. coli* as described in Example 5 supra. As shown in FIG. 6B, the putative phylogenetic tree of the coat protein and coat protein duplicate of GLRaV-2 with those of other *closteroviruses* showed that GLRaV-2 is more closely related to aphid transmissible *closteroviruses* (BYV, BYSV, and CTV) (Candresse, "*Closteroviruses* and *Clostero*-like Elongated Plant Viruses," in *Encyclopedia of Virology*, pp. 242–48, Webster and Granoff, eds., Academic Press, New York (1994), which is hereby incorporated by reference) than to whitefly (LIYV) or mealybug transmissible *closteroviruses* (LChV and GLRaV-3) (Raine et al., "Transmission of the Agent Causing Little Cherry Disease by the Apple Mealybug *Phenacoccus aceris* and the Dodder *Cuscuta Lupuliformis*," *Canadian J. Plant Pathology* 8:6–11 (1986); Jelkmann et al., "Complete Genome Structure and Phylogenetic Analysis of Little Cherry Virus, a Mealybug-Transmissible *Closterovirus*," *J. General Virology* 78:2067–71 (1997); Rosciglione and Gugerli, "Transmission of Grapevine Leafroll Disease and an Associated *Closterovirus* to Healthy Grapevine by the Mealybug *Planococcus ficus*," *Phytoparasitica* 17:63 (1989); Engelbrecht and Kasdorf, "Transmission of Grapevine Leafroll Disease and Associated *Closteroviruses* by the Vine Mealybug *planococcus-ficus*," *Phytophlactica*, 22:34)1–46 (1990); Cabaleiro and Segura, 1997; Petersen and Charles, "Transmission of Grapevine Leafroll-Associated *Closteroviruses* by *Pseudococcus longispinus* and *P. calceolariae*. *Plant Pathology* 46:509–15 (1997), all of which are hereby incorporated by reference).

Figure 7:
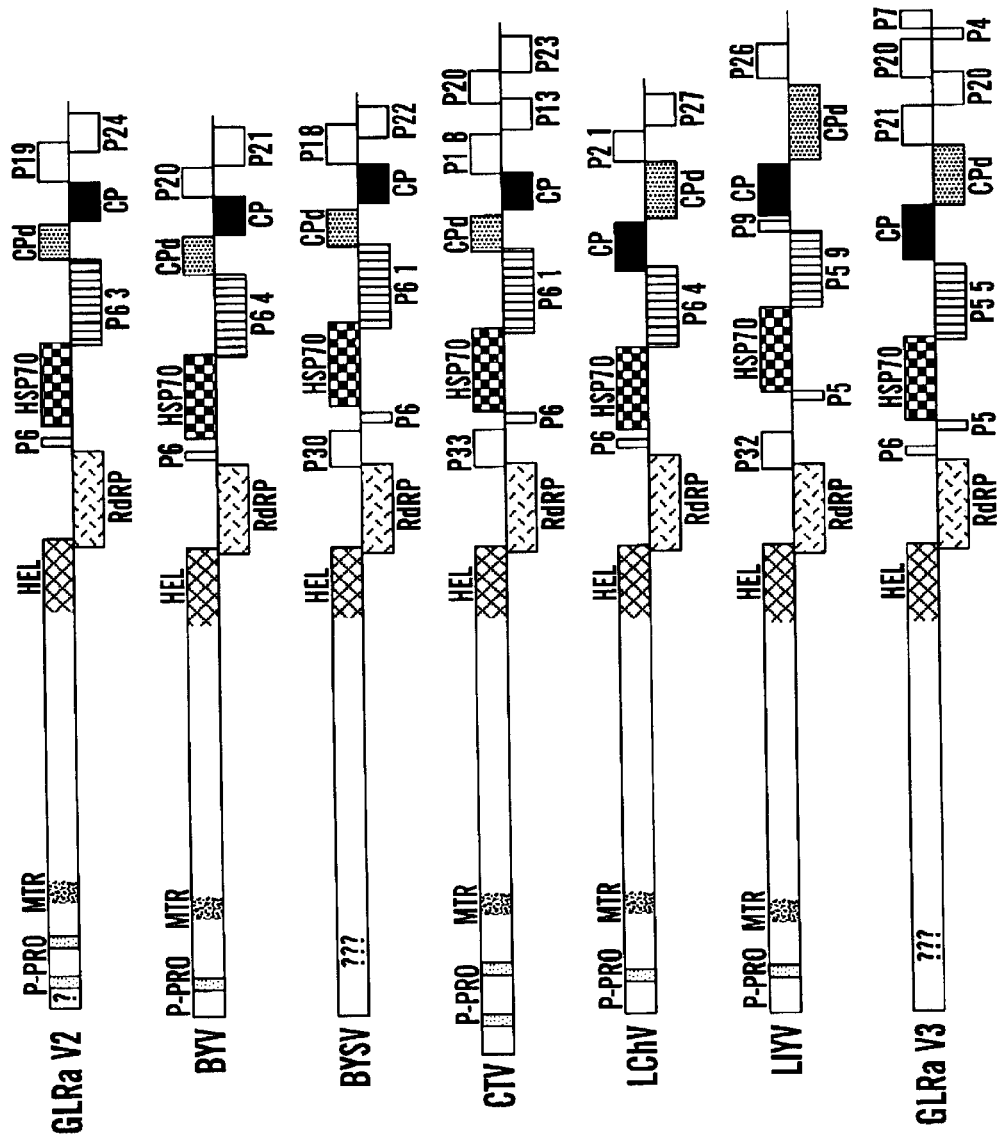

ORF7 and ORF8 encode polypeptides of 162 amino acid with a molecular mass of 18,800 Da and of 206 amino acid with a molecular mass of 23,659 Da, respectively. Database searching with the ORF7 and ORF8 showed no significant similarity with any other proteins. Nevertheless, these genes were of similar in size and location as those observed in the sequence of other *closteroviruses*, BYV (P20, P21), BYSV (P18, P22), and LChV (P21, P27) (FIG. 7). However, conserved regions were not observed between the ORF7 or ORF8 and its counterparts in BYV, BYSV, and LChV.

The 3' terminal untranslated region (3'-UTR) consists of 216 nucleotides. Nucleotide sequence analysis revealed a long oligo(A) tract close to the end of the GLRaV-2 genome which is similar to that observed in the genome of BYV and BYSV (Agranovsky et al. "Nucleotide Sequence of the 3'-Terminal Half of Beet Yellows *Closterovirus* RNA Genome Unique Arrangement of Eight Virus Genes," *J. General Virology* 72:15–24 (1991); Karasev et al., "Organization of the 3'-Terminal Half of Beet Yellow Stunt Virus Genome and Implications for the Evolution of *Closteroviruses*," *Virology* 221:199–207 (1996), both of which are hereby incorporated by reference). The genome of BYV ends in CCC, BYSV, and CTV ends in CC with an additional G or A in the double-stranded replicative form of BYSV (Karasev et al., "Organization of the 3'-Terminal Half of Beet Yellow Stunt Virus Genome and Implications for the Evolution of *Closteroviruses*," *Virology* 221:199–207 (1996), which is hereby incorporated by reference) and CTV (Karasev et al., "Complete Sequence of the *Citrus* Tristeza Virus RNA Genome," *Virology* 208:511–20 (1995), which is hereby incorporated by reference), respectively . GLRaV-2 had CGC at the 3' terminus of the genome. Recently, a conserved 60 nt cis-element was identified in the 3'-UTR of three monopartite *closteroviruses*, which included a prominent conserved stem and loop structure (Karasev et al., 1996). As shown in FIG. 10, alignment of the 3'-UTR sequence of GLRaV-2 with the same regions of BYV, BYSV, and CTV showed the presence of the same conserved 60 nt stretch. Besides this cis-element, conserved sequences were not found in the 3' UTRs of GLRaV-2, BYV, BYSV, and CTV.

The *closteroviruses* studied so far (e.g., BYV, BYSV, CTV, LIYV, LChV, and GLRaV-3) have apparent similarities in genome organization, which include replication associated genes that consist of MT, HEL, and RdRP conserved domains and a five-gene array unique for *closteroviruses* (Dolja et al. "Molecular Biology and Evolution of *Closteroviruses*: Sophisticated Build-up of Large RNA Genomes," *Annual Rev. Photopathology* 32:261–85 (1994); Agranovsky "Principles of Molecular Organization, Expression, and Evolution of *Closteroviruses*: Over the Barriers," *Adv. in Virus Res.* 47:119–218 (1996); Jelkmann et al., "Complete Genome Structure and Phylogenetic Analysis of Little Cherry Virus, a Mealybug-Transmissible *Closterovirus*," *J. General Virology* 78:2067–71 (1997); Ling et al., "Nucleotide Sequence of the 3' Terminal Two-Thirds of the Grapevine Leafroll Associated Virus-3 Genome Reveals a Typical Monopartite *Closterovirus*," *J. General Virology* 79(5) :1289–1301 (1998), all of which are hereby incorporated by reference).

The above data clearly shows that GLRaV-2 is a *closterovirus*. In the genome of GLRaV-2, two putative papain-like proteases were identified and an autoproteolytic cleavage process was predicted. The replication associated proteins consisting of MT, HEL, and RdRP conserved motifs were also identified, which were phylogenetically closely related to the replication associated proteins of other *closteroviruses*. A unique gene array including a small hydrophobic transmembrane protein, HSP70 homolog, HSP90 homolog, diverged CP and CP was also preserved in GLRaV-2. In addition, the calculated molecular mass (21,661 Da) of the coat protein (ORF6) of GLRaV-2 is in good agreement with that of the other *closteroviruses* (22 to 28 kDa) (Martelli and Bar-Joseph, "*Closteroviruses*: Classification and Nomenclature of Viruses," *Fifth Report of the International Committee on Taxonomy of Viruses*, Francki et al., eds., Springer-Verlag Wein, New York, p. 345–47 (1991); Candresse and Martelli, "Genus *Closterovirus*," in *Virus Taxonomy, Report of the International Committee on Taxonomy of Viruses*, Murphy et al., eds., Springer-Verlag., NY, p. 461–63 (1995), both of which are hereby incorporated by reference). Two ORFs downstream of the CP are of similar, in size and location, to those observed in the genome of BYV. Furthermore, lack of a poly(A) tail at the 3' end of GLRaV-2 is also in good agreement with other *closteroviruses*. Like all other *closteroviruses*, the expression of ORF1b is suspected to occur via a +1 ribosomal frameshift and the 3' proximal ORFs are probably expressed via formation of a nested set of subgenomic RNAs. Since the slippery sequence, stem-loop and pseudoknot structure involved in the frameshift of BYV were absent in GLRaV-2, the +1 frameshift of GLRaV-2 might be the same as proposed for CTV (Karasev et al., "Complete Sequence of the *Citrus* Tristeza Virus RNA Genome," *Virology* 208:511–20 (1995), which is hereby incorporated by reference) and BYSV (Karasev et al., "Organization of the 3'-Terminal Half of Beet Yellow Stunt Virus Genome and Implications for the Evolution of *Closteroviruses*," *Virology* 221:199–207 (1996), which is hereby incorporated by reference).

Overall, GLRaV-2 is more closely related to monopartite *closteroviruses* BYV, BYSV, and CTV than to GLRaV-3 (FIG. 7) (Ling et al., "Nucleotide Sequence of the 3' Terminal Two-Thirds of the Grapevine Leafroll Associated Virus-3 Genome Reveals a Typical Monopartite *Closterovirus*," *J. General Virology* 79(5):1289–1301 (1998), which is hereby incorporated by reference), even though the latter causes similar leafroll symptoms in grapevine (Rosciglione and Gugerli, "Maladies de l'Enroulement et du Bois Strie de la Vigne: Analyse Microscopique et Serologique (Leafroll and Stem Pitting of Grapevine: Microscopical and Serological Analysis)," *Rev Suisse Viticult Arboricult Horticulture* 18:207–11 (1986); Hu et al., "Characterization of *Closterovirus*-Like Particles Associated with Grapevine Leafroll Disease," *J. Phytopathology* 128:1–14 (1990), both of which are hereby incorporated by reference).

*Closteroviruses* are a diverse group with complex and heterogeneous genome organizations. So far, GLRaV-2 is the only *closterovirus* that matches with the genome organization of BYV, the type member of the genus *Closterovirus*. In addition, the genomic RNA of GLRaV-2 is about the same size as that of BYV; however, the transmission vector of GLRaV-2 is unknown. The genome organization of GLRaV-2 is more closely related to the aphid transmissible *closteroviruses* (BYV and CTV) than to whitefly (LIYV) or mealybug transmissible *closteroviruses* (LChV and GLRaV-3). Thus, it is possible that GLRaV-2 is transmitted by aphids. Aphid transmission experiments with GLRaV-2 should provide information that might help develop methods for further control of GLRaV-2.

A total of 15,500 nucleotides or over 95% of the estimated GLRaV-2 genome has been cloned and sequenced. GLRaV-2 and GLRaV-3 (Ling et al., "Nucleotide Sequence of the 3' Terminal Two-Thirds of the Grapevine Leafroll Associated Virus-3 Genome Reveals a Typical Monopartite *Closterovirus*," *J. General Virology* 79(5):1289–1301 (1998), which is hereby incorporated by reference) are the first grapevine leafroll associated *closteroviruses* that have been almost completely sequenced. The above data clearly justify the inclusion of GLRaV-2 into the genus *Closterovirus*. In addition, the information regarding the genome of GLRaV-2 would provide a better understanding of this and related GLRaVs, and add fundamental knowledge to the group of *closteroviruses*.

Example 7

Construction of the CP Gene of GLRaV-2 in Plant Expression Vector

GLRaV-2 infected *Vitis vinifera*, cv Pinot Noir grapevines originated from a vineyard in central New York was used as the virus isolate, from which the cp gene of GLRaV-2 was identified. Based on the sequence information, two oligonucleotide primers have been designed. The sense primer CP-96F (SEQ. ID. No. 21) starts from the ATG initiation codon of the coat protein gene and the complementary primer CP-96R (SEQ. ID. No. 22) starts from 56 nucleotides downstream of the stop codon of the CP gene. A NcoI restriction site (11 bp in SEQ. ID. No. 21 and 13 bp in SEQ. ID. No. 22) is introduced in the beginning of both primers to facilitate the cloning. The coat protein gene of GLRaV-2 was amplified from dsRNA extracted from GLRaV-2 infected grapevine using reverse transcriptase polymerase chain reaction (RT-PCR). The PCR-amplified CP product was purified from low melting temperature agarose gel, digested with NcoI and cloned into the same enzyme digested plant expression vector pEPT8 (shown at FIG. 11). After screening, the orientation of recombinant construct was checked by using the internal restriction site of the CP gene and directly sequencing the CP gene. The recombinant construct with translatable (sense) full length coat protein gene, pEPT8CP-GLRaV2, was going through for the further cloning. The plant expression cassette, which consisted of a double cauliflower mosaic virus (CaMV) 35S-enhancer, a CaMV 35S-promoter, an alfalfa mosaic virus (ALMV) RNA4 5' leader sequence, a coat protein gene of GLRaV-2 (CP-GLRaV-2), and a CaMV 35S 3' untranslated region as a terminator, was cut using the EcoRI restriction enzyme, isolated from low melting point temperature agarose gel, and cloned into the same restriction enzyme treated binary vector pGA482GG or pGA482G (a derivative of pGA482 (An et al., "Binary Vectors," in *Plant Molecular Biology Manual*, pp. A3:1–19, Gelvin and Schilperoot, eds., Kinwer Academic Publishers, Dordrecht, Netherlands (1988), which is hereby incorporated by reference). The resulting recombinants constructs are pGA482GG/EPT8CP-GLRaV2 (shown at FIG. 11A), which contain both neomycin phosphotransferase (npt II) and β-glucuronidase (GUS) at the internal region of the T-DNA, and pGA482G/EPT8CP-GLRaV2 (shown at FIG. 11B) without GUS. These recombinants constructs were separately introduced by electroporation into disarmed avirulent *Agrobacterium tumefaciens* strain C58Z707. The *Agrobacterium tumefaciens* containing the vector was used to infect *Nicotiana benthamiana* wounded leaf disks according to the procedure essentially described by Horsch et al., "A Simple and General Method for Transferring Genes into Plants," *Science* 277:1229–1231 (1985), which is incorporated herein by reference.

Example 8

Analysis of Transgenic *Nicotiana benthamiana* Plants with the CP Gene of GLRaV-2

NPT II-ELISA: Double-antibody sandwich enzyme linked immunosorbent assay (DAS-ELISA) was used to detect the npt II enzyme with an NPT II-ELISA kit (5' prime to 3' prime, Inc., Boulder, Colo.).

Indirect ELISA: Polyclonal antibodies to GLRaV-2, which were prepared from the coat protein expressed in *E. coli*, were used. Plates were coated with homogenized samples in extraction buffer (1:10, w/v) (phosphate buffered saline containing 0.05% Tween 20 and 2% polyvinyl pyrrolidone) and incubated overnight at 4° C. After washing with phosphate buffered saline containing 0.05% Tween 20 (PBST), the plates were blocked with blocking buffer (phosphate buffered saline containing 2% BSA) and incubated at room temperature for 1 hr. The anti-GLRaV-2 IgG was added at 2 µg/ml after washing with PBST. After incubation at 30 C for 4 hr, the plates were washed with PBST, and the goat anti-rabbit IgG conjugate of alkaline phosphotase (Sigma) was added at 1:10,000 dilution. The absorbance was measured at 405 nm with a MicroELISA AutoReader. In addition, Western blot was also performed according to the method described by Hu et al., "Characterization of *Closterovirus*-like Particle Associated Grapevine Leafroll Disease," *J. Phytophathology* 128:1–14, (1990), which is incorporated herein by reference.

PCR analysis: Genomic DNA was extracted from leaves of putative transgenic and non-transgenic plants according to the method described by Cheung et al., "A Simple and Rapid DNA Microextraction Method for Plants, Animal, and Insect Suitable for RAPD and other PCR analysis," *PCR Methods and Applications* 3:69 (1996), which is incorporated herein by reference. The extracted total DNA served as the template for PCR reaction. The primers CP-96F and CP-96R (SEQ. ID. Nos. 21 and 22, respectively,) for the CP gene of GLRaV-2, as well as npt II 5'- and 3'-primers were used for PCR analysis. PCR reaction was performed at the 94° C.×3 min for one cycle, followed by 30 cycles of 94° C.×1 min, 50° C.×1 min, and 72° C.×2:30 min with an additional extension at 72° C. for 10 min. The PCR product was analyzed on agarose gel.

After transformation, a total of 42 kanamycin resistant *Nicotiana benthamiana* lines ($R_0$) were obtained, of which the leaf samples were tested by NPT II enzyme activity. Among them, 37 lines were NPT II positive by ELISA, which took about 88.0% of total transformants. However, some of NPT II negative plants were obtained among these selected kanamycin resistant plants. All of the transgenic plants were self-pollinated in a greenhouse, and the seeds from these transgenic lines were germinated for further analysis.

Figure 12:
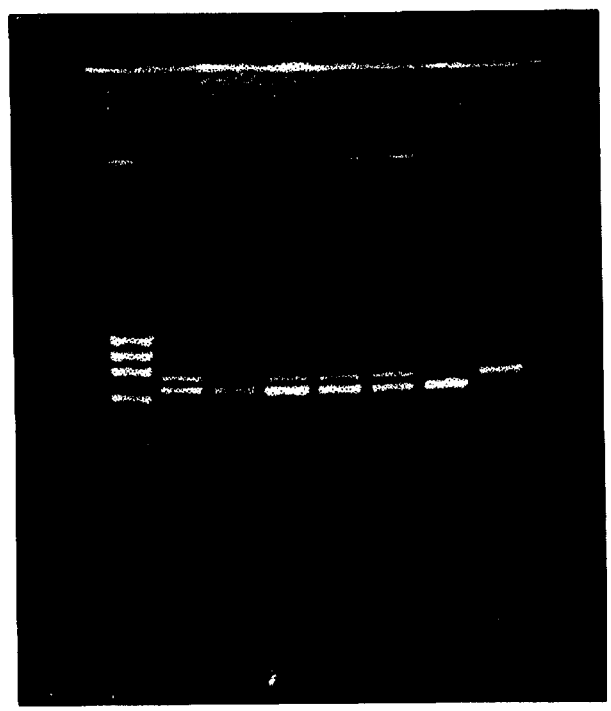

The production of GLRaV-2 CP in transgenic plants was detected by indirect ELISA prior to inoculation, and the results showed that GLRaV-2 CP gene expression was not detectable in all transgenic plants tested. This result was further confirmed with Western blot. Using the antibody to GLRaV-2, the production of the CP was not detected in the transgenic and nontransgenic control plants. However, a protein of expected size (~22 kDa) was detected in GLRaV-2 infected positive control plants. This result was consistent with the ELISA result. The presence of the CP gene of GLRaV-2 in transgenic plants was detected from total genomic DNA extracted from plants tissue by PCR analysis (FIG. 12). The DNA product of expected size (653 bp) was amplified from twenty tested transgenic lines, but not in non-transgenic plants. The result indicated that the CP gene of GLRaV-2 was present at these transgenic lines, which was also confirmed by Northern blot analysis.

Example 9

$R_1$ and R2 transgenic *Nicotiana benthamiana* Plants Are Resistant to GLRaV-2

Inoculation of transgenic plants: GLRaV-2 isolate 94/970, which was originally identified and transmitted from grapevine to *Nicotiana benthamiana* in South Africa (Goszczynski et al., "Detection of Two Strains of Grapevine Leafroll-Associated Virus 2," *Vitis* 35:133–35 (1996), which is incorporated herein by reference), was used as inoculum. The CP gene of isolate 94/970 was sequenced; and it is identical to the CP gene used in construction. *Nicotiana benthamiana* is an experimental host of GLRaV-2. The infection on it produces chlorotic and occasional necrotic lesions followed by systemic vein clearing. The vein clearing results in vein necrosis. Eventually the infected plants died, starting from the top to the bottom.

At five to seven leaf stage, two youngest apical leaves were challenged with GLRaV-2 isolate 94/970. Inoculum was prepared by grinding 1.0 g GLRaV-2 infected *Nicotiana benthamiana* leaf tissue in 5 ml of phosphate buffer (0.01 M K2HPO4, PH7.0). The tested plants were dusted with carborundum and rubbed with the prepared inoculum. Non-transformed plants were simultaneously inoculated as above. The plants were observed for symptom development every other day for 60 days after inoculation. Resistant R1 transgenic plants were carried on to R2 generation for further evaluation.

Transgenic progenies from 20 $R_0$ lines were initially screened for the resistance to GLRaV-2 followed by inoculation with GLRaV-2 isolate 94/970. The seedlings of the transgenic plants (NPT II positive), and nontransformed control plants were inoculated with GLRaV-2. After inoculation, the reaction of tested plants were divided into three types: highly susceptible (i.e. typical symptoms were observed two to four weeks postinoculation); tolerant (i.e. no symptom was developed in the early stage and typical symptoms was shown four to eight weeks postinoculation); and resistant (i.e. the plants remained asymptomatic eight weeks postinoculation). Based on the plant reaction, the resistant plants were obtained from fourteen different lines (listed in Table 1 below). In each of these fourteen lines, there was no virus detected within these plants by ELISA at 6 weeks postinoculation. In contrast, GLRaV-2 was detected in symptomatic plants by indirect ELISA. In the other six lines, although there were a few plants with some kind of delay in symptom development, all the inoculated transgenic plants died at three to eight weeks postinoculation. Based o(n the initial screening results, five representative lines consisting of three resistant lines (1, 4, and 19) and two susceptible lines (12 and 13) were selected for the further analysis.

TABLE 1

| No. Line | No. | Reaction of Tested Plants | | |
| --- | --- | --- | --- | --- |
| | | HS | T | HR |
| line 1 | 39 | 14 | 3 | 22 |
| line 2 | 36 | 7 | 6 | 23 |
| line 3 | 38 | 11 | 4 | 23 |
| line 4 | 31 | 4 | 5 | 22 |
| line 5 | 33 | 6 | 13 | 14 |
| line 6 | 36 | 4 | 16 | 16 |
| line 7 | 32 | 5 | 9 | 18 |
| line 8 | 37 | 22 | 9 | 6 |
| line 9 | 36 | 9 | 12 | 15 |
| line 10 | 14 | 13 | 1 | 0 |
| line 11 | 13 | 11 | 2 | 0 |
| line 12 | 17 | 16 | 1 | 0 |
| line 13 | 16 | 14 | 0 | 0 |
| line 14 | 17 | 17 | 0 | 0 |
| line 15 | 32 | 30 | 2 | 0 |
| line 16 | 33 | 6 | 13 | 14 |
| line 17 | 12 | 0 | 1 | 11 |
| line 19 | 15 | 0 | 0 | 15 |
| line 20 | 19 | 3 | 0 | 16 |
| line 21 | 14 | 1 | 3 | 10 |
| control | 15 | 15 | 0 | 0 |

No. Line: include transgenic lines and nontransformed control;
No.: the number of transgenic and nontransformed plants;
HS: highly susceptible, typical symptoms were observed two to four weeks after inoculation;
T: tolerant, the symptoms were observed five to eight weeks after inoculation; and
HR: plants remain without asymptoms after eight weeks inoculation.

Figure 13:
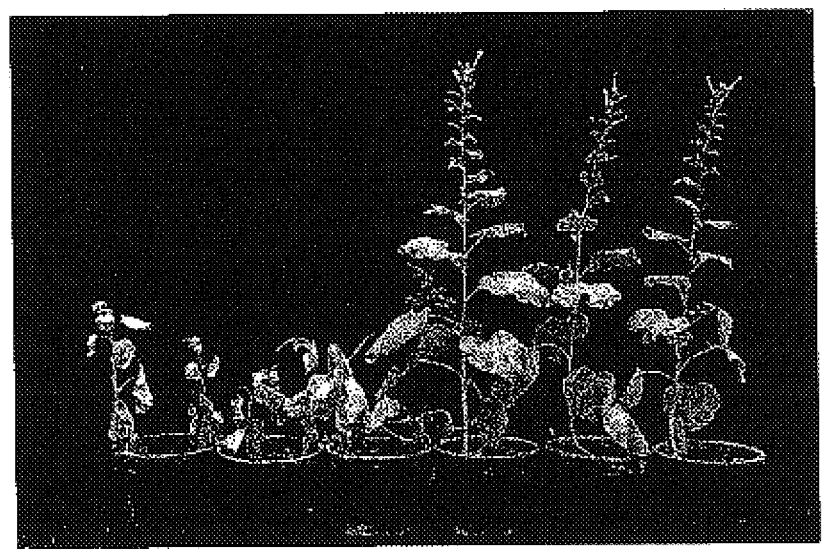

Table 2 below shows the symptom development in transgenic plants relative to non-transgenic control plants in the five selected lines in separate experiments. Non-transgenic control plants were all infected two to four weeks after inoculation, which showed typical GLRaV-2 symptoms on *Nicotiana benthamiana*, including chlorotic and local lesions followed by systemic vein clearing and vein necrosis on the leaves. Three of the tested lines (1, 4, and 19) showed some resistance that was manifested by either an absence or a delay in symptom development. Two other lines, 12 and 13, developed symptoms at nearly the same time as the non-transformed control plants. From top to bottom, the leaves of infected plants gradually became yellow, wilted, and dried, and, eventually, the whole plants died. No matter when infection occurred, the eventual result was the same. Six weeks after inoculation, all non-transgenic plants and the susceptible plants were dead. Some tolerant plants started to die. In contrast, the asymptomatic plants were flowering normally and pollinating as the non-inoculated healthy control plants (FIG. 13).

TABLE 2

| No. Line | No. | Reaction of Tested Plants | | |
| --- | --- | --- | --- | --- |
| | | HS | T | HR |
| line 1 | 19 | 5 | 6 | 8 |
| line 4 | 15 | 9 | 1 | 5 |
| line 12 | 16 | 14 | 2 | 0 |
| line 13 | 18 | 13 | 5 | 0 |
| line 19 | 13 | 10 | 0 | 3 |
| non-transgenic | 24 | 23 | 1 | 0 |

No. Line: include transgenic lines and nontransformed control;
No.: Number of transgenic and nontransformed plants tested;
HS: highly susceptible; typical symptoms were observed two to four weeks after inoculation;
T: tolerant, the symptoms were observed five to eight weeks postinoculation; and
HR: plants remain without asymptoms after eight weeks inoculation.

ELISA was performed at 6 weeks postinoculation to test the GLRaV-2 replication in the plants. Presumably, the increased level of CP reflected virus replication. The result showed that the absorbance value in symptomatic plants reached (OD) 0.7 to 3.2, compared to (OD) 0.10–0.13 prior to inoculation. In contrast, GLRaV-2 was not detected in asymptomatic plants, of which the absorbance value was the same or nearly the same as that of healthy nontransformed control plants. The data confirmed that virus replicated in symptomatic plants, but not in asymptomatic plants. The replication of GLRaV-2 was suppressed in asymptomatic plants. This result implicated that another mechanism other than the CP-mediated resistance was probably involved.

Three 2 progenies derived from transgenic resistant plants of lines 1, 4, and 19 were generated and utilized to examine the stable transmission and whether resistance was maintained in R2 generation. These results are shown in Table 3 below. NPT II analysis revealed that R2 progeny were still segregating. The CP expression in R2 progeny was still undetectable. After inoculation, all the nontransgenic plants were infected and showed GLRaV-2 symptoms on the leaves after 24 days postinoculation. In contrast, the inoculated transgenic $R_2$ progeny showed different levels of resistance from those highly susceptible to highly resistant. The tolerant and resistant plants were manifested by a delay in symptom development and absence of symptoms, respectively. At 6 weeks postinoculation, GLRaV-2 was detected in the tolerant symptomatic infected plants by indirect ELISA; but not in asymptomatic plants. This result indicated that virus replication was suppressed in these resistant plants, which was confirmed by Western blot. These resistant plants remained asymptomatic eight weeks postinoculation, and they were flowering normally and pollinating.

TABLE 3

| No. Line | No. Plants | NPT II positive/ negative | Reaction of Tested Plants | | |
|---|---|---|---|---|---|
| | | | HS | T | HR |
| line 1/22 | 12 | 12/20 | 3 | 3 | 6 |
| line 1/30 | 11 | 8/3 | 7 | 2 | 2 |
| line 1/31 | 11 | 10/1 | 6 | 3 | 2 |
| line 1/35 | 10 | 10/0 | 4 | 6 | 0 |
| line 1/41 | 8 | 7/1 | 2 | 2 | 4 |
| line 4/139 | 12 | 11/1 | 4 | 4 | 3 |
| line 4/149 | 10 | 7/3 | 4 | 5 | 1 |
| line 4/152 | 10 | 8/2 | 9 | 0 | 1 |
| line 4/174 | 9 | 8/1 | 4 | 0 | 4 |
| line 19/650 | 11 | 10/1 | 7 | 0 | 2 |
| line 19/657 | 12 | 12/0 | 6 | 2 | 4 |
| line 19/659 | 12 | 8/4 | 5 | 2 | 5 |
| line 19/660 | 10 | 8/2 | 3 | 6 | 1 |
| non-transformed CK | 12 | 0/12 | 12 | 0 | 0 |

HS: highly susceptible, typical symptoms were observed two to four weeks after inoculation;
T: tolerant, the symptoms were observed five to eight weeks postinoculation; and
HR: plants remain asymptomatic at eight weeks postinoculation.

Example 10

Evidence for RNA-mediated Protection in Transgenic Plants

Northern blot analysis: Total RNA was extracted from leaves prior to inoculation following the method described by Napoli et al., Plant Cell 2:279–89 (1990), which is hereby incorporated by reference. The concentration of the extracted RNA was measured by spectrophotometer at OD 260. About 10 g of total RNA was used for each sample. The probe used was the 3' one third of GLRaV-2 CP gene, which was randomly labeled with $^{32}P$ ($\alpha$-dATP) using Klenow fragment of DNA polymerase I.

Figure 14:
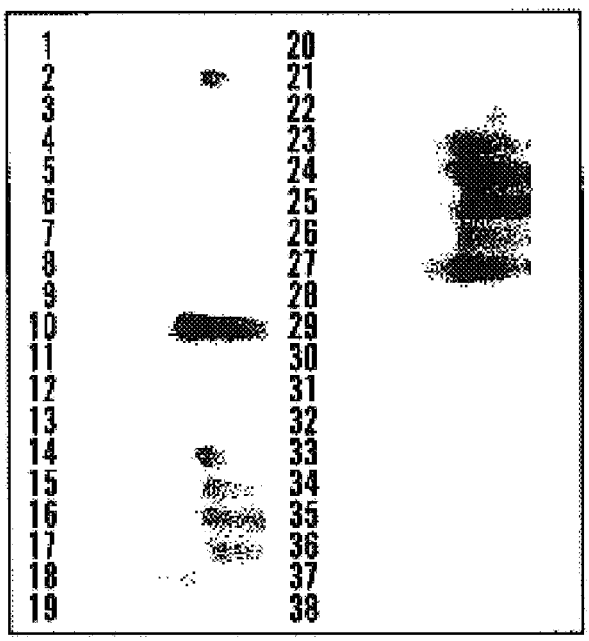

Using a DNA corresponding to the 3' one third CP gene sequence as probe, a single band was detected in the RNA extracted from susceptible plants from R1 progeny of lines 5, 12, and 13 by Northern hybridization. There was little or no signal detected in the transgenic plants from R1 progeny of line 1, 4, and 19. This RNA is not present in nontransformed control plants. The size of the hybridization signal was estimated to an approximately 0.9 kb nucleic acid, which was about the same as estimated (FIG. 14). In lines of 1, 4, and 19, the steady state level of RNA expression was also low in R2 progeny. This data showed that susceptible plants from lines 12 and 13 had high mRNA level and all transgenic plants from lines 1, 4, and 19 had low mRNA level.

Example 11

Transformation and Analysis of Transgenic Grapevines with the CP Gene of GLRaV-2

Plant materials: The rootstock cultivars Couderc 3309 (3309C) (V. riparia×V. rupestris), Vitis riparia 'Gloire de Montpellier' (Gloire), Teleki 5C (5C) (V. berlandieri×V. riparia), Millardet et De Grasset 101–14 (101–14 MGT) (V. riparia×V. rupestris), and Richter 110 (110R) (V. rupestris× V. berlandieri) were utilized. Initial embryogenic calli of Gloire were provided by Mozsar and Süle (Plant Protection Institute, Hungarian Academy of Science, Budapest). All other plant materials came from a vineyard at the New York State Agricultural Experiment Station, Geneva, N.Y. Buds were removed from the clusters and surface sterilized in 70% ethanol for 1–2 min. The buds (from the greenhouse and the field) were transferred to 1% sodium hypochlorite for 15 min, then rinsed three times in sterile, double-distilled water. Anthers were excised aseptically from flower buds with the aid of a stereo microscope. The pollen was crushed on a microscope slide under a coverslip with a drop of acetocarmine to observe the cytological stage. This was done to determine which stage was most favorable for callus induction.

Somatic embryogenesis and regeneration: Anthers were plated under aseptic conditions at a density of 40 to 50 per 9 cm diameter Petri dish containing MSE. Plates were cultured at 28° C. in the dark. Callus was initiated, and, after 60 days, embryos were induced and were transferred to hormone-free HMG medium for differentiation. Torpedo stage embryos were then transferred from HMG to MGC medium to promote embryo germination. Cultures were maintained in the dark at 26–28° C. and transferred to fresh medium at 34 week intervals. Elongated embryos were transferred to rooting medium in baby food jars (5–8 embryos per jar). The embryos were grown in a tissue culture room at 25° C. with a daily 16 h photoperiod (76:mol. s) to induce shoot and root formation. After plants developed roots, they were transplanted to soil in the greenhouse.

Transformation: The protocols used for transformation were modified from those described by Scorza et. al., "Transformation of Grape (Vitis vinifera L.) Zygotic-derived Somatic Embryos and Regeneration of Transgenic Plants," Plant Cell Rpt. 14:589–92 (1995), which is hereby incorporated by reference. Overnight cultures of Agrobacterium strain C58Z707 or LBA4404 were grown in LB medium at 28° C. in a shaking incubator. Bacteria were centrifuged for 5 min at 3000–5000 rpm and resuspended in MS liquid medium (OD 1.0 at A600 nm ). Calli with embryos were immersed in the bacterial suspension for 15–30 min, blotted dry, and transferred to HMG medium with or without acetosyringone (100 $\mu$M). Embryogenic calli were co-cultivated with the bacteria for 48 h in the dark at 28° C. Then, the plant material was washed in MS liquid plus cefotaxime (300 mg/ml) and carbenicillin (200 mg/ml) 2–3 times. To select transgenic embryos, the material was transferred to HMG medium containing either 20 or 40 mg/L kanamycin, 300 mg/L cefotaxime, and 200 mg/L carbenicillin. Alternatively, after co-cultivation, embryogenic calli were transferred to initiation MSE medium containing 25 mg/l kanamycin plus the same antibiotics listed above. All plant materials were incubated in continuous dark at 28° C. After growth on selection medium for 3 months, embryos were transferred to HMG or MGC without kanamycin to promote elongation of embryos. They were then transferred to rooting medium Without antibiotics. Nontransformed calli were grown on the same media with and without kanamycin to verify the efficiency of the kanamycin selection process.

Although the invention has been described in detail for the purpose of illustration, it is understood that such detail is solely for that purpose, and variations can be made therein by those skilled in the art without departing from the spirit and scope of the invention which is defined by the following claims.

We claim:

1. An expression system comprising a DNA molecule in a vector heterologous to said DNA molecule, wherein said DNA molecule encodes a protein or polypeptide comprising the amino acid sequence of SEQ ID NO:15.

2. A host cell transformed with a heterologous DNA molecule, wherein said DNA molecule encodes a protein or polypeptide comprising the amino acid sequence of SEQ ID NO:15.

3. The host cell according to claim 2, wherein the host cell is selected from the group consisting of *Agrobacterium vitis* and *Agrobacterium tumefaciens*.

4. The host cell according to claim 2, wherein the host cell is selected from a group consisting of a grape cell, a citrus cell, a beet cell, and a tobacco cell.

5. The expression system of claim 1, wherein said DNA molecule comprises the nucleic acid sequence of SEQ ID NO:14.

6. The host cell of claim 2, wherein said DNA molecule comprises the nucleic acid sequence of SEQ ID NO:14.

* * * * *

UNITED STATES PATENT AND TRADEMARK OFFICE
CERTIFICATE OF CORRECTION

PATENT NO.     : 6,858,426 B1
DATED          : February 22, 2005
INVENTOR(S)    : Hai-Ying Zhu, Kai-Shu Ling and Dennis Gonsalves It is certified that error appears in the above-identified patent and that said Letters Patent is hereby corrected as shown below:

Title page,
Item [56], References Cited, OTHER PUBLICATIONS, "Habill et al. reference, replace "Habill" with -- Habili --; and
"Wetzel et al." reference, "A Highly Sensitive Immunocapture Polymerase Chain Reaction Method for Plum Pox Virus Detection," should be flanked by quotation marks.
Item [57], ABSTRACT, replace "leafroll resistance, to grape" with -- leafroll resistance to grape --.

Column 2,
Line 10, replace "48:51-54 (1958)," with -- 48:51-54 (1958) --; and
Line 22, replace "(1936)." with -- (1936) ). --; and
Line 57, replace "2:23-39" with --; 22:23-39 and
Line 58, replace "(Castellano" with -- ("Castellano --; and
Line 58, before "A Small" insert -- " --; and
Line 60, "Grapevine," insert -- " --; and
Line 60, replace "45: -70-73" with -- 45:70-73 --; and
Line 63, replace "*phytopathol, Soc. Japan*, 45." with -- phytopathol. Soc. Japan, 45: --.

Column 3
Line 19, replace "*Phyopathol.*" with -- *Phytopathol.* --.

Column 4,
Line 2, replace "Serotype III, "*phytopathology*" with -- Serotype III," *phytopathology* --; and
Line 12, replace "*Viticult, Arboricult,*" with -- Viticult. Arboricult. --; and
Line 15, before "Detection" insert -- " --; and
Line 18, before "Characterization" insert -- " --; and
Line 35, replace "3Cloning" with -- 3: Cloning --; and
Line 44, replace "been sequences" with -- been sequenced --.

Column 5,
Line 43, before "Leafroll" insert -- ( --.

Column 6,
Line 26, replace "polypeptide, corresponding" with -- polypeptide corresponding --.

UNITED STATES PATENT AND TRADEMARK OFFICE
CERTIFICATE OF CORRECTION

PATENT NO. : 6,858,426 B1
DATED : February 22, 2005
INVENTOR(S) : Hai-Ying Zhu, Kai-Shu Ling and Dennis Gonsalves It is certified that error appears in the above-identified patent and that said Letters Patent is hereby corrected as shown below:

Column 8,
Line 11, before "Organization" insert -- " --; and
Line 23, after "respectively" insert -- . --.

Signed and Sealed this

Nineteenth Day of July, 2005

JON W. DUDAS
*Director of the United States Patent and Trademark Office*